United States Patent
Martin et al.

(10) Patent No.: US 9,439,422 B2
(45) Date of Patent: *Sep. 13, 2016

(54) USE OF MACROCYCLIC PICOLINAMIDES AS FUNGICIDES

(71) Applicant: DOW AGROSCIENCES LLC, Indianapolis, IN (US)

(72) Inventors: Timothy P. Martin, Noblesville, IN (US); Kevin G. Meyer, Zionsville, IN (US); Benjamin Nugent, Brownsburg, IN (US); Chenglin Yao, Westfield, IN (US); W. John Owen, Carmel, IN (US); Anne M. Wilson, Indianapolis, IN (US); Ian O'Callaghan, Kinsale (IE); Jeremy Wilmot, Zionsville, IN (US); Johnathan E. DeLorbe, Pearland, TX (US); William Dent, III, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/500,628

(22) Filed: Sep. 29, 2014

(65) Prior Publication Data

US 2015/0094340 A1    Apr. 2, 2015

Related U.S. Application Data

(60) Provisional application No. 61/885,380, filed on Oct. 1, 2013, provisional application No. 61/885,391, filed on Oct. 1, 2013.

(51) Int. Cl.

| A01N 43/24 | (2006.01) |
|---|---|
| A01N 47/18 | (2006.01) |
| C07D 405/12 | (2006.01) |
| C07D 321/00 | (2006.01) |
| A01N 43/40 | (2006.01) |
| A01N 53/00 | (2006.01) |

(52) U.S. Cl.
CPC ............ *A01N 43/24* (2013.01); *A01N 43/40* (2013.01); *A01N 47/18* (2013.01); *A01N 53/00* (2013.01); *C07D 321/00* (2013.01); *C07D 405/12* (2013.01)

(58) Field of Classification Search
CPC .... A61K 31/44; A61K 31/355; A01N 43/40; A01N 43/24; A01N 47/18; A01N 53/00; C07D 405/12; C07D 321/00
See application file for complete search history.

(56) References Cited

U.S. PATENT DOCUMENTS

| 6,355,660 B1 | 3/2002 | Ricks |
|---|---|---|
| 6,521,622 B1 | 2/2003 | Ricks |
| 6,706,740 B2 | 3/2004 | Ricks |
| 6,861,390 B2 | 3/2005 | Meyer |
| 6,927,225 B2 | 8/2005 | Ricks |
| 7,034,035 B2 | 4/2006 | Ricks |
| 7,183,278 B1 | 2/2007 | Imamura |
| 7,250,389 B1 | 7/2007 | Sakanaka |
| 8,785,479 B2 | 7/2014 | Meyer |
| 8,835,462 B2 | 9/2014 | Meyer |
| 8,883,811 B2 | 11/2014 | Owen |
| 2002/0177578 A1 | 11/2002 | Ricks |
| 2003/0018012 A1 | 1/2003 | Ricks |
| 2003/0018052 A1 | 1/2003 | Ricks |
| 2003/0022902 A1 | 1/2003 | Ricks |
| 2004/0034025 A1 | 2/2004 | Ricks |
| 2004/0048864 A1 | 3/2004 | Ricks |
| 2004/0171838 A1 | 9/2004 | Meyer |
| 2004/0186296 A1 | 9/2004 | Nyaz |
| 2004/0192924 A1 | 9/2004 | Meyer |
| 2005/0239873 A1 | 10/2005 | Hockenbery |
| 2007/0060579 A1 | 3/2007 | Wachendorff-Neumann |
| 2007/0066629 A1 | 3/2007 | Tormo I Blasco |
| 2009/0306142 A1 | 12/2009 | Carson |
| 2013/0296371 A1 | 11/2013 | Meyer |
| 2014/0187588 A1 | 7/2014 | Lalonde |
| 2014/0275171 A1 | 9/2014 | Meyer |
| 2015/0065529 A1 | 3/2015 | Owen |

FOREIGN PATENT DOCUMENTS

| EP | 1516874 | 3/2005 |
|---|---|---|
| WO | 01/14339 | 3/2001 |
| WO | 01/14339 A2 | 3/2001 |

(Continued)

OTHER PUBLICATIONS

Koyanagi, T.,"Bioisosterism in agrochemicals." In Synthesis and chemistry of agrochemicals IV., pp. 15-24. American Chemical Society, 1995.*

(Continued)

*Primary Examiner* — Samantha Shterengarts
*Assistant Examiner* — Matt Mauro
(74) *Attorney, Agent, or Firm* — Charles W. Arnett; Faegre Baker Daniels LLP

(57) ABSTRACT

The invention relates to macrocyclic picolinamides of Formula I and their use as fungicides.

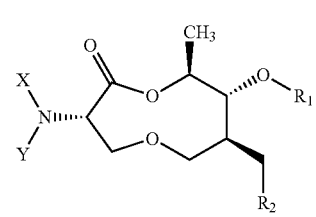

20 Claims, No Drawings

(56) References Cited

FOREIGN PATENT DOCUMENTS

| WO | 2009040397 | 9/2008 |
| WO | 2012/070015 | 5/2012 |
| WO | 2012/070015 A1 | 5/2012 |

OTHER PUBLICATIONS

Thomas, S., International Search Report for PCT/US14/58061, Dec. 15, 2014, pp. 1-4, ISA/US.

Thomas, S., International Search Report for PCT/US14/58065, Dec. 22, 2014, pp. 1-4, ISA/US.

Thomas, S., Written Opinion for PCT/US14/58061, Dec. 15, 2014, pp. 1-5, ISA/US.

Thomas, S., Written Opinion for PCT/US14/58065, Dec. 22, 2014, pp. 1-5, ISA/US.

Anonymous, Synergistic Fungicidal Composition of Heterocyclic Aromatic Amides and Trizaoles, IP.com, Electronic Publication, 2004, 11 pages.

Anonymous, Synergistic Fungicidal Composition of Heterocyclic Aromatic Amides and Triazoles, IP.com Journal, IP.com Inc., West Henrietta, NY, US, Dates Jul. 2004, 10 pages.

K. Tani, et al, Journal of Antibiotics, vol. 55, No. 3, Mar. 2002, pp. 315-321.

Z. Hu, et al, Synthesis of Novel Analogues of Antimycin A3, Tetrahedron Letters 49 (2008) pp. 5192-5195.

Y. Usuki, et al, Journal of Antibiotics, vol. 55, No. 6, Jun. 2002, pp. 607-610.

* cited by examiner

USE OF MACROCYCLIC PICOLINAMIDES AS FUNGICIDES

CROSS REFERENCE TO RELATED APPLICATIONS

This application claims the benefit of U.S. Provisional Patent Application Ser. No. 61/885,380, and U.S. Provisional Patent Application Ser. No. 61/885,391, each filed Oct. 1, 2013, the disclosure of each of which is expressly incorporated by reference herein.

BACKGROUND & SUMMARY

Fungicides are compounds, of natural or synthetic origin, which act to protect and/or cure plants against damage caused by agriculturally relevant fungi. Generally, no single fungicide is useful in all situations. Consequently, research is ongoing to produce fungicides that may have better performance, are easier to use, and cost less.

The present disclosure relates to macrocyclic picolinamides and their use as fungicides. The compounds of the present disclosure may offer protection against ascomycetes, basidiomycetes, deuteromycetes and oomycetes.

One embodiment of the present disclosure may include compounds of Formula I:

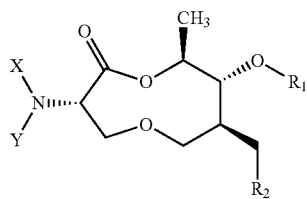

X is H or C(O)R$_3$;
Y is H, C(O)R$_3$, or Q;
Q is

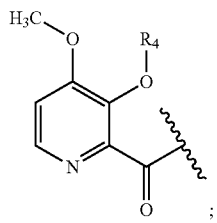

R$_1$ is H, alkyl, alkenyl, aryl, —Si(R$_6$)$_3$, —C(O)R$_6$, each substituted with 0, 1 or multiple R$_5$;
R$_2$ is H, alkyl, aryl, heteroaryl, arylalkyl, each substituted with 0, 1 or multiple R$_5$;
R$_3$ is alkoxy, benzyloxy, each substituted with 0, 1, or multiple R$_5$;
R$_4$ is H, —C(O)R$_7$, or —CH$_2$OC(O)R$_7$;
R$_5$ is H, alkyl, alkenyl, halo, haloalkyl, alkoxy, aryl, heteroaryl, heterocyclyl, —C(O)R$_6$;
R$_6$ is alkyl, alkenyl, haloalkyl, alkoxy, aryl or heteroaryl; and
R$_7$ is alkyl or alkoxy, each substituted with 0, 1, or multiple R$_6$;
with the proviso that R$_2$ is not unsubstituted phenyl or unsubstituted cyclohexyl.

Another embodiment of the present disclosure may include a fungicidal composition for the control or prevention of fungal attack comprising the compounds described above and a phytologically acceptable carrier material.

Yet another embodiment of the present disclosure may include a method for the control or prevention of fungal attack on a plant, the method including the steps of applying a fungicidally effective amount of one or more of the compounds described above to at least one of the fungus, the plant, and an area adjacent to the plant.

It will be understood by the those skilled in the art that the following terms may include generic "R"-groups within their definitions, e.g., "the term alkoxy refers to an —OR substituent". It is also understood that within the definitions for the following terms, these "R" groups are included for illustration purposes and should not be construed as limiting or being limited by substitutions about Formula I.

The term "alkyl" refers to a branched, unbranched, or saturated cyclic carbon chain, including, but not limited to, methyl, ethyl, propyl, butyl, isopropyl, isobutyl, tertiary butyl, pentyl, hexyl, cyclopropyl, cyclobutyl, cyclopentyl, cyclohexyl and the like.

The term "alkenyl" refers to a branched, unbranched or cyclic carbon chain containing one or more double bonds including, but not limited to, ethenyl, propenyl, butenyl, isopropenyl, isobutenyl, cyclobutenyl, cyclopentenyl, cyclohexenyl, and the like.

The term "alkynyl" refers to a branched or unbranched carbon chain containing one or more triple bonds including, but not limited to, propynyl, butynyl and the like.

The term "aryl" refers to any aromatic, mono- or bi-cyclic, containing 0 heteroatoms.

The term "unsubstituted phenyl" refers to a phenyl ring in which the 5 available bonding sites are all occupied by a hydrogen atom.

The term "unsubstituted cyclohexyl" refers to a 6-membered, saturated carbocycle in which the 11 available bonding sites are all occupied by a hydrogen atom.

The term "heterocycle" refers to any aromatic or non-aromatic ring, mono- or bi-cyclic, containing one or more heteroatoms.

The term "alkoxy" refers to an —OR substituent.
The term "cyano" refers to a —C≡N substituent.
The term "hydroxyl" refers to an —OH substituent.
The term "amino" refers to a —NH$_2$ substituent.
The term "arylalkoxy" refers to —O(CH$_2$)$_n$Ar where n is an integer selected from the list 1, 2, 3, 4, 5, or 6.
The term "haloalkoxy" refers to an —OR—X substituent, wherein X is Cl, F, Br, or I, or any combination thereof.
The term "haloalkyl" refers to an alkyl, which is substituted with Cl, F, I, or Br or any combination thereof.
The term "halogen" or "halo" refers to one or more halogen atoms, defined as F, Cl, Br, and I.
The term "nitro" refers to a —NO$_2$ substituent.

Throughout the disclosure, reference to the compounds of Formula I is read as also including diastereomers, enantiomers, and mixtures thereof. In another embodiment, Formula (I) is read as also including salts or hydrates thereof. Exemplary salts include, but are not limited to: hydrochloride, hydrobromide, and hydroiodide.

It is also understood by those skilled in the art that additional substitution is allowable, unless otherwise noted, as long as the rules of chemical bonding and strain energy are satisfied and the product still exhibits fungicidal activity.

Another embodiment of the present disclosure is a use of a compound of Formula I, for protection of a plant against attack by a phytopathogenic organism or the treatment of a plant infested by a phytopathogenic organism, comprising the application of a compound of Formula I, or a composition comprising the compound to soil, a plant, a part of a plant, foliage, and/or roots.

Additionally, another embodiment of the present disclosure is a composition useful for protecting a plant against attack by a phytopathogenic organism and/or treatment of a plant infested by a phytopathogenic organism comprising a compound of Formula I and a phytologically acceptable carrier material.

DETAILED DESCRIPTION

The compounds of the present disclosure may be applied by any of a variety of known techniques, either as the compounds or as formulations comprising the compounds. For example, the compounds may be applied to the roots or foliage of plants for the control of various fungi, without damaging the commercial value of the plants. The materials may be applied in the form of any of the generally used formulation types, for example, as solutions, dusts, wettable powders, flowable concentrate, or emulsifiable concentrates.

Preferably, the compounds of the present disclosure are applied in the form of a formulation, comprising one or more of the compounds of Formula I with a phytologically acceptable carrier. Concentrated formulations may be dispersed in water, or other liquids, for application, or formulations may be dust-like or granular, which may then be applied without further treatment. The formulations can be prepared according to procedures that are conventional in the agricultural chemical art.

The present disclosure contemplates all vehicles by which one or more of the compounds may be formulated for delivery and use as a fungicide. Typically, formulations are applied as aqueous suspensions or emulsions. Such suspensions or emulsions may be produced from water-soluble, water-suspendible, or emulsifiable formulations which are solids, usually known as wettable powders; or liquids, usually known as emulsifiable concentrates, aqueous suspensions, or suspension concentrates. As will be readily appreciated, any material to which these compounds may be added may be used, provided it yields the desired utility without significant interference with the activity of these compounds as antifungal agents.

Wettable powders, which may be compacted to form water-dispersible granules, comprise an intimate mixture of one or more of the compounds of Formula I, an inert carrier and surfactants. The concentration of the compound in the wettable powder may be from about 10 percent to about 90 percent by weight based on the total weight of the wettable powder, more preferably about 25 weight percent to about 75 weight percent. In the preparation of wettable powder formulations, the compounds may be compounded with any finely divided solid, such as prophyllite, talc, chalk, gypsum, Fuller's earth, bentonite, attapulgite, starch, casein, gluten, montmorillonite clays, diatomaceous earths, purified silicates or the like. In such operations, the finely divided carrier and surfactants are typically blended with the compound(s) and milled.

Emulsifiable concentrates of the compounds of Formula I may comprise a convenient concentration, such as from about 1 weight percent to about 50 weight percent of the compound, in a suitable liquid, based on the total weight of the concentrate. The compounds may be dissolved in an inert carrier, which is either a water-miscible solvent or a mixture of water-immiscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, for example, terpenic solvents, including rosin derivatives, aliphatic ketones, such as cyclohexanone, and complex alcohols, such as 2-ethoxyethanol.

Emulsifiers which may be advantageously employed herein may be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil-soluble salts or sulfated polyglycol ethers and appropriate salts of phosphated polyglycol ether.

Representative organic liquids which may be employed in preparing the emulsifiable concentrates of the compounds of the present disclosure are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, the methyl ether of triethylene glycol, petroleum fractions or hydrocarbons such as mineral oil, aromatic solvents, paraffinic oils, and the like; vegetable oils such as soy bean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable oils; and the like. Mixtures of two or more organic liquids may also be employed in the preparation of the emulsifiable concentrate. Organic liquids include xylene, and propyl benzene fractions, with xylene being most preferred in some cases. Surface-active dispersing agents are typically employed in liquid formulations and in an amount of from 0.1 to 20 percent by weight based on the combined weight of the dispersing agent with one or more of the compounds. The formulations can also contain other compatible additives, for example, plant growth regulators and other biologically active compounds used in agriculture.

Aqueous suspensions comprise suspensions of one or more water-insoluble compounds of Formula I, dispersed in an aqueous vehicle at a concentration in the range from about 1 to about 50 weight percent, based on the total weight of the aqueous suspension. Suspensions are prepared by finely grinding one or more of the compounds, and vigorously mixing the ground material into a vehicle comprised of water and surfactants chosen from the same types discussed above. Other components, such as inorganic salts and synthetic or natural gums, may also be added to increase the density and viscosity of the aqueous vehicle.

The compounds of Formula I can also be applied as granular formulations, which are particularly useful for applications to the soil. Granular formulations generally contain from about 0.5 to about 10 weight percent, based on the total weight of the granular formulation of the compound(s), dispersed in an inert carrier which consists entirely or in large part of coarsely divided inert material such as attapulgite, bentonite, diatomite, clay or a similar inexpensive substance. Such formulations are usually prepared by dissolving the compounds in a suitable solvent and applying it to a granular carrier which has been preformed to the appropriate particle size, in the range of from about 0.5 to about 3 mm. A suitable solvent is a solvent in which the compound is substantially or completely soluble. Such formulations may also be prepared by making a dough or paste of the carrier and the compound and solvent, and crushing and drying to obtain the desired granular particle.

Dusts containing the compounds of Formula I may be prepared by intimately mixing one or more of the compounds in powdered form with a suitable dusty agricultural carrier, such as, for example, kaolin clay, ground volcanic rock, and the like. Dusts can suitably contain from about 1 to about 10 weight percent of the compounds, based on the total weight of the dust.

The formulations may additionally contain adjuvant surfactants to enhance deposition, wetting and penetration of the compounds onto the target crop and organism. These adjuvant surfactants may optionally be employed as a component of the formulation or as a tank mix. The amount of adjuvant surfactant will typically vary from 0.01 to 1.0 percent by volume, based on a spray-volume of water, preferably 0.05 to 0.5 volume percent. Suitable adjuvant surfactants include, but are not limited to ethoxylated nonyl phenols, ethoxylated synthetic or natural alcohols, salts of the esters or sulphosuccinic acids, ethoxylated organosilicones, ethoxylated fatty amines, blends of surfactants with mineral or vegetable oils, crop oil concentrate (mineral oil (85%)+emulsifiers (15%)); nonylphenol ethoxylate; benzyl-cocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO-PO block copolymer; polysiloxane-methyl cap; nonylphenol ethoxylate+urea ammonium nitrrate; emulsified methylated seed oil; tridecyl alcohol (synthetic) ethoxylate (8EO); tallow amine ethoxylate (15 EO); PEG(400) dioleate-99. The formulations may also include oil-in-water emulsions such as those disclosed in U.S. patent application Ser. No. 11/495,228, the disclosure of which is expressly incorporated by reference herein.

The formulations may optionally include combinations that contain other pesticidal compounds. Such additional pesticidal compounds may be fungicides, insecticides, herbicides, nematocides, miticides, arthropodicides, bactericides or combinations thereof that are compatible with the compounds of the present disclosure in the medium selected for application, and not antagonistic to the activity of the present compounds. Accordingly, in such embodiments, the other pesticidal compound is employed as a supplemental toxicant for the same or for a different pesticidal use. The compounds of Formula I and the pesticidal compound in the combination can generally be present in a weight ratio of from 1:100 to 100:1.

The compounds of the present disclosure may also be combined with other fungicides to form fungicidal mixtures and synergistic mixtures thereof. The fungicidal compounds of the present disclosure are often applied in conjunction with one or more other fungicides to control a wider variety of undesirable diseases. When used in conjunction with other fungicide(s), the presently claimed compounds may be formulated with the other fungicide(s), tank-mixed with the other fungicide(s) or applied sequentially with the other fungicide(s). Such other fungicides may include 2-(thiocyanatomethylthio)-benzothiazole, 2-phenylphenol, 8-hydroxyquinoline sulfate, ametoctradin, amisulbrom, antimycin, *Ampelomyces quisqualis*, azaconazole, azoxystrobin, *Bacillus subtilis, Bacillus subtilis* strain QST713, benalaxyl, benomyl, benthiavalicarb-isopropyl, benzylaminobenzenesulfonate (BABS) salt, bicarbonates, biphenyl, bismerthiazol, bitertanol, bixafen, blasticidin-S, borax, Bordeaux mixture, boscalid, bromuconazole, bupirimate, calcium polysulfide, captafol, captan, carbendazim, carboxin, carpropamid, carvone, chlazafenone, chloroneb, chlorothalonil, chlozolinate, *Coniothyrium minitans*, copper hydroxide, copper octanoate, copper oxychloride, copper sulfate, copper sulfate (tribasic), cuprous oxide, cyazofamid, cyflufenamid, cymoxanil, cyproconazole, cyprodinil, dazomet, debacarb, diammonium ethylenebis-(dithiocarbamate), dichlofluanid, dichlorophen, diclocymet, diclomezine, dichloran, diethofencarb, difenoconazole, difenzoquat ion, diflumetorim, dimethomorph, dimoxystrobin, diniconazole, diniconazole-M, dinobuton, dinocap, diphenylamine, dithianon, dodemorph, dodemorph acetate, dodine, dodine free base, edifenphos, enestrobin, enestroburin, epoxiconazole, ethaboxam, ethoxyquin, etridiazole, famoxadone, fenamidone, fenarimol, fenbuconazole, fenfuram, fenhexamid, fenoxanil, fenpiclonil, fenpropidin, fenpropimorph, fenpyrazamine, fentin, fentin acetate, fentin hydroxide, ferbam, ferimzone, fluazinam, fludioxonil, flumorph, fluopicolide, fluopyram, fluoroimide, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, guazatine, guazatine acetates, GY-81, hexachlorobenzene, hexaconazole, hymexazol, imazalil, imazalil sulfate, imibenconazole, iminoctadine, iminoctadine triacetate, iminoctadine tris(albesilate), iodocarb, ipconazole, ipfenpyrazolone, iprobenfos, iprodione, iprovalicarb, isoprothiolane, isopyrazam, isotianil, kasugamycin, kasugamycin hydrochloride hydrate, kresoxim-methyl, laminarin, mancopper, mancozeb, mandipropamid, maneb, mefenoxam, mepanipyrim, mepronil, meptyl-dinocap, mercuric chloride, mercuric oxide, mercurous chloride, metalaxyl, metalaxyl-M, metam, metam-ammonium, metam-potassium, metam-sodium, metconazole, methasulfocarb, methyl iodide, methyl isothiocyanate, metiram, metominostrobin, metrafenone, mildiomycin, myclobutanil, nabam, nitrothal-isopropyl, nuarimol, octhilinone, ofurace, oleic acid (fatty acids), orysastrobin, oxadixyl, oxine-copper, oxpoconazole fumarate, oxycarboxin, pefurazoate, penconazole, pencycuron, penflufen, pentachlorophenol, pentachlorophenyl laurate, penthiopyrad, phenylmercury acetate, phosphonic acid, phthalide, picoxystrobin, polyoxin B, polyoxins, polyoxorim, potassium bicarbonate, potassium hydroxyquinoline sulfate, probenazole, prochloraz, procymidone, propamocarb, propamocarb hydrochloride, propiconazole, propineb, proquinazid, prothioconazole, pyraclostrobin, pyrametostrobin, pyraoxystrobin, pyrazophos, pyribencarb, pyributicarb, pyrifenox, pyrimethanil, pyriofenone, pyroquilon, quinoclamine, quinoxyfen, quintozene, *Reynoutria sachalinensis* extract, sedaxane, silthiofam, simeconazole, sodium 2-phenylphenoxide, sodium bicarbonate, sodium pentachlorophenoxide, spiroxamine, sulfur, SYP-Z048, tar oils, tebuconazole, tebufloquin, tecnazene, tetraconazole, thiabendazole, thifluzamide, thiophanate-methyl, thiram, tiadinil, tolclofos-methyl, tolylfluanid, triadimefon, triadimenol, triazoxide, tricyclazole, tridemorph, trifloxystrobin, triflumizole, triforine, triticonazole, validamycin, valifenalate, valiphenal, vinclozolin, zineb, ziram, zoxamide, *Candida oleophila, Fusarium oxysporum, Gliocladium* spp., *Phlebiopsis gigantea, Streptomyces griseoviridis, Trichoderma* spp., (RS)-N-(3,5-dichlorophenyl)-2-(methoxymethyl)-succinimide, 1,2-dichloropropane, 1,3-dichloro-1,1,3,3-tetrafluoroacetone hydrate, 1-chloro-2,4-dinitronaphthalene, 1-chloro-2-nitropropane, 2-(2-heptadecyl-2-imidazolin-1-yl)ethanol, 2,3-dihydro-5-phenyl-1,4-dithi-ine 1,1,4,4-tetraoxide, 2-methoxyethylmercury acetate, 2-methoxyethylmercury chloride, 2-methoxyethylmercury silicate, 3-(4-chlorophenyl)-5-methylrhodanine, 4-(2-nitroprop-1-enyl)phenyl thiocyanateme, ampropylfos, anilazine, azithiram, barium polysulfide, Bayer 32394, benodanil, benquinox, bentaluron, benzamacril; benzamacril-isobutyl, benzamorf, binapacryl, bis(methylmercury) sulfate, bis(tributyltin) oxide, buthiobate, cadmium calcium copper zinc chromate sulfate, carbamorph, CECA, chlobenthiazone, chloraniformethan, chlorfenazole, chlorquinox, climbazole, copper bis(3-phenylsalicylate), copper zinc chromate, cufraneb, cupric hydrazinium sulfate, cuprobam, cyclafuramid, cypendazole, cyprofuram, decafentin, dichlone, dichlozoline, diclobutrazol, dimethirimol, dinocton, dinosulfon, dinoterbon, dipyrithione, ditalimfos, dodicin, drazoxolon, EBP, ESBP, etaconazole, etem, ethirim, fenaminosulf, fenapanil, fenitropan, fluotrimazole, furcarbanil, furconazole, furconazole-cis, furmecyclox, furophanate, glyodine, griseofulvin, halacrinate, Hercules 3944, hexylthiofos, ICIA0858, isopamphos, isovaledione, mebenil, mecarbinzid, metazoxolon, methfuroxam, methylmercury dicyandiamide, metsulfovax, milneb, mucochloric anhydride, myclozolin, N-3,5-dichlorophenyl-succinimide, N-3-nitrophenylitaconimide, natamycin, N-ethylmercurio-4-toluenesulfonanilide, nickel bis(dimethyldithiocarbamate), OCH, phenylmercury dimethyldithiocarbamate, phenylmercury nitrate, phosdiphen, prothiocarb; prothiocarb hydrochloride, pyracarbolid, pyridinitril, pyroxychlor, pyroxyfur, quinacetol; quinacetol sulfate, quinazamid, quinconazole, rabenzazole, salicylanilide, SSF-109, sultropen, tecoram, thiadifluor, thicyofen, thiochlorfenphim, thiophanate, thioquinox, tioxymid, triamiphos, triarimol, triazbutil, trichlamide, urbacid, zarilamid, and any combinations thereof.

Additionally, the compounds described herein may be combined with other pesticides, including insecticides, nematocides, miticides, arthropodicides, bactericides or combinations thereof that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more other pesticides to control a wider variety of undesirable pests. When used in conjunction with other pesticides, the presently claimed compounds may be formulated with the other pesticide(s), tank-mixed with the other pesticide(s) or applied sequentially with the other pesticide(s). Typical insecticides include, but are not limited to: 1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluoron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, flpronil, flonicamid, flubendiamide, flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, mephosfolan, mercurous chloride, mesulfenfos, metaflumizone, methacrifos, methamidophos, methidathion, methiocarb, methocrotophos, methomyl, methoprene, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluoron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, promacyl, promecarb, propaphos, propetamphos, propoxur, prothidathion, prothiofos, prothoate, protrifenbute, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos, and any combinations thereof.

Additionally, the compounds described herein may be combined with herbicides that are compatible with the compounds of the present disclosure in the medium selected for application, and not antagonistic to the activity of the present compounds to form pesticidal mixtures and synergistic mixtures thereof. The fungicidal compounds of the present disclosure may be applied in conjunction with one or more herbicides to control a wide variety of undesirable plants. When used in conjunction with herbicides, the presently claimed compounds may be formulated with the herbicide(s), tank-mixed with the herbicide(s) or applied sequentially with the herbicide(s). Typical herbicides include, but are not limited to: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, amino cyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, diallate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, triafamone, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

Another embodiment of the present disclosure is a method for the control or prevention of fungal attack. This method comprises applying to the soil, plant, roots, foliage, or locus of the fungus, or to a locus in which the infestation is to be prevented (for example applying to cereal or grape plants), a fungicidally effective amount of one or more of the compounds of Formula I. The compounds are suitable for treatment of various plants at fungicidal levels, while exhibiting low phytotoxicity. The compounds may be useful both in a protectant and/or an eradicant fashion.

The compounds have been found to have significant fungicidal effect particularly for agricultural use. Many of the compounds are particularly effective for use with agricultural crops and horticultural plants.

It will be understood by those in the art that the efficacy of the compound for the foregoing fungi establishes the general utility of the compounds as fungicides.

The compounds have broad ranges of activity against fungal pathogens. Exemplary pathogens may include, but are not limited to, causing agent of wheat leaf blotch (*Mycosphaerella graminicola*; inperfect stage: *Septoria tritici*), wheat brown rust (*Puccinia triticina*), wheat stripe rust (*Puccinia striiformis*), scab of apple (*Venturia inaequalis*), powdery mildew of grapevine (*Uncinula necator*), barley scald (*Rhynchosporium secalis*), blast of rice (*Magnaporthe grisea*), rust of soybean (*Phakopsora pachyrhizi*), glume blotch of wheat (*Leptosphaeria nodorum*), powdery mildew of wheat (*Blumeria graminis* f. sp. *tritici*), powdery mildew of barley (*Blumeria graminis* f. sp. *hordei*), powdery mildew of cucurbits (*Erysiphe cichoracearum*), anthracnose of cucurbits (*Glomerella lagenarium*), leaf spot of beet (*Cercospora beticola*), early blight of tomato (*Alternaria solani*), and spot blotch of barley (*Cochliobolus sativus*). The exact amount of the active material to be applied is dependent not only on the specific active material being applied, but also on the particular action desired, the fungal species to be controlled, and the stage of growth thereof, as well as the part of the plant or other product to be contacted with the compound. Thus, all the compounds, and formulations containing the same, may not be equally effective at similar concentrations or against the same fungal species.

The compounds are effective in use with plants in a disease-inhibiting and phytologically acceptable amount. The term "disease-inhibiting and phytologically acceptable amount" refers to an amount of a compound that kills or inhibits the plant disease for which control is desired, but is not significantly toxic to the plant. This amount will generally be from about 0.1 to about 1000 ppm (parts per million), with 1 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre (about 0.01 to 0.45 grams per square meter, $g/m^2$).

Any range or desired value given herein may be extended or altered without losing the effects sought, as is apparent to the skilled person for an understanding of the teachings herein.

The compounds of Formula I may be made using well-known chemical procedures. Intermediates not specifically mentioned in this disclosure are either commercially available, may be made by routes disclosed in the chemical literature, or may be readily synthesized from commercial starting materials utilizing standard procedures.

General Schemes

The following schemes illustrate approaches to generating picolinamide compounds of Formula (I). It may be understood by those skilled in the art that each $R_2$ may be differentially substituted. The following descriptions and examples are provided for illustrative purposes and should not be construed as limiting in terms of substituents or substitution patterns.

Compounds of Formula 1.4, where $R_2$ is as originally defined, can be prepared according to the methods outlined in Scheme 1, steps a-b. Compounds of Formula 1.2 can be obtained by reaction of an acid chloride prepared from carboxylic acids of Formula 1.1, where $R_2$ is as originally defined, using a chlorinating agent, such as oxalyl chloride or thionyl chloride, in a solvent such as dichloroethane (DCE) in the presence of a catalytic amount of N,N-dimethylformamide (DMF), with the amide anion of a chiral oxazolidinone prepared by treating compound 1.0 with n-butyllithium (n-BuLi) in an anhydrous solvent such as tetrahydrofuran (THF) at −78° C., as shown in a. Compounds of Formula 1.4, can be prepared by treating the boron enolate of compounds of Formula 1.2, formed using dibutyl(((trifluoromethyl)-sulfonyl)oxy)borane and an amine base such as triethylamine, with a benzyl- or triisopropylsilyl protected lactate-derived aldehyde of Formula 1.3, prepared as described by Enders et al. *Organic Syntheses*, 2004, 10, 66; 2002, 78, 177, in a solvent such as dichloromethane ($CH_2Cl_2$, DCM) at −78° C. to −10° C., as shown in b.

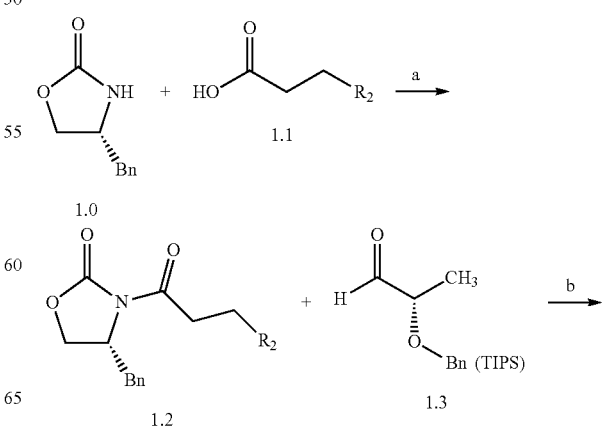

Scheme 1

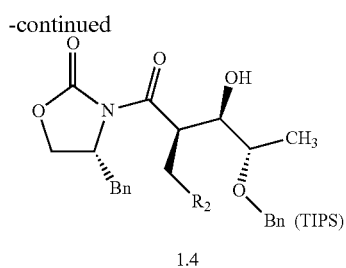

1.4

Compounds of Formula 2.6, where $R_1$ is alkyl, $R_2$ is as originally defined, and X is tert-butoxycarbonyl (Boc) can be prepared according to the methods outlined in Scheme 2, steps a-e. Compounds of Formula 2.1, where $R_1$ possesses an allylic functionality and $R_2$ is as originally defined, can be prepared by treating compounds of Formula 2.0, where $R_2$ is as originally defined, with an allyl carbonate, such as tert-butyl(2-methylallyl)carbonate, in the presence of a palladium (0) catalyst with or without the addition of a phosphine ligand, such as tris(dibenzylideneacetone)-dipalladium(0) ($Pd_2(dba)_3$) and 1,1'-bis(diphenylphosphino) ferrocene (dppf), in an aprotic solvent such as THF, at elevated temperatures, such as 45 to 60° C., as depicted in a. Primary alcohols of Formula 2.2, where $R_1$ possesses an allylic functionality and $R_2$ is as originally defined, can be obtained from compounds of Formula 2.1, where $R_1$ and $R_2$ are as defined above, by treatment with a reducing agent such as lithium borohydride ($LiBH_4$) in a mixed solvent system consisting of THF and water ($H_2O$), as shown in b. Compounds of Formula 2.4, where $R_1$ possesses an allylic functionality and $R_2$ is as originally defined and X is Boc or Cbz, can be prepared from compounds of Formula 2.2, where $R_1$ and $R_2$ are as defined above, by treatment with a protected aziridine of Formula 2.3, wherein X is Boc or Cbz, such as (S)-1-tert-butyl 2-methyl aziridine-1,2-dicarboxylate, in the presence of a Lewis acid such as boron trifluoride diethyl etherate ($BF_3$-$Et_2O$), in an aprotic solvent such as DCM, as shown in c. Compounds of Formulas 2.5 or 2.6, wherein the allylic functionality in $R_1$ has been reduced to an alkyl functionality, $R_2$ is as originally defined, and X is Boc, can be prepared from compounds of Formula 2.4, where $R_1$, $R_2$, and X are as defined above, by treatment with hydrogen in the presence of a catalyst, such as palladium on carbon (Pd/C), in a solvent such as ethyl acetate (EtOAc), as shown in d. Treating compounds of Formula 2.4, where $R_1$, $R_2$, and X are as defined above and the carboxylic acid is protected as the benzyl (Bn) ester, as described in d affords compounds of Formula 2.6 directly, whereas treatment of compounds of Formula 2.4 wherein the carboxylic acid is protected as the methyl (Me) ester, as described in d affords compounds of Formula 2.5, which require an additional hydrolysis step, as shown in e. In step e compounds of Formula 2.5 are converted to compounds of Formula 2.6, using a hydroxide base, such as lithium hydroxide (LiOH), in an aqueous THF solvent mixture.

Scheme 2

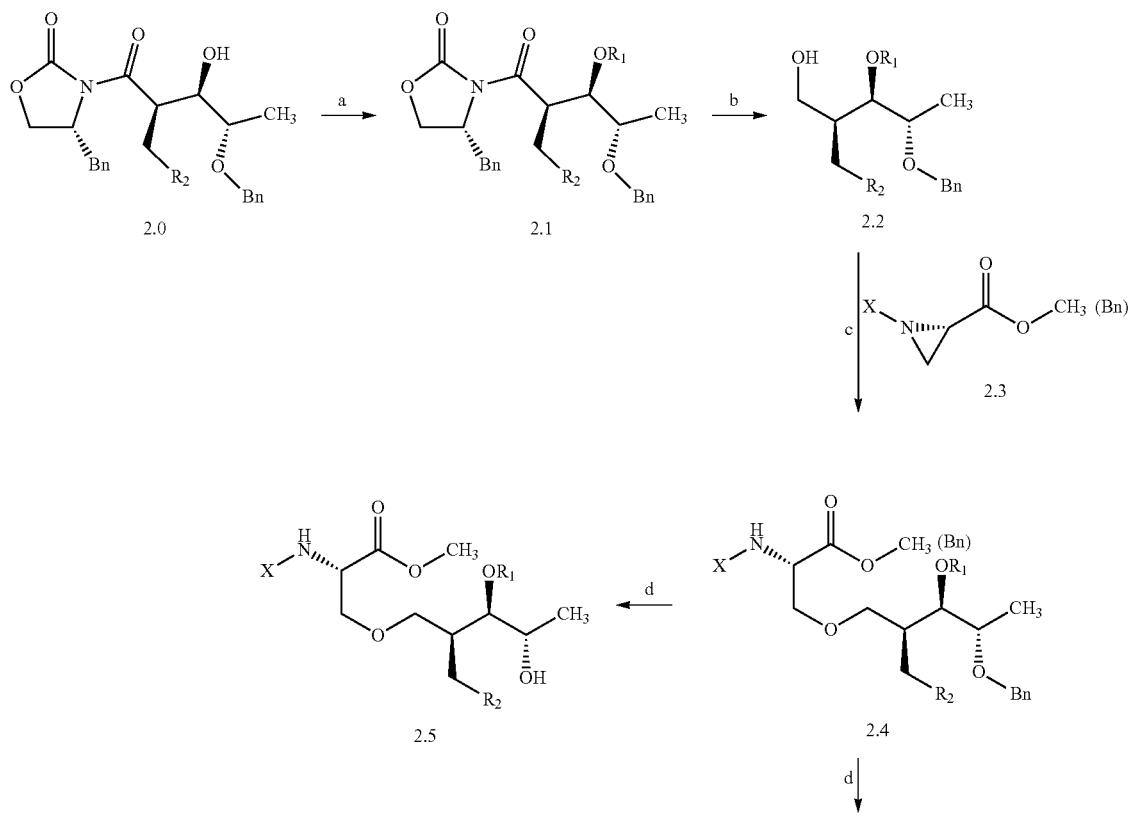

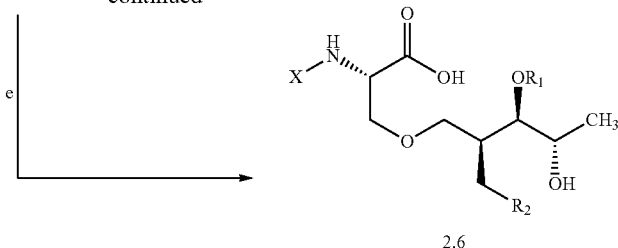

2.6

Compounds of Formula 3.5, where R₁ is triisopropylsilyl (TIPS), R₂ is as originally defined, and X is as originally defined, but not hydrogen, can be prepared according to the methods outlined in Scheme 3, steps a-f. Compounds of Formula 3.1, where R₂ is as originally defined, can be obtained from compounds of Formula 3.0, where R₂ is as originally defined, using an aqueous acid solution such as hydrochloric acid (HCl) in a solvent such as ethanol (EtOH) at an elevated temperature, such as 80° C., as shown in a. Compounds of Formula 3.2, where R₁ is TIPS and R₂ is as originally defined, can be obtained from compounds of Formula 3.1, where R₂ is as defined above, by exposure to triisopropylsilyl trifluoro-methanesulfonate and an amine base, such as 4-N,N-dimethylamino pyridine (DMAP), in a solvent such as DCM, as shown in b. Compounds of Formula 3.3, where R₁ is TIPS and R₂ is as originally defined, can be prepared from compounds of Formula 3.2, where R₁ and R₂ are as defined above, by treatment with a reducing agent such as diisobutylaluminum hydride (DIBAl-H) in a solvent such as DCM, as shown in c. Compounds of Formula 3.4, where R₁ is TIPS and R₂ is as originally defined and X is Boc or Cbz, can be prepared from compounds of Formula 3.3, where R₁ and R₂ are as defined above, by treatment with a protected aziridine of Formula 2.3, wherein X is Boc or Cbz, such as (S)-1-tert-butyl 2-methyl aziridine-1,2-dicarboxylate, in the presence of a Lewis acid such as BF₃-Et₂O, in an aprotic solvent such as DCM, as shown in d. Compounds of Formula 3.5, where R₁, R₂, and X are as defined above, can be prepared from compounds of Formula 3.4, where R₁, R₂, and X are as defined above and the carboxylic acid is protected as either the methyl (Me) or benzyl (Bn) ester, by treating with a hydroxide base, such as LiOH, in an aqueous THF solvent mixture, as shown in e. Additionally, compounds of Formula 3.5, where R₁ and R₂ are as defined above and X is Boc, can be prepared from compounds of Formula 3.4, where R₁ and R₂ are as defined above, X is Boc, and the carboxylic acid is protected as the benzyl (Bn) ester by treatment with hydrogen in the presence of a catalyst such as Pd/C, in a solvent such as EtOAc, as shown in f.

Scheme 3

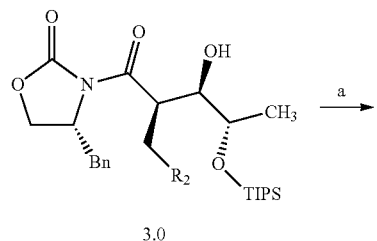

3.0

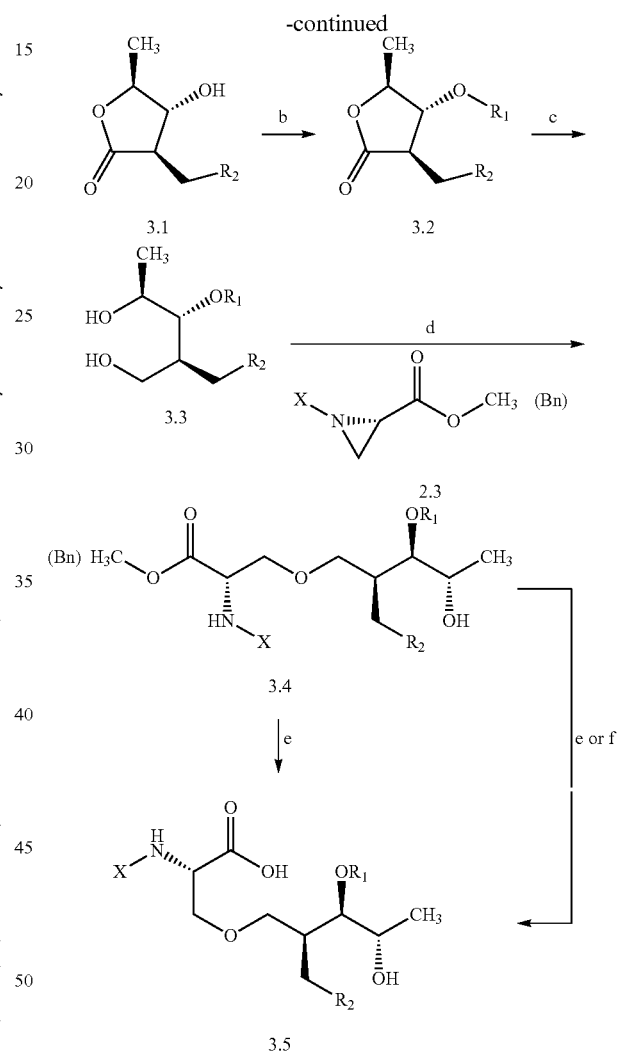

Compounds of Formula 4.1, where R₁ is TIPS, alkyl, or an allylic functionality and R₂ is as originally defined and X is Boc or Cbz, can be prepared according to the methods outlined in Scheme 4. Compounds of Formula 4.1, can be obtained from compounds of Formula 4.0, where R₁ is TIPS, alkyl, or an allylic functionality and R₂ is as originally defined and X is Boc or Cbz, by the addition of a solution of compounds of Formula 4.0 in a halogenated solvent such as DCM or an aromatic solvent such as toluene to a mixture of a base, such as DMAP, and a mixed anhydride, such as 2-methyl-6-nitrobenzoic anhydride (MNBA), in either a halogenated solvent such as DCM or an aromatic solvent such as toluene over a period of 4-12 hours, as shown in a.

Scheme 4

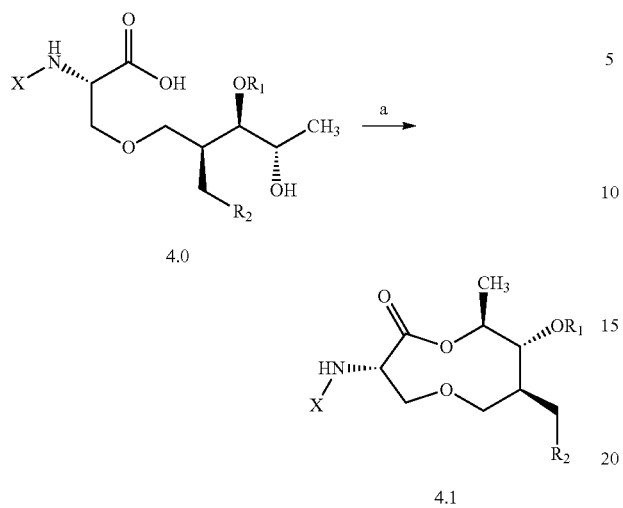

Compounds of formulas 5.1 and 5.2 can be prepared through the methods shown in Scheme 5, steps a-b. Compounds of Formula 5.1, where $R_1$ is an allylic or alkyl functionality, $R_2$ is as originally defined, and X and Y are hydrogen, can be obtained from compounds of Formula 5.0, where $R_1$ is an allylic or alkyl functionality, $R_2$ is as originally defined, X is Boc, and Y is hydrogen, by treating with an acid, such as a 4.0 M hydrogen chloride (HCl) solution in dioxane, in a solvent such as DCM, as shown in a. The resulting hydrochloride salt may be neutralized prior to use to give the free amine or neutralized in situ in step b. Compounds of Formula 5.2, where $R_1$ is an allylic or alkyl functionality and $R_2$ is as originally defined, can be prepared from compounds of Formula 5.1 by treatment with 3-hydroxy-4-methoxypicolinic acid in the presence of a base, such as 4-methylmorpholine, and a peptide coupling reagent, such as O-(7-azabenzotriazol-1-yl)-N,N,N',N'-tetramethyluronium hexafluorophosphate (HATU) or benzotriazol-1-yl-oxytripyrrolidinophosphonium hexafluorophosphate (PyBOP), in an aprotic solvent such as DCM, as shown in b.

Scheme 5

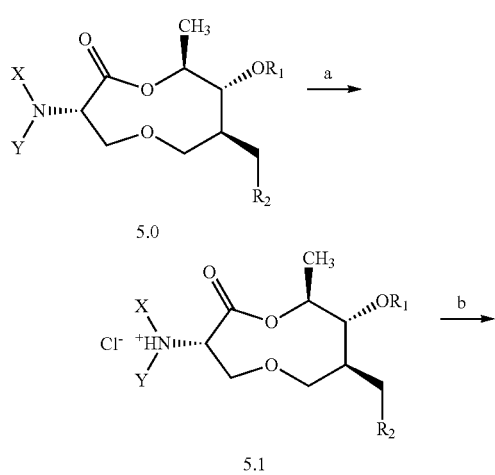

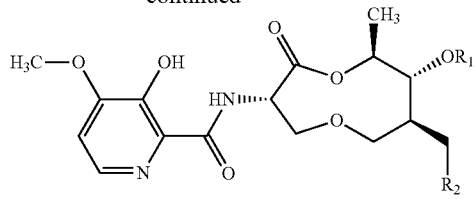

5.2

Compounds of Formulas 6.1-6.8 can be prepared as described in Scheme 6, steps a-h. Compounds of Formula 6.1, where $R_1$ is a trialkyl silyl group like TIPS, $R_2$ is as originally defined, and X and Y are Boc, can be prepared from compounds of Formula 6.0, where $R_1$ is a trialkyl silyl group like TIPS, $R_2$ is as originally defined, X is Boc, and Y is H, by treatment with a dicarbonate, such as di-tert-butyl dicarbonate ($Boc_2O$) in the presence of an amine base, such as DMAP, in a polar aprotic solvent such as acetonitrile ($CH_3CN$), as shown in a. Secondary alcohols of Formula 6.2, where $R_1$ is H, $R_2$ is as originally defined, and X and Y are Boc, can be prepared by treating compounds of Formula 6.1, where $R_1$, $R_2$, X, and Y are as defined above, with a fluoride source, such as tetrabutylammonium fluoride (TBAF), in an aprotic solvent such as THF, as shown in b. Compounds of Formula 6.3, where $R_1$ possesses an allylic functionality, $R_2$ is as originally defined, and X and Y are Boc, can be prepared from compounds of Formula 6.2, where $R_1$, $R_2$, X, and Y are as defined above, by treating with an allyl carbonante, such as tert-butyl(cyclopent-2-en-1-yl) carbonate, in the presence of a palladium catalyst with or without the addition of a phosphine ligand, such as tetrakis (triphenylphosphine)palladium(0) ($Pd(PPh_3)_4$), or ($Pd_2$ $(dba)_3$), and dppf, in an aprotic solvent such as toluene or THF, at elevated temperatures, such as 60-95° C., as shown in c. Compounds of Formula 6.4, where $R_1$ is alkyl, $R_2$ is as originally defined, and X and Y are Boc, can be prepared from compounds of Formula 6.3, where $R_1$, $R_2$, X, and Y are as defined above, by treating with hydrogen in the presences of a catalyst such as Pd/C or $PtO_2$ (platinum (IV) oxide), in a solvent such as EtOAc, as shown in f. Compounds of Formula 6.5, where $R_1$ is acyl, $R_2$ is as originally defined, and X and Y are Boc, can be prepared from compounds of Formula 6.2, where $R_1$, $R_2$, X, and Y are as defined above, by treating with a carbonyl chloride such as isobutyryl chloride in the presence of an amine base such as DMAP, in a solvent such as DCM, as shown in d. Compounds of Formula 6.6, where $R_1$ is aryl, $R_2$ is as originally defined, and X and Y are Boc, can be prepared from compounds of Formula 6.2, where $R_1$, $R_2$, X, and Y are as defined above, by treating with a triarylbismuth reagent, such as tritoluoyl-bismuth diacetate, in the presence of a copper catalyst, such as diacetoxycopper, and an amine base, such as N,N-dicyclohexyl-methylamine, in an aprotic solvent such as toluene at an elevated temperature of about 50° C., as shown in e. Compounds of Formula 6.7, where $R_1$ and $R_2$ are as originally defined, and X and Y are H, can be prepared from a variety of precursors, including, but not limited to, compounds of Formulas 6.3, 6.4, 6.5, and 6.6, wherein $R_1$, $R_2$, X, and Y have been previously defined above, by treating with an acid, such as a 4.0 M HCl solution in dioxane, in a solvent such as DCM, as shown in g. The resulting hydrochloride salt may be neutralized prior to use to give the free amine or neutralized in situ in step h. Compounds of Formula 6.8, where $R_1$ and $R_2$ are as originally defined, can be prepared from compounds of Formula 6.7, where $R_1$, $R_2$, X, and Y are H, by treating with 3-hydroxy-4-methoxypicolinic acid in the presence of a base, such as N-ethyl-N-isopropylpropan-2-amine, and a peptide coupling reagent, such as HATU or PyBOP, in an aprotic solvent such as DCM, as shown in h.

defined, and X is Boc (7.0), X and Y are Boc (7.1), and X is CBz (7.2), respectively. Treating compounds of Formulas 7.0 and 7.1 with an acid, such as a 4.0 M HCl solution in dioxane, in a solvent such as DCM affords the hydrochloride salt of compounds of Formula 7.3, which may be neutralized

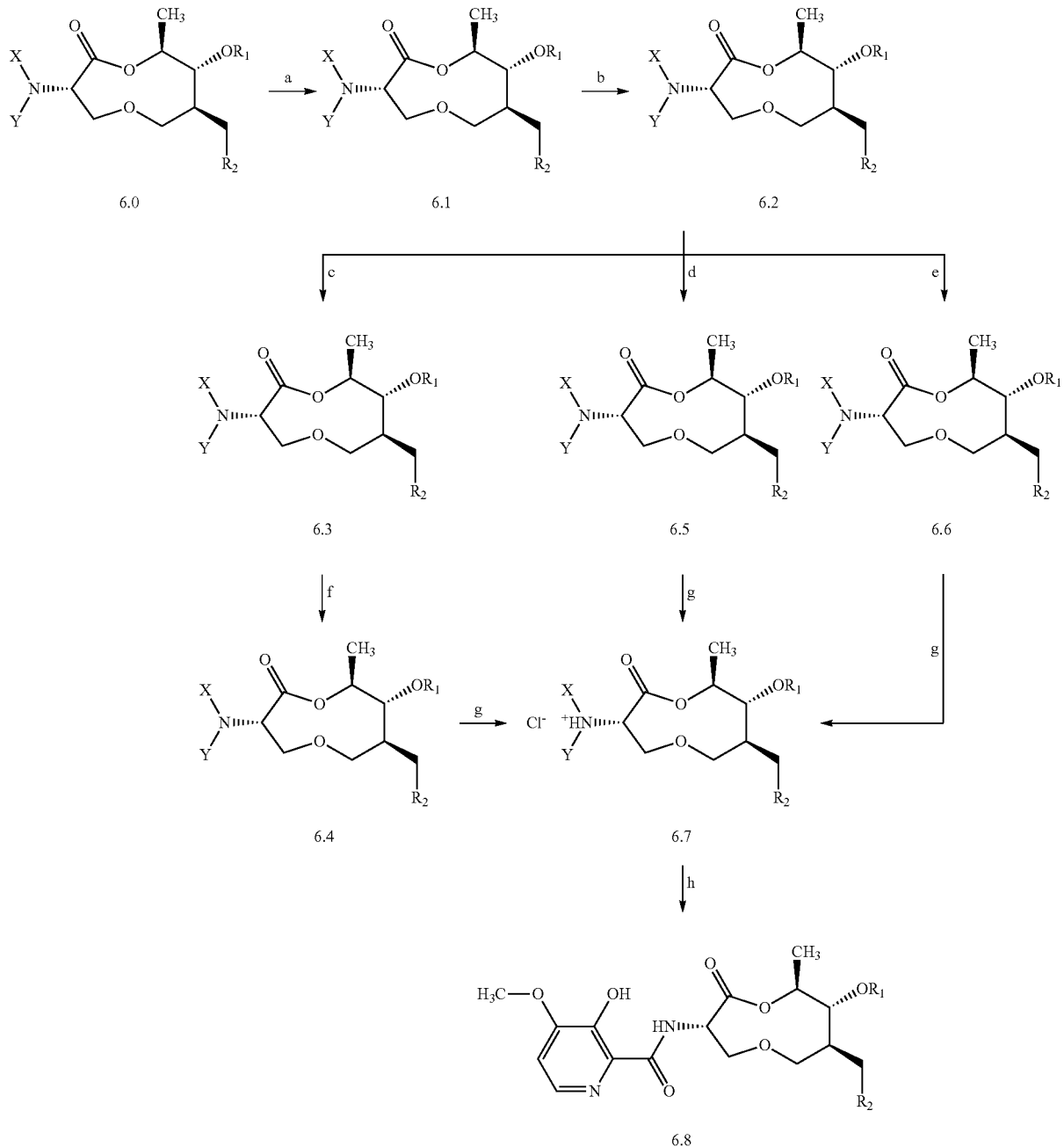

Scheme 6

Compounds of Formulas 7.3 and 7.4 can be prepared through the methods shown in Scheme 7, steps a-d. Compounds of Formula 7.3, where $R_1$ and $R_2$ are as originally defined and X and Y are H, can be prepared from a variety or precursors, including, but not limited to, compounds of Formulas 7.0, 7.1, and 7.2, where $R_1$ and $R_2$ are as originally defined, and X is Boc (7.0), X and Y are Boc (7.1), and X is CBz (7.2), respectively. Treating compounds of Formulas 7.0 and 7.1 with an acid, such as a 4.0 M HCl solution in dioxane, in a solvent such as DCM affords the hydrochloride salt of compounds of Formula 7.3, which may be neutralized in situ in step d or neutralized prior to use to give the free amine, as shown in a. Additionally, compounds of Formula 7.3, where $R_1$ and $R_2$ are as originally defined, can be prepared from compounds of Formulas 7.0 and 7.1, where $R_1$, $R_2$, are as originally defined and X and Y are Boc or Cbz, by treatment with trimethylsilyl trifluoromethanesulfonate in the presence of a base, such as 2,6-lutidine, in an aprotic solvent such as DCM, followed by treatment with a protic solvent such as MeOH, as shown in b. Alternatively, compounds of Formula 7.3, where $R_1$ and $R_2$ are as originally defined and X and Y are H, can be prepared from compounds of Formula 7.2, where $R_1$ and $R_2$ are as originally defined and X is CBz, by treatment with hydrogen in the presence of a catalyst, such as Pd/C, in a solvent such as EtOAc, as shown in c. Compounds of Formula 7.4, where $R_1$ and $R_2$ are as originally defined, can be prepared from compounds of Formula 7.3, where $R_1$ and $R_2$ are as defined above, by treatment with 3-hydroxy-4-methoxypicolinic acid in the presence of a base, such as 4-methylmorpholine, and a peptide coupling reagent, such as HATU or PyBOP, in an aprotic solvent such as DCM, as shown in step d.

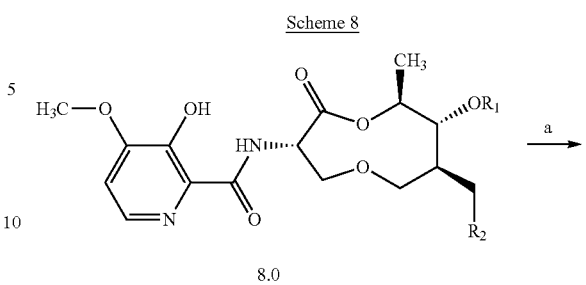

Scheme 8

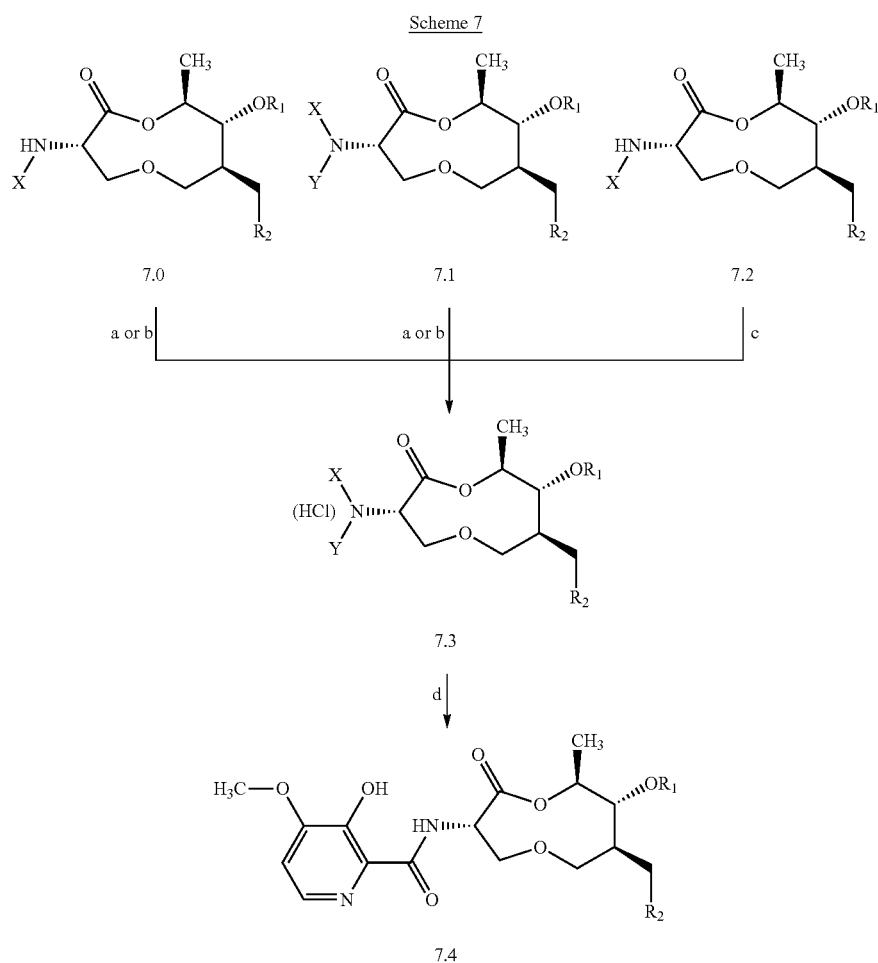

Scheme 7

Compounds of Formula 8.1, where $R_1$, $R_2$ and $R_4$ are as originally defined, can be prepared by the method shown in Scheme 8. Compounds of Formula 8.1 can be prepared from compounds of Formula 8.0, where $R_1$ and $R_2$ are as originally defined, by treatment with the appropriate alkyl halide with or without a reagent such as sodium iodide (NaI) and an alkali carbonate base such as sodium carbonate ($Na_2CO_3$) or potassium carbonate ($K_2CO_3$) in a solvent such as acetone or by treatment with an acyl halide in the presence of an amine base, such as pyridine, triethylamine, DMAP, or mixtures thereof in an aprotic solvent such as DCM, as shown in a.

-continued

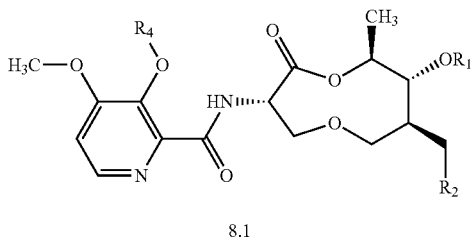

The following examples are presented to illustrate the various aspects of the compounds of the present disclosure and should not be construed as limitations to the claims.

EXAMPLES

Example 1

Step 1: Preparation of (R)-4-benzyl-3-(3-(p-tolyl)propanoyl)-oxazolidin-2-one

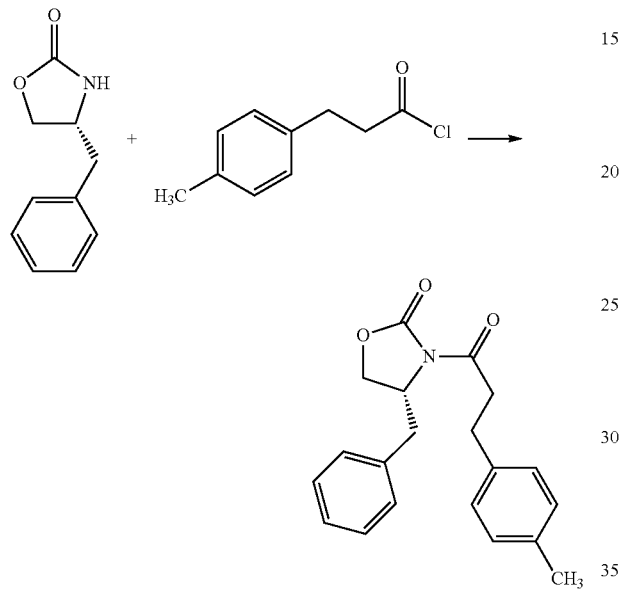

To a solution of 3-(p-tolyl)propanoic acid (8.0 grams (g), 48.7 millimoles (mmol)) in dichloroethane (DCE, 100 milliliters (mL)) was added oxalyl chloride (30.9 g, 20.6 mL, 243 mmol) followed by 1 drop of DMF, and the resulting gold colored mixture was stirred at room temperature. Within 90 minutes (min) all of the solids had dissolved and gas evolution had subsided. The solution was stirred for an additional 2 hours (h) and then the solvent and excess oxalyl chloride were evaporated on the rotary evaporator. The resulting yellow oil was dissolved in anhydrous THF (25 mL) and the solvent was evaporated (repeated 2×). The residual yellow oil was dissolved in anhydrous THF (5 mL) and used immediately in the next step.

To a solution of (R)-4-benzyloxazolidin-2-one (7.5 g, 42.3 mmol) in anhydrous THF (140 mL) was added n-BuLi (17.8 mL of 2.5 M in hexanes, 44.4 mmol) dropwise at −78° C. over a 20 min period. The solution was clear to light yellow during most of the addition and then gradually turns orange upon completion. The resulting orange solution was stirred at −78° C. for 45 min and was then treated dropwise with the propanoyl chloride prepared above at −75 to −78° C. The resulting light brown solution was stirred at −78° C. for 2 h, slowly warmed to room temperature, and stirred for 16 h at room temperature. The homogeneous brown solution was neutralized with saturated aqueous ammonium chloride (NH$_4$Cl, 100 mL), and the majority of the THF was removed on the rotary evaporator. The aqueous residue was extracted with CH$_2$Cl$_2$ (3×100 mL), and the combined organic extracts were washed with brine (100 mL), dried over sodium sulfate (Na$_2$SO$_4$), filtered, and concentrated to a tan solid. The solid was recrystallized from 25% ethyl acetate (EtOAc) in hexanes (150 mL), and the resulting crystals were collected by vacuum filtration, washed with ice cold 20% EtOAc in hexanes, and dried under vacuum to give (R)-4-benzyl-3-(3-(p-tolyl)propanoyl)oxazolidin-2-one (10.57 g, 77%) as pale yellow needles: mp 124-126° C.; $^1$H NMR (400 MHz, CDCl$_3$) δ 7.29 (m, 3H), 7.17 (m, 4H), 7.11 (m, 2H), 4.65 (m, 1H), 4.16 (m, 2H), 3.26 (m, 3H), 2.99 (m, 2H), 2.75 (m, 1H), 2.32 (s, 3H); ESIMS m/z 346 ([M+Na]$^+$).

Example 1

Step 2: Preparation of (R)-4-benzyl-3-((2R,3R,4S)-4-(benzyloxy)-3-hydroxy-2-(4-methylbenzyl)pentanoyl)oxazolidin-2-one

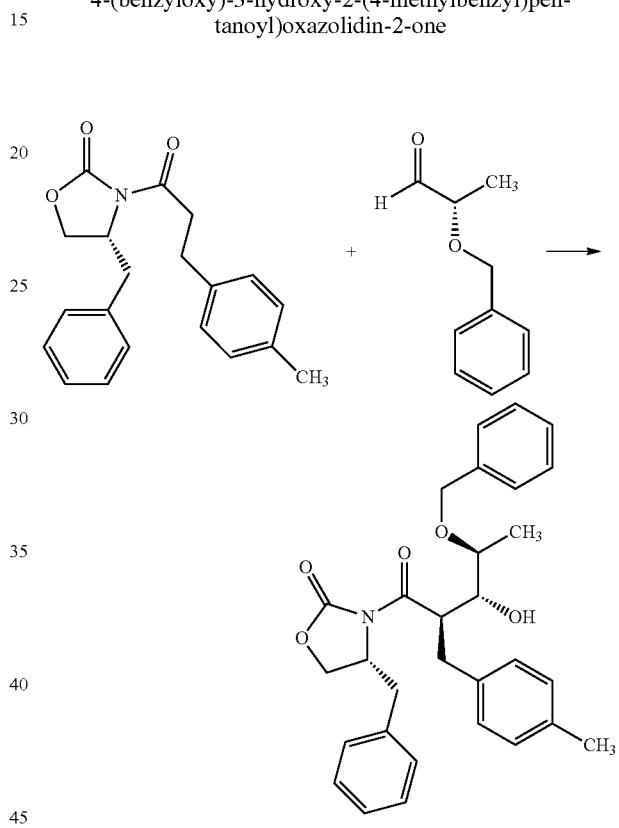

To a solution of (R)-4-benzyl-3-(3-(p-tolyl)propanoyl)oxazolidin-2-one (2.5 g, 7.73 mmol) in CH$_2$Cl$_2$ (30 mL) was added dibutyl(((trifluoromethyl)sulfonyl)oxy)borane (8.5 mL of 1M in CH$_2$Cl$_2$, 8.5 mmol) dropwise at 0° C., and the resulting brown solution was stirred for 10 min. Triethylamine (TEA, 1.1 g, 10.82 mmol) was added dropwise, and the resulting light yellow solution was stirred for 1 h, and then cooled to −78° C. A solution of (S)-2-(benzyloxy)propanal (1.65 g, 10.05 mmol), prepared according to the method described in Enders, D., von Berg, S., Jandeleit, B. *Organic Synthesis* 2002, 78, 177, in CH$_2$Cl$_2$ (3 mL) was added dropwise and the reaction was stirred at −78° C. for 1 h. The dry ice/acetone bath was replaced with an ice/acetone bath and the reaction was stirred at −10° C. for 1 h. The reaction was quenched with a 2:1 solution of MeOH/pH=7 phosphate buffer (24 mL total) followed by a 2:1 solution of MeOH/30% hydrogen peroxide (H$_2$O$_2$; 6 mL total, 2 mL peroxide, ~20 mmol), and then stirred at 0° C. for 1 h. The phases were separated and the aqueous phase was extracted with additional CH$_2$Cl$_2$ (2×50 mL). The combined organic phases were washed with aqueous sodium bicarbonate (NaHCO$_3$), washed with brine, dried over magnesium sulfate (MgSO$_4$), filtered, and concentrated to give 4.6 g of a light yellow oil. Purification by flash chromatography (silica gel (SiO$_2$), 0→40% EtOAc/hexanes) afforded (R)-4-benzyl-3-((2R,3R,4S)-4-(benzyloxy)-3-hydroxy-2-(4-methylbenzyl)pentanoyl)-oxazolidin-2-one (3.18 g, 84%) as a colorless, sticky glass: $^1$H NMR (400 MHz, CDCl$_3$) δ 7.26 (m, 10H), 7.04 (d, J=7.8 Hz, 2H), 6.92 (dd, J=7.6, 1.6 Hz, 2H), 4.74 (m, 1H), 4.63 (d, J=11.6 Hz, 1H), 4.31 (d, J=11.6 Hz, 1H), 4.23 (ddt, J=8.1, 6.6, 3.3 Hz, 1H), 3.97 (td, J=6.8, 4.9 Hz, 1H), 3.68 (dd, J=9.0, 3.1 Hz, 1H), 3.55 (m, 1H), 3.38 (t, J=8.4 Hz, 1H), 3.24 (dd, J=13.4, 5.4 Hz, 1H), 2.95 (dd, J=13.4, 10.4 Hz, 1H), 2.80 (dd, J=13.6, 3.4 Hz, 1H), 2.59 (d, J=4.9 Hz, 1H), 2.27 (s, 3H), 1.81 (dd, J=13.6, 10.3 Hz, 1H), 1.34 (d, J=6.1 Hz, 3H); $^{13}$C NMR (101 MHz, CDCl$_3$) δ 175.08, 152.94, 138.43, 135.87, 135.57, 135.18, 129.54, 129.09, 128.91, 128.79, 128.27, 127.48, 127.33, 127.03, 76.78, 75.35, 70.27, 65.30, 54.66, 46.15, 37.20, 34.73, 21.00, 15.88; ESIMS m/z 511 ([M+Na]$^+$).

Example 2

Step 1: Preparation of (R)-4-benzyl-3-((2R,3R,4S)-4-(benzyloxy)-3-((2-methylallyl)oxy)-2-(4-methylbenzyl)pentanoyl)oxazolidin-2-one To a 250 mL round bottom flask were added (R)-4-benzyl-3-((2R,3R,4S)-4-(benzyloxy)-3-hydroxy-2-(4-methylbenzyl)pentanoyl)oxazolidin-2-one (11.2 g, 23 mmol) and anhydrous THF (145 mL). The solution was sparged with N$_2$ for 5 min and then tris(dibenzylideneacetone)-dipalladium (0) (Pd$_2$(dba)$_3$; 2.10 g, 2.3 mmol) and 1,1'-bis(diphenylphosphino)ferrocene (dppf; 2.55 g, 4.59 mmol) were added, and the resulting dark solution was sparged with N$_2$ for an additional 5 minutes. The reaction mixture was warmed to 55° C. under N$_2$ and treated with a solution of tert-butyl (2-methylallyl)carbonate (7.9 g, 45.9 mmol) in THF (5 mL). The dark mixture was stirred at 55° C. for 1 h and then cooled to room temperature. The reaction mixture was filtered through paper, rinsing with CH$_2$Cl$_2$, and the filtrate was evaporated to give a dark oil. The oil was partially purified by flash chromatography (SiO$_2$, 0→30% acetone/hexanes) to give (R)-4-benzyl-3-((2R,3R,4S)-4-(benzyloxy)-3-((2-methylallyl)oxy)-2-(4-methylbenzyl)pentanoyl)oxazolidin-2-one (9.36 g) as a yellow oil that is contaminated with dibenzylideneacetone (dba): $^1$H NMR (400 MHz, CDCl$_3$) δ 7.22 (m, 10H), 7.02 (d, J=7.8 Hz, 2H), 6.87 (m, 2H), 5.06 (m, 1H), 4.91 (s, 1H), 4.77 (ddd, J=11.7, 9.3, 4.7 Hz, 1H), 4.64 (d, J=11.9 Hz, 1H), 4.31 (d, J=11.9 Hz, 1H), 4.16 (s, 2H), 3.96 (m, 1H), 3.74 (dd, J=9.2, 7.1 Hz, 1H), 3.62 (p, J=6.1 Hz, 1H), 3.41 (m, 2H), 2.85 (m, 2H), 2.70 (dd, J=13.7, 3.5 Hz, 1H), 2.26 (s, 3H), 2.17 (s, 3H), 1.49 (dd, J=13.7, 10.6 Hz, 1H), 1.34 (d, J=6.1 Hz, 3H); ESIMS m/z 565 ([M+Na]$^+$).

Example 2

Step 2: Preparation of (2S,3R,4S)-4-(benzyloxy)-3-(2-methylallyl)-oxy)-2-(4-methylbenzyl)pentan-1-ol

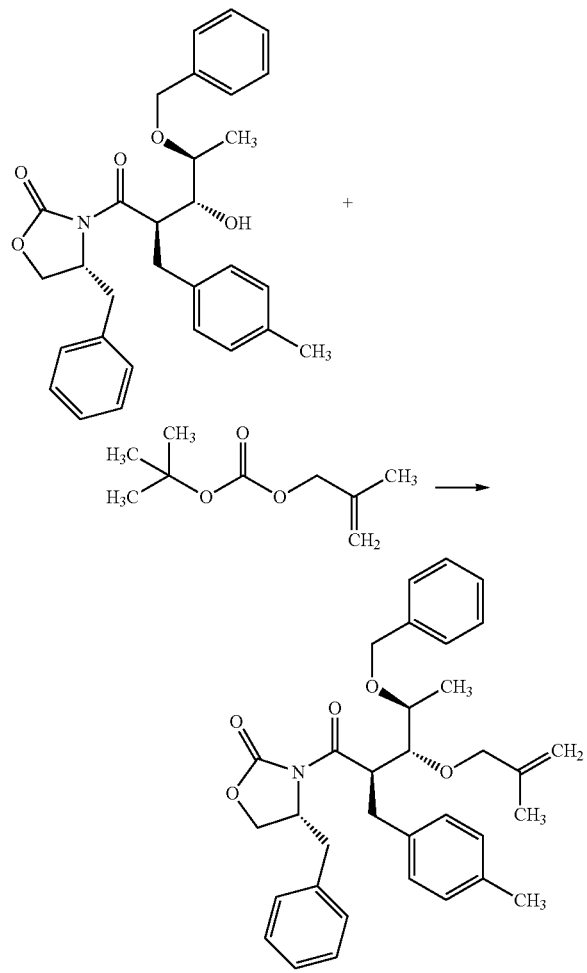

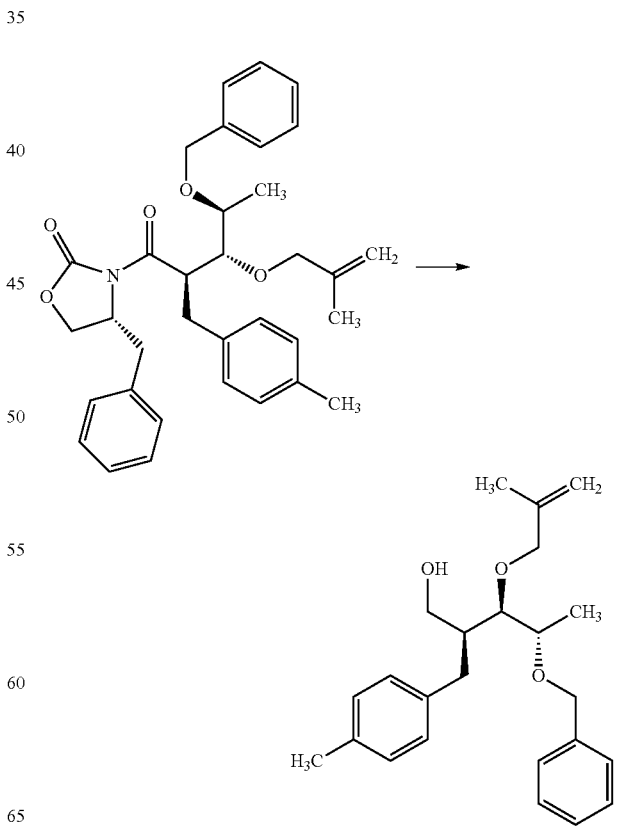

To a solution of (R)-4-benzyl-3-((2R,3R,4S)-4-(benzyloxy)-3-((2-methylallyl)oxy)-2-(4-methylbenzyl)pentanoyl)oxazolidin-2-one (9.36 g, 17.3 mmol) in aqueous THF (4:1 THF/H$_2$O; 86 mL) was added lithium borohydride (34.6 mL of 2.0 M in THF, 69.1 mmol) dropwise at −5° C., and the resulting yellow solution was vigorously stirred. After 1 h the yellow color (dba) had dissipated and the reaction was allowed to slowly warm to room temperature. The reaction was stirred for an additional 5 h and then poured into ice cold saturated aqueous NH$_4$Cl (250 mL). The phases were separated and the aqueous was extracted with CH$_2$Cl$_2$ (3×100 mL). The combined organics phases were dried over Na$_2$SO$_4$, filtered, and concentrated to a light yellow oil (10.11 g), which was purified by both reverse phase (RP; C18, 0→100% CH$_3$CN/H$_2$O) and normal phase (NP: SiO$_2$, 0→30% EtOAc/CH$_2$Cl$_2$) to give (2S,3R,4S)-4-(benzyloxy)-3-((2-methylallyl)oxy)-2-(4-methylbenzyl)pentan-1-ol (4.04 g, 48% from Ex. 2, Step 1) as a colorless liquid: $^1$H NMR (400 MHz, CDCl$_3$) δ 7.32 (m, 5H), 7.06 (m, 4H), 4.98 (m, 1H), 4.87 (m, 1H), 4.64 (d, J=11.6 Hz, 1H), 4.44 (d, J=11.6 Hz, 1H), 4.08 (d, J=11.6 Hz, 1H), 3.97 (d, J=12.1 Hz, 1H), 3.78 (p, J=6.2 Hz, 1H), 3.56 (m, 3H), 2.88 (dd, J=13.8, 4.7 Hz, 1H), 2.53 (dd, J=13.8, 10.1 Hz, 1H), 2.30 (s, 3H), 2.18 (ddd, J=14.4, 7.7, 4.3 Hz, 1H), 2.01 (dd, J=6.2, 4.9 Hz, 1H), 1.76 (s, 3H), 1.33 (d, J=6.2 Hz, 3H); $^{13}$C NMR (101 MHz, CDCl$_3$) δ 142.41, 138.50, 137.87, 135.28, 129.00, 128.37, 127.75, 127.57, 111.86, 83.08, 75.92, 75.73, 70.79, 62.83, 44.60, 32.63, 21.05, 20.99, 19.84, 16.33; ESIMS m/z 391 ([M+Na]$^+$).

Example 2

Step 3: Preparation of (S)-methyl 3-((2S,3R,4S)-4-(benzyloxy)-3-((2-methylallyl)oxy)-2-(4-methylbenzyl)pentyl)oxy)-2-((tert-butoxycarbonyl)amino)propanoate

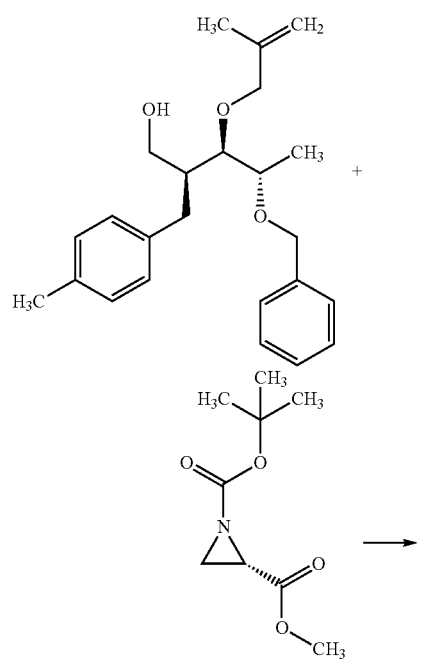

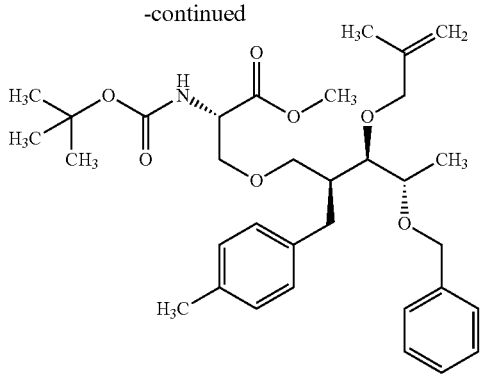

To a solution of (2S,3R,4S)-4-(benzyloxy)-3-((2-methylallyl)oxy)-2-(4-methylbenzyl)pentan-1-ol (0.51 g, 1.38 mmol) and (diethyloxonio)trifluoroborate (BF$_3$(OEt)$_2$), 0.02 g, 0.14 mmol) in CH$_2$Cl$_2$ (9 mL) was added a solution of (S)-1-tert-butyl 2-methylaziridine-1,2-dicarboxylate (0.40 g, 1.99 mmol) in CH$_2$Cl$_2$ (4.0 mL) slowly (syringe pump: 1.0 mL/h) at room temperature. After 3 h, the reaction mixture was treated with 2 μL of BF$_3$(OEt)$_2$, while the aziridine addition was continued, and at the 4 and 5 h time points HPLC-MS indicated 74 and 84% conversion to desired product. An additional 2 μL of BF$_3$(OEt)$_2$ were added and the reaction mixture was stirred for 1 h and then treated with a final 2 μL dose of BF$_3$(OEt)$_2$ and 0.1 equivalents of the aziridine. After 1 h of stirring, the reaction mixture was adsorbed to Celite® (3.3 g) and purified by flash chromatography (SiO$_2$, 0→20% acetone/hexanes) to give (S)-methyl 3-((2S,3R,4S)-4-(benzyloxy)-3-((2-methylallyl)oxy)-2-(4-methylbenzyl)pentyl)oxy)-2-((tert-butoxycarbonyl)amino)propanoate (0.46 g, 58%) as a colorless oil: $^1$H NMR (400 MHz, CDCl$_3$) δ 7.32 (m, 5H), 7.05 (d, J=7.8 Hz, 2H), 6.98 (d, J=8.0 Hz, 2H), 5.30 (d, J=9.0 Hz, 1H), 5.00 (m, 1H), 4.87 (m, 1H), 4.61 (d, J=11.7 Hz, 1H), 4.44 (d, J=11.7 Hz, 1H), 4.39 (m, 1H), 4.09 (d, J=12.0 Hz, 1H), 3.88 (d, J=12.0 Hz, 1H), 3.72 (s, 3H), 3.68 (m, 2H), 3.49 (dt, J=8.8, 4.3 Hz, 2H), 3.23 (m, 2H), 2.92 (dd, J=13.7, 3.9 Hz, 1H), 2.38 (dd, J=13.7, 10.7 Hz, 1H), 2.31 (s, 3H), 2.21 (dq, J=6.9, 3.7 Hz, 1H), 1.78 (s, 3H), 1.43 (s, 9H), 1.27 (d, J=6.2 Hz, 3H); $^{13}$C NMR (101 MHz, CDCl$_3$) δ 171.14, 155.49, 142.79, 138.73, 137.86, 135.23, 128.94, 128.33, 127.68, 127.47, 111.54, 81.57, 79.98, 77.22, 76.34, 75.57, 70.78, 70.66, 70.52, 53.94, 52.35, 42.09, 32.26, 28.31, 21.00, 19.89, 16.01; ESIMS m/z 594 ([M+Na+H]$^+$).

Example 2

Step 4: Preparation of (S)-methyl 2-((tert-butoxycarbonyl)amino)-3-(((2S,3R,4S)-4-hydroxy-3-isobutoxy-2-(4-methylbenzyl)pentyl)oxy)propanoate

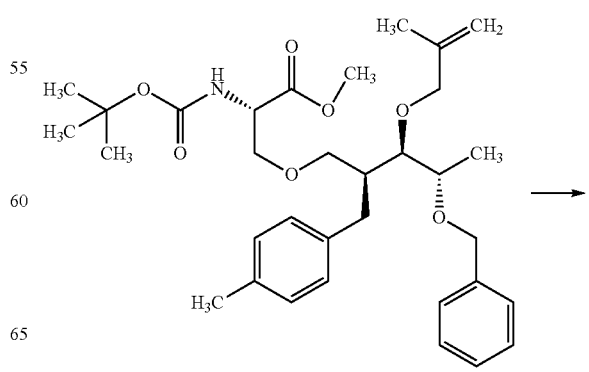

-continued

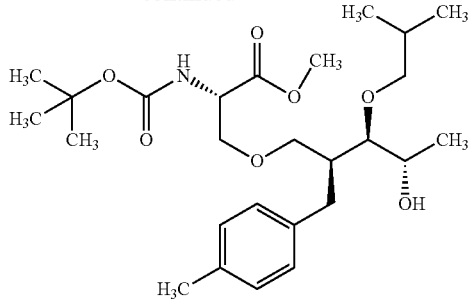

To a solution of (S)-methyl 3-((2S,3R,4S)-4-(benzyloxy)-3-((2-methylallyl)oxy)-2-(4-methylbenzyl)pentyl)oxy)-2-((tert-butoxycarbonyl)amino)propanoate (3.0 g, 5.27 mmol) in ethyl alcohol (EtOH; 21 mL) was added Pd/C (10%, ~200 mg), and the mixture was sparged with $N_2$. The reaction flask was evacuated and backfilled with $N_2$ three times, evacuated and backfilled with $H_2$ three times, and then stirred under 1 atmosphere (atm) of $H_2$ for 16 h. The reaction mixture was treated with additional catalyst (0.2 g) and resubjected to the hydrogenation/hydrogenolysis conditions as described above for an additional 5 h. The reaction flask was evacuated and backfilled with $N_2$ (4×) and then the reaction mixture was sparged with $N_2$ for 10 min. The mixture was filtered through Celite®, rinsing with EtOH, and the filtrate was passed through a 2 µm syringe filter, and then concentrated to a colorless oil. The oil was purified by flash chromatography ($SiO_2$, 0→30% acetone/hexanes) to give (S)-methyl 2-((tert-butoxycarbonyl)amino)-3-(2S,3R,4S)-4-hydroxy-3-isobutoxy-2-(4-methylbenzyl)pentyl)-oxy)propanoate (2.099 g, 83%) as a colorless oil: $^1$H NMR (400 MHz, $CDCl_3$) δ 7.05 (m, 4H), 5.36 (d, J=8.7 Hz, 1H), 4.43 (dd, J=5.4, 3.3 Hz, 1H), 3.90 (m, 1H), 3.76 (s, 3H), 3.72 (m, 1H), 3.56 (dd, J=9.3, 3.0 Hz, 1H), 3.24 (m, 5H), 2.94 (dd, J=13.8, 4.4 Hz, 1H), 2.47 (dd, J=13.7, 10.8 Hz, 1H), 2.32 (s, 3H), 2.12 (dq, J=6.7, 3.4 Hz, 1H), 1.84 (dq, J=13.2, 6.6 Hz, 1H), 1.45 (s, 9H), 1.26 (d, J=6.3 Hz, 4H), 0.93 (dd, J=6.7, 2.7 Hz, 6H); $^{13}$C NMR (101 MHz, $CDCl_3$) δ 171.06, 155.40, 137.83, 135.36, 129.04, 128.87, 83.26, 80.07, 78.59, 71.11, 70.00, 68.47, 53.94, 52.47, 42.56, 34.67, 33.20, 31.60, 29.09, 28.32, 22.66, 21.01, 19.57, 19.52, 19.49; ESIMS m/z 505 ([M+Na]$^+$).

Example 2

Step 5: Preparation of (S)-2-((tert-butoxycarbonyl)amino)-3-(((2S,3R,4S)-4-hydroxy-3-isobutoxy-2-(4-methylbenzyl)pentyl)oxy)propanoic acid

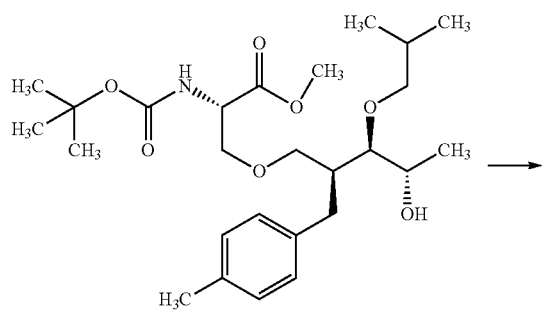

To a solution of (S)-methyl 2-((tert-butoxycarbonyl)amino)-3-(((2S,3R,4S)-4-hydroxy-3-isobutoxy-2-(4-methylbenzyl)pentyl)oxy)propanoate (2.06 g, 4.28 mmol) in aqueous THF (16 THF:5$H_2O$; 21 mL total volume) was added LiOH—$H_2O$ (0.54 g, 12.83 mmol) and the reaction was stirred for 4 h at room temperature. The reaction was diluted with $H_2O$ (50 mL) and the majority of the THF was removed on the rotovap. The aqueous residue was acidified with 2 N HCl and extracted with $CH_2Cl_2$ (6×50 mL) until the aqueous phase was nearly clear. The combined organic extracts were washed with brine (2×50 mL), dried over $Na_2SO_4$, filtered, and concentrated to a colorless oil (1.96 g). The oil was purified by RP flash chromatography (C18; 0→85% $CH_3CN/H_2O$) to give (S)-2-((tert-butoxycarbonyl)amino)-3-(((2S,3R,4S)-4-hydroxy-3-isobutoxy-2-(4-methyl-benzyl)pentyl)oxy)-propanoic acid (1.71 g, 85%) as a colorless oil: $^1$H NMR (400 MHz, $CDCl_3$) δ 7.05 (m, 4H), 6.57 (s, 2H), 5.47 (d, J=8.1 Hz, 1H), 4.44 (m, 1H), 3.92 (m, 1H), 3.77 (m, 1H), 3.58 (m, 1H), 3.41 (d, J=7.2 Hz, 1H), 3.24 (m, 4H), 2.91 (dd, J=13.7, 4.0 Hz, 1H), 2.46 (dd, J=13.7, 10.8 Hz, 1H), 2.31 (s, 3H), 2.10 (dd, J=6.8, 3.3 Hz, 1H), 1.81 (dp, J=13.2, 6.6 Hz, 1H), 1.44 (s, 9H), 1.25 (d, J=6.2 Hz, 3H), 0.91 (dd, J=6.7, 2.7 Hz, 6H); $^{13}$C NMR (101 MHz, $CDCl_3$) δ 171.72, 153.71, 135.81, 133.44, 127.15, 127.02, 81.61, 78.33, 76.81, 69.13, 68.31, 67.08, 51.93, 40.98, 31.48, 27.16, 26.42, 19.12, 17.65, 17.58, 17.38; ESIMS m/z 491 ([M+Na]$^+$).

Example 3

Step 1: Preparation of (3R,4R,5S)-4-hydroxy-5-methyl-3-phenethyldihydro-furan-2(3H)-one and (R)-4-benzyloxazolidin-2-one

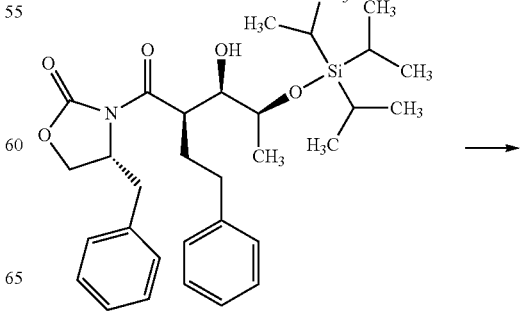

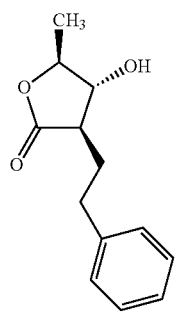

To a solution of (R)-4-benzyl-3-((2R,3R,4S)-3-hydroxy-2-phenethyl-4-((triisopropylsilyl)oxy)pentanoyl)-oxazolidin-2-one (2.52 g, 4.55 mmol) in EtOH (18 mL) was added 1 N HCl (2 mL, 2 mmol) and the mixture heated to 80° C. for a 3 h. The solution was concentrated in vacuo, and the residue was dissolved in $CH_2Cl_2$, loaded onto a pre-packed Celite® cartridge, and purified by flash chromatography ($SiO_2$, 0→100% EtOAc/hexanes) gave (3R,4R,5S)-4-hydroxy-5-methyl-3-phenethyldihydrofuran-2(3H)-one (840 mg, 3.81 mmol, 84% yield) and (R)-4-benzyloxazolidin-2-one (710 mg, 4.01 mmol, 88% yield). The title product was obtained as a colorless, amorphous solid: $^1$H NMR (600 MHz, $CDCl_3$) δ 7.33-7.28 (m, 2H), 7.25-7.19 (m, 3H), 4.20-4.13 (m, 1H), 3.80 (dd, J=8.9, 7.3 Hz, 1H), 2.96-2.88 (m, 1H), 2.86-2.79 (m, 1H), 2.59-2.52 (m, 1H), 2.28-2.17 (m, 2H), 1.97-1.88 (m, 1H), 1.43 (d, J=6.3 Hz, 3H); $^{13}$C NMR (151 MHz, $CDCl_3$) δ 175.91, 140.94, 128.64, 128.51, 126.34, 79.89, 79.36, 47.98, 32.81, 30.25, 18.19; ESIMS m/z 221 ([M+H]$^+$).

Example 3

Step 2: Preparation of (3R,4R,5S)-5-methyl-3-phenethyl-4-((triisopropylsilyl)oxy)dihydrofuran-2(3H)-one

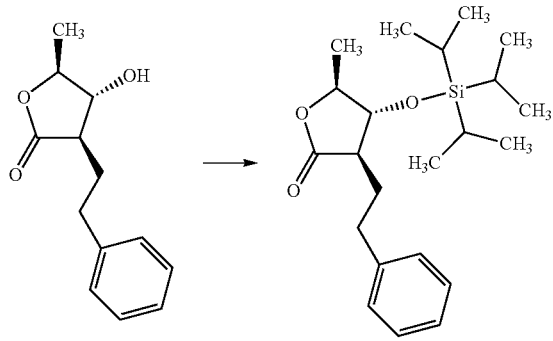 [SMILES: C[C@@H]1OC(=O)[C@H](CCc2ccccc2)[C@H]1O ; CC(C)[Si](O[C@H]1[C@H](C)OC(=O)[C@@H]1CCc1ccccc1)(C(C)C)C(C)C]

To a solution of (3R,4R,5S)-4-hydroxy-5-methyl-3-phenethyldihydrofuran-2(3H)-one (800 mg, 3.63 mmol) in $CH_2Cl_2$ (20 mL) were added 2,6-dimethylpyridine (592 μl, 5.08 mmol) and triisopropylsilyl trifluoromethanesulfonate (1171 μL, 4.36 mmol) at 0° C., and the mixture was warmed to room temperature while stirring overnight. The reaction mixture was poured onto 50 mL saturated sodium bicarbonate solution and mixed thoroughly. The phases were separated, and the aqueous extracted with $CH_2Cl_2$ (2×25 mL). The combined $CH_2Cl_2$ extracts were dried and concentrated to a colorless oil which was purified by flash chromatography ($SiO_2$, 0→50% EtOAc/hexanes) to give (3R,4R,5S)-5-methyl-3-phenethyl-4-((triisopropylsilyl)oxy)dihydrofuran-2(3H)-one (809 mg, 53%): $^1$H NMR (400 MHz, $CDCl_3$) δ 7.33-7.25 (m, 2H), 7.25-7.17 (m, 3H), 3.98 (dd, J=5.9, 4.8 Hz, 1H), 4.34-4.24 (m, 1H), 2.99-2.88 (m, 1H), 2.88-2.76 (m, 1H), 2.61-2.51 (m, 1H), 2.04-1.94 (m, 2H), 1.43 (d, J=6.5 Hz, 3H), 1.09-0.99 (m, 21H); $^{13}$C NMR (101 MHz, $CDCl_3$) δ 176.64, 140.98, 128.57, 128.51, 126.16, 82.10, 79.45, 49.17, 32.96, 31.14, 19.10, 18.00, 17.71; ESIMS m/z 378 ([M+H]$^+$).

Example 3

Step 3: Preparation of (2S,3R,4S)-2-phenethyl-3-((triisopropylsilyl)-oxy)pentane-1,4-diol

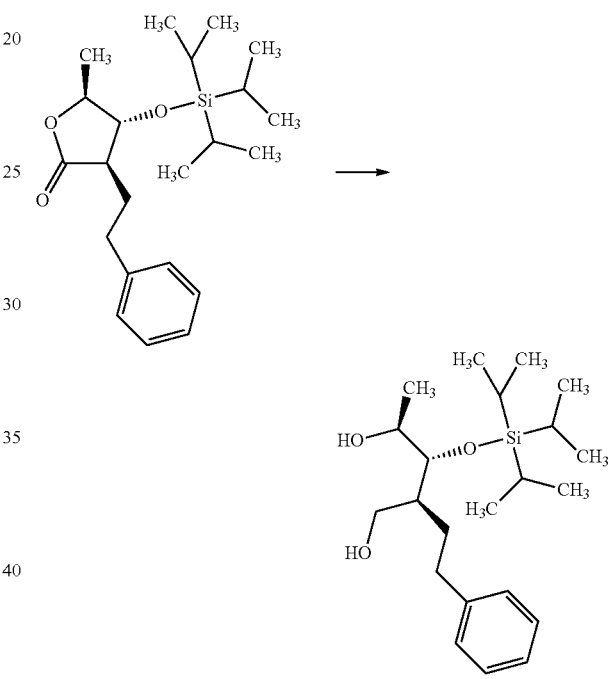

To an oven-dried flask were added (3R,4R,5S)-5-methyl-3-phenethyl-4-((triisopropyl-silyl)oxy)dihydrofuran-2(3H)-one (670 mg, 1.601 mmol) and $CH_2Cl_2$ (8 mL)) and the mixture was cooled to −78° C. and treated with DIBAL-H (1.0 M in $CH_2Cl_2$, 4.00 mL, 4.00 mmol) dropwise over 10 min. The dry ice/acetone bath was removed and the mixture allowed to warm to room temperature while stirring overnight. The reaction was cooled to 0° C. and quenched by addition of saturated potassium sodium tartrate solution (50 mL). The mixture was diluted with $CH_2Cl_2$ (25 mL) and stirred until two clean-splitting phases were formed. The phases were separated, and the aqueous extracted further with $CH_2Cl_2$. The combined organic extracts were dried and concentrated to a colorless oil which was purified by flash chromatography ($SiO_2$, 030% EtOAc/hexanes) to give (2S,3R,4S)-2-phenethyl-3-((triisopropylsilyl)oxy)pentane-1,4-diol (422 mg, 69%): $^1$H NMR (400 MHz, $CDCl_3$) δ 7.30-7.23 (m, 2H), 7.21-7.14 (m, 3H), 4.02-3.92 (m, 2H), 3.77 (dd, J=4.3, 3.1 Hz, 1H), 3.72-3.61 (m, 1H), 3.18 (s, 1H), 2.92-2.76 (m, 2H), 2.62-2.51 (m, 1H), 2.10-1.96 (m, 1H), 1.80-1.62 (m, 2H), 1.27 (d, J=6.7 Hz, 3H), 1.07-0.93 (m, 21H); $^{13}$C NMR (101 MHz, CDCl$_3$) δ 141.94, 128.48, 128.36, 125.86, 78.18, 71.24, 59.48, 45.39, 34.24, 29.69, 18.64, 18.14, 18.10, 12.54; ESIMS m/z 403 ([M+Na]$^+$).

Example 4

Step 1: Preparation of tert-butyl ((3S,7S,8R,9S)-8-isobutoxy-9-methyl-7-(4-methylbenzyl)-2-oxo-1,5-dioxonan-3-yl)carbamate (F170)

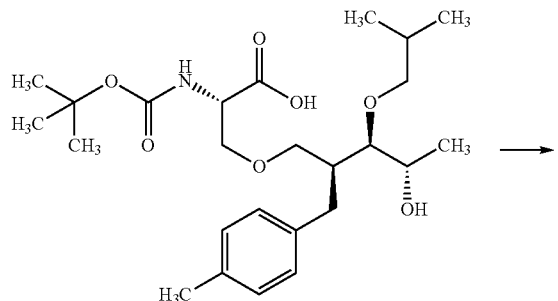

To a magnetically stirred solution of DMAP (3.22 g, 26.3 mmol) and MNBA (2.07 g, 6.02 mmol) in anhydrous toluene (750 mL) was added a solution of (S)-2-((tert-butoxycarbonyl)amino)-3-(2S,3R,4S)-4-hydroxy-3-isobutoxy-2-(4-methylbenzyl)pentyl)oxy)-propanoic acid (1.76 g, 3.76 mmol) in anhydrous toluene (60 mL) dropwise over 5.5 h (syringe pump), and the resulting turbid mixture was stirred for 16 h. The reaction mixture was filtered through paper and the filtrate was concentrated to a pale yellow solid which was purified by flash chromatography (SiO$_2$, 0→30% acetone/hexanes) to give tert-butyl ((3S,7S,8R,9S)-8-isobutoxy-9-methyl-7-(4-methylbenzyl)-2-oxo-1,5-dioxonan-3-yl)carbamate (1.48 g, 87%) as a white foam: $^1$H NMR (400 MHz, CDCl$_3$) δ 7.09 (d, J=8.2 Hz, 2H), 7.06 (d, J=8.2 Hz, 2H), 5.14 (d, J=8.2 Hz, 1H), 4.95 (dq, J=9.2, 6.4 Hz, 1H), 4.59 (q, J=7.3 Hz, 1H), 3.87 (dd, J=11.5, 7.3 Hz, 1H), 3.44 (t, J=7.4 Hz, 2H), 3.32 (tdd, J=16.8, 10.6, 5.2 Hz, 3H), 3.10 (dd, J=10.4, 6.6 Hz, 2H), 2.31 (s, 3H), 2.24 (t, J=12.7 Hz, 1H), 1.88 (dq, J=13.2, 6.6 Hz, 2H), 1.47 (d, J=6.4 Hz, 3H), 1.41 (s, 9H), 0.95 (d, J=6.7 Hz, 6H); $^{13}$C NMR (101 MHz, CDCl$_3$) δ 172.24, 154.95, 136.81, 135.52, 129.10, 129.01, 84.66, 80.02, 79.21, 75.57, 72.86, 72.48, 52.97, 47.40, 34.56, 29.17, 28.27, 21.01, 19.48, 18.80; ESIMS m/z 473 ([M+Na]$^+$).

Step 2: Preparation of tert-butyl N-tert-butoxycarbonyl-N-[(3S,7S,8R,9S)-9-methyl-7-(1-naphthylmethyl)-2-oxo-8-triisopropylsilyloxy-1,5-dioxonan-3-yl]carbamate

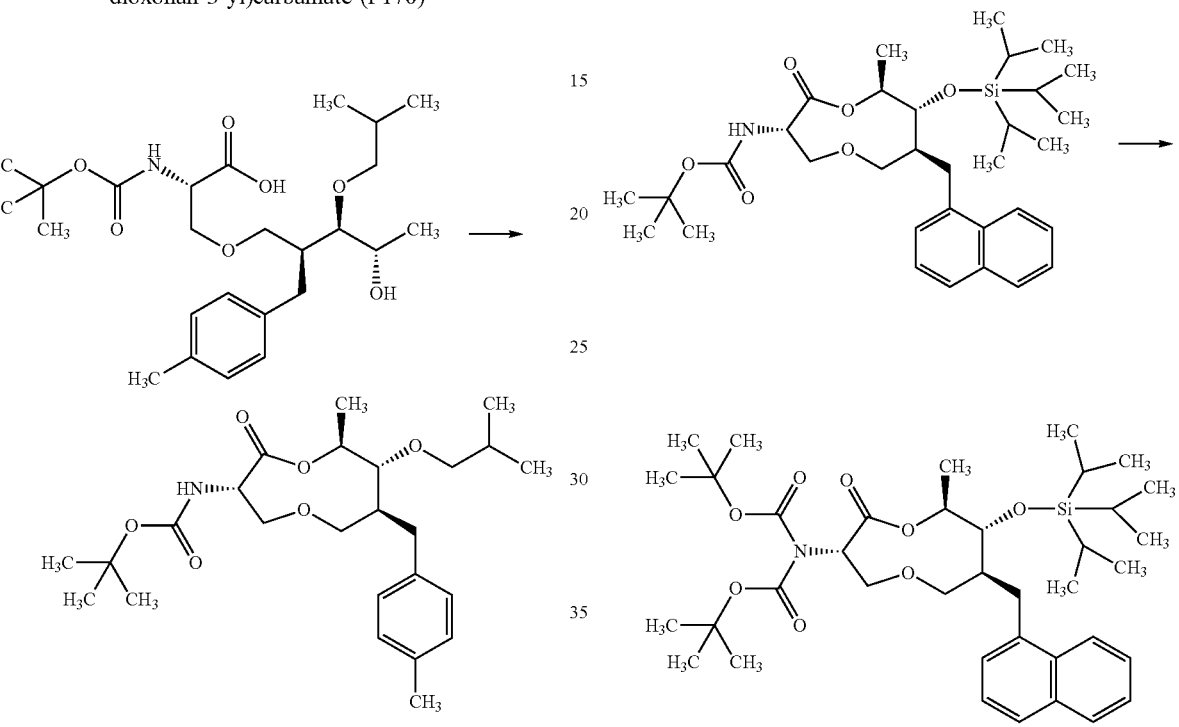

To a solution of tert-butyl ((3S,7S,8R,9S)-9-methyl-7-(naphthalen-1-ylmethyl)-2-oxo-8-((triisopropylsilyl)oxy)-1,5-dioxonan-3-yl)carbamate (2.8 g, 4.78 mmol) and DMAP (0.292 g, 2.39 mmol) in CH$_3$CN (23.9 mL) was added di-tert-butyl dicarbonate (4.17 g, 19.1 mmol) at room temperature and the reaction was stirred for 16 h at room temperature. The crude reaction mixture was adsorbed to Celite® and purified via flash chromatography (SiO$_2$, 0→20% EtOAc/hexanes) to give tert-butyl N-tert-butoxycarbonyl-N-[(3S,7S,8R,9S)-9-methyl-7-(1-naphthylmethyl)-2-oxo-8-triisopropylsilyloxy-1,5-dioxonan-3-yl]carbamate (2.85 g, 87%) as a white foam: $^1$H NMR (400 MHz, CDCl$_3$) δ 8.04-7.96 (m, 1H), 7.87-7.80 (m, 1H), 7.71 (dd, J=8.2, 1.3 Hz, 1H), 7.52-7.36 (m, 4H), 5.24 (app q, J=3.1 Hz, 1H), 5.06 (app t, J=7.9 Hz, 1H), 4.11 (dd, J=5.9, 2.9 Hz, 1H), 4.08 (d, J=7.9 Hz, 2H), 3.75-3.63 (m, 2H), 3.37 (m, 2H), 2.32-2.22 (m, 1H), 1.52 (d, J=7.0 Hz, 3H), 1.47 (s, 18H), 1.04 (m, 21H); $^{13}$C NMR (101 MHz, CDCl$_3$) δ 169.53, 152.75, 136.39, 134.08, 131.92, 128.95, 127.65, 126.82, 125.70, 125.45, 125.37, 123.68, 82.84, 78.92, 76.93, 73.31, 71.12, 58.06, 48.83, 30.74, 27.91, 19.92, 18.17, 18.14, 12.73; ESIMS m/z 709 ([M+Na]$^+$).

Example 5

Steps 1a and 1b: Preparation of 3-hydroxy-N-((3S, 7S,8R,9S)-8-isobutoxy-9-methyl-7-(4-methylbenzyl)-2-oxo-1,5-dioxonan-3-yl)-4-methoxypicolinamide (F48)

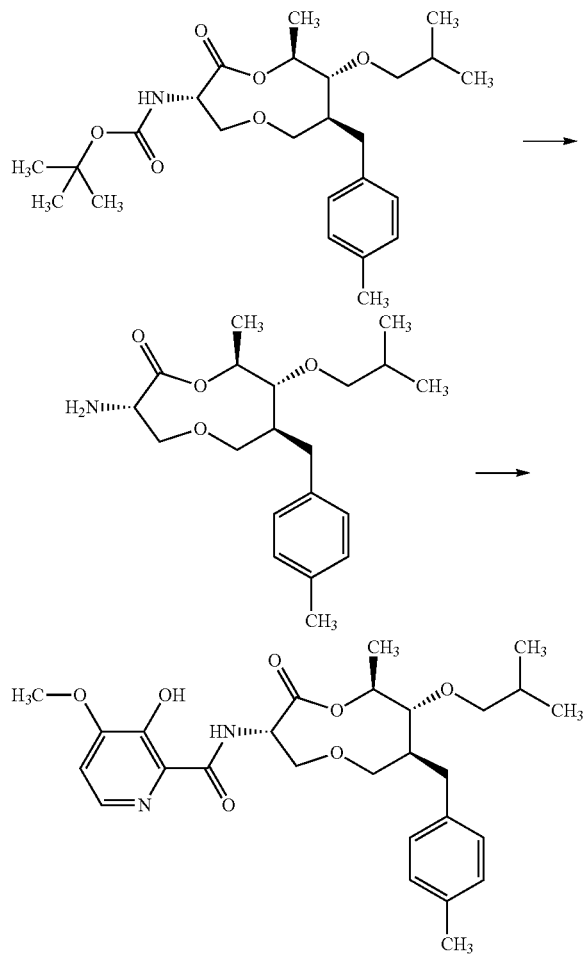

Step 1a

To a solution of tert-butyl ((3S,7S,8R,9S)-8-isobutoxy-9-methyl-7-(4-methylbenzyl)-2-oxo-1,5-dioxonan-3-yl)carbamate (0.03 g, 0.07 mmol) in CH$_2$Cl$_2$ (0.7 mL) was added a 4 M solution of HCl in dioxane (0.33 mL, 1.34 mmol), and the resulting colorless solution was stirred at room temperature for 1.5 h. The solvent was evaporated under a positive stream of N$_2$ and the residue was dissolved in CH$_2$Cl$_2$, washed with saturated aqueous NaHCO$_3$, dried by passing through a phase separator cartridge, and concentrated to give (3S,7S,8R,9S)-3-amino-8-isobutoxy-9-methyl-7-(4-methylbenzyl)-1,5-dioxonan-2-one (0.021 g, 90%) as a white solid: mp 81-84° C.; $^1$H NMR (400 MHz, CDCl$_3$) δ 7.08 (t, J=2.7 Hz, 4H), 4.91 (dq, J=9.2, 6.4 Hz, 1H), 3.84 (dd, J=11.6, 7.5 Hz, 1H), 3.74 (m, 2H), 3.64 (m, 1H), 3.47 (dd, J=8.3, 6.4 Hz, 1H), 3.41 (dd, J=10.7, 6.1 Hz, 1H), 3.31 (m, 2H), 3.07 (m, 3H), 2.31 (s, 3H), 1.87 (m, 2H), 1.59 (m, 1H), 1.47 (d, J=6.4 Hz, 3H), 0.95 (dd, J=6.7, 1.6 Hz, 6H); ESIMS m/z 351 ([M+H]$^+$).

Step 1b

To a mixture of 3-hydroxy-4-methoxypicolinic acid (0.198 g, 1.17 mmol), HATU (0.47 g, 1.25 mmol), and N-methylmorpholine (0.47 g, 4.7 mmol) in CH$_2$Cl$_2$ (9 mL) was added (3S,7S,8R,9S)-3-amino-8-isobutoxy-9-methyl-7-(4-methylbenzyl)-1,5-dioxonan-2-one (272 mg, 0.78 mmol), and the tan mixture was stirred at room temperature for 7 h. The resulting homogeneous solution was adsorbed to Celite® and purified by flash chromatography (SiO$_2$, 0→30% acetone/hexanes) to give 3-hydroxy-N-((3S,7S,8R, 9S)-8-isobutoxy-9-methyl-7-(4-methylbenzyl)-2-oxo-1,5-dioxonan-3-yl)-4-methoxypicolinamide (0.30 g, 77%) as a white foam: $^1$H NMR (400 MHz, CDCl$_3$) δ 11.95 (s, 1H), 8.54 (d, J=8.3 Hz, 1H), 7.97 (d, J=5.2 Hz, 1H), 7.09 (d, J=2.1 Hz, 4H), 6.85 (d, J=5.2 Hz, 1H), 5.01 (m, 2H), 4.02 (dd, J=11.7, 7.3 Hz, 1H), 3.92 (s, 3H), 3.46 (m, 4H), 3.34 (dd, J=8.3, 6.5 Hz, 1H), 3.13 (m, 2H), 2.31 (s, 4H), 1.93 (m, 2H), 1.50 (d, J=6.4 Hz, 3H), 0.96 (d, J=6.7 Hz, 6H); $^{13}$C NMR (101 MHz, CDCl$_3$) δ 171.15, 168.90, 155.31, 148.71, 140.62, 136.76, 135.58, 130.20, 129.15, 129.05, 109.56, 84.61, 79.28, 75.92, 72.53, 72.16, 56.08, 51.53, 47.47, 34.60, 29.20, 21.03, 19.50, 18.83; HRMS-ESI (m/z) [M+H]$^+$ calcd for C$_{27}$H$_{36}$N$_2$O$_7$, 500.2523. found, 500.2529.

Example 6

Step 1: Preparation of tert-butyl N-tert-butoxycarbonyl-N-[(3S,7S,8R,9S)-8-hydroxy-9-methyl-7-(1-naphthylmethyl)-2-oxo-1,5-dioxonan-3-yl]carbamate

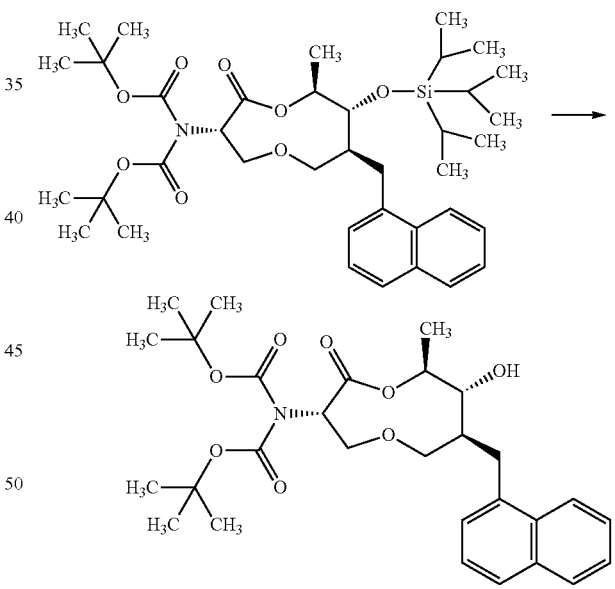

To a solution of tert-butyl N-tert-butoxycarbonyl-N-[(3S, 7S,8R,9S)-9-methyl-7-(1-naphthylmethyl)-2-oxo-8-triisopropylsilyloxy-1,5-dioxonan-3-yl]carbamate (2.54 g, 3.70 mmol) in THF (18.5 ml) was added TBAF (1.94 g, 7.41 mmol, 1M in THF) at room temperature. The reaction was stirred for 3.5 h, diluted with a ½ sat. aqueous NaCl solution (10 mL), and extracted with EtOAc (3×10 mL). The combined extracts were dried over Na$_2$SO$_4$, filtered, and concentrated to dryness under reduced pressure. The resulting clear oil was purified by flash chromatography (SiO$_2$, 0→50% acetone/hexanes) to afford tert-butyl N-tert-butoxycarbonyl-N-[(3S,7S,8R,9S)-8-hydroxy-9-methyl-7-(1- naphthylmethyl)-2-oxo-1,5-dioxonan-3-yl]carbamate (1.41 g, 72%) as a white solid: $^1$H NMR (400 MHz, CDCl$_3$) δ 8.11 (dd, J=8.5, 1.4 Hz, 1H), 7.87-7.79 (m, 1H), 7.72 (d, J=8.1 Hz, 1H), 7.54-7.41 (m, 2H), 7.42-7.27 (m, 2H), 5.19 (dd, J=8.8, 5.7 Hz, 1H), 5.00-4.88 (m, 1H), 4.10 (dd, J=11.9, 5.8 Hz, 1H), 3.89 (dd, J=12.0, 8.7 Hz, 1H), 3.68-3.51 (m, 4H), 2.79 (t, J=12.2 Hz, 1H), 2.58-2.51 (m, 1H), 2.15 (q, J=8.7, 7.4 Hz, 1H), 1.51 (d, J=6.4 Hz, 3H), 1.46 (s, 18H); $^{13}$C NMR (101 MHz, CDCl$_3$) δ 169.95, 152.69, 135.84, 134.02, 132.04, 128.77, 127.46, 127.16, 126.03, 125.56, 125.25, 124.04, 83.17, 77.69, 76.26, 73.23, 70.87, 57.38, 46.90, 33.38, 27.92, 18.67; ESIMS m/z 553 ([M+Na]$^+$).

Example 6

Step 2a-1: Preparation of tert-butyl N-tert-butoxycarbonyl-N-[(3S,7S,8R,9S)-8-cyclopent-2-en-1-yloxy-9-methyl-7-(1-naphthylmethyl)-2-oxo-1,5-dioxonan-3-yl]carbamate

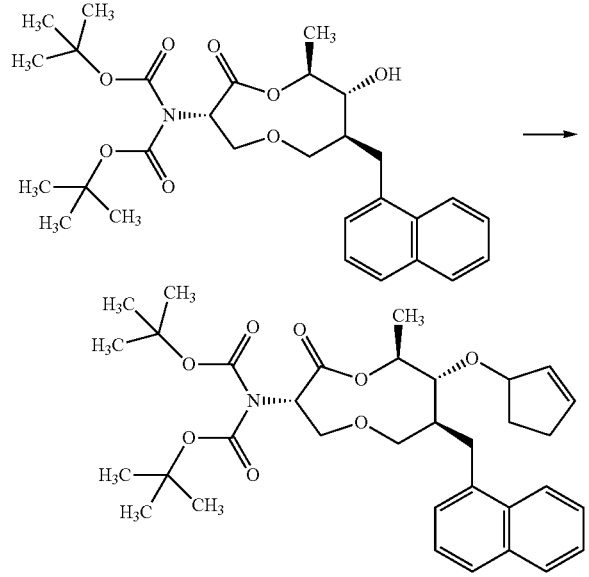

To a solution of tert-butyl N-tert-butoxycarbonyl-N-[(3S,7S,8R,9S)-8-hydroxy-9-methyl-7-(1-naphthylmethyl)-2-oxo-1,5-dioxonan-3-yl]carbamate (205 mg, 0.387 mmol), [Pd$_2$(dba)$_3$] (26.6 mg, 0.029 mmol), and dppf (32.5 mg, 0.058 mmol) in toluene (1.94 mL) was added (E) tert-butyl cyclopent-2-en-1-yl carbonate (250 mg, 1.355 mmol), and the mixture was warmed to 95° C. and stirred for 2 h. An additional portion of (E)-tert-butyl pent-2-en-1-yl carbonate (150 mg, 0.6 equiv.) was added to the reaction and stirring continued for an additional 2 h. The mixture was cooled to room temperature and the toluene was removed under reduced pressure. The residue was dissolved in CH$_2$Cl$_2$ (12 mL), adsorbed to Celite® and purified by flash chromatography (SiO$_2$, 35 mL/min, 0→25 EtOAc/hexanes) to provide tert-butyl N-tert-butoxycarbonyl-N-[(3S,7S,8R,9S)-8-cyclopent-2-en-1-yloxy-9-methyl-7-(1-naphthylmethyl)-2-oxo-1,5-dioxonan-3-yl]carbamate (205 mg, 89%) as a mixture of diastereomers (about 1:1) in the form of a white solid: IR (thin film) 2928, 1755, 1709, 1117 cm$^{-1}$; $^1$H NMR (400 MHz, CDCl$_3$) δ 8.09 (m, 1H), 7.82 (m, 1H), 7.74-7.66 (m, 1H), 7.53-7.39 (m, 2H), 7.42-7.28 (m, 2H), 6.13-6.01 (m, 1.5H), 6.01-5.92 (m, 0.5H), 5.07 (app t, J=7.7 Hz, 1H), 4.90-4.79 (m, 2H), 4.02-3.83 (m, 2H), 3.76 (dd, J=13.6, 2.8 Hz, 1H), 3.55-3.39 (m, 3H), 2.82-2.66 (m, 1H), 2.60-2.47 (m, 1H), 2.34-2.17 (m, 2H), 2.11-1.92 (m, 3H), 1.57 (app dd, J=12.6, 6.4 Hz, 3H), 1.39 (app d, J=5.9 Hz, 18H); ESIMS m/z 618 ([M+Na]$^+$).

Example 6

Step 2a-2: Preparation of tert-butyl N-tert-butoxycarbonyl-N-[(3S,7S,8R,9S)-8-(cyclopentoxy)-9-methyl-7-(1-naphthylmethyl)-2-oxo-1,5-dioxonan-3-yl]carbamate (F132)

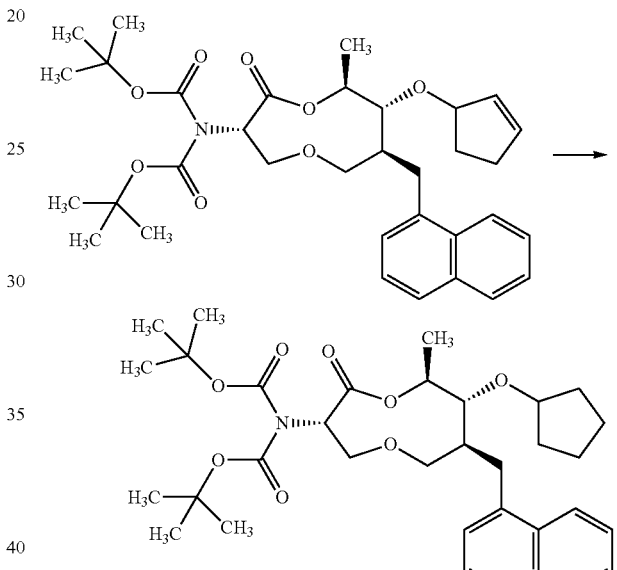

To a solution of tert-butyl N-tert-butoxycarbonyl-N-[(3S,7S,8R,9S)-8-cyclopent-2-en-1-yloxy-9-methyl-7-(1-naphthylmethyl)-2-oxo-1,5-dioxonan-3-yl]carbamate (210 mg, 0.353 mmol) in EtOAc (3.5 mL) was added 10% Pd/C (37.5 mg, 0.035 mmol). The reaction was put under a H$_2$ atmosphere (balloon) and stirred at room temperature for 5 h, whereupon the H$_2$ was purged from system and the reaction was filtered through a pad of Celite®. The pad was washed with EtOAc (2×6 mL) and the organics were combined and concentrated to dryness to afford tert-butyl N-tert-butoxycarbonyl-N-[(3S,7S,8R,9S)-8-(cyclopentoxy)-9-methyl-7-(1-naphthyl-methyl)-2-oxo-1,5-dioxonan-3-yl]carbamate (193 mg, 92%) as a white powder: mp 49-55° C.; $^1$H NMR (400 MHz, CDCl$_3$) δ 8.09 (d, J=8.3 Hz, 1H), 7.82 (dd, J=8.1, 1.5 Hz, 1H), 7.74-7.67 (m, 1H), 7.54-7.41 (m, 2H), 7.40-7.31 (m, 2H), 5.05 (app t, J=7.7 Hz, 1H), 4.90-4.79 (m, 1H), 4.21-4.12 (m, 1H), 3.94 (dd, J=11.7, 7.5 Hz, 1H), 3.88 (dd, J=11.7, 8.0 Hz, 1H), 3.73 (dd, J=13.6, 2.9 Hz, 1H), 3.53-3.35 (m, 3H), 2.71 (app t, J=12.8 Hz, 1H), 2.07-1.96 (m, 1H), 1.90-1.70 (m, 6H), 1.63-1.49 (m, 5H), 1.38 (s, 18H); ESIMS m/z 620 ([M+Na]$^+$).

Example 6

Step 2b: Preparation of [(3S,6S,7R,8S)-3-[bis(tert-butoxycarbonyl)amino]-6-methyl-8-(1-naphthylmethyl)-4-oxo-1,5-dioxonan-7-yl]2-methylpropanoate (F128)

Example 6

Step 2c: Preparation of tert-butyl N-tert-butoxycarbonyl-N-[(3S,7S,8R,9S)-9-methyl-8-(4-methylphenoxy)-7-(1-naphthylmethyl)-2-oxo-1,5-dioxonan-3-yl]carbamate (F131)

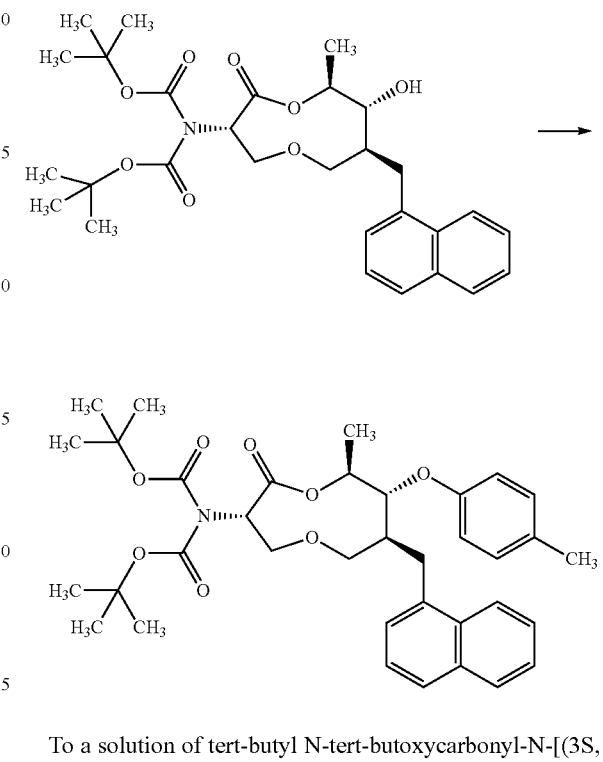

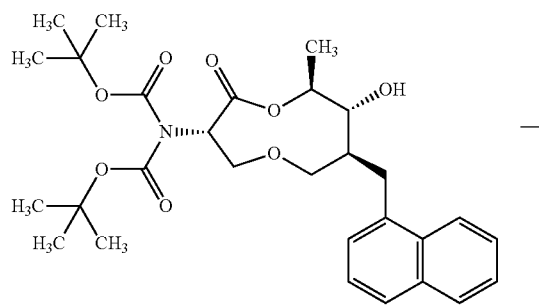

To a solution of tert-butyl N-tert-butoxycarbonyl-N-[(3S,7S,8R,9S)-8-hydroxy-9-methyl-7-(1-naphthylmethyl)-2-oxo-1,5-dioxonan-3-yl]carbamate (290 mg, 0.548 mmol) and DMAP (201 mg, 1.64 mmol) in $CH_2Cl_2$ (2.7 mL) was added isobutyryl chloride (86 μL, 0.821 mmol) slowly to the flask and the resulting solution was stirred at room temperature for 20 h. The reaction mixture was dissolved in $CH_2Cl_2$ (4 mL), treated with Celite®, the solvent evaporated, and the adsorbed crude material purified by flash chromatography ($SiO_2$, 0→15% EtOAc/hexanes) to provide [(3S,6S,7R,8S)-3-[bis(tert-butoxycarbonyl)amino]-6-methyl-8-(1-naphthylmethyl)-4-oxo-1,5-dioxonan-7-yl]2-methylpropanoate (270 mg, 82%) as a white powder: mp 130-132° C.; $^1$H NMR (400 MHz, $CDCl_3$) δ 8.01-7.93 (m, 1H), 7.84 (dd, J=8.0, 1.5 Hz, 1H), 7.72 (d, J=8.1 Hz, 1H), 7.54-7.41 (m, 2H), 7.37 (dd, J=8.2, 7.0 Hz, 1H), 7.28 (dd, J=7.0, 1.3 Hz, 1H), 5.20 (dd, J=8.7, 5.7 Hz, 1H), 5.11 (app t, J=9.3 Hz, 1H), 5.08-4.97 (m, 1H), 4.06 (dd, J=11.8, 5.7 Hz, 1H), 3.86 (dd, J=11.9, 8.7 Hz, 1H), 3.66 (d, J=11.0 Hz, 1H), 3.50 (dd, J=10.8, 6.4 Hz, 1H), 3.23 (dd, J=14.0, 3.1 Hz, 1H), 2.74-2.55 (m, 2H), 2.37-2.20 (m, 1H), 1.42 (s, 18H), 1.37 (d, J=6.2 Hz, 3H), 1.26 (app dd, J=7.0, 4.4 Hz, 6H); ESIMS m/z 622 ([M+Na]$^+$).

To a solution of tert-butyl N-tert-butoxycarbonyl-N-[(3S,7S,8R,9S)-8-hydroxy-9-methyl-7-(1-naphthylmethyl)-2-oxo-1,5-dioxonan-3-yl]carbamate (150 mg, 0.283 mmol), tritoluoylbismuth diacetate (255 mg, 0.425 mmol), and diacetoxycopper (7.72 mg, 0.042 mmol) was added N-cyclohexyl-N-methylcyclohexanamine (120 μL, 0.566 mmol). The mixture was warmed to 50° C. and stirring continued at this temperature for 14 h. The resulting thick slurry, was cooled to room temperature and loaded directly onto a silica gel precolumn and purified by flash chromatography ($SiO_2$, 30 mL/min, 0% EtOAc 1 min, 0→50% EtOAc/hexanes) to afford tert-butyl N-tert-butoxycarbonyl-N-[(3S,7S,8R,9S)-9-methyl-8-(4-methylphenoxy)-7-(1-naphthylmethyl)-2-oxo-1,5-dioxonan-3-yl]carbamate (45 mg, 26%) as a colorless solid: $^1$H NMR (400 MHz, $CDCl_3$) δ 8.11-8.03 (m, 1H), 7.81 (dd, J=7.9, 1.6 Hz, 1H), 7.69 (d, J=8.1 Hz, 1H), 7.54-7.39 (m, 2H), 7.39-7.30 (m, 1H), 7.27 (dd, J=7.0, 1.4 Hz, 1H), 7.16-7.08 (m, 2H), 7.03-6.95 (m, 2H), 5.17 (dd, J=8.7, 6.5 Hz, 1H), 5.09-4.99 (m, 1H), 4.40 (app t, J=9.0 Hz, 1H), 4.08 (dd, J=11.7, 6.6 Hz, 1H), 3.91 (dd, J=11.7, 8.7 Hz, 1H), 3.63-3.48 (m, 3H), 2.69-2.64 (m, 1H), 2.37-2.26 (m, 4H), 1.47-1.38 (m, 21H); $^{13}$C NMR (101 MHz, $CDCl_3$) δ 169.99, 157.28, 152.59, 135.48, 133.98, 131.99, 130.55, 130.22, 128.67, 127.79, 127.09, 125.91, 125.43, 125.14, 124.04, 115.18, 83.05, 82.23, 75.40, 72.08, 70.65, 57.24, 46.50, 32.68, 27.84, 20.43, 19.10; ESIMS m/z 642 ([M+Na]$^+$).

Example 6

Steps 3a and 3b: Preparation of (3S,6S,7R,8S)-3-(3-hydroxy-4-methoxypicolin-amido)-6-methyl-8-(naphthalen-1-ylmethyl)-4-oxo-1,5-dioxonan-7-yl isobutyrate (F5)

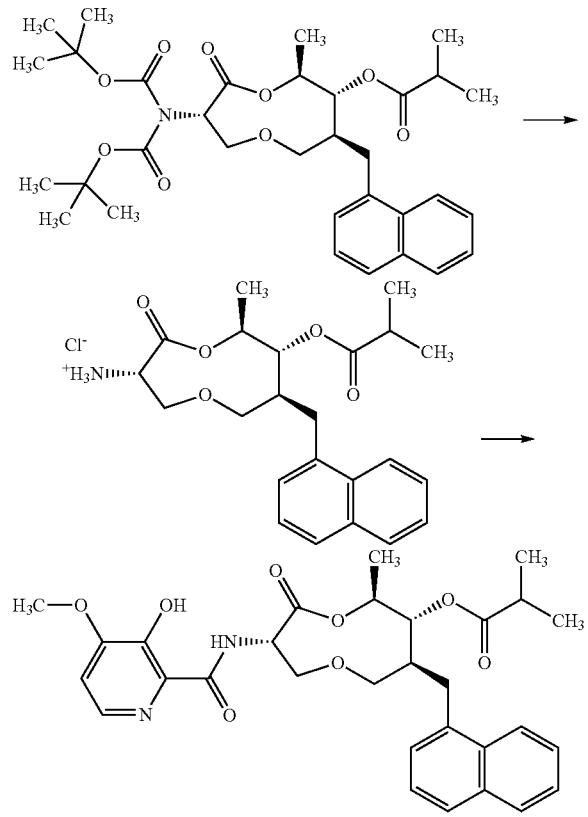

Step 3a

To a solution of [(3S,6S,7R,8S)-3-[bis(tert-butoxycarbonyl)amino]-6-methyl-8-(1-naphthylmethyl)-4-oxo-1,5-dioxonan-7-yl]2-methylpropanoate (260 mg, 0.434 mmol) in CH$_2$Cl$_2$ (1 mL) was added 4 M HCl in dioxane (2.17 mL, 8.67 mmol) slowly (gas evolution) and the resulting solution was stirred at room temperature for 2.5 h. The solvent was evaporated under a stream of N$_2$ to give (3S,7S,8R,9S)-8-(isobutyryloxy)-9-methyl-7-(naphthalen-1-ylmethyl)-2-oxo-1,5-dioxonan-3-aminium chloride as a white powder. The powder was dried under high vacuum for 20 h to remove residual HCl and was used without further purification for the amide picolinamide formation: ESIMS m/z 400 ([M+H]$^+$).

Step 3b

To a suspension of (3S,7S,8R,9S)-8-(isobutyryloxy)-9-methyl-7-(naphthalen-1-ylmethyl)-2-oxo-1,5-dioxonan-3-aminium chloride in CH$_2$Cl$_2$ (2 mL) were added PyBOP (248 mg, 0.477 mmol) and 3-hydroxy-4-methoxypicolinic acid (81 mg, 0.477 mmol) followed by the dropwise addition of N-ethyl-N-isopropylpropan-2-amine (249 μL, 1.43 mmol). After 10 min everything solubilized and stirring was continued for 2 h. The reaction was treated with Celite®, the solvent removed under reduced pressure, and the resulting adsorbed crude material was purified by flash chromatography (SiO$_2$, 0→100% EtOAc/hexanes) to provide (3S,6S,7R, 8S)-3-(3-hydroxy-4-methoxypicolin-amido)-6-methyl-8-(naphthalen-1-ylmethyl)-4-oxo-1,5-dioxonan-7-yl isobutyrate as a white powder (210 mg, 88%): mp 139-142° C.; $^1$H NMR (400 MHz, CDCl$_3$) δ 11.91 (s, 1H), 8.50 (d, J=8.3 Hz, 1H), 8.01-7.92 (m, 2H), 7.89-7.82 (m, 1H), 7.74 (d, J=8.2 Hz, 1H), 7.49 (dddd, J=14.7, 8.1, 6.9, 1.5 Hz, 2H), 7.40 (dd, J=8.2, 7.0 Hz, 1H), 7.30 (dd, J=6.9, 1.2 Hz, 1H), 6.84 (d, J=5.2 Hz, 1H), 5.20-5.02 (m, 3H), 4.04 (dd, J=11.7, 7.3 Hz, 1H), 3.92 (s, 3H), 3.60 (d, J=4.1 Hz, 2H), 3.43 (dd, J=11.7, 7.1 Hz, 1H), 3.23 (dd, J=14.2, 3.2 Hz, 1H), 2.79-2.64 (m, 2H), 2.36-2.23 (m, 1H), 1.43-1.37 (m, 3H), 1.29 (dd, J=7.0, 3.6 Hz, 6H); $^{13}$C NMR (101 MHz, CDCl$_3$) δ 176.37, 171.12, 168.88, 155.32, 148.71, 140.60, 134.68, 133.97, 131.94, 130.09, 128.97, 127.76, 127.35, 126.02, 125.57, 125.37, 123.45, 109.55, 76.95, 74.38, 72.09, 56.07, 51.42, 44.93, 34.37, 32.19, 19.14, 19.07, 18.26; HRMS-ESI (m/z) [M+H]$^+$ calcd for C$_{30}$H$_{35}$N$_2$O$_8$ expected, 551.2388. found 551.2388.

Example 7

Preparation of (3S,6S,7R,8S)-3-(3-(acetoxymethoxy)-4-methoxypicolin-amido)-6-methyl-8-(naphthalen-1-ylmethyl)-4-oxo-1,5-dioxonan-7-yl isobutyrate (F83)

To a mixture of (3S,6S,7R,8S)-3-(3-hydroxy-4-methoxypicolinamido)-6-methyl-8-(naphthalen-1-ylmethyl)-4-oxo-1,5-dioxonan-7-yl isobutyrate (85 mg, 0.154 mmol) and K$_2$CO$_3$ (42.7 mg, 0.309 mmol) in acetone (2.0 mL) was added bromomethyl acetate (21.2 μL, 0.216 mmol), and the reaction was stirred vigorously at 50° C. under N$_2$ for 1 h. The reaction was cooled to room temperature, diluted with CH$_2$Cl$_2$ (10 mL), filtered, and treated with Celite®. The solvent was removed under reduced pressure and the resulting adsorbed crude material was purified by flash chromatography (SiO$_2$, 0→50% acetone/hexanes) to afford (3S,6S,7R,8S)-3-(3-(acetoxymethoxy)-4-methoxypicolinamido)-6-methyl-8-(naphthalen-1-ylmethyl)-4-oxo-1,5-dioxonan-7-yl isobutyrate (70 mg, 0.112 mmol, 73% yield) as a white powder: mp 58-64° C.; $^1$H NMR (400

MHz, CDCl$_3$) δ 8.37 (d, J=8.1 Hz, 1H), 8.24 (d, J=5.3 Hz, 1H), 8.02-7.94 (m, 1H), 7.89-7.81 (m, 1H), 7.74 (d, J=8.2 Hz, 1H), 7.56-7.43 (m, 2H), 7.40 (dd, J=8.2, 7.0 Hz, 1H), 7.30 (dd, J=7.1, 1.2 Hz, 1H), 6.92 (d, J=5.4 Hz, 1H), 5.71 (d, J=6.5 Hz, 2H), 5.17-5.06 (m, 3H), 4.04 (dd, J=11.6, 7.4 Hz, 1H), 3.89 (s, 3H), 3.60 (d, J=4.2 Hz, 2H), 3.40 (dd, J=11.7, 7.1 Hz, 1H), 3.23 (dd, J=14.2, 3.1 Hz, 1H), 2.77-2.63 (m, 2H), 2.29 (ddt, J=12.2, 8.1, 3.9 Hz, 1H), 2.04 (s, 3H), 1.39 (d, J=5.6 Hz, 3H), 1.29 (dd, J=7.0, 3.9 Hz, 6H); $^{13}$C NMR (101 MHz, CDCl$_3$) δ 176.38, 171.75, 170.27, 163.15, 160.19, 145.74, 143.97, 142.01, 134.75, 133.97, 131.96, 128.95, 127.78, 127.32, 125.99, 125.54, 125.38, 123.50, 109.70, 89.40, 74.18, 72.32, 71.93, 56.18, 51.77, 44.97, 34.38, 32.25, 20.85, 19.14, 19.07, 18.28; HRMS-ESI (m/z) [M+H]+ calcd for C$_{33}$H$_{39}$N$_2$O$_{10}$ expected, 623.2599. found, 623.2611.

Example 8

Preparation of (3S,6S,7R,8S)-3-(3-acetoxy-4-methoxypicolinamido)-6-methyl-8-(naphthalen-1-ylmethyl)-4-oxo-1,5-dioxonan-7-yl isobutyrate (F51)

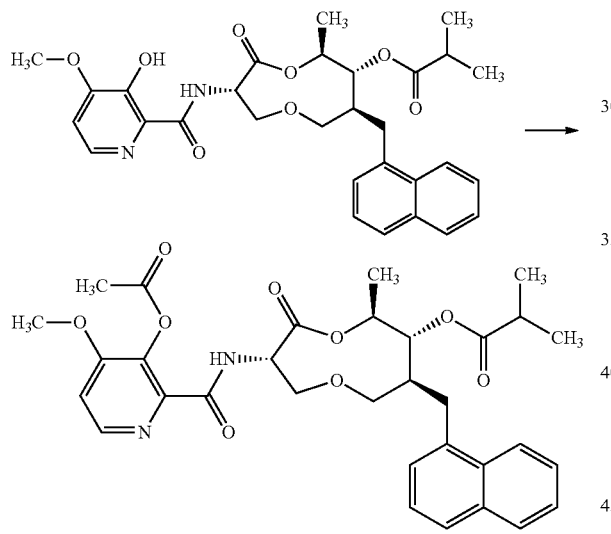

To a solution of (3S,6S,7R,8S)-3-(3-hydroxy-4-methoxypicolinamido)-6-methyl-8-(naphthalen-1-ylmethyl)-4-oxo-1,5-dioxonan-7-yl isobutyrate (80 mg, 0.145 mmol) and DMAP (28.4 mg, 0.232 mmol) in CH$_2$Cl$_2$ (1.45 mL) was added acetyl chloride (218 μL, 0.218 mmol) slowly and the resulting mixture was stirred at room temperature for 14 h. The reaction mixture was treated with Celite®, the solvent removed under reduced pressure, and the resulting adsorbed crude material was purified by flash chromatography (SiO$_2$, 0→100% acetone/hexanes) to afford (3S,6S,7R, 8S)-3-(3-acetoxy-4-methoxypicolinamido)-6-methyl-8-(naphthalen-1-ylmethyl)-4-oxo-1,5-dioxonan-7-yl isobutyrate as a white powder (80 mg, 93%): mp 104-108° C.; $^1$H NMR (400 MHz, CDCl$_3$) δ 8.53 (d, J=8.2 Hz, 1H), 8.27 (d, J=5.4 Hz, 1H), 8.01-7.94 (m, 1H), 7.88-7.81 (m, 1H), 7.73 (d, J=8.2 Hz, 1H), 7.55-7.43 (m, 2H), 7.39 (dd, J=8.2, 7.0 Hz, 1H), 7.29 (dd, J=7.0, 1.2 Hz, 1H), 6.96 (d, J=5.4 Hz, 1H), 5.18-5.02 (m, 3H), 4.00 (dd, J=11.7, 7.4 Hz, 1H), 3.86 (s, 3H), 3.58 (d, J=4.2 Hz, 2H), 3.37 (dd, J=11.7, 7.2 Hz, 1H), 3.22 (dd, J=14.1, 3.1 Hz, 1H), 2.76-2.63 (m, 2H), 2.38 (s, 3H), 2.34-2.22 (m, 1H), 1.38 (d, J=5.7 Hz, 3H), 1.29 (d, J=3.7 Hz, 3H), 1.27 (d, J=3.7 Hz, 3H); $^{13}$C NMR (101 MHz, CDCl$_3$) δ 176.38, 171.66, 168.84, 162.67, 159.42, 146.73, 141.03, 137.53, 134.77, 133.99, 131.98, 128.97, 127.78, 127.34, 126.01, 125.57, 125.39, 123.50, 109.95, 77.05, 74.20, 72.26, 71.84, 56.29, 51.51, 44.99, 34.38, 32.26, 20.73, 19.15, 19.08, 18.28; HRMS-ESI (m/z) [M+H]+ calcd for C$_{32}$H$_{37}$N$_2$O$_9$ expected, 593.2494. found, 593.2502.

Example 9

Preparation of ((4-methoxy-2-(((3S,7S,8R,9S)-9-methyl-2-oxo-8-propoxy-7-(4-(trifluoromethyl)benzyl)-1,5-dioxonan-3-yl)carbamoyl)pyridin-3-yl)oxy) methyl 2-ethoxyacetate (F120)

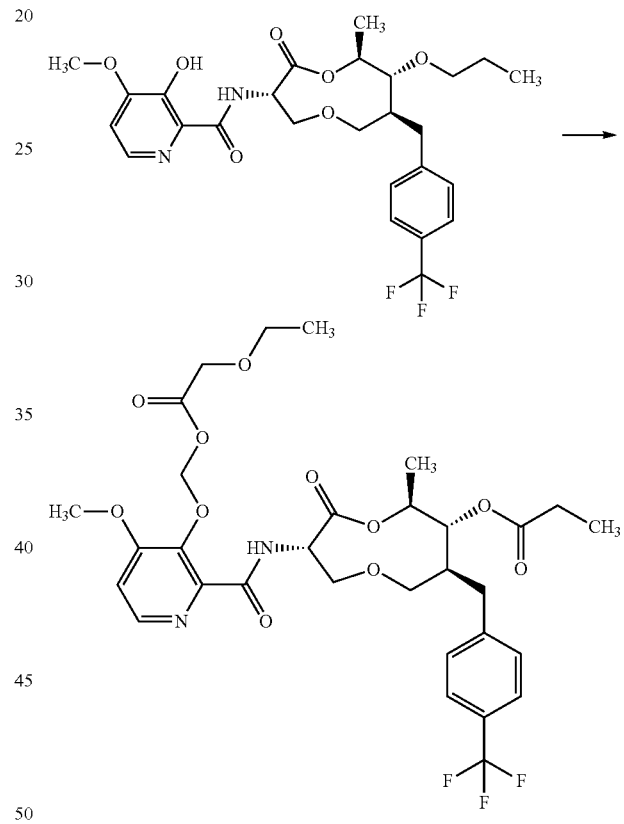

To a solution of 3-hydroxy-4-methoxy-N-((3S,7S,8R,9S)-9-methyl-2-oxo-8-propoxy-7-(4-(trifluoromethyl)benzyl)-1, 5-dioxonan-3-yl)picolinamide (83 mg, 0.154 mmol) in acetone (2 mL) were added Na$_2$CO$_3$ (24.4 mg, 0.230 mmol), NaI (4.60 mg, 0.031 mmol), and chloromethyl 2-ethoxyacetate (30.5 mg, 0.200 mmol), and the mixture was stirred for 7 hours at 40° C. The reaction was cooled to room temperature and purified directly by flash chromatography (SiO$_2$, 0→100% EtOAc/hexanes) to give ((4-methoxy-2-(((3S,7S, 8R,9S)-9-methyl-2-oxo-8-propoxy-7-(4-(trifluoromethyl) benzyl)-1,5-dioxonan-3-yl)carbamoyl)pyridin-3-yl)oxy) methyl 2-ethoxyacetate as a colorless oil (94 mg, 93%): $^1$H NMR (400 MHz, CDCl$_3$) δ 8.41 (d, J=8.2 Hz, 1H), 8.26 (d, J=5.4 Hz, 1H), 7.61-7.50 (m, 2H), 7.32 (d, J=8.0 Hz, 2H), 6.95 (d, J=5.4 Hz, 1H), 5.80 (s, 2H), 5.04-4.95 (m, 2H), 4.08 (s, 2H), 4.03 (dd, J=11.7, 7.3 Hz, 1H), 3.90 (s, 3H), 3.66 (dt, J=8.6, 6.6 Hz, 1H), 3.63-3.47 (m, 3H), 3.47-3.36 (m, 3H), 3.23-3.12 (m, 2H), 2.43 (dd, J=13.7, 11.7 Hz, 1H), 2.01-1.90 (m, 1H), 1.69-1.58 (m, 2H), 1.51 (d, J=6.4 Hz, 3H), 1.22 (t, J=7.0 Hz, 3H), 0.97 (t, J=7.4 Hz, 3H); $^{19}$F NMR (376 MHz, CDCl$_3$) δ −62.35; HRMS-ESI (m/z) [M]$^+$ calcd for C$_{31}$H$_{39}$F$_3$N$_2$O$_{10}$ expected, 656.2557. found, 656.2569.

Example A

Evaluation of Fungicidal Activity: Leaf Blotch of Wheat (*Mycosphaerella graminicola*; Anamorph: *Septoria tritici*; Bayer Code SEPTTR)

Technical grades of materials were dissolved in acetone, which were then mixed with nine volumes of water containing 110 ppm Triton X-100. The fungicide solutions were applied onto wheat seedlings using an automated booth sprayer to run-off. All sprayed plants were allowed to air dry prior to further handling. All fungicides were evaluated using the aforementioned method for their activity vs. all target diseases. Wheat leaf blotch and brown rust activity were also evaluated using track spray applications, in which case the fungicides were formulated as EC formulations, containing 0.1% Trycol 5941 in the spray solutions.

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Septoria tritici* either prior to or after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a greenhouse set at 20° C. for disease to develop. When disease symptoms were fully expressed on the $1^{st}$ leaves of untreated plants, infection levels were assessed on a scale of 0 to 100 percent disease severity. Percent disease control was calculated using the ratio of disease severity on treated plants relative to untreated plants.

Example B

Evaluation of Fungicidal Activity: Wheat Brown Rust (*Puccinia triticina*; Synonym: *Puccinia recondite* f. sp. *tritici*; Bayer Code PUCCRT)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Puccinia triticina* either prior to or after fungicide treatments. After inoculation the plants were kept in a dark dew room at 22° C. with 100% relative humidity overnight to permit spores to germinate and infect the leaf. The plants were then transferred to a greenhouse set at 24° C. for disease to develop. Fungicide formulation, application and disease assessment followed the procedures as described in the Example A.

Example C

Evaluation of Fungicidal Activity: Wheat Glume Blotch (*Leptosphaeria nodorum*; Bayer Code LEPTNO)

Wheat plants (variety Yuma) were grown from seed in a greenhouse in 50% mineral soil/50% soil-less Metro mix until the first leaf was fully emerged, with 7-10 seedlings per pot. These plants were inoculated with an aqueous spore suspension of *Leptosphaeria nodorum* 24 hr after fungicide treatments. After inoculation the plants were kept in 100% relative humidity (one day in a dark dew chamber followed by two days in a lighted dew chamber at 20° C.) to permit spores to germinate and infect the leaf. The plants were then transferred to a greenhouse set at 20° C. for disease to develop. Fungicide formulation, application and disease assessment followed the procedures as described in the Example A.

Example D

Evaluation of Fungicidal Activity: Apple Scab (*Venturia inaequalis*; Bayer Code VENTIN)

Apple seedlings (variety McIntosh) were grown in soil-less Metro mix, with one plant per pot. Seedlings with two expanding young leaves at the top (older leaves at bottom of the plants were trimmed) were used in the test. Plants were inoculated with a spore suspension of *Venturia inaequalis* 24 hr after fungicide treatment and kept in a 22° C. dew chamber with 100% RH for 48 hr, and then moved to a greenhouse set at 20° C. for disease to develop. Fungicide formulation, application and disease assessment on the sprayed leaves followed the procedures as described in the Example A.

Example E

Evaluation of Fungicidal Activity: Grape Powdery Mildew (*Uncinula necator*; Bayer Code UNCINE)

Grape seedlings (variety Carignane) were grown in soil-less Metro mix, with one plant per pot, and used in the test when approximately one month old. Plants were inoculated 24 hr after fungicide treatment by shaking spores from infected leaves over test plants. Plants were maintained in a greenhouse set at 20° C. until disease was fully developed. Fungicide formulation, application and disease assessment on the sprayed leaves followed the procedures as described in the Example A.

Example F

Evaluation of Fungicidal Activity: Powdery Mildew of Cucumber (*Erysiphe cichoracearum*; Bayer Code ERYSCI)

Cucumber seedlings (variety Bush Pickle) were grown in soil-less Metro mix, with one plant per pot, and used in the test when 12 to 14 days old. Plants were inoculated with a spore suspension 24 hr following fungicide treatments. After inoculation the plants remained in the greenhouse set at 20° C. until disease was fully expressed. Fungicide formulation, application and disease assessment on the sprayed leaves followed the procedures as described in the Example A.

Example G

Evaluation of Fungicidal Activity: Leaf Spot of Sugar Beets (*Cercospora beticola*; Bayer Code CERCBE)

Sugar beet plants (variety HH88) were grown in soil-less Metro mix and trimmed regularly to maintain a uniform plant size prior to test. Plants were inoculated with a spore suspension 24 hr after fungicide treatments. Inoculated plants were kept in a dew chamber at 22° C. for 48 hr then incubated in a greenhouse set at 24° C. under a clear plastic hood with bottom ventilation until disease symptoms were fully expressed. Fungicide formulation, application and disease assessment on the sprayed leaves followed the procedures as described in the Example A.

Example H

Evaluation of Fungicidal Activity: Asian Soybean Rust (*Phakopsora pachyrhizi*; Bayer Code PHAKPA)

Technical grades of materials were dissolved in acetone, which were then mixed with nine volumes of water containing 0.011% Tween 20. The fungicide solutions were applied onto soybean seedlings using an automated booth sprayer to run-off. All sprayed plants were allowed to air dry prior to further handling.

Soybean plants (variety Williams 82) were grown in soil-less Metro mix, with one plant per pot. Two weeks old seedlings were used for testing. Plants were inoculated either 3 days prior to or 1 day after fungicide treatments. Plants were incubated for 24 h in a dark dew room at 22° C. and 100% RH then transferred to a growth room at 23° C. for disease to develop. Disease severity was assessed on the sprayed leaves.

Example I

Evaluation of Fungicidal Activity: Wheat Powdery Mildew (*Blumeria graminis* f. sp. *tritici*; Synonym: *Erysiphe graminis* f. sp. *tritici*; Bayer Code ERYSGT)

Wheat plants (variety Yuma) were grown from seed in a greenhouse in 50% mineral soil/50% soil-less Metro mix until the first leaf was fully emerged, with 7-10 seedlings per pot. These plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example J

Evaluation of Fungicidal Activity: Barley Powdery Mildew (*Blumeria graminis* f. sp. *hordei*; Synonym: *Erysiphe graminis* f. sp. *hordei*; Bayer Code ERYSGH)

Barley seedlings (variety Harrington) were propagated in soil-less Metro mix, with each pot having 8 to 12 plants, and used in the test when first leaf was fully emerged. Test plants were inoculated by dusting with infected stock plants 24 hr after fungicide treatments. After inoculation the plants were kept in a greenhouse set at 20° C. for disease to develop. Fungicide formulation, application and disease assessment on the sprayed leaves followed the procedures as described in the Example A.

Example K

Evaluation of Fungicidal Activity: Barley Scald (*Rhyncosporium secalis*; Bayer Code RHYNSE)

Barley seedlings (variety Harrington) were propagated in soil-less Metro mix, with each pot having 8 to 12 plants, and used in the test when first leaf was fully emerged. Test plants were inoculated by an aqueous spore suspension of *Rhyncosporium secalis* 24 hr after fungicide treatments. After inoculation the plants were kept in a dew room at 20° C. with 100% relative humidity for 48 hr. The plants were then transferred to a greenhouse set at 20° C. for disease to develop. Fungicide formulation, application and disease assessment on the sprayed leaves followed the procedures as described in the Example A.

Example L

Evaluation of Fungicidal Activity: Rice Blast (*Magnaporthe grisea*; Anamorph: *Pyricularia oryzae*; Bayer Code PYRIOR)

Rice seedlings (variety Japonica) were propagated in soil-less Metro mix, with each pot having 8 to 14 plants, and used in the test when 12 to 14 days old. Test plants were inoculated with an aqueous spore suspension of *Pyricularia oryzae* 24 hr after fungicide treatments. After inoculation the plants were kept in a dew room at 22° C. with 100% relative humidity for 48 hr to permit spores to germinate and infect the leaf. The plants were then transferred to a greenhouse set at 24° C. for disease to develop. Fungicide formulation, application and disease assessment on the sprayed leaves followed the procedures as described in the Example A.

Example M

Evaluation of Fungicidal Activity: Tomato Early Blight (*Alternaria solani*; Bayer Code ALTESO)

Tomato plants (variety Outdoor girl) were propagated in soil-less Metro mix, with each pot having one plant, and used when 12 to 14 days old. Test plants were inoculated with an aqueous spore suspension of *Alternaria solani* 24 hr after fungicide treatments. After inoculation the plants were kept in 100% relative humidity (one day in a dark dew chamber followed by two to three days in a lighted dew chamber at 20° C.) to permit spores to germinate and infect the leaf. The plants were then transferred to a growth room at 22° C. for disease to develop. Fungicide formulation, application and disease assessment on the sprayed leaves followed the procedures as described in the Example A.

Example N

Evaluation of Fungicidal Activity: Cucumber Anthracnose (*Glomerella lagenarium*; Anamorph: *Colletotrichum lagenarium*; Bayer Code COLLLA)

Cucumber seedlings (variety Bush Pickle) were propagated in soil-less Metro mix, with each pot having one plant, and used in the test when 12 to 14 days old. Test plants were inoculated with an aqueous spore suspension of *Colletotrichum lagenarium* 24 hr after fungicide treatments. After inoculation the plants were kept in a dew room at 22° C. with 100% relative humidity for 48 hr to permit spores to germinate and infect the leaf. The plants were then transferred to a growth room set at 22° C. for disease to develop. Fungicide formulation, application and disease assessment on the sprayed leaves followed the procedures as described in the Example A.

TABLE 1

Compound Structure and Appearance

| Compound Number | Structure | Prepared According to Example | Appearance |
|---|---|---|---|
| F1 | 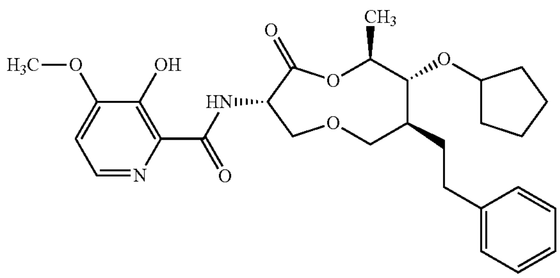 [SMILES: COc1ccnc(C(=O)N[C@H]2COC[C@H](CCc3ccccc3)[C@@H](OC3CCCC3)[C@H](C)OC2=O)c1O] | Example 6, Step 3b | White Powder |
| F2 | 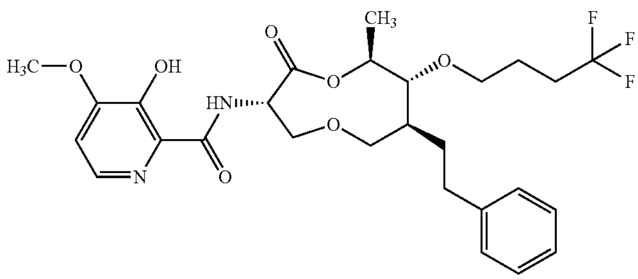 [SMILES: COc1ccnc(C(=O)N[C@H]2COC[C@H](CCc3ccccc3)[C@@H](OCCCC(F)(F)F)[C@H](C)OC2=O)c1O] | Example 6, Step 3b | White Solid |
| F3 | 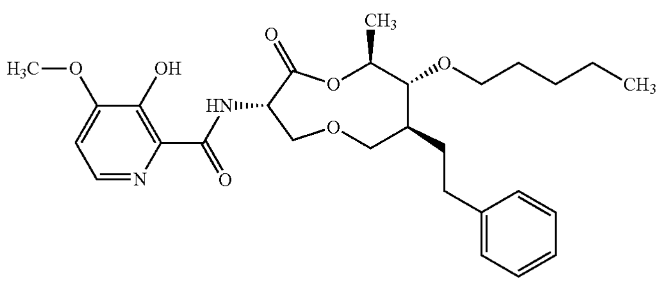 [SMILES: CCCCCO[C@@H]1[C@@H](CCc2ccccc2)COC[C@H](NC(=O)c2nccc(OC)c2O)C(=O)O[C@H]1C] | Example 6, Step 3b | White Solid |
| F4 | 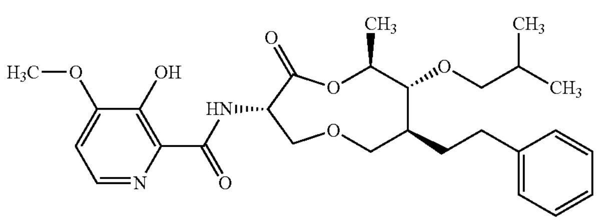 [SMILES: COc1ccnc(C(=O)N[C@H]2COC[C@H](CCc3ccccc3)[C@@H](OCC(C)C)[C@H](C)OC2=O)c1O] | Example 6, Step 3b | White Powder |
| F5 | 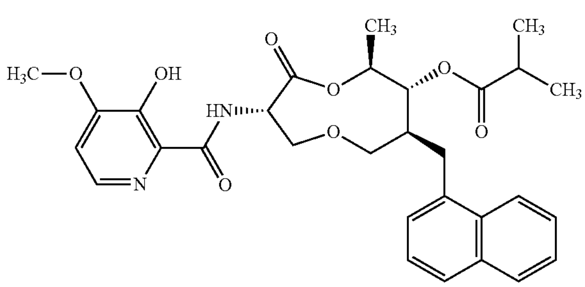 [SMILES: COc1ccnc(C(=O)N[C@H]2COC[C@H](Cc3cccc4ccccc34)[C@@H](OC(=O)C(C)C)[C@H](C)OC2=O)c1O] | Example 6, Step 3b | White Powder |

TABLE 1-continued

Compound Structure and Appearance

| Compound Number | Structure | Prepared According to Example | Appearance |
|---|---|---|---|
| F6 | 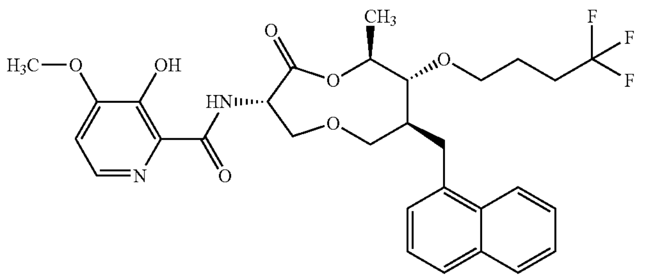 [SMILES: COc1ccnc(C(=O)N[C@H]2COC[C@H](Cc3cccc4ccccc34)[C@@H](OCCCC(F)(F)F)[C@H](C)OC2=O)c1O] | Example 6, Step 3b | White Solid |
| F7 | 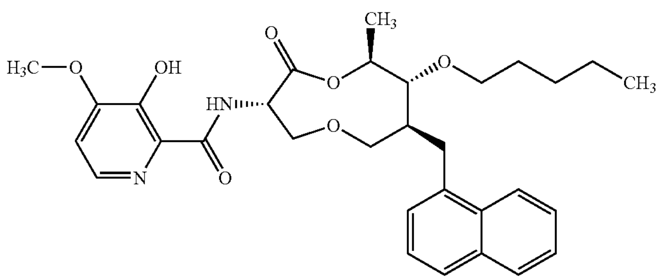 [SMILES: CCCCCO[C@@H]1[C@@H](Cc2cccc3ccccc23)COC[C@H](NC(=O)c2nccc(OC)c2O)C(=O)O[C@H]1C] | Example 6, Step 3b | White Powder |
| F8 | 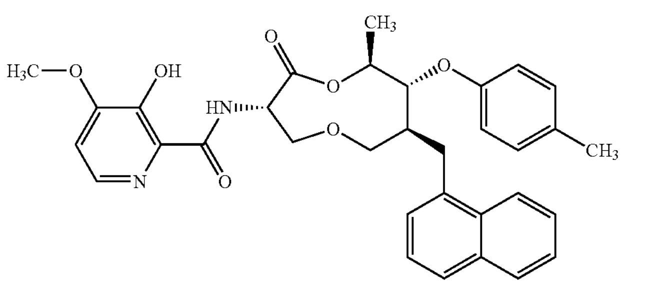 | Example 6, Step 3b | White Solid |
| F9 | 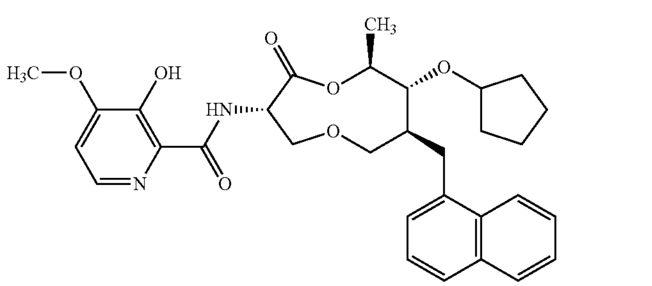 [SMILES: COc1ccnc(C(=O)N[C@H]2COC[C@H](Cc3cccc4ccccc34)[C@@H](OC3CCCC3)[C@H](C)OC2=O)c1O] | Example 6, Step 3b | White Powder |
| F10 | 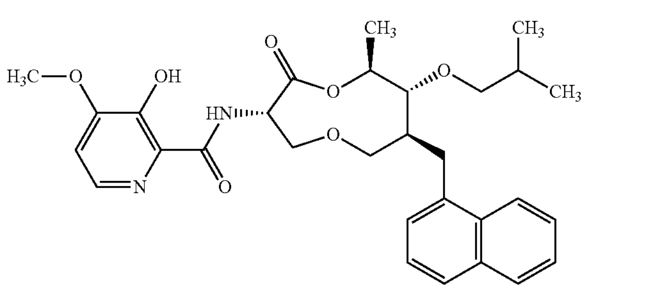 [SMILES: COc1ccnc(C(=O)N[C@H]2COC[C@H](Cc3cccc4ccccc34)[C@@H](OCC(C)C)[C@H](C)OC2=O)c1O] | Example 6, Step 3b | White Solid |

TABLE 1-continued

Compound Structure and Appearance

| Compound Number | Structure | Prepared According to Example | Appearance |
|---|---|---|---|
| F11 | 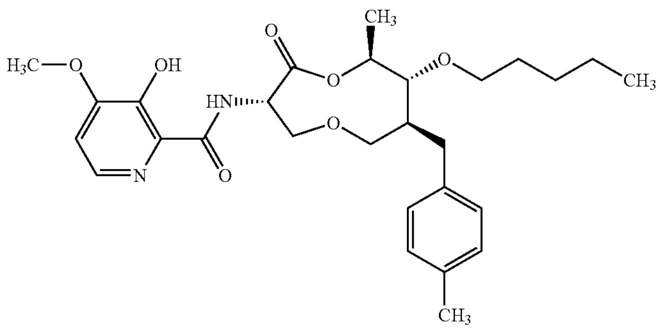 [SMILES: CCCCCO[C@@H]1[C@@H](Cc2ccc(C)cc2)COC[C@H](NC(=O)c2nccc(OC)c2O)C(=O)O[C@H]1C] | Example 6, Step 3b | White Powder |
| F12 | 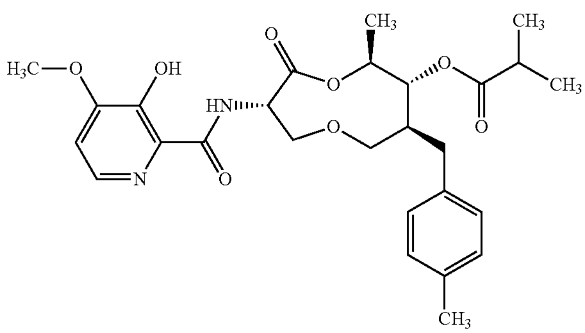 [SMILES: COc1ccnc(C(=O)N[C@H]2COC[C@H](Cc3ccc(C)cc3)[C@@H](OC(=O)C(C)C)[C@H](C)OC2=O)c1O] | Example 6, Step 3b | White Powder |
| F13 | 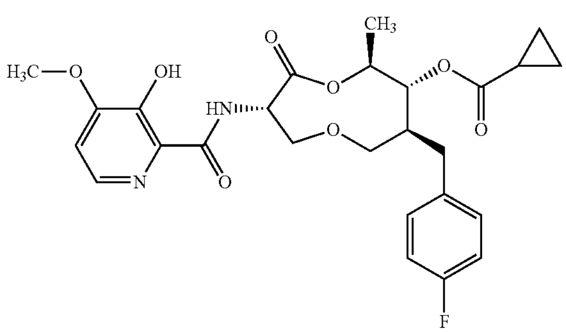 [SMILES: COc1ccnc(C(=O)N[C@H]2COC[C@H](Cc3ccc(F)cc3)[C@@H](OC(=O)C3CC3)[C@H](C)OC2=O)c1O] | Example 6, Step 3b | White Powder |
| F14 | 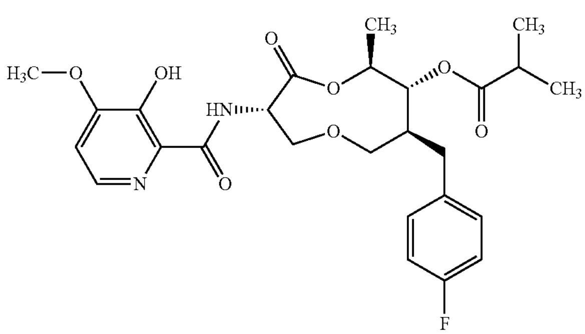 [SMILES: COc1ccnc(C(=O)N[C@H]2COC[C@H](Cc3ccc(F)cc3)[C@@H](OC(=O)C(C)C)[C@H](C)OC2=O)c1O] | Example 6, Step 3b | White Powder |

TABLE 1-continued

Compound Structure and Appearance

| Compound Number | Structure | Prepared According to Example | Appearance |
|---|---|---|---|
| F15 | 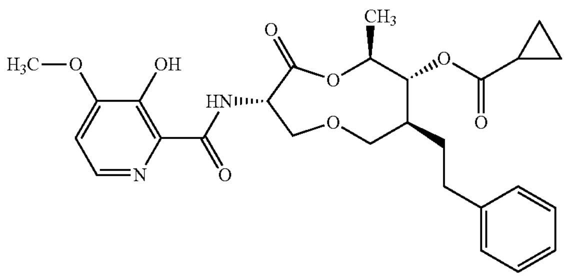 [SMILES: COc1ccnc(C(=O)N[C@H]2COC[C@H](CCc3ccccc3)[C@@H](OC(=O)C3CC3)[C@H](C)OC2=O)c1O] | Example 6, Step 3b | Colorless Oil |
| F16 | 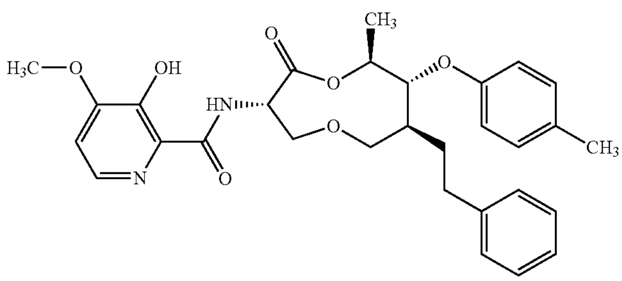 | Example 6, Step 3b | Colorless Oil |
| F17 | 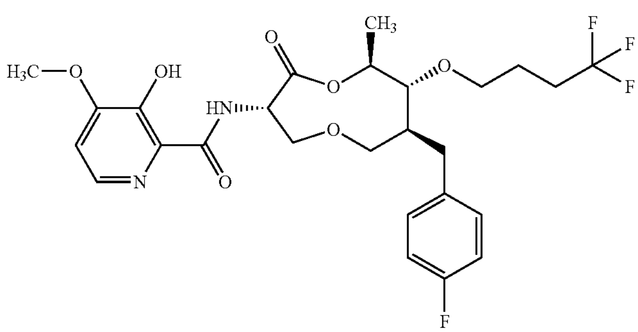 [SMILES: COc1ccnc(C(=O)N[C@H]2COC[C@H](Cc3ccc(F)cc3)[C@@H](OCCCC(F)(F)F)[C@H](C)OC2=O)c1O] | Example 6, Step 3b | Colorless Oil |
| F18 | 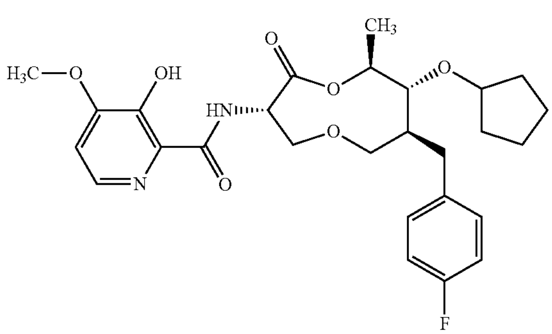 [SMILES: COc1ccnc(C(=O)N[C@H]2COC[C@H](Cc3ccc(F)cc3)[C@@H](OC3CCCC3)[C@H](C)OC2=O)c1O] | Example 6, Step 3b | Colorless Oil |

TABLE 1-continued

Compound Structure and Appearance

| Compound Number | Structure | Prepared According to Example | Appearance |
|---|---|---|---|
| F19 | 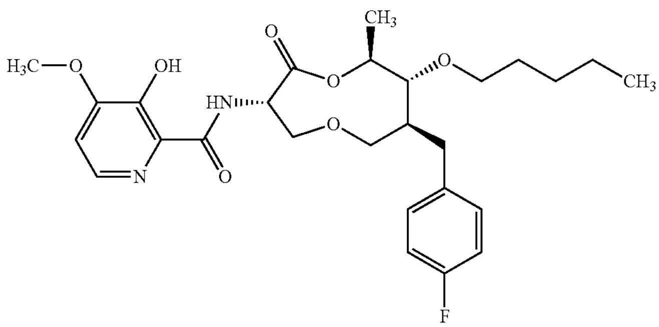 [SMILES: CCCCCO[C@@H]1[C@@H](Cc2ccc(F)cc2)COC[C@H](NC(=O)c2nccc(OC)c2O)C(=O)O[C@H]1C] | Example 6, Step 3b | Colorless Oil |
| F20 | 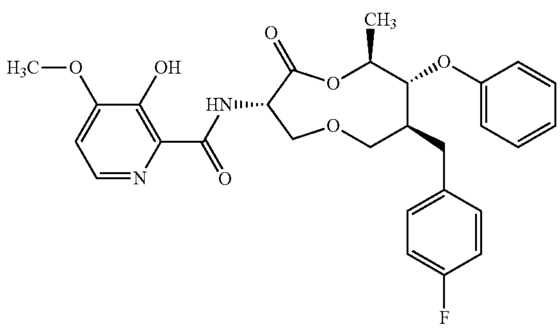 [SMILES: COc1ccnc(C(=O)N[C@H]2COC[C@H](Cc3ccc(F)cc3)[C@@H](Oc3ccccc3)[C@H](C)OC2=O)c1O] | Example 6, Step 3b | Colorless Film |
| F21 | 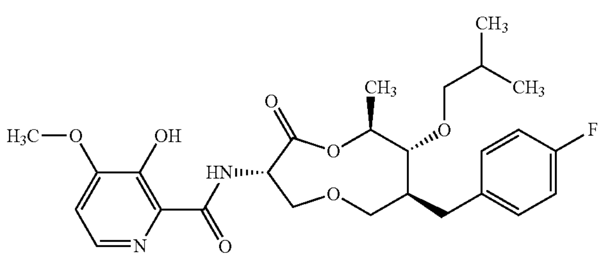 [SMILES: COc1ccnc(C(=O)N[C@H]2COC[C@H](Cc3ccc(F)cc3)[C@@H](OCC(C)C)[C@H](C)OC2=O)c1O] | Example 5, Step 1b | Colorless Oil |
| F22 | 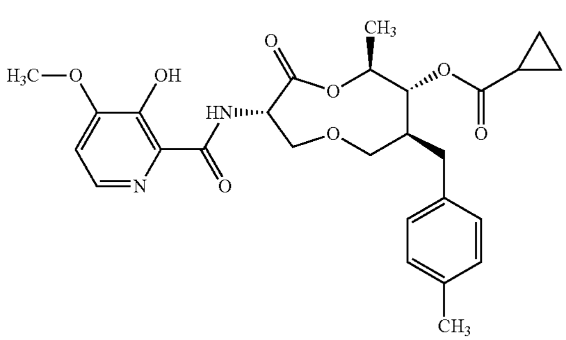 [SMILES: COc1ccnc(C(=O)N[C@H]2COC[C@H](Cc3ccc(C)cc3)[C@@H](OC(=O)C3CC3)[C@H](C)OC2=O)c1O] | Example 6, Step 3b | Colorless Oil |

TABLE 1-continued

Compound Structure and Appearance

| Compound Number | Structure | Prepared According to Example | Appearance |
|---|---|---|---|
| F23 | 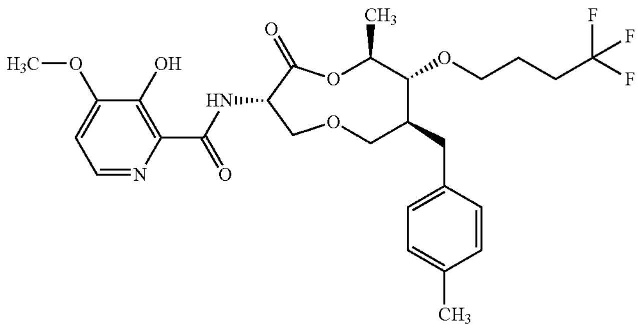 [SMILES: COc1ccnc(C(=O)N[C@H]2COC[C@H](Cc3ccc(C)cc3)[C@@H](OCCCC(F)(F)F)[C@H](C)OC2=O)c1O] | Example 6, Step 3b | Colorless Oil |
| F24 | 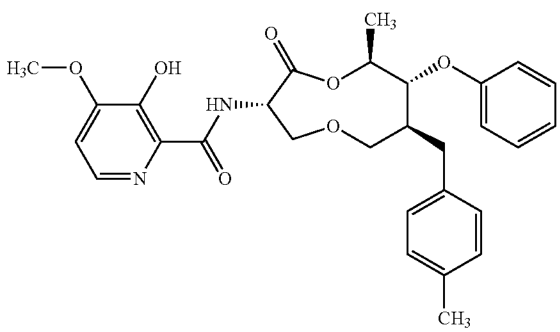 | Example 6, Step 3b | Colorless Oil |
| F25 | 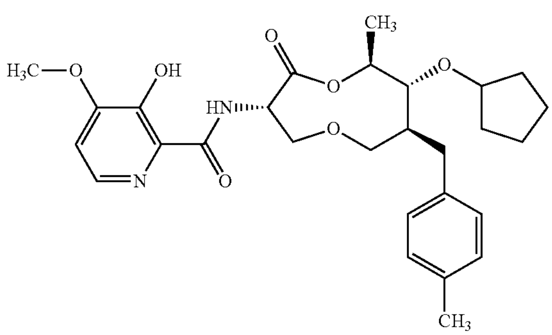 [SMILES: COc1ccnc(C(=O)N[C@H]2COC[C@H](Cc3ccc(C)cc3)[C@@H](OC3CCCC3)[C@H](C)OC2=O)c1O] | Example 6, Step 3b | Colorless Oil |
| F26 | 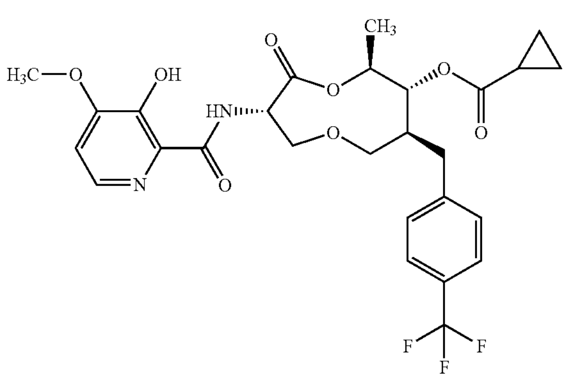 [SMILES: COc1ccnc(C(=O)N[C@H]2COC[C@H](Cc3ccc(C(F)(F)F)cc3)[C@@H](OC(=O)C3CC3)[C@H](C)OC2=O)c1O] | Example 6, Step 3b | Colorless Amorphous Solid |

TABLE 1-continued

Compound Structure and Appearance

| Compound Number | Structure | Prepared According to Example | Appearance |
|---|---|---|---|
| F27 | 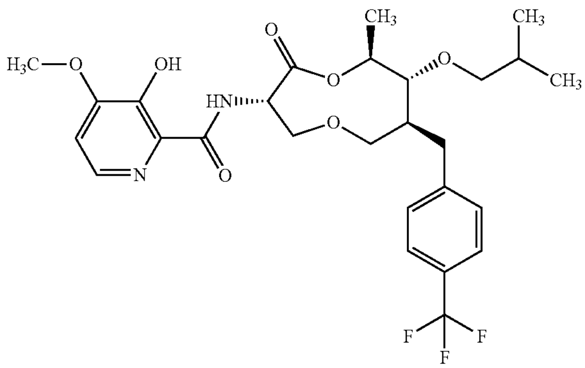 [SMILES: COc1ccnc(C(=O)N[C@H]2COC[C@H](Cc3ccc(C(F)(F)F)cc3)[C@@H](OCC(C)C)[C@H](C)OC2=O)c1O] | Example 6, Step 3b | Colorless Oil |
| F28 | 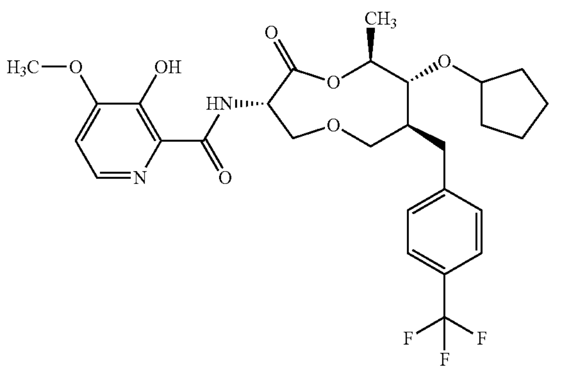 [SMILES: COc1ccnc(C(=O)N[C@H]2COC[C@H](Cc3ccc(C(F)(F)F)cc3)[C@@H](OC3CCCC3)[C@H](C)OC2=O)c1O] | Example 6, Step 3b | Colorless Oil |
| F29 | 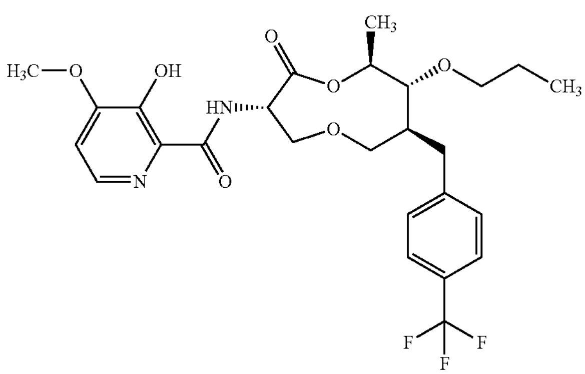 [SMILES: CCCO[C@@H]1[C@@H](Cc2ccc(C(F)(F)F)cc2)COC[C@H](NC(=O)c2nccc(OC)c2O)C(=O)O[C@H]1C] | Example 6, Step 3b | Colorless Oil |
| F30 | 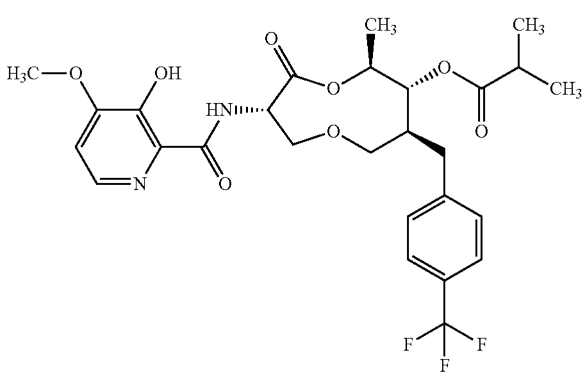 [SMILES: COc1ccnc(C(=O)N[C@H]2COC[C@H](Cc3ccc(C(F)(F)F)cc3)[C@@H](OC(=O)C(C)C)[C@H](C)OC2=O)c1O] | Example 6, Step 3b | Colorless Oil |

TABLE 1-continued

Compound Structure and Appearance

| Compound Number | Structure | Prepared According to Example | Appearance |
|---|---|---|---|
| F31 | 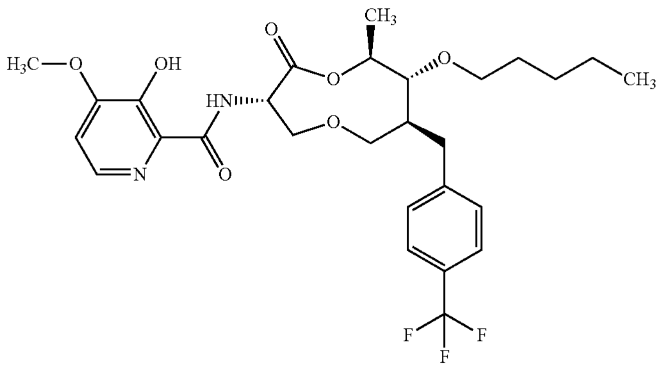 [SMILES: CCCCCO[C@@H]1[C@@H](Cc2ccc(C(F)(F)F)cc2)COC[C@H](NC(=O)c2nccc(OC)c2O)C(=O)O[C@H]1C] | Example 6, Step 3b | Colorless Oil |
| F32 | 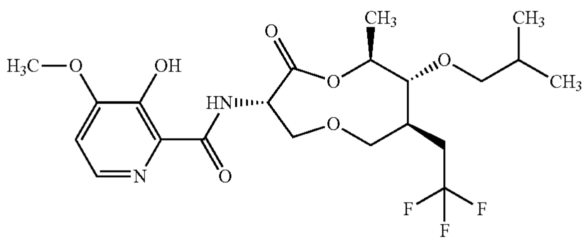 [SMILES: COc1ccnc(C(=O)N[C@H]2COC[C@H](CC(F)(F)F)[C@@H](OCC(C)C)[C@H](C)OC2=O)c1O] | Example 6, Step 3b | Colorless Oil |
| F33 | 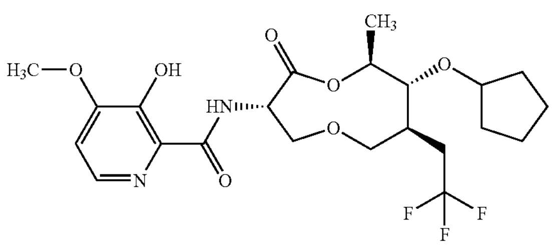 [SMILES: COc1ccnc(C(=O)N[C@H]2COC[C@H](CC(F)(F)F)[C@@H](OC3CCCC3)[C@H](C)OC2=O)c1O] | Example 6, Step 3b | Colorless Solid |
| F34 | 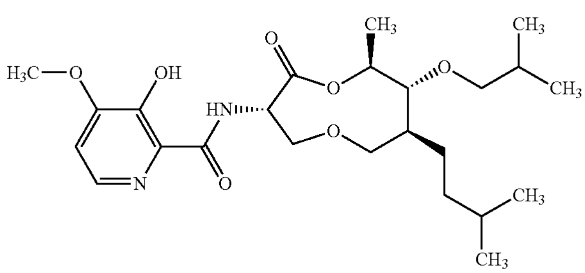 [SMILES: COc1ccnc(C(=O)N[C@H]2COC[C@H](CCC(C)C)[C@@H](OCC(C)C)[C@H](C)OC2=O)c1O] | Example 6, Step 3b | Colorless Oil |
| F35 | 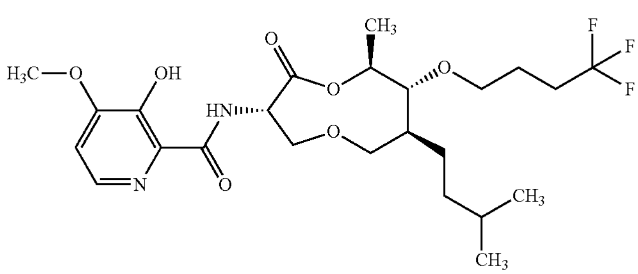 [SMILES: COc1ccnc(C(=O)N[C@H]2COC[C@H](CCC(C)C)[C@@H](OCCCC(F)(F)F)[C@H](C)OC2=O)c1O] | Example 6, Step 3b | Colorless Solid |

TABLE 1-continued

Compound Structure and Appearance

| Compound Number | Structure | Prepared According to Example | Appearance |
|---|---|---|---|
| F36 | 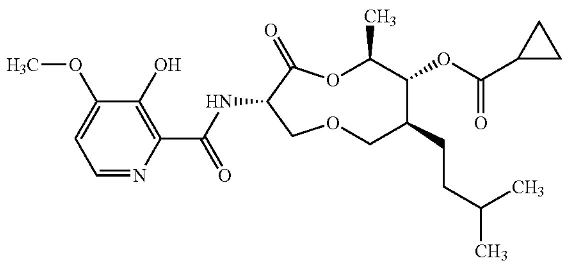 [SMILES: COc1ccnc(C(=O)N[C@H]2COC[C@H](CCC(C)C)[C@@H](OC(=O)C3CC3)[C@H](C)OC2=O)c1O] | Example 6, Step 3b | Colorless Oil |
| F37 | 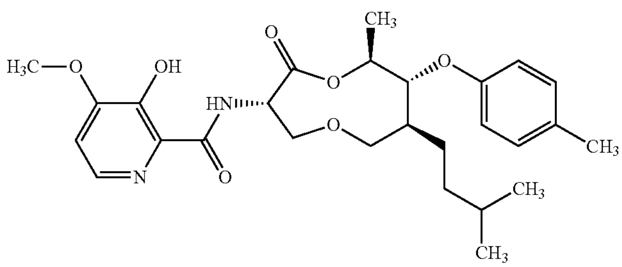 | Example 6, Step 3b | Colorless Oil |
| F38 | 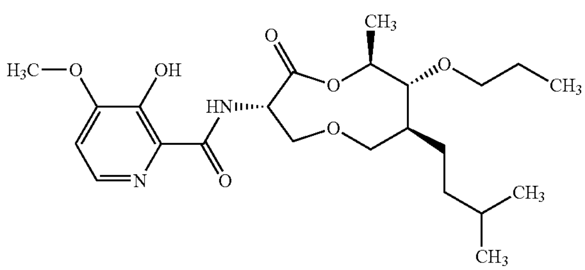 [SMILES: CCCO[C@@H]1[C@@H](CCC(C)C)COC[C@H](NC(=O)c2nccc(OC)c2O)C(=O)O[C@H]1C] | Example 6, Step 3b | Colorless Solid |
| F39 | 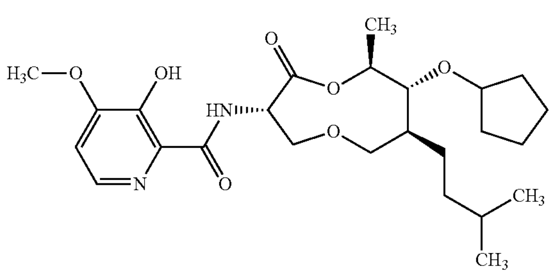 [SMILES: COc1ccnc(C(=O)N[C@H]2COC[C@H](CCC(C)C)[C@@H](OC3CCCC3)[C@H](C)OC2=O)c1O] | Example 6, Step 3b | Colorless Oil |
| F40 | 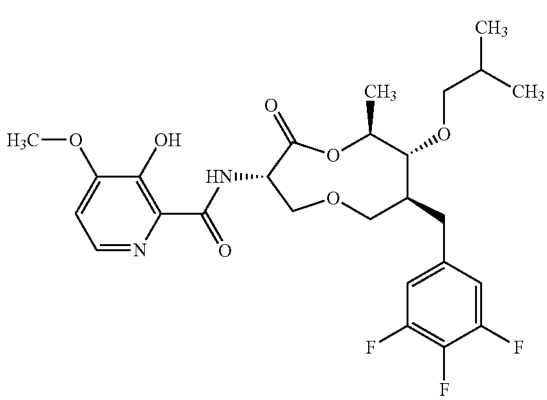 [SMILES: COc1ccnc(C(=O)N[C@H]2COC[C@H](Cc3cc(F)c(F)c(F)c3)[C@@H](OCC(C)C)[C@H](C)OC2=O)c1O] | Example 5, Step 1b | Colorless Oil |

TABLE 1-continued

Compound Structure and Appearance

| Compound Number | Structure | Prepared According to Example | Appearance |
|---|---|---|---|
| F41 | 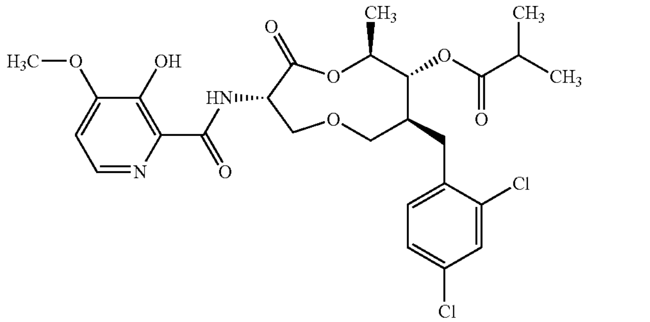 [SMILES: COc1ccnc(C(=O)N[C@H]2COC[C@H](Cc3ccc(Cl)cc3Cl)[C@@H](OC(=O)C(C)C)[C@H](C)OC2=O)c1O] | Example 6, Step 3b | White Solid |
| F42 | 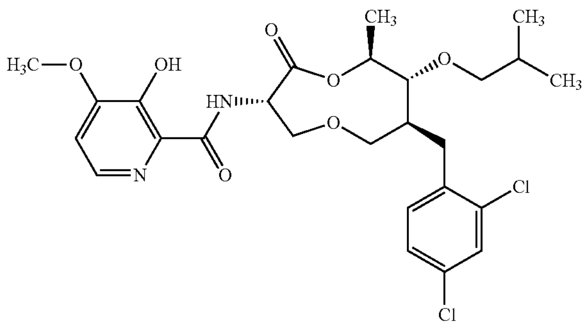 [SMILES: COc1ccnc(C(=O)N[C@H]2COC[C@H](Cc3ccc(Cl)cc3Cl)[C@@H](OCC(C)C)[C@H](C)OC2=O)c1O] | Example 6, Step 3b | White Solid |
| F43 | 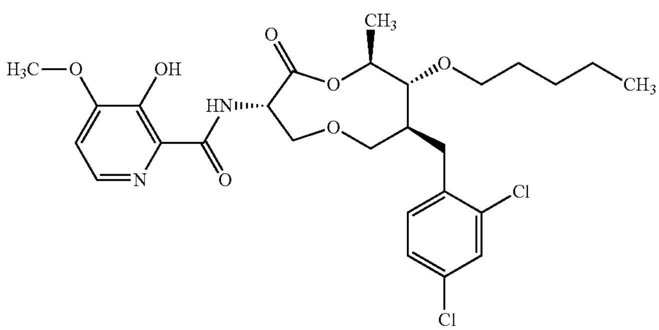 [SMILES: CCCCCO[C@@H]1[C@@H](Cc2ccc(Cl)cc2Cl)COC[C@H](NC(=O)c2nccc(OC)c2O)C(=O)O[C@H]1C] | Example 6, Step 3b | White Solid |
| F44 | 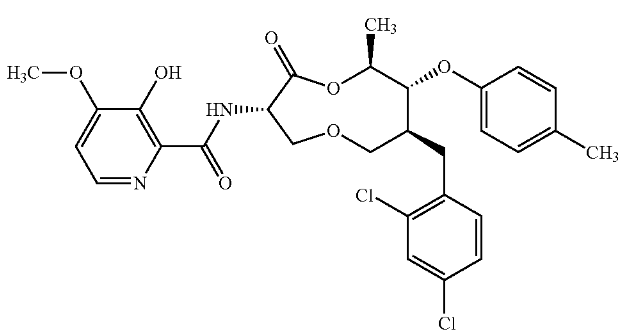 | Example 6, Step 3b | White Solid |

TABLE 1-continued

Compound Structure and Appearance

| Compound Number | Structure | Prepared According to Example | Appearance |
|---|---|---|---|
| F45 | 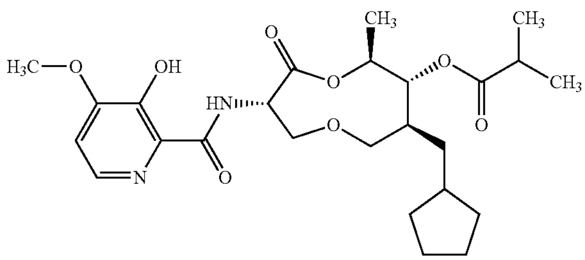 [SMILES: COc1ccnc(C(=O)N[C@H]2COC[C@H](CC3CCCC3)[C@@H](OC(=O)C(C)C)[C@H](C)OC2=O)c1O] | Example 6, Step 3b | White Solid |
| F46 | 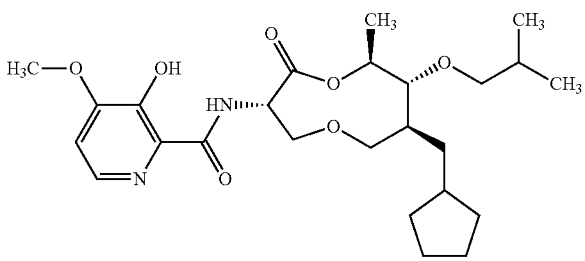 [SMILES: COc1ccnc(C(=O)N[C@H]2COC[C@H](CC3CCCC3)[C@@H](OCC(C)C)[C@H](C)OC2=O)c1O] | Example 6, Step 3b | White Solid |
| F47 | 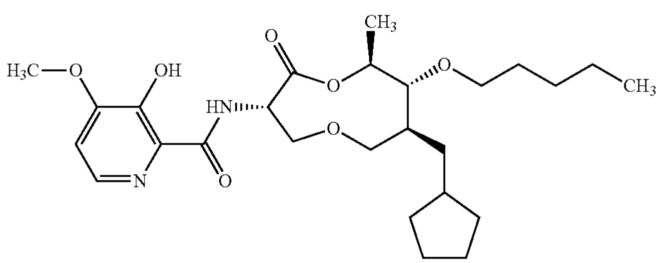 [SMILES: CCCCCO[C@@H]1[C@@H](CC2CCCC2)COC[C@H](NC(=O)c2nccc(OC)c2O)C(=O)O[C@H]1C] | Example 6, Step 3b | White Solid |
| F48 | 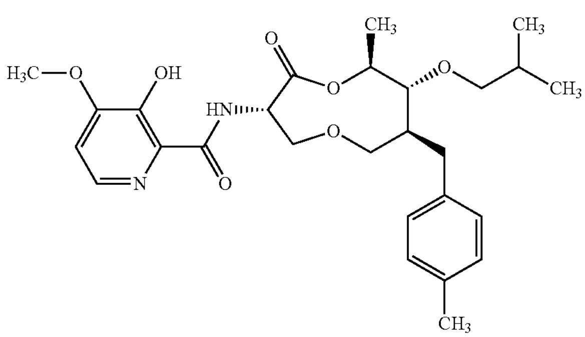 [SMILES: COc1ccnc(C(=O)N[C@H]2COC[C@H](Cc3ccc(C)cc3)[C@@H](OCC(C)C)[C@H](C)OC2=O)c1O] | Example 5, Step 1b | White Foam |
| F49 | 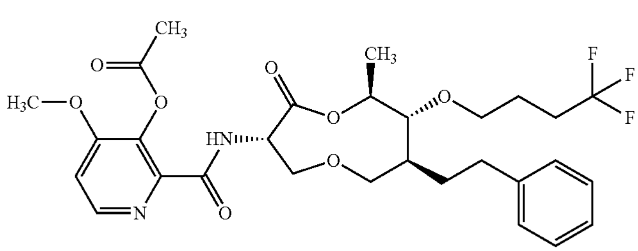 [SMILES: COc1ccnc(C(=O)N[C@H]2COC[C@H](CCc3ccccc3)[C@@H](OCCCC(F)(F)F)[C@H](C)OC2=O)c1OC(C)=O] | Example 8 | White Powder |

TABLE 1-continued

Compound Structure and Appearance

| Compound Number | Structure | Prepared According to Example | Appearance |
|---|---|---|---|
| F50 | 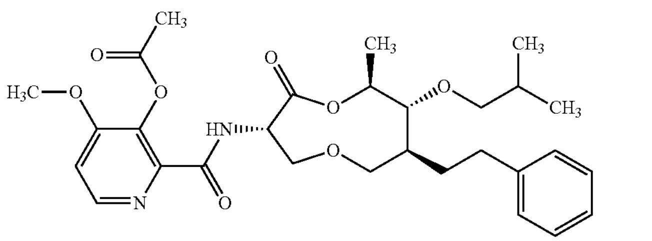 [SMILES: COc1ccnc(C(=O)N[C@H]2COC[C@H](CCc3ccccc3)[C@@H](OCC(C)C)[C@H](C)OC2=O)c1OC(C)=O] | Example 8 | White Solid |
| F51 | 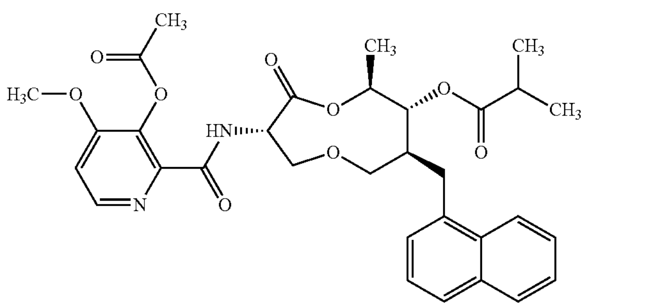 [SMILES: COc1ccnc(C(=O)N[C@H]2COC[C@H](Cc3cccc4ccccc34)[C@@H](OC(=O)C(C)C)[C@H](C)OC2=O)c1OC(C)=O] | Example 8 | White Powder |
| F52 | 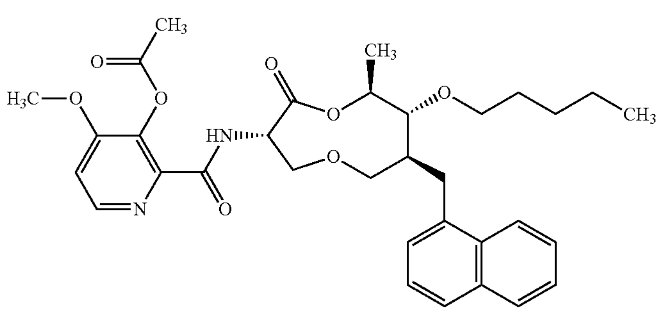 [SMILES: CCCCCO[C@@H]1[C@@H](Cc2cccc3ccccc23)COC[C@H](NC(=O)c2nccc(OC)c2OC(C)=O)C(=O)O[C@H]1C] | Example 8 | White Powder |
| F53 | 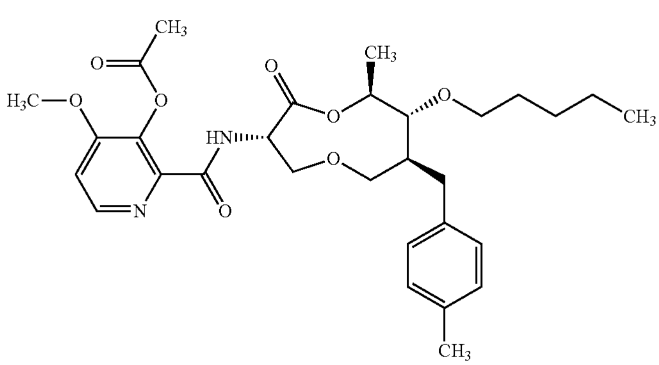 [SMILES: CCCCCO[C@@H]1[C@@H](Cc2ccc(C)cc2)COC[C@H](NC(=O)c2nccc(OC)c2OC(C)=O)C(=O)O[C@H]1C] | Example 8 | Sticky White Solid |

TABLE 1-continued
Compound Structure and Appearance
| Compound Number | Structure | Prepared According to Example | Appearance |
|---|---|---|---|
| F54 | 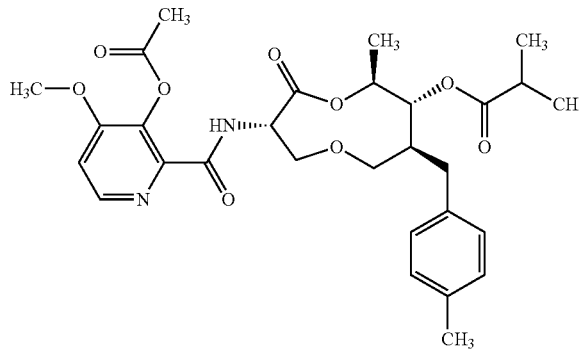 | Example 8 | White Powder |
| F55 | 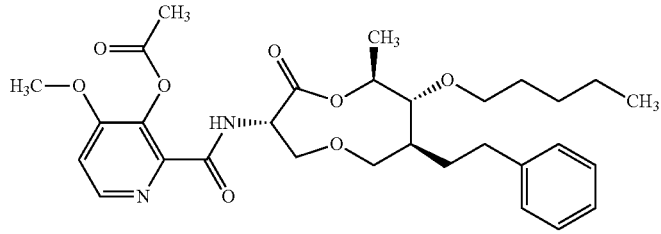 [SMILES: CCCCCO[C@@H]1[C@@H](CCc2ccccc2)COC[C@H](NC(=O)c2nccc(OC)c2OC(C)=O)C(=O)O[C@H]1C] | Example 8 | Colorless Oil |
| F56 | 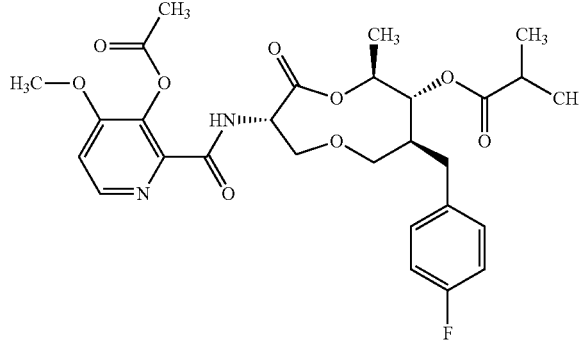 | Example 8 | White Powder |
| F57 | 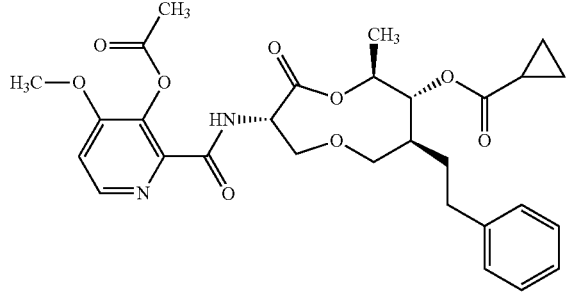 [SMILES: COc1ccnc(C(=O)N[C@H]2COC[C@H](CCc3ccccc3)[C@@H](OC(=O)C3CC3)[C@H](C)OC2=O)c1OC(C)=O] | Example 8 | White Solid |

TABLE 1-continued

Compound Structure and Appearance

| Compound Number | Structure | Prepared According to Example | Appearance |
|---|---|---|---|
| F58 | 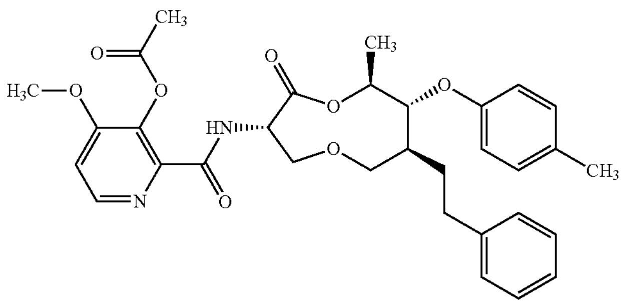 | Example 8 | Colorless Amorphous Solid |
| F59 | 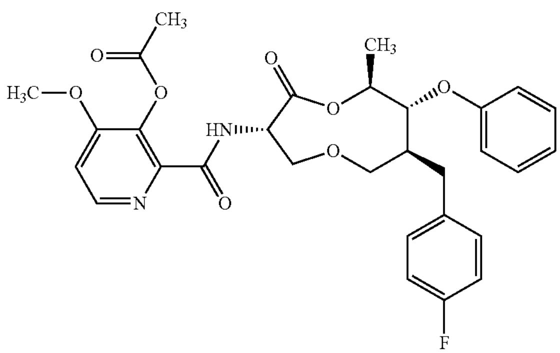 [SMILES: COc1ccnc(C(=O)N[C@H]2COC[C@H](Cc3ccc(F)cc3)[C@@H](Oc3ccccc3)[C@H](C)OC2=O)c1OC(C)=O] | Example 8 | Colorless Oil |
| F60 | 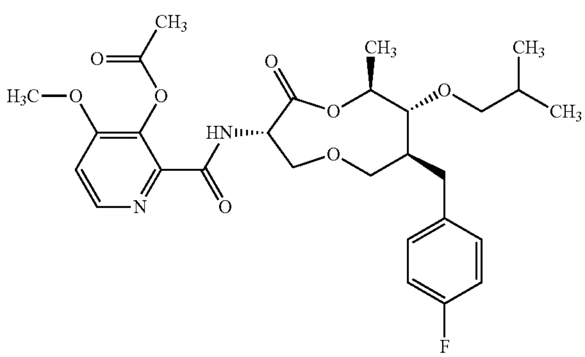 [SMILES: COc1ccnc(C(=O)N[C@H]2COC[C@H](Cc3ccc(F)cc3)[C@@H](OCC(C)C)[C@H](C)OC2=O)c1OC(C)=O] | Example 8 | Colorless Oil |
| F61 | 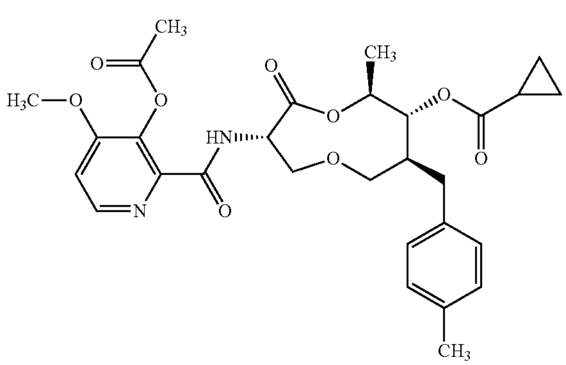 [SMILES: COc1ccnc(C(=O)N[C@H]2COC[C@H](Cc3ccc(C)cc3)[C@@H](OC(=O)C3CC3)[C@H](C)OC2=O)c1OC(C)=O] | Example 8 | Colorless Amorphous Solid |

TABLE 1-continued

Compound Structure and Appearance

| Compound Number | Structure | Prepared According to Example | Appearance |
|---|---|---|---|
| F62 | 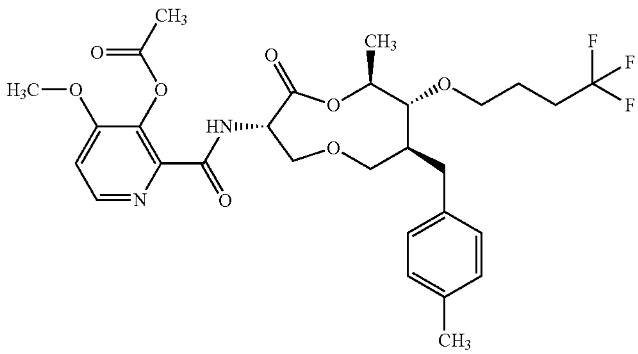 [SMILES: COc1ccnc(C(=O)N[C@H]2COC[C@H](Cc3ccc(C)cc3)[C@@H](OCCCC(F)(F)F)[C@H](C)OC2=O)c1OC(C)=O] | Example 8 | Colorless Oil |
| F63 | 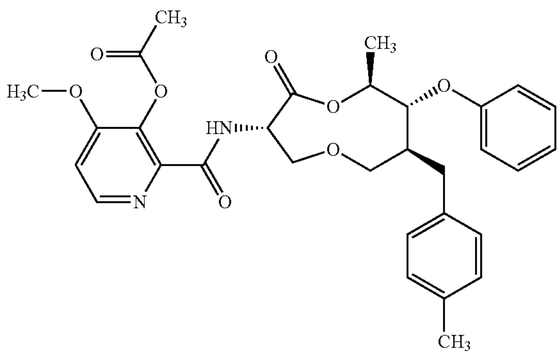 [SMILES: COc1ccnc(C(=O)N[C@H]2COC[C@H](Cc3ccc(C)cc3)[C@@H](Oc3ccccc3)[C@H](C)OC2=O)c1OC(C)=O] | Example 8 | Colorless Amorphous Solid |
| F64 | 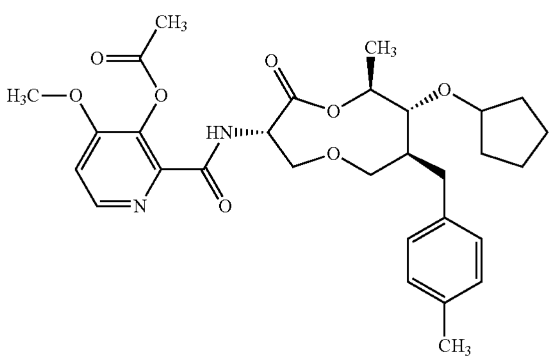 [SMILES: COc1ccnc(C(=O)N[C@H]2COC[C@H](Cc3ccc(C)cc3)[C@@H](OC3CCCC3)[C@H](C)OC2=O)c1OC(C)=O] | Example 8 | Colorless Film |
| F65 | 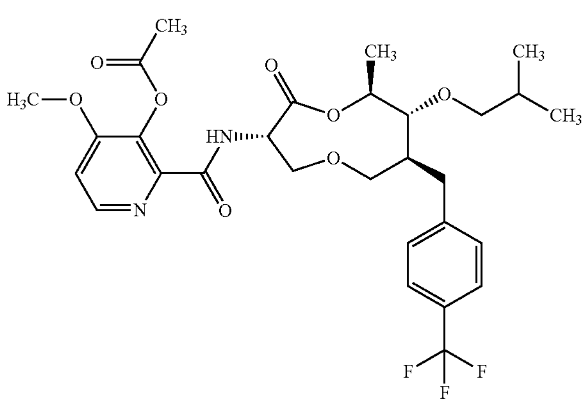 [SMILES: COc1ccnc(C(=O)N[C@H]2COC[C@H](Cc3ccc(C(F)(F)F)cc3)[C@@H](OCC(C)C)[C@H](C)OC2=O)c1OC(C)=O] | Example 8 | Colorless Oil |

TABLE 1-continued

Compound Structure and Appearance

| Compound Number | Structure | Prepared According to Example | Appearance |
|---|---|---|---|
| F66 | 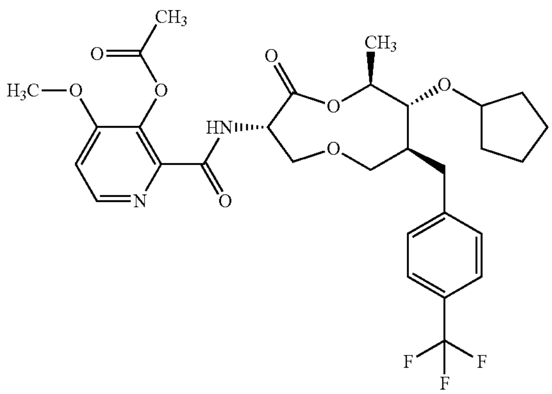 [SMILES: COc1ccnc(C(=O)N[C@H]2COC[C@H](Cc3ccc(C(F)(F)F)cc3)[C@@H](OC3CCCC3)[C@H](C)OC2=O)c1OC(C)=O] | Example 8 | Colorless Amorphous Solid |
| F67 | 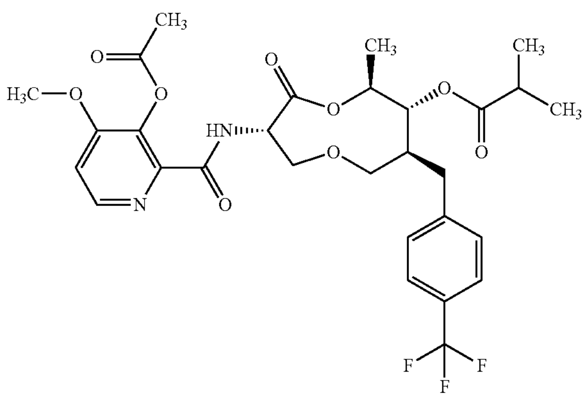 [SMILES: COc1ccnc(C(=O)N[C@H]2COC[C@H](Cc3ccc(C(F)(F)F)cc3)[C@@H](OC(=O)C(C)C)[C@H](C)OC2=O)c1OC(C)=O] | Example 8 | Colorless Oil |
| F68 | 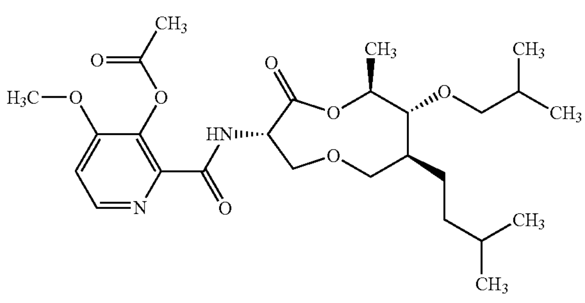 [SMILES: COc1ccnc(C(=O)N[C@H]2COC[C@H](CCC(C)C)[C@@H](OCC(C)C)[C@H](C)OC2=O)c1OC(C)=O] | Example 8 | Colorless Oil |
| F69 | 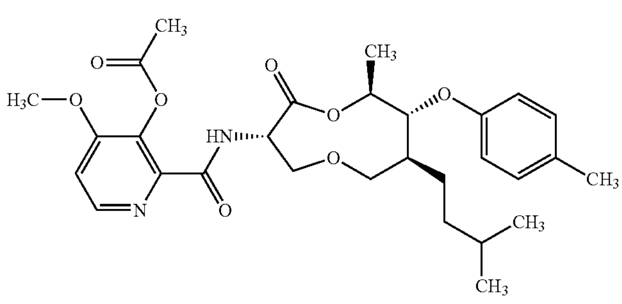 | Example 8 | Colorless Oil |

TABLE 1-continued

Compound Structure and Appearance

| Compound Number | Structure | Prepared According to Example | Appearance |
|---|---|---|---|
| F70 | 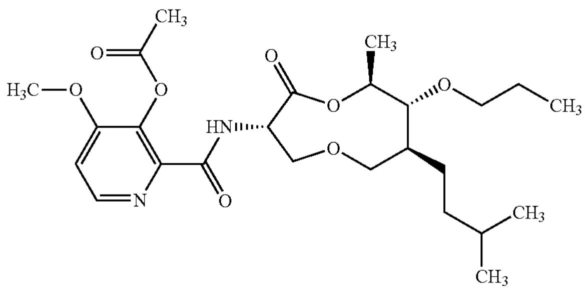 [SMILES: CCCO[C@@H]1[C@@H](CCC(C)C)COC[C@H](NC(=O)c2nccc(OC)c2OC(C)=O)C(=O)O[C@H]1C] | Example 8 | Colorless Oil |
| F71 | 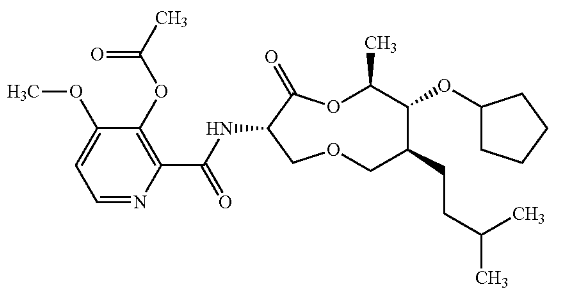 [SMILES: COc1ccnc(C(=O)N[C@H]2COC[C@H](CCC(C)C)[C@@H](OC3CCCC3)[C@H](C)OC2=O)c1OC(C)=O] | Example 8 | Colorless Oil |
| F72 | 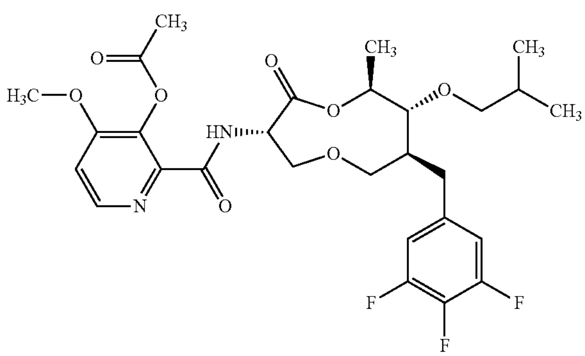 [SMILES: COc1ccnc(C(=O)N[C@H]2COC[C@H](Cc3cc(F)c(F)c(F)c3)[C@@H](OCC(C)C)[C@H](C)OC2=O)c1OC(C)=O] | Example 8 | Colorless Oil |
| F73 | 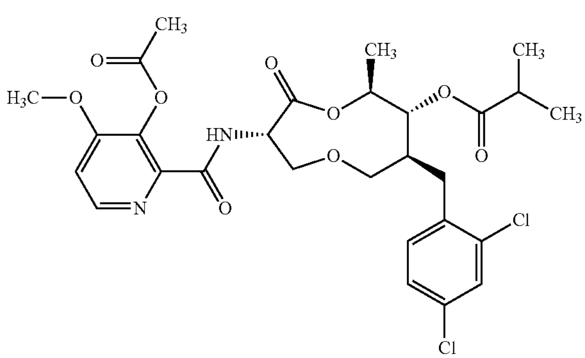 [SMILES: COc1ccnc(C(=O)N[C@H]2COC[C@H](Cc3ccc(Cl)cc3Cl)[C@@H](OC(=O)C(C)C)[C@H](C)OC2=O)c1OC(C)=O] | Example 8 | White Solid |

TABLE 1-continued

Compound Structure and Appearance

| Compound Number | Structure | Prepared According to Example | Appearance |
|---|---|---|---|
| F74 | 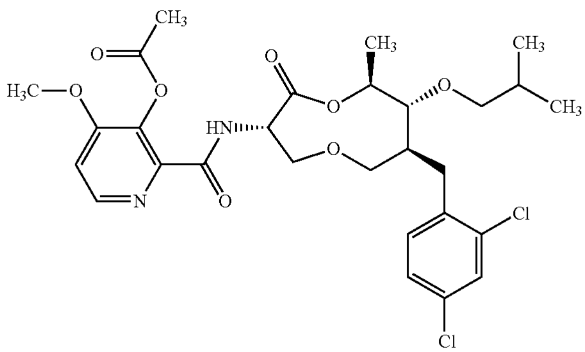 [SMILES: COc1ccnc(C(=O)N[C@H]2COC[C@H](Cc3ccc(Cl)cc3Cl)[C@@H](OCC(C)C)[C@H](C)OC2=O)c1OC(C)=O] | Example 8 | White Solid |
| F75 | 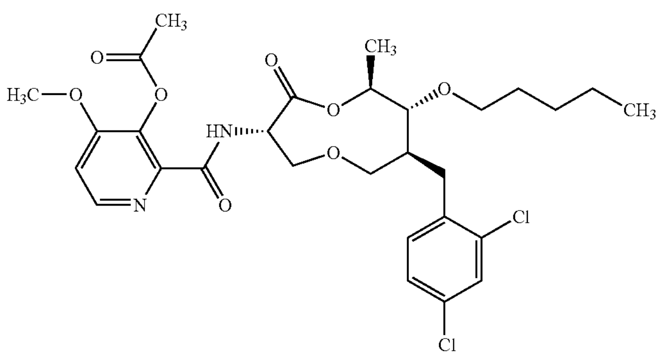 [SMILES: CCCCCO[C@@H]1[C@@H](Cc2ccc(Cl)cc2Cl)COC[C@H](NC(=O)c2nccc(OC)c2OC(C)=O)C(=O)O[C@H]1C] | Example 8 | White Solid |
| F76 | 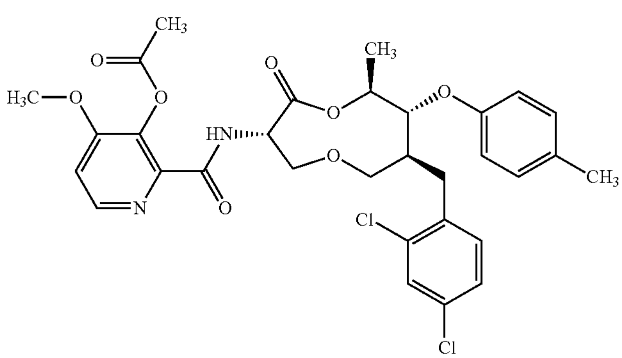 | Example 8 | White Solid |
| F77 | 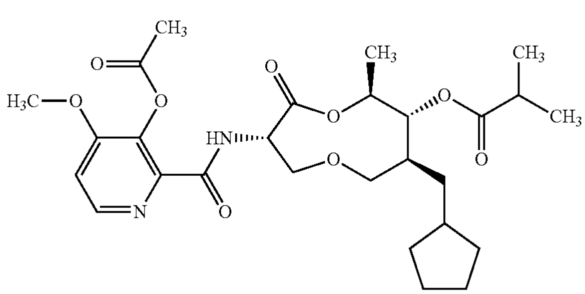 [SMILES: COc1ccnc(C(=O)N[C@H]2COC[C@H](CC3CCCC3)[C@@H](OC(=O)C(C)C)[C@H](C)OC2=O)c1OC(C)=O] | Example 8 | White Solid |

TABLE 1-continued

Compound Structure and Appearance

| Compound Number | Structure | Prepared According to Example | Appearance |
|---|---|---|---|
| F78 | 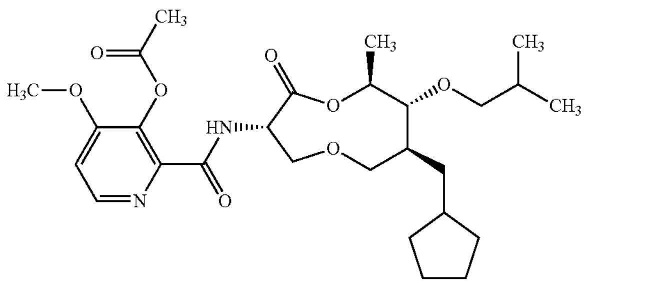 [SMILES: COc1ccnc(C(=O)N[C@H]2COC[C@H](CC3CCCC3)[C@@H](OCC(C)C)[C@H](C)OC2=O)c1OC(C)=O] | Example 8 | White Solid |
| F79 | 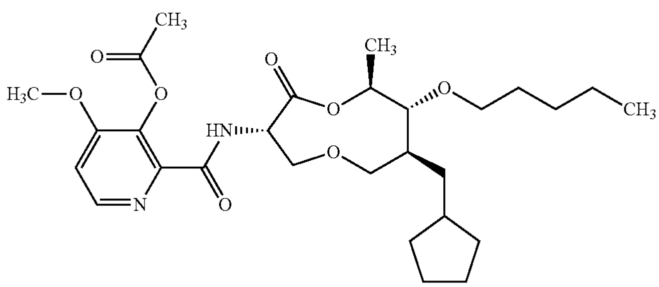 [SMILES: CCCCCO[C@@H]1[C@@H](CC2CCCC2)COC[C@H](NC(=O)c2nccc(OC)c2OC(C)=O)C(=O)O[C@H]1C] | Example 8 | White Solid |
| F80 | 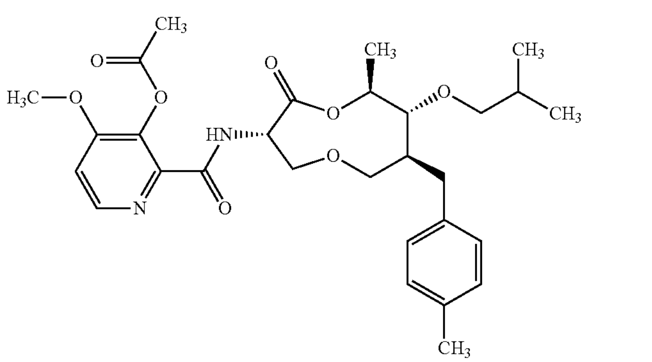 [SMILES: COc1ccnc(C(=O)N[C@H]2COC[C@H](Cc3ccc(C)cc3)[C@@H](OCC(C)C)[C@H](C)OC2=O)c1OC(C)=O] | Example 8 | White Foam |
| F81 | 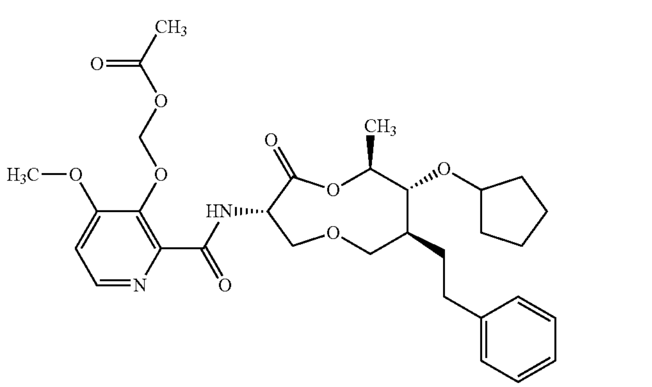 [SMILES: COc1ccnc(C(=O)N[C@H]2COC[C@H](CCc3ccccc3)[C@@H](OC3CCCC3)[C@H](C)OC2=O)c1OCOC(C)=O] | Example 7 | White Powder |

TABLE 1-continued

Compound Structure and Appearance

| Compound Number | Structure | Prepared According to Example | Appearance |
|---|---|---|---|
| F82 | 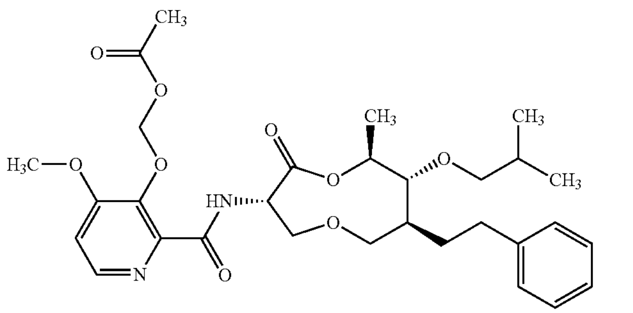 [SMILES: COc1ccnc(C(=O)N[C@H]2COC[C@H](CCc3ccccc3)[C@@H](OCC(C)C)[C@H](C)OC2=O)c1OCOC(C)=O] | Example 7 | Viscous Oil |
| F83 | 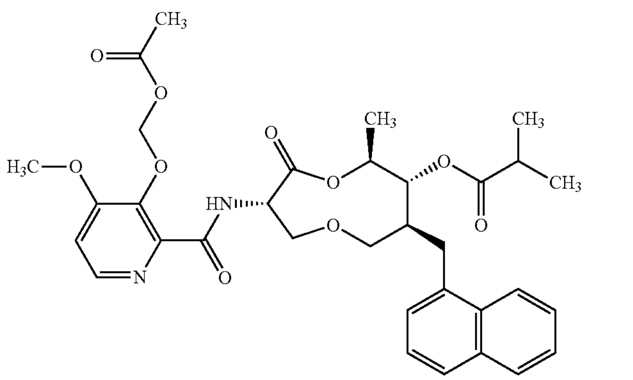 [SMILES: COc1ccnc(C(=O)N[C@H]2COC[C@H](Cc3cccc4ccccc34)[C@@H](OC(=O)C(C)C)[C@H](C)OC2=O)c1OCOC(C)=O] | Example 7 | White Powder |
| F84 | 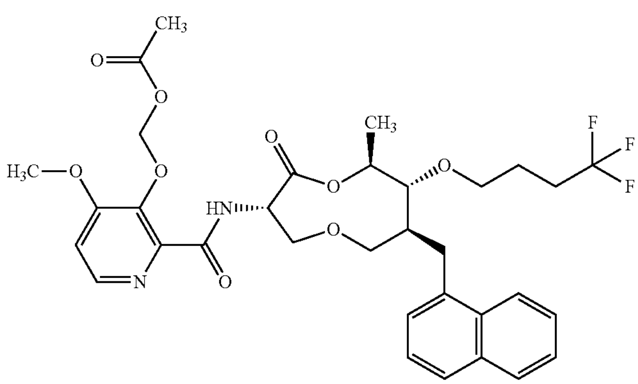 [SMILES: COc1ccnc(C(=O)N[C@H]2COC[C@H](Cc3cccc4ccccc34)[C@@H](OCCCC(F)(F)F)[C@H](C)OC2=O)c1OCOC(C)=O] | Example 7 | White Powder |
| F85 | 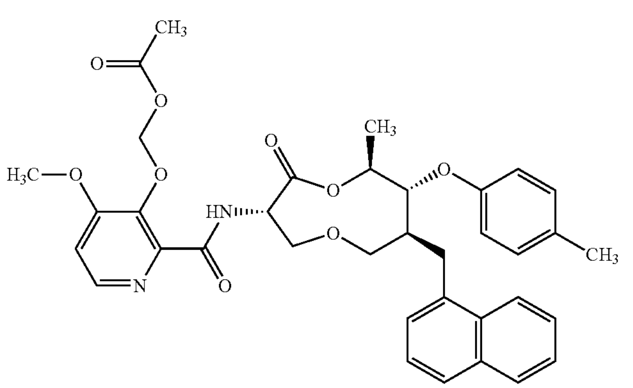 | Example 7 | White Solid |

TABLE 1-continued

Compound Structure and Appearance

| Compound Number | Structure | Prepared According to Example | Appearance |
|---|---|---|---|
| F86 | 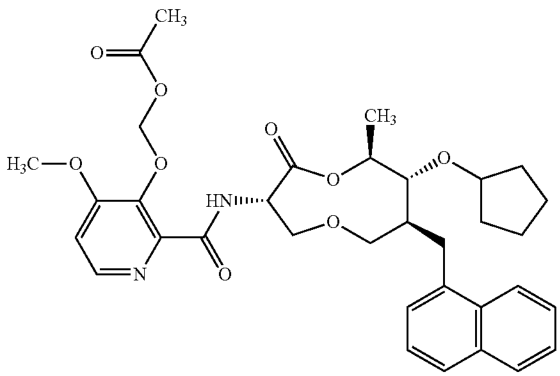 [SMILES: COc1ccnc(C(=O)N[C@H]2COC[C@H](Cc3cccc4ccccc34)[C@@H](OC3CCCC3)[C@H](C)OC2=O)c1OCOC(C)=O] | Example 7 | Slightly Yellow Oil |
| F87 | 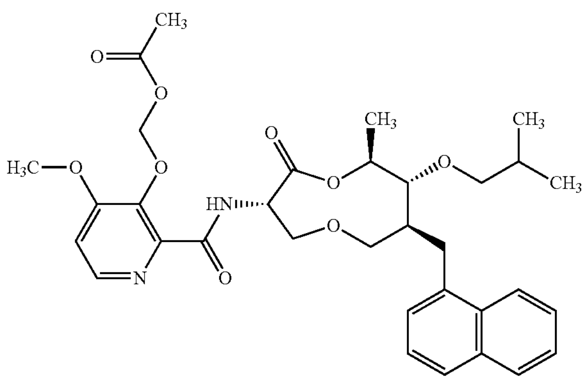 [SMILES: COc1ccnc(C(=O)N[C@H]2COC[C@H](Cc3cccc4ccccc34)[C@@H](OCC(C)C)[C@H](C)OC2=O)c1OCOC(C)=O] | Example 7 | Colorless Oil |
| F88 | 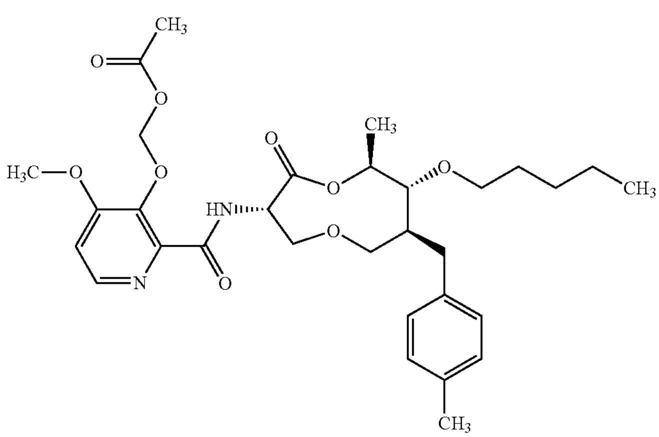 [SMILES: CCCCCO[C@@H]1[C@@H](Cc2ccc(C)cc2)COC[C@H](NC(=O)c2nccc(OC)c2OCOC(C)=O)C(=O)O[C@H]1C] | Example 7 | White Powder |

TABLE 1-continued

Compound Structure and Appearance

| Compound Number | Structure | Prepared According to Example | Appearance |
|---|---|---|---|
| F89 | 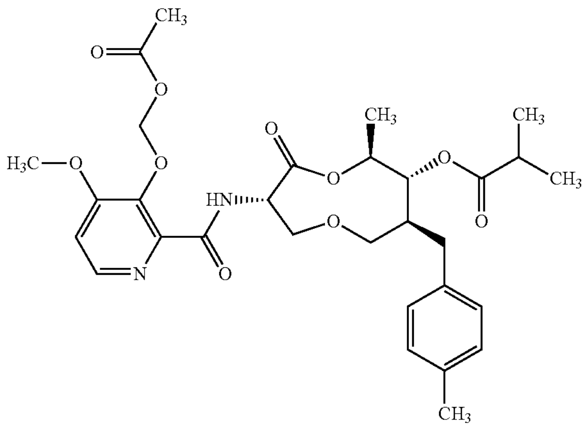 [SMILES: COc1ccnc(C(=O)N[C@H]2COC[C@H](Cc3ccc(C)cc3)[C@@H](OC(=O)C(C)C)[C@H](C)OC2=O)c1OCOC(C)=O] | Example 7 | White Powder |
| F90 | 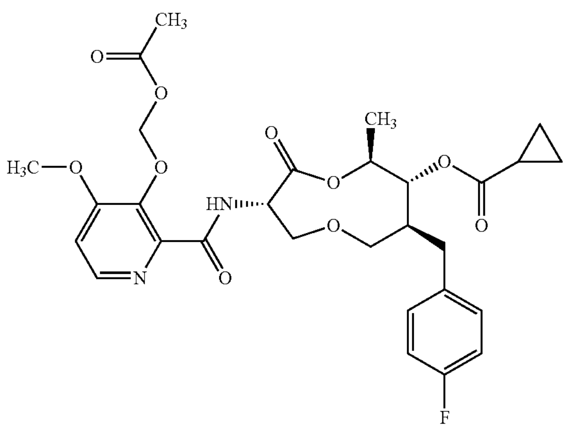 [SMILES: COc1ccnc(C(=O)N[C@H]2COC[C@H](Cc3ccc(F)cc3)[C@@H](OC(=O)C3CC3)[C@H](C)OC2=O)c1OCOC(C)=O] | Example 7 | White Powder |
| F91 | 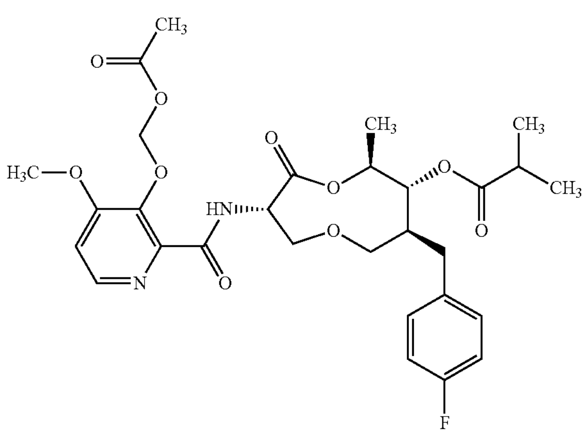 [SMILES: COc1ccnc(C(=O)N[C@H]2COC[C@H](Cc3ccc(F)cc3)[C@@H](OC(=O)C(C)C)[C@H](C)OC2=O)c1OCOC(C)=O] | Example 7 | White Powder |

TABLE 1-continued

Compound Structure and Appearance

| Compound Number | Structure | Prepared According to Example | Appearance |
|---|---|---|---|
| F92 | 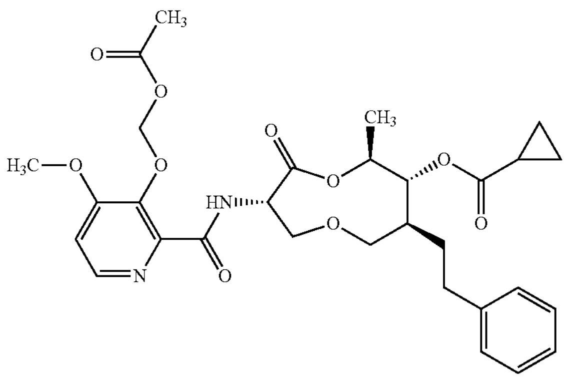 [SMILES: COc1ccnc(C(=O)N[C@H]2COC[C@H](CCc3ccccc3)[C@@H](OC(=O)C3CC3)[C@H](C)OC2=O)c1OCOC(C)=O] | Example 7 | Colorless Oil |
| F93 | 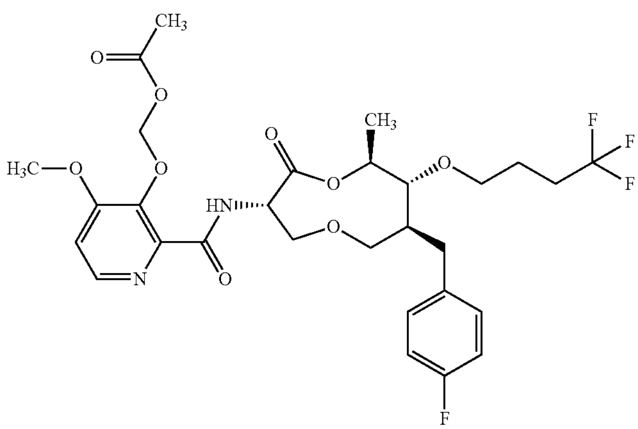 [SMILES: COc1ccnc(C(=O)N[C@H]2COC[C@H](Cc3ccc(F)cc3)[C@@H](OCCCC(F)(F)F)[C@H](C)OC2=O)c1OCOC(C)=O] | Example 7 | Colorless Oil |
| F94 | 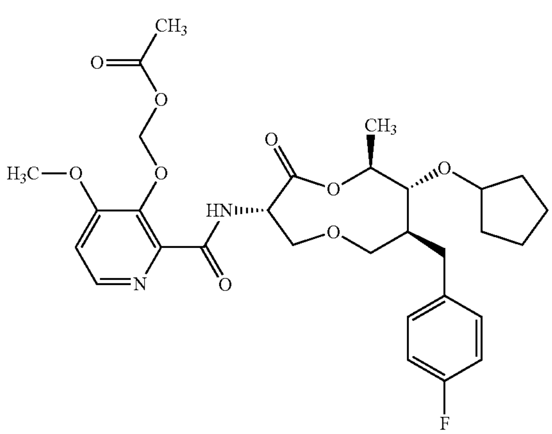 [SMILES: COc1ccnc(C(=O)N[C@H]2COC[C@H](Cc3ccc(F)cc3)[C@@H](OC3CCCC3)[C@H](C)OC2=O)c1OCOC(C)=O] | Example 7 | Colorless Oil |

TABLE 1-continued

Compound Structure and Appearance

| Compound Number | Structure | Prepared According to Example | Appearance |
|---|---|---|---|
| F95 | 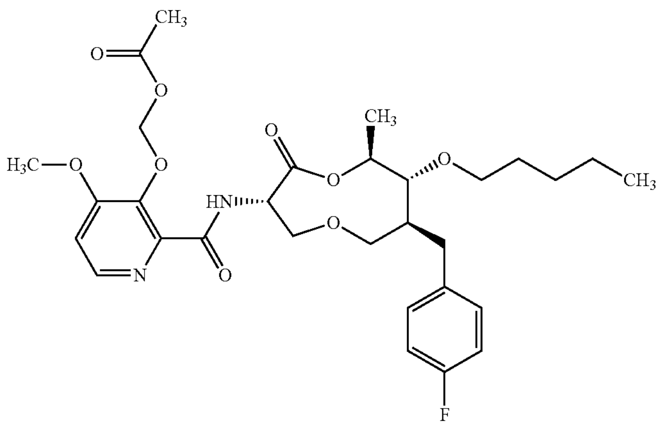 [SMILES: CCCCCO[C@@H]1[C@@H](Cc2ccc(F)cc2)COC[C@H](NC(=O)c2nccc(OC)c2OCOC(C)=O)C(=O)O[C@H]1C] | Example 7 | Colorless Oil |
| F96 | 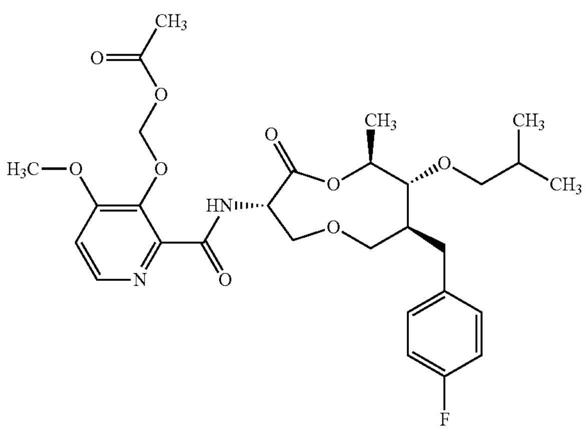 [SMILES: COc1ccnc(C(=O)N[C@H]2COC[C@H](Cc3ccc(F)cc3)[C@@H](OCC(C)C)[C@H](C)OC2=O)c1OCOC(C)=O] | Example 7 | Colorless Oil |
| F97 | 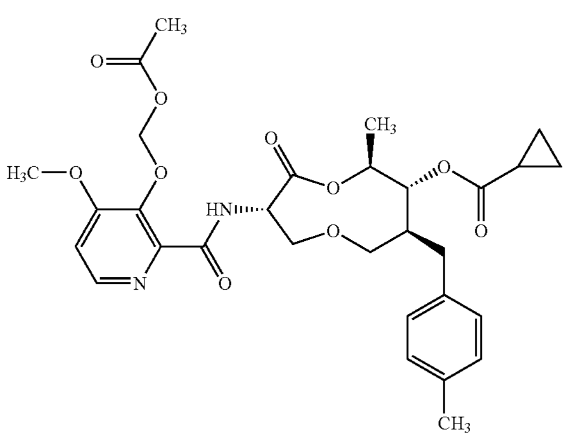 [SMILES: COc1ccnc(C(=O)N[C@H]2COC[C@H](Cc3ccc(C)cc3)[C@@H](OC(=O)C3CC3)[C@H](C)OC2=O)c1OCOC(C)=O] | Example 7 | Colorless Oil |

TABLE 1-continued

Compound Structure and Appearance

| Compound Number | Structure | Prepared According to Example | Appearance |
|---|---|---|---|
| F98 | 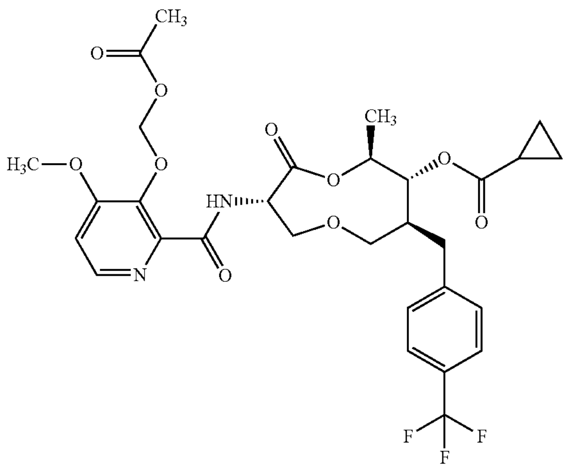 [SMILES: COc1ccnc(C(=O)N[C@H]2COC[C@H](Cc3ccc(C(F)(F)F)cc3)[C@@H](OC(=O)C3CC3)[C@H](C)OC2=O)c1OCOC(C)=O] | Example 7 | Colorless Oil |
| F99 | 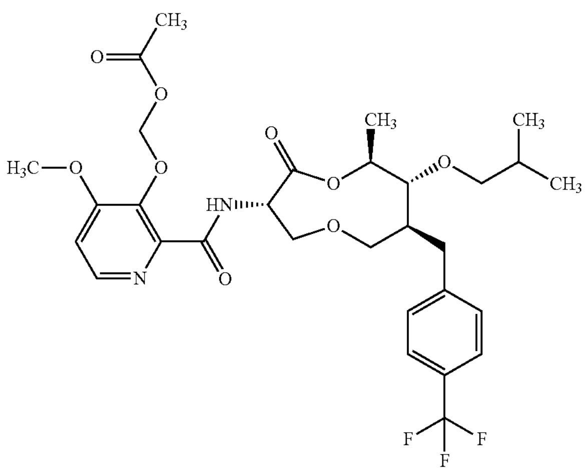 [SMILES: COc1ccnc(C(=O)N[C@H]2COC[C@H](Cc3ccc(C(F)(F)F)cc3)[C@@H](OCC(C)C)[C@H](C)OC2=O)c1OCOC(C)=O] | Example 7 | Colorless Oil |
| F100 | 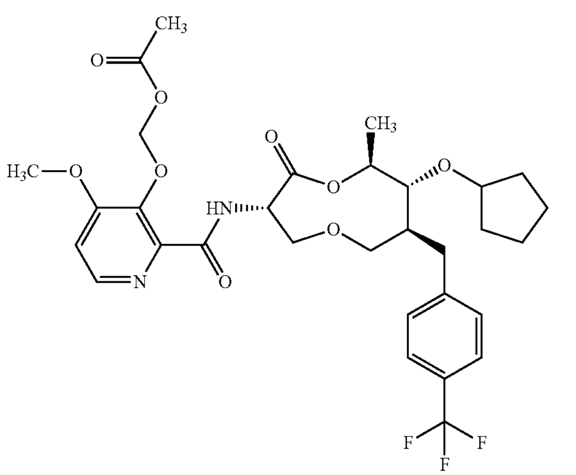 [SMILES: COc1ccnc(C(=O)N[C@H]2COC[C@H](Cc3ccc(C(F)(F)F)cc3)[C@@H](OC3CCCC3)[C@H](C)OC2=O)c1OCOC(C)=O] | Example 7 | Colorless Oil |

TABLE 1-continued

Compound Structure and Appearance

| Compound Number | Structure | Prepared According to Example | Appearance |
|---|---|---|---|
| F101 | 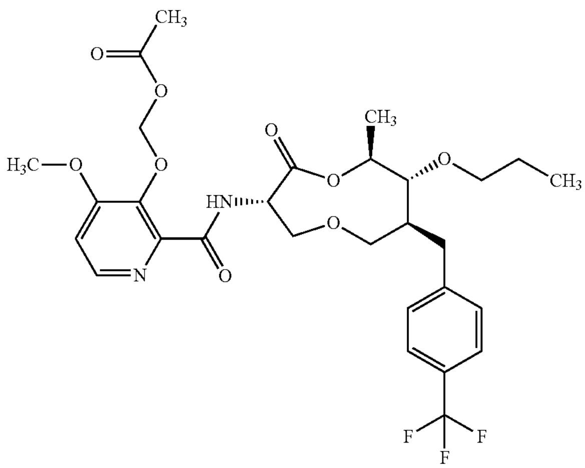 [SMILES: CCCO[C@@H]1[C@@H](Cc2ccc(C(F)(F)F)cc2)COC[C@H](NC(=O)c2nccc(OC)c2OCOC(C)=O)C(=O)O[C@H]1C] | Example 7 | Colorless Oil |
| F102 | 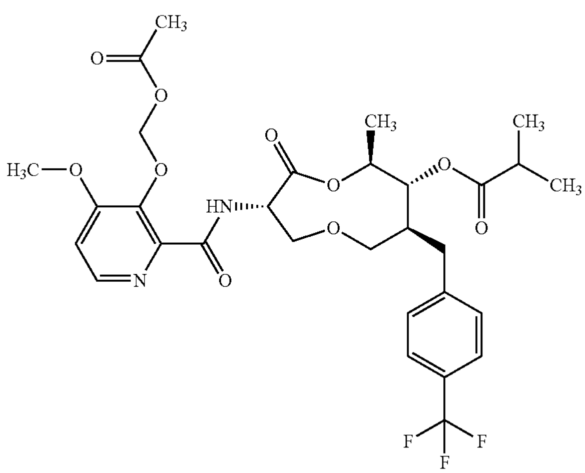 [SMILES: COc1ccnc(C(=O)N[C@H]2COC[C@H](Cc3ccc(C(F)(F)F)cc3)[C@@H](OC(=O)C(C)C)[C@H](C)OC2=O)c1OCOC(C)=O] | Example 7 | Colorless Oil |
| F103 | 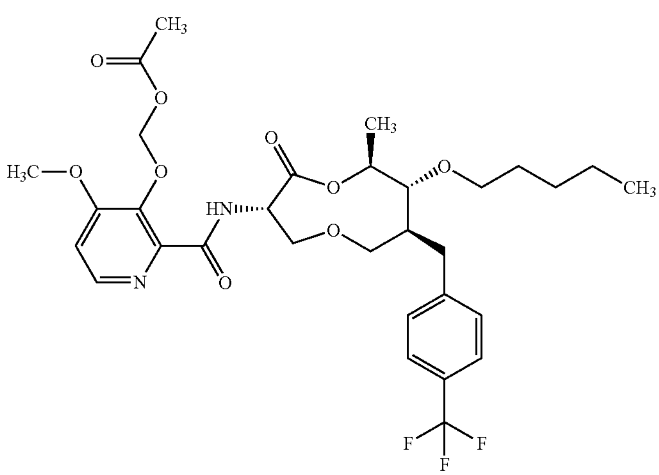 [SMILES: CCCCCO[C@@H]1[C@@H](Cc2ccc(C(F)(F)F)cc2)COC[C@H](NC(=O)c2nccc(OC)c2OCOC(C)=O)C(=O)O[C@H]1C] | Example 7 | Colorless Oil |

TABLE 1-continued

Compound Structure and Appearance

| Compound Number | Structure | Prepared According to Example | Appearance |
|---|---|---|---|
| F104 | 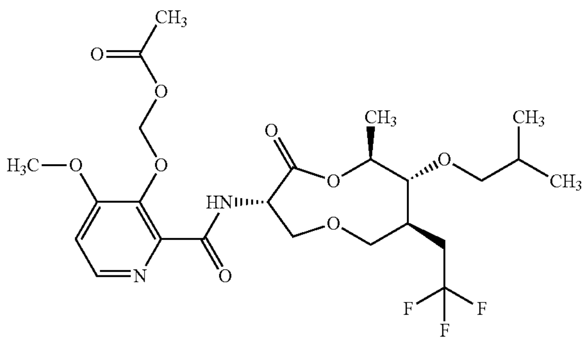 [SMILES: COc1ccnc(C(=O)N[C@H]2COC[C@H](CC(F)(F)F)[C@@H](OCC(C)C)[C@H](C)OC2=O)c1OCOC(C)=O] | Example 7 | Pale Pink Oil |
| F105 | 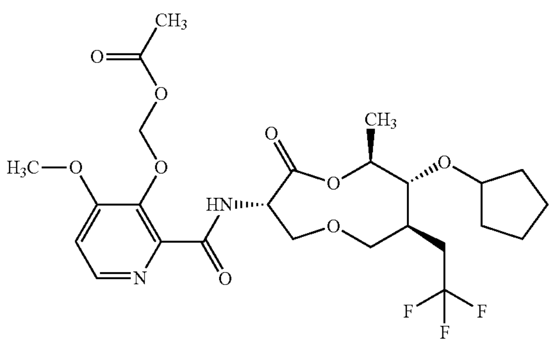 [SMILES: COc1ccnc(C(=O)N[C@H]2COC[C@H](CC(F)(F)F)[C@@H](OC3CCCC3)[C@H](C)OC2=O)c1OCOC(C)=O] | Example 7 | Colorless Oil |
| F106 | 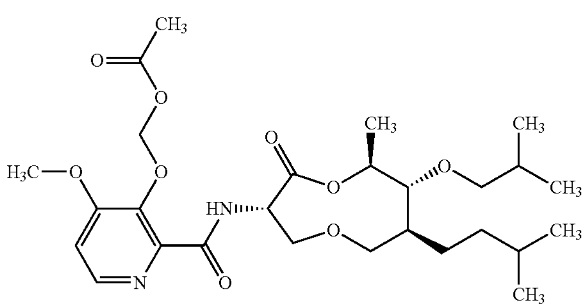 [SMILES: COc1ccnc(C(=O)N[C@H]2COC[C@H](CCC(C)C)[C@@H](OCC(C)C)[C@H](C)OC2=O)c1OCOC(C)=O] | Example 7 | Colorless Oil |
| F107 | 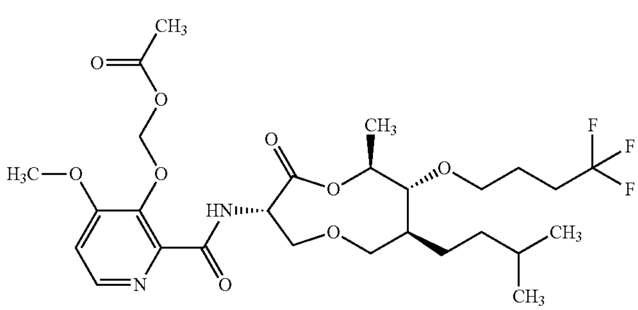 [SMILES: COc1ccnc(C(=O)N[C@H]2COC[C@H](CCC(C)C)[C@@H](OCCCC(F)(F)F)[C@H](C)OC2=O)c1OCOC(C)=O] | Example 7 | Colorless Oil |

TABLE 1-continued

Compound Structure and Appearance

| Compound Number | Structure | Prepared According to Example | Appearance |
|---|---|---|---|
| F108 | 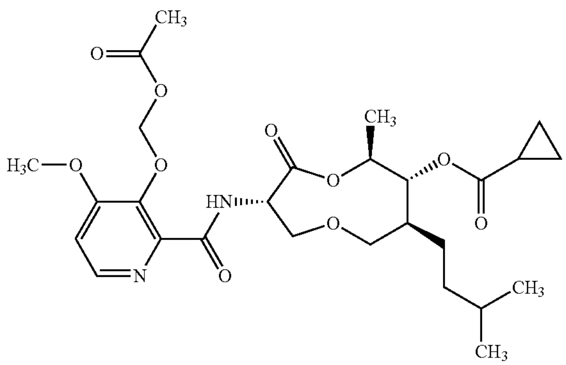 [SMILES: COc1ccnc(C(=O)N[C@H]2COC[C@H](CCC(C)C)[C@@H](OC(=O)C3CC3)[C@H](C)OC2=O)c1OCOC(C)=O] | Example 7 | Colorless Oil |
| F109 | 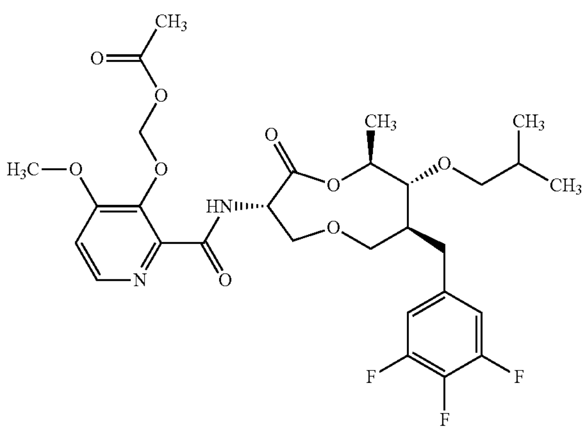 [SMILES: COc1ccnc(C(=O)N[C@H]2COC[C@H](Cc3cc(F)c(F)c(F)c3)[C@@H](OCC(C)C)[C@H](C)OC2=O)c1OCOC(C)=O] | Example 7 | Colorless Oil |
| F110 | 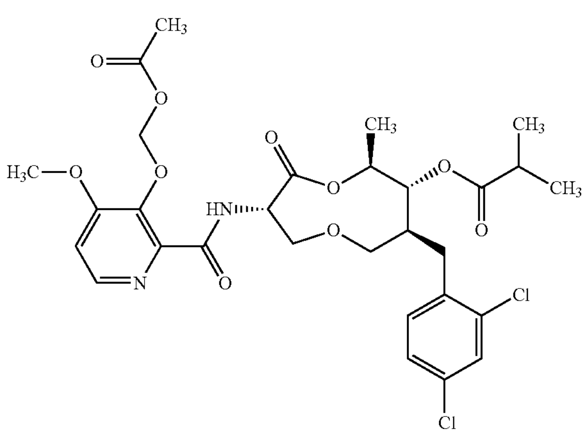 [SMILES: COc1ccnc(C(=O)N[C@H]2COC[C@H](Cc3ccc(Cl)cc3Cl)[C@@H](OC(=O)C(C)C)[C@H](C)OC2=O)c1OCOC(C)=O] | Example 7 | White Solid |

TABLE 1-continued

Compound Structure and Appearance

| Compound Number | Structure | Prepared According to Example | Appearance |
|---|---|---|---|
| F111 | 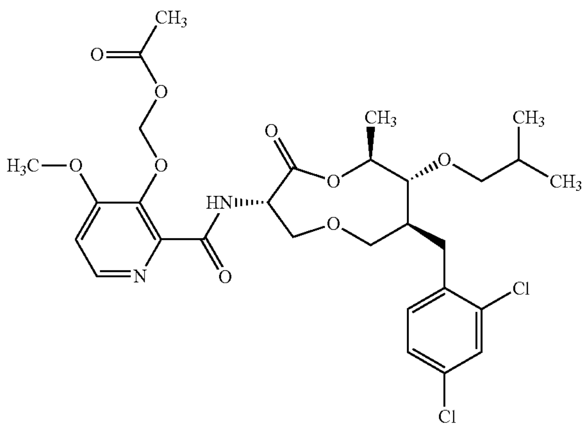 [SMILES: COc1ccnc(C(=O)N[C@H]2COC[C@H](Cc3ccc(Cl)cc3Cl)[C@@H](OCC(C)C)[C@H](C)OC2=O)c1OCOC(C)=O] | Example 7 | White Solid |
| F112 | 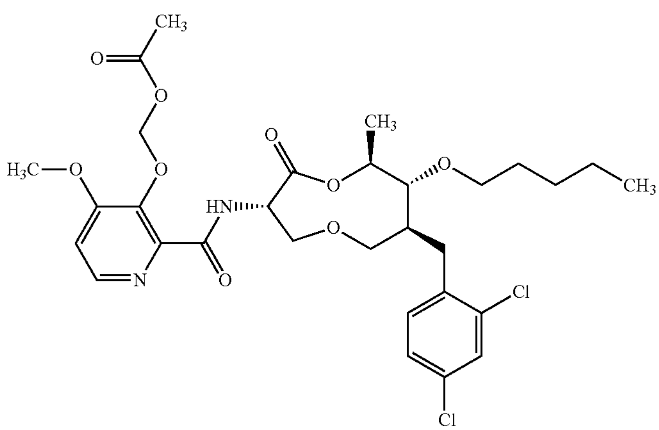 [SMILES: CCCCCO[C@@H]1[C@@H](Cc2ccc(Cl)cc2Cl)COC[C@H](NC(=O)c2nccc(OC)c2OCOC(C)=O)C(=O)O[C@H]1C] | Example 7 | Yellow Solid |
| F113 | 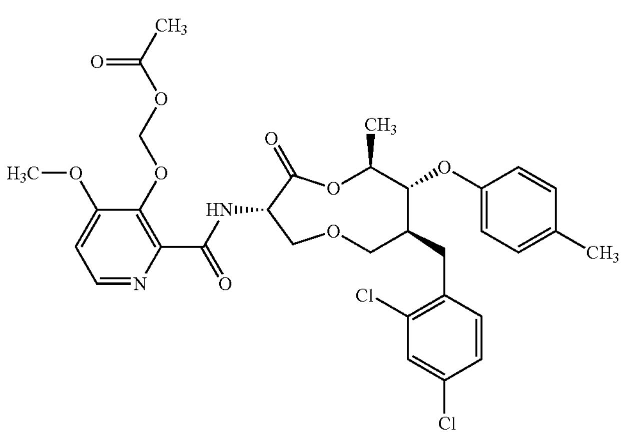 | Example 7 | White Solid |

TABLE 1-continued

Compound Structure and Appearance

| Compound Number | Structure | Prepared According to Example | Appearance |
|---|---|---|---|
| F114 | 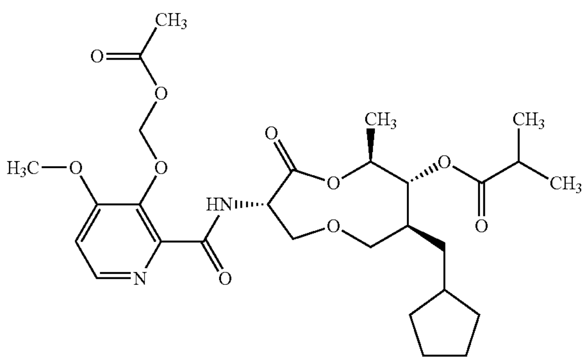 [SMILES: COc1ccnc(C(=O)N[C@H]2COC[C@H](CC3CCCC3)[C@@H](OC(=O)C(C)C)[C@H](C)OC2=O)c1OCOC(C)=O] | Example 7 | Yellow Solid |
| F115 | 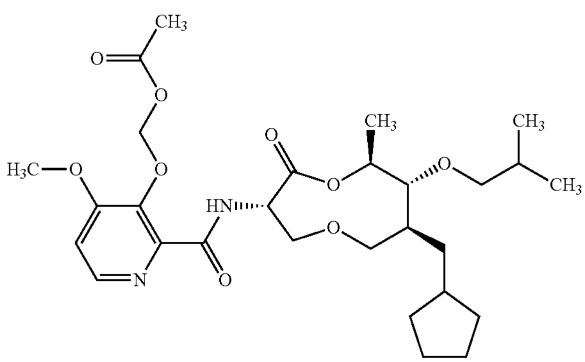 [SMILES: COc1ccnc(C(=O)N[C@H]2COC[C@H](CC3CCCC3)[C@@H](OCC(C)C)[C@H](C)OC2=O)c1OCOC(C)=O] | Example 7 | Sticky Yellow Solid |
| F116 | 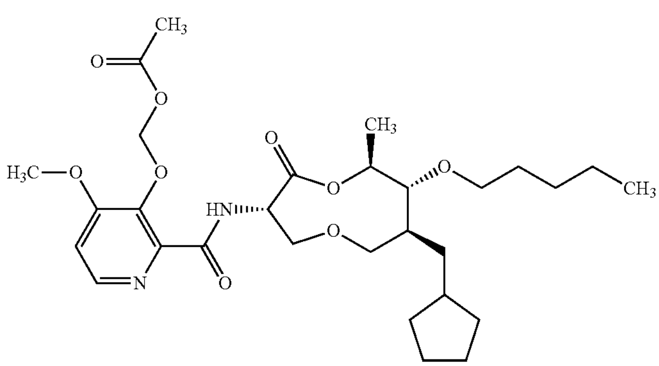 [SMILES: CCCCCO[C@@H]1[C@@H](CC2CCCC2)COC[C@H](NC(=O)c2nccc(OC)c2OCOC(C)=O)C(=O)O[C@H]1C] | Example 7 | Yellow Oil |
| F117 | 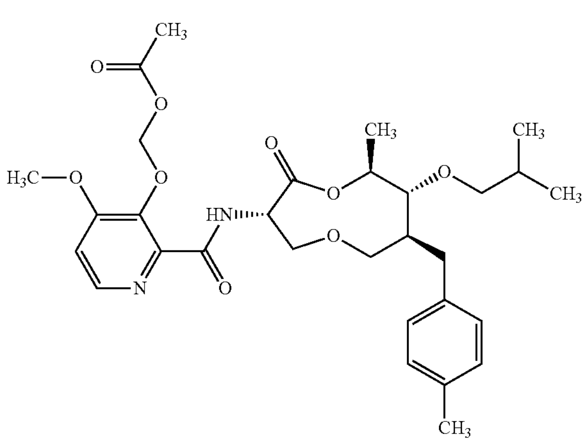 [SMILES: COc1ccnc(C(=O)N[C@H]2COC[C@H](Cc3ccc(C)cc3)[C@@H](OCC(C)C)[C@H](C)OC2=O)c1OCOC(C)=O] | Example 7 | White Foam |

TABLE 1-continued

Compound Structure and Appearance

| Compound Number | Structure | Prepared According to Example | Appearance |
|---|---|---|---|
| F118 | 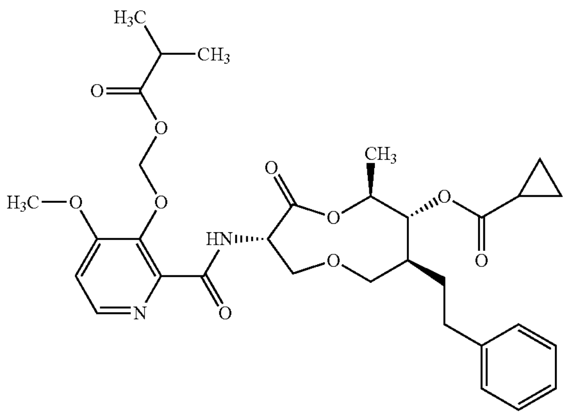 [SMILES: COc1ccnc(C(=O)N[C@H]2COC[C@H](CCc3ccccc3)[C@@H](OC(=O)C3CC3)[C@H](C)OC2=O)c1OCOC(=O)C(C)C] | Example 7 | Colorless Oil |
| F119 | 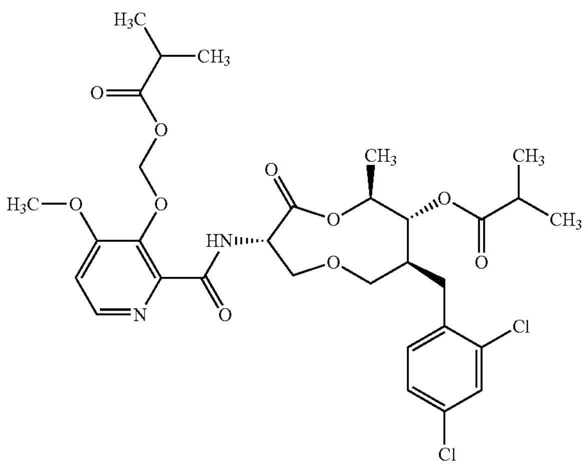 [SMILES: COc1ccnc(C(=O)N[C@H]2COC[C@H](Cc3ccc(Cl)cc3Cl)[C@@H](OC(=O)C(C)C)[C@H](C)OC2=O)c1OCOC(=O)C(C)C] | Example 7 | White Solid |
| F120 | 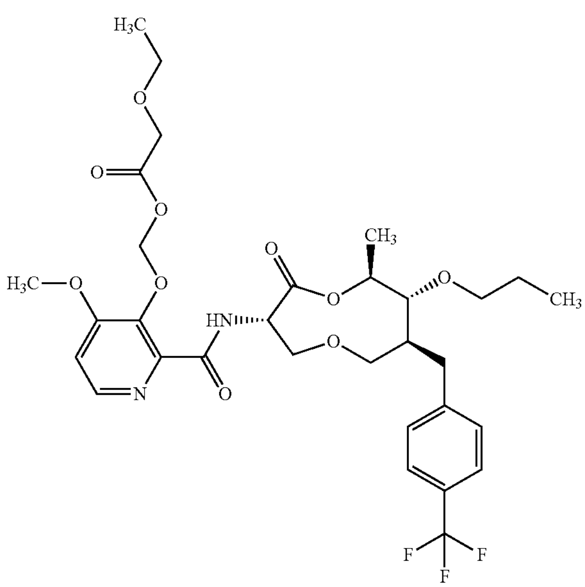 [SMILES: CCCO[C@@H]1[C@@H](Cc2ccc(C(F)(F)F)cc2)COC[C@H](NC(=O)c2nccc(OC)c2OCOC(=O)COCC)C(=O)O[C@H]1C] | Example 9 | Colorless Oil |

TABLE 1-continued
| Compound Number | Structure | Prepared According to Example | Appearance |
|---|---|---|---|
| F121 | 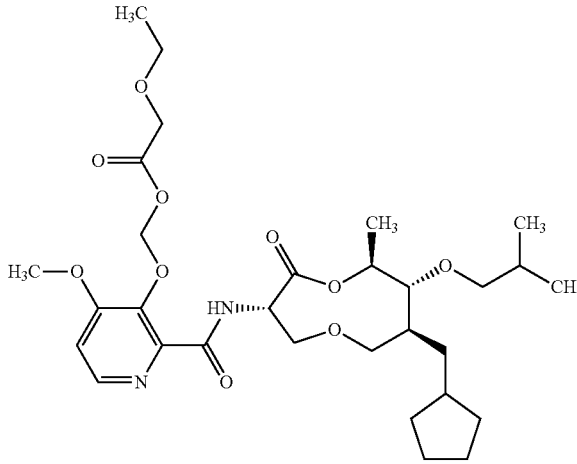 [SMILES: CCOCC(=O)OCOc1c(OC)ccnc1C(=O)N[C@H]1COC[C@H](CC2CCCC2)[C@@H](OCC(C)C)[C@H](C)OC1=O] | Example 9 | Clear Gel |
| F122 | 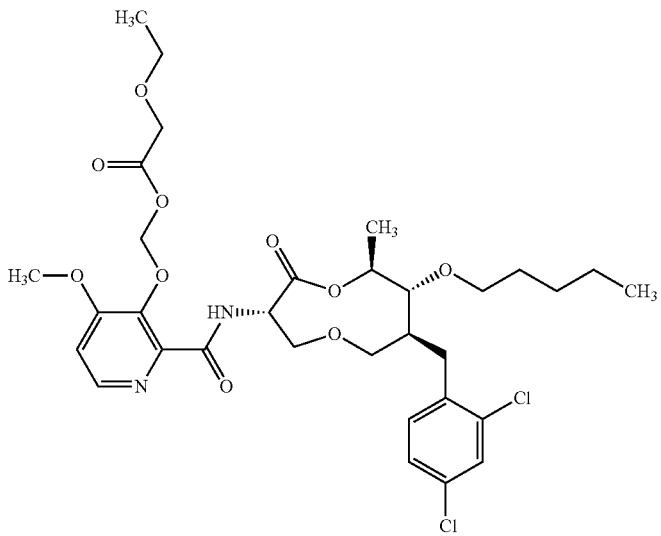 [SMILES: CCCCCO[C@@H]1[C@@H](Cc2ccc(Cl)cc2Cl)COC[C@H](NC(=O)c2nccc(OC)c2OCOC(=O)COCC)C(=O)O[C@H]1C] | Example 9 | Clear Gel |
| F123 | 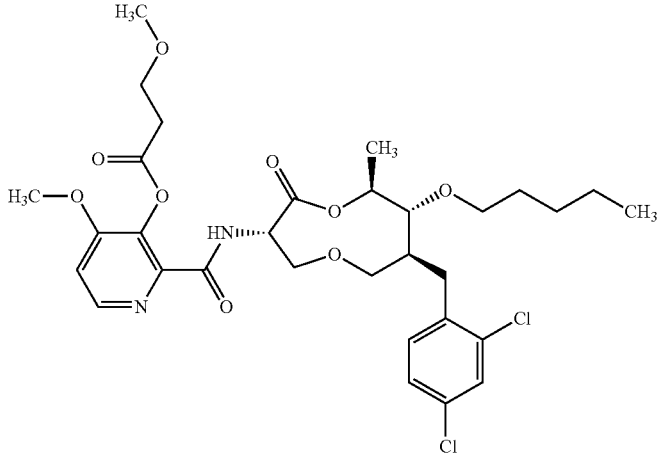 [SMILES: CCCCCO[C@@H]1[C@@H](Cc2ccc(Cl)cc2Cl)COC[C@H](NC(=O)c2nccc(OC)c2OC(=O)CCOC)C(=O)O[C@H]1C] | Example 8 | White Solid |

TABLE 1-continued

Compound Structure and Appearance

| Compound Number | Structure | Prepared According to Example | Appearance |
|---|---|---|---|
| F124 | 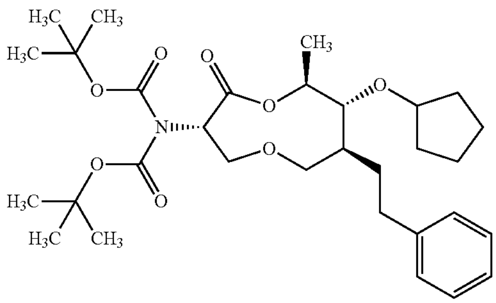 [SMILES: C[C@@H]1OC(=O)[C@@H](N(C(=O)OC(C)(C)C)C(=O)OC(C)(C)C)COC[C@H](CCc2ccccc2)[C@H]1OC1CCCC1] | Example 6, Step 2a-2 | Colorless Oil |
| F125 | 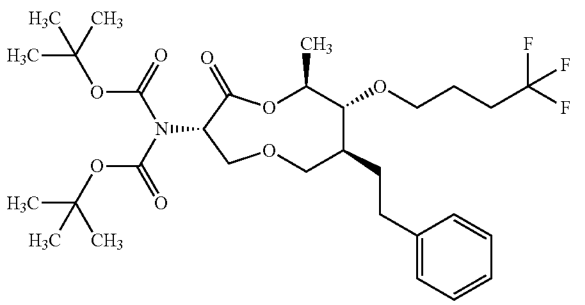 [SMILES: C[C@@H]1OC(=O)[C@@H](N(C(=O)OC(C)(C)C)C(=O)OC(C)(C)C)COC[C@H](CCc2ccccc2)[C@H]1OCCCC(F)(F)F] | Example 6, Step 2a-2 | Oil |
| F126 | 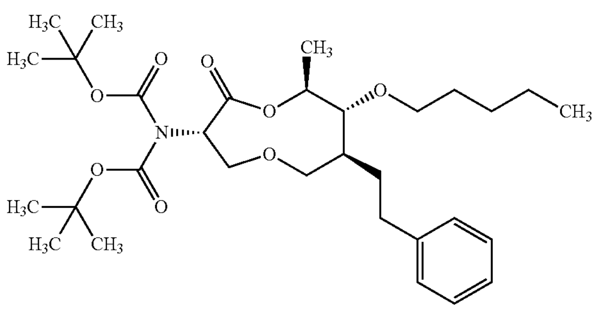 [SMILES: CCCCCO[C@@H]1[C@@H](CCc2ccccc2)COC[C@H](N(C(=O)OC(C)(C)C)C(=O)OC(C)(C)C)C(=O)O[C@H]1C] | Example 6, Step 2a-2 | Colorless Oil |
| F127 | 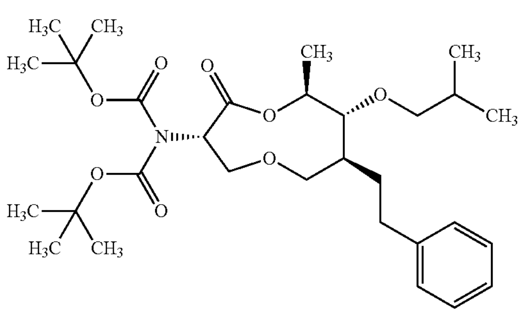 [SMILES: CC(C)CO[C@@H]1[C@@H](CCc2ccccc2)COC[C@H](N(C(=O)OC(C)(C)C)C(=O)OC(C)(C)C)C(=O)O[C@H]1C] | Example 6, Step 2a-2 | Colorless Oil |

TABLE 1-continued

Compound Structure and Appearance

| Compound Number | Structure | Prepared According to Example | Appearance |
|---|---|---|---|
| F128 | 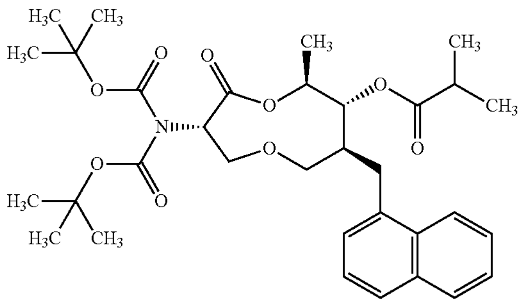 [SMILES: CC(C)C(=O)O[C@@H]1[C@@H](Cc2cccc3ccccc23)COC[C@H](N(C(=O)OC(C)(C)C)C(=O)OC(C)(C)C)C(=O)O[C@H]1C] | Example 6, Step 2b | White Powder |
| F129 | 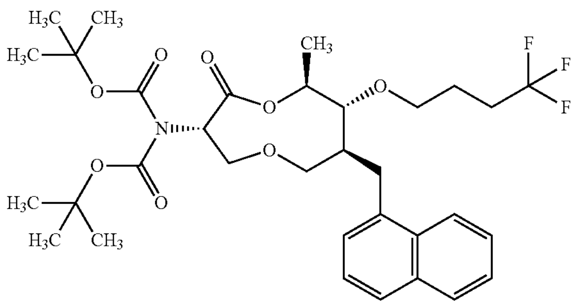 [SMILES: C[C@@H]1OC(=O)[C@@H](N(C(=O)OC(C)(C)C)C(=O)OC(C)(C)C)COC[C@H](Cc2cccc3ccccc23)[C@H]1OCCCC(F)(F)F] | Example 6, Step 2a-2 | Off-White Solid |
| F130 | 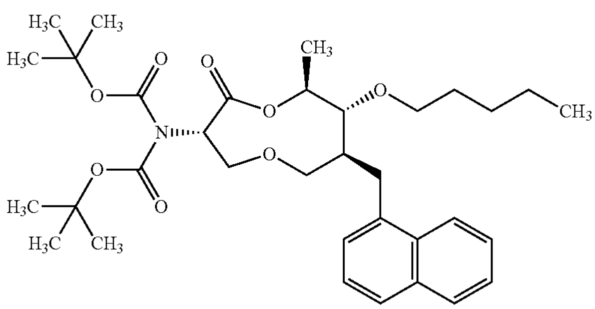 [SMILES: CCCCCO[C@@H]1[C@@H](Cc2cccc3ccccc23)COC[C@H](N(C(=O)OC(C)(C)C)C(=O)OC(C)(C)C)C(=O)O[C@H]1C] | Example 6, Step 2a-2 | Colorless Oil |
| F131 | 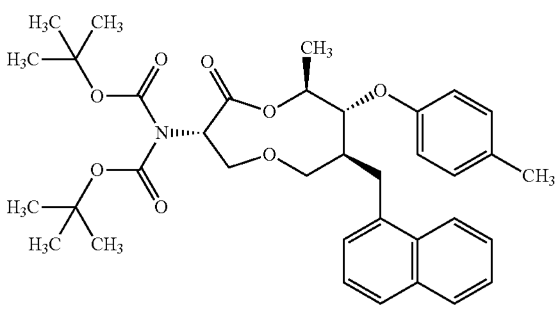 [SMILES: Cc1ccc(O[C@@H]2[C@@H](Cc3cccc4ccccc34)COC[C@H](N(C(=O)OC(C)(C)C)C(=O)OC(C)(C)C)C(=O)O[C@H]2C)cc1] | Example 6, Step 2c | Colorless Solid |

TABLE 1-continued

Compound Structure and Appearance

| Compound Number | Structure | Prepared According to Example | Appearance |
|---|---|---|---|
| F132 | 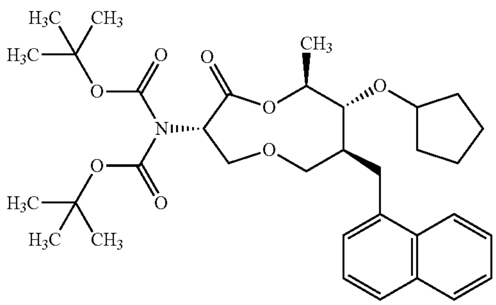 [SMILES: C[C@@H]1OC(=O)[C@@H](N(C(=O)OC(C)(C)C)C(=O)OC(C)(C)C)COC[C@H](Cc2cccc3ccccc23)[C@H]1OC1CCCC1] | Example 6, Step 2a-2 | White Powder |
| F133 | 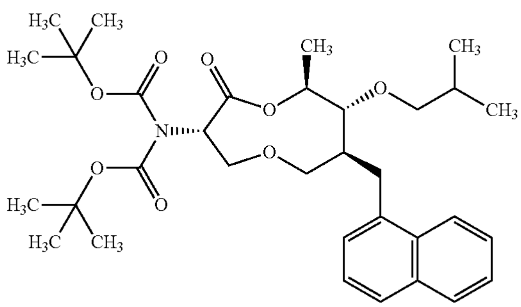 [SMILES: CC(C)CO[C@@H]1[C@@H](Cc2cccc3ccccc23)COC[C@H](N(C(=O)OC(C)(C)C)C(=O)OC(C)(C)C)C(=O)O[C@H]1C] | Example 6, Step 2a-2 | White Powder |
| F134 | 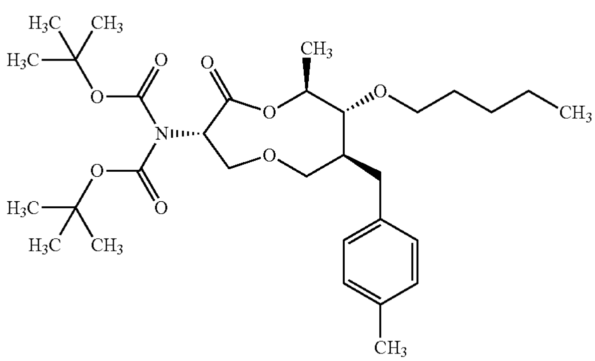 [SMILES: CCCCCO[C@@H]1[C@@H](Cc2ccc(C)cc2)COC[C@H](N(C(=O)OC(C)(C)C)C(=O)OC(C)(C)C)C(=O)O[C@H]1C] | Example 6, Step 2a-2 | White Solid |
| F135 | 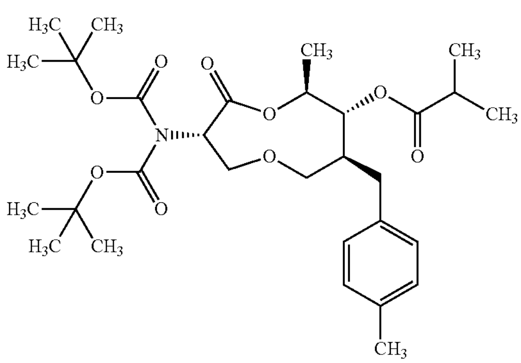 [SMILES: Cc1ccc(C[C@H]2COC[C@H](N(C(=O)OC(C)(C)C)C(=O)OC(C)(C)C)C(=O)O[C@@H](C)[C@@H]2OC(=O)C(C)C)cc1] | Example 6, Step 2b | White Powder |

TABLE 1-continued

Compound Structure and Appearance

| Compound Number | Structure | Prepared According to Example | Appearance |
|---|---|---|---|
| F136 | 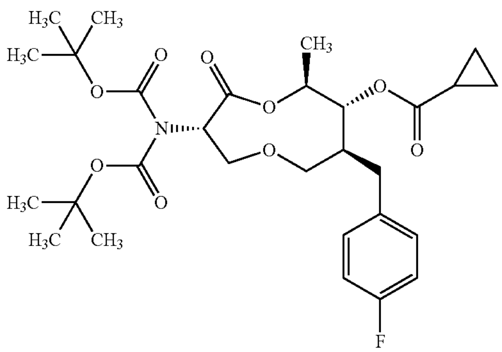 [SMILES: C[C@@H]1OC(=O)[C@@H](N(C(=O)OC(C)(C)C)C(=O)OC(C)(C)C)COC[C@H](Cc2ccc(F)cc2)[C@H]1OC(=O)C1CC1] | Example 6, Step 2b | White Solid |
| F137 | 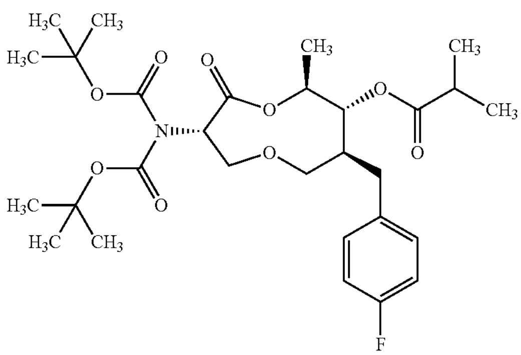 [SMILES: CC(C)C(=O)O[C@@H]1[C@@H](Cc2ccc(F)cc2)COC[C@H](N(C(=O)OC(C)(C)C)C(=O)OC(C)(C)C)C(=O)O[C@H]1C] | Example 6, Step 2b | White Solid |
| F138 | 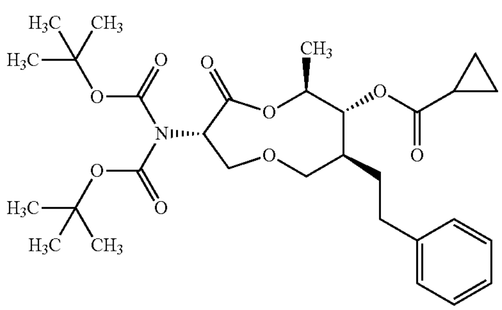 [SMILES: C[C@@H]1OC(=O)[C@@H](N(C(=O)OC(C)(C)C)C(=O)OC(C)(C)C)COC[C@H](CCc2ccccc2)[C@H]1OC(=O)C1CC1] | Example 6, Step 2b | Colorless Oil |
| F139 | 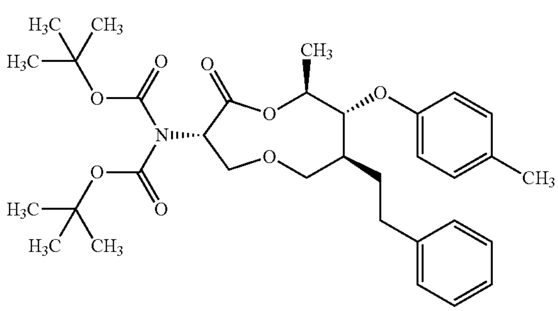 [SMILES: Cc1ccc(O[C@@H]2[C@@H](CCc3ccccc3)COC[C@H](N(C(=O)OC(C)(C)C)C(=O)OC(C)(C)C)C(=O)O[C@H]2C)cc1] | Example 6, Step 2c | Colorless Film |

TABLE 1-continued

Compound Structure and Appearance

| Compound Number | Structure | Prepared According to Example | Appearance |
|---|---|---|---|
| F140 | 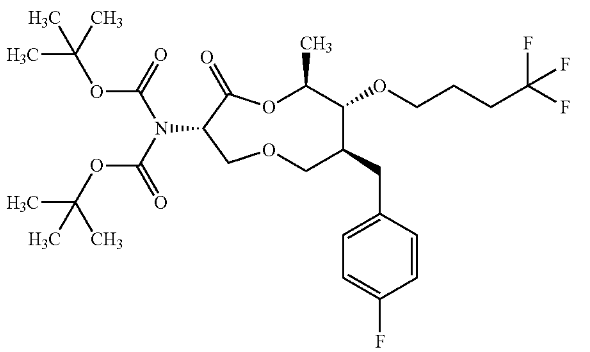 [SMILES: C[C@@H]1OC(=O)[C@@H](N(C(=O)OC(C)(C)C)C(=O)OC(C)(C)C)COC[C@H](Cc2ccc(F)cc2)[C@H]1OCCCC(F)(F)F] | Example 6, Step 2a-2 | Colorless Oil |
| F141 | 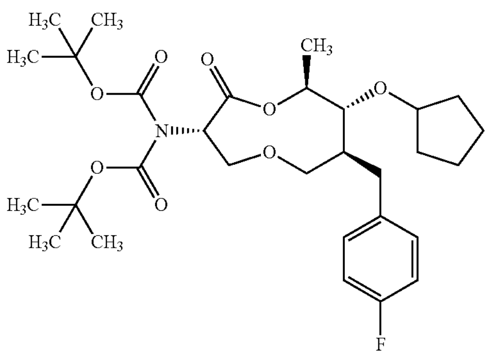 [SMILES: C[C@@H]1OC(=O)[C@@H](N(C(=O)OC(C)(C)C)C(=O)OC(C)(C)C)COC[C@H](Cc2ccc(F)cc2)[C@H]1OC1CCCC1] | Example 6, Step 2a-2 | Colorless Oil |
| F142 | 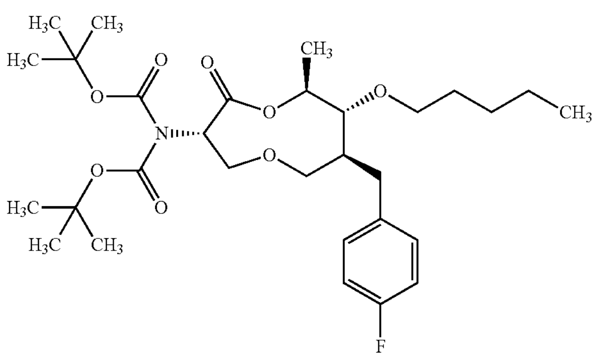 [SMILES: CCCCCO[C@@H]1[C@@H](Cc2ccc(F)cc2)COC[C@H](N(C(=O)OC(C)(C)C)C(=O)OC(C)(C)C)C(=O)O[C@H]1C] | Example 6, Step 2a-2 | Colorless Oil |
| F143 | 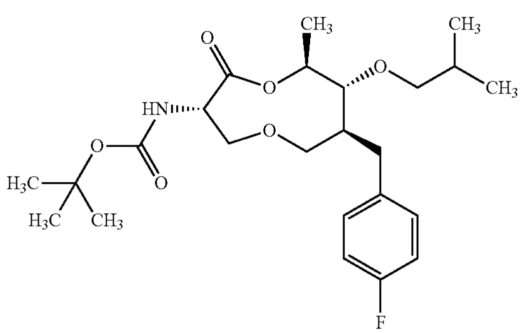 [SMILES: CC(C)CO[C@@H]1[C@@H](Cc2ccc(F)cc2)COC[C@H](NC(=O)OC(C)(C)C)C(=O)O[C@H]1C] | Example 4, Step 1 | Colorless Oil |

TABLE 1-continued

Compound Structure and Appearance

| Compound Number | Structure | Prepared According to Example | Appearance |
|---|---|---|---|
| F144 | 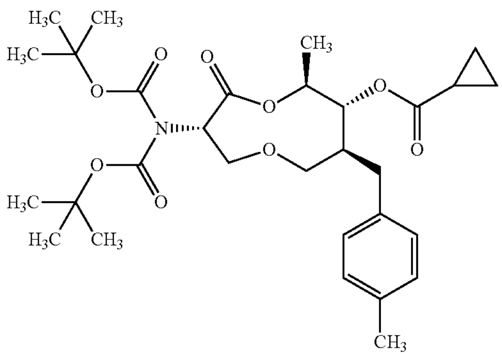 [SMILES: Cc1ccc(C[C@H]2COC[C@H](N(C(=O)OC(C)(C)C)C(=O)OC(C)(C)C)C(=O)O[C@@H](C)[C@@H]2OC(=O)C2CC2)cc1] | Example 6, Step 2b | Colorless Oil |
| F145 | 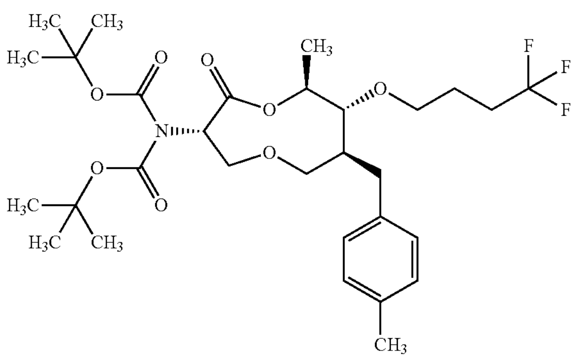 [SMILES: Cc1ccc(C[C@H]2COC[C@H](N(C(=O)OC(C)(C)C)C(=O)OC(C)(C)C)C(=O)O[C@@H](C)[C@@H]2OCCCC(F)(F)F)cc1] | Example 6, Step 2a-2 | Colorless Oil |
| F146 | 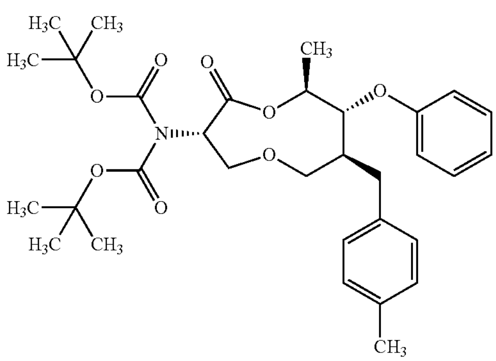 [SMILES: Cc1ccc(C[C@H]2COC[C@H](N(C(=O)OC(C)(C)C)C(=O)OC(C)(C)C)C(=O)O[C@@H](C)[C@@H]2Oc2ccccc2)cc1] | Example 6, Step 2c | Colorless Film |
| F147 | 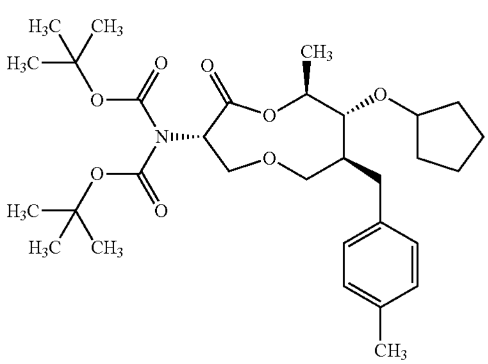 [SMILES: Cc1ccc(C[C@H]2COC[C@H](N(C(=O)OC(C)(C)C)C(=O)OC(C)(C)C)C(=O)O[C@@H](C)[C@@H]2OC2CCCC2)cc1] | Example 6, Step 2a-2 | Colorless Oil |

TABLE 1-continued

Compound Structure and Appearance

| Compound Number | Structure | Prepared According to Example | Appearance |
|---|---|---|---|
| F148 | 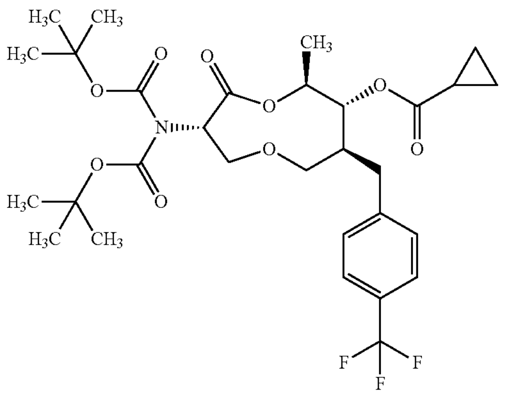 [SMILES: C[C@@H]1OC(=O)[C@@H](N(C(=O)OC(C)(C)C)C(=O)OC(C)(C)C)COC[C@H](Cc2ccc(C(F)(F)F)cc2)[C@H]1OC(=O)C1CC1] | Example 6, Step 2b | Colorless Oil |
| F149 | 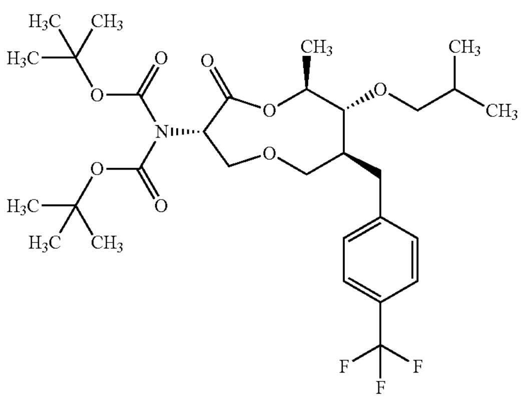 [SMILES: CC(C)CO[C@@H]1[C@@H](Cc2ccc(C(F)(F)F)cc2)COC[C@H](N(C(=O)OC(C)(C)C)C(=O)OC(C)(C)C)C(=O)O[C@H]1C] | Example 6, Step 2a-2 | Colorless Oil |
| F150 | 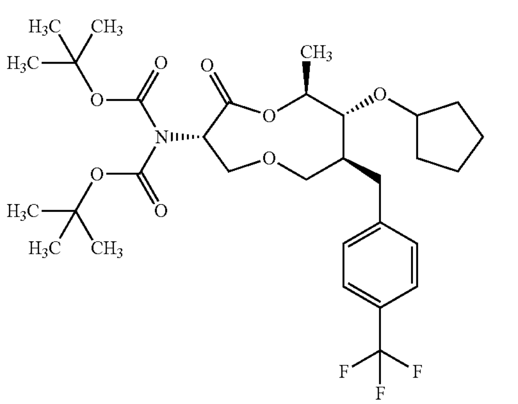 [SMILES: C[C@@H]1OC(=O)[C@@H](N(C(=O)OC(C)(C)C)C(=O)OC(C)(C)C)COC[C@H](Cc2ccc(C(F)(F)F)cc2)[C@H]1OC1CCCC1] | Example 6, Step 2a-2 | Colorless Oil |

TABLE 1-continued

Compound Structure and Appearance

| Compound Number | Structure | Prepared According to Example | Appearance |
|---|---|---|---|
| F151 | 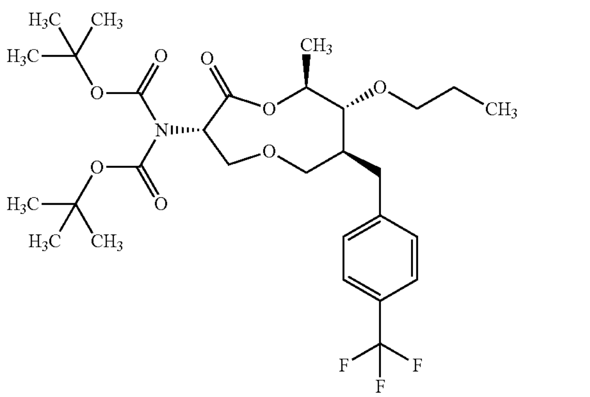 [SMILES: CCCO[C@@H]1[C@@H](Cc2ccc(C(F)(F)F)cc2)COC[C@H](N(C(=O)OC(C)(C)C)C(=O)OC(C)(C)C)C(=O)O[C@H]1C] | Example 6, Step 2a-2 | Colorless Oil |
| F152 | 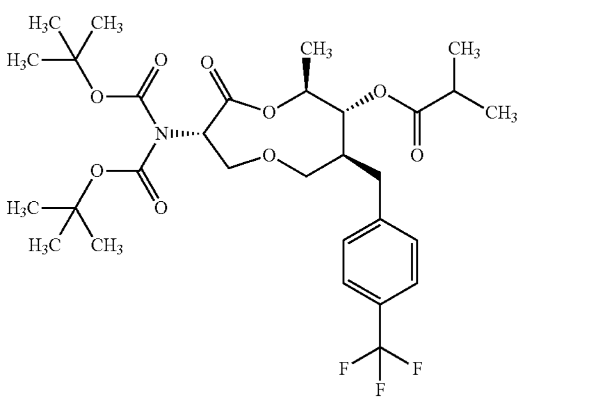 [SMILES: CC(C)C(=O)O[C@@H]1[C@@H](Cc2ccc(C(F)(F)F)cc2)COC[C@H](N(C(=O)OC(C)(C)C)C(=O)OC(C)(C)C)C(=O)O[C@H]1C] | Example 6, Step 2b | Colorless Oil |
| F153 | 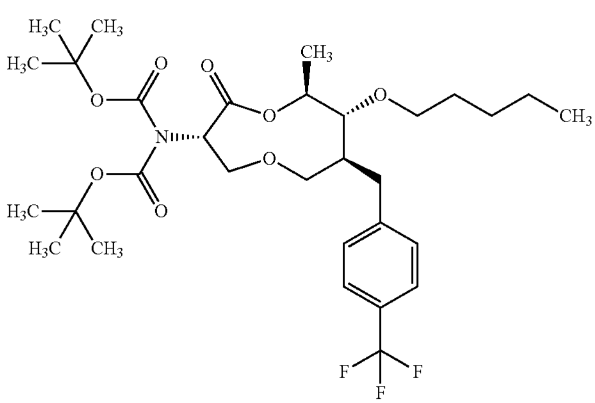 [SMILES: CCCCCO[C@@H]1[C@@H](Cc2ccc(C(F)(F)F)cc2)COC[C@H](N(C(=O)OC(C)(C)C)C(=O)OC(C)(C)C)C(=O)O[C@H]1C] | Example 6, Step 2a-2 | Colorless Oil |
| F154 | 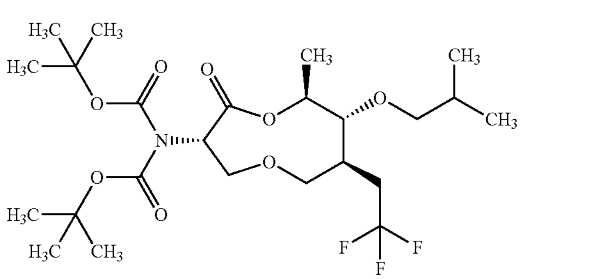 [SMILES: CC(C)CO[C@@H]1[C@@H](CC(F)(F)F)COC[C@H](N(C(=O)OC(C)(C)C)C(=O)OC(C)(C)C)C(=O)O[C@H]1C] | Example 6, Step 2a-2 | Colorless Oil |

TABLE 1-continued

Compound Structure and Appearance

| Compound Number | Structure | Prepared According to Example | Appearance |
|---|---|---|---|
| F155 | 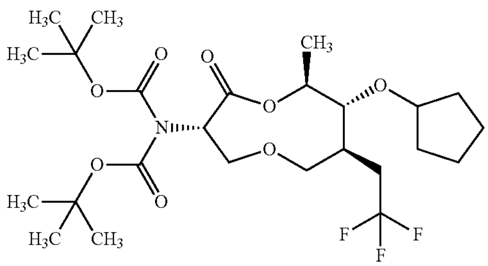 [SMILES: C[C@@H]1OC(=O)[C@@H](N(C(=O)OC(C)(C)C)C(=O)OC(C)(C)C)COC[C@H](CC(F)(F)F)[C@H]1OC1CCCC1] | Example 6, Step 2a-2 | Colorless Oil |
| F156 | 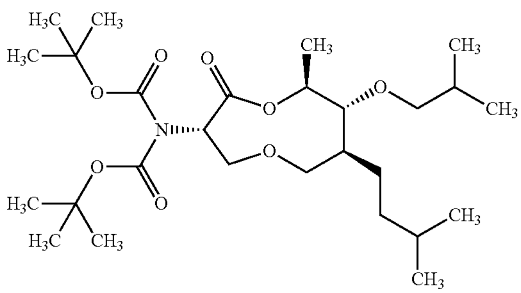 [SMILES: CC(C)CC[C@H]1COC[C@H](N(C(=O)OC(C)(C)C)C(=O)OC(C)(C)C)C(=O)O[C@@H](C)[C@@H]1OCC(C)C] | Example 6, Step 2a-2 | Colorless Oil |
| F157 | 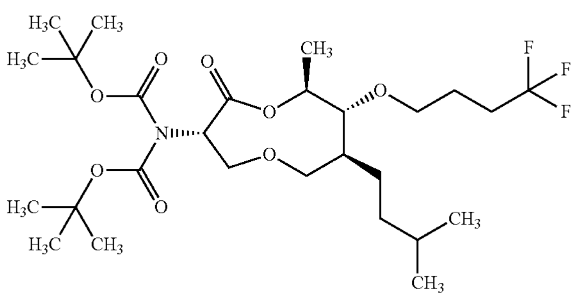 [SMILES: CC(C)CC[C@H]1COC[C@H](N(C(=O)OC(C)(C)C)C(=O)OC(C)(C)C)C(=O)O[C@@H](C)[C@@H]1OCCCC(F)(F)F] | Example 6, Step 2a-2 | Colorless Oil |
| F158 | 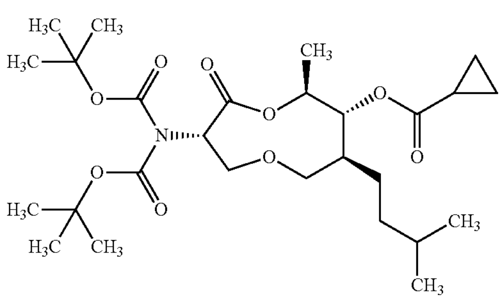 [SMILES: CC(C)CC[C@H]1COC[C@H](N(C(=O)OC(C)(C)C)C(=O)OC(C)(C)C)C(=O)O[C@@H](C)[C@@H]1OC(=O)C1CC1] | Example 6, Step 2b | Colorless Oil |
| F159 | 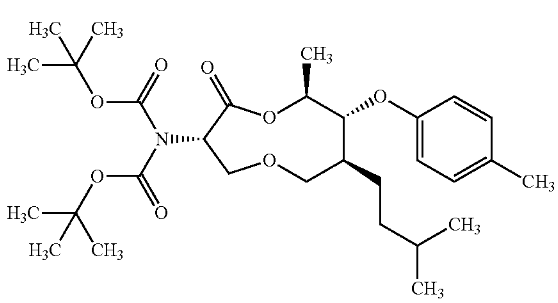 [SMILES: Cc1ccc(O[C@@H]2[C@@H](CCC(C)C)COC[C@H](N(C(=O)OC(C)(C)C)C(=O)OC(C)(C)C)C(=O)O[C@H]2C)cc1] | Example 6, Step 2c | Colorless Oil |

TABLE 1-continued

Compound Structure and Appearance

| Compound Number | Structure | Prepared According to Example | Appearance |
|---|---|---|---|
| F160 | 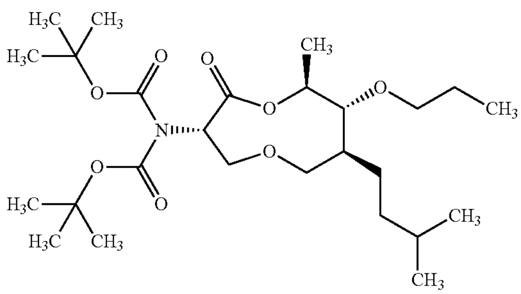 [SMILES: CCCO[C@@H]1[C@@H](CCC(C)C)COC[C@H](N(C(=O)OC(C)(C)C)C(=O)OC(C)(C)C)C(=O)O[C@H]1C] | Example 6, Step 2a-2 | Colorless Oil |
| F161 | 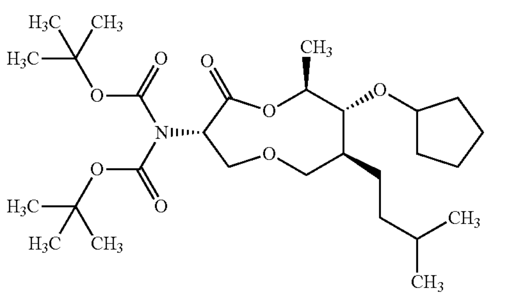 [SMILES: CC(C)CC[C@H]1COC[C@H](N(C(=O)OC(C)(C)C)C(=O)OC(C)(C)C)C(=O)O[C@@H](C)[C@@H]1OC1CCCC1] | Example 6, Step 2a-2 | Colorless Oil |
| F162 | 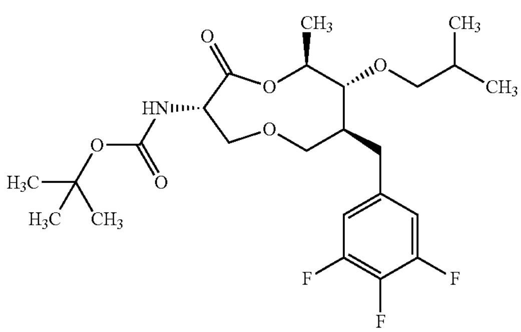 [SMILES: CC(C)CO[C@@H]1[C@@H](Cc2cc(F)c(F)c(F)c2)COC[C@H](NC(=O)OC(C)(C)C)C(=O)O[C@H]1C] | Example 4, Step 1 | Colorless Oil |
| F163 | 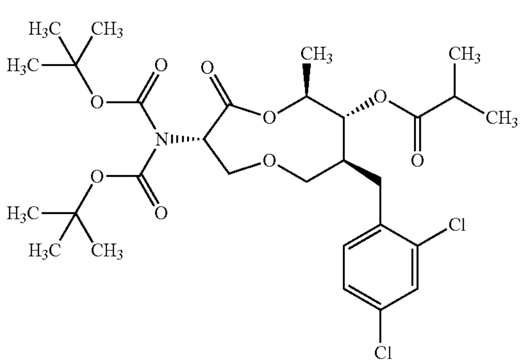 [SMILES: CC(C)C(=O)O[C@@H]1[C@@H](Cc2ccc(Cl)cc2Cl)COC[C@H](N(C(=O)OC(C)(C)C)C(=O)OC(C)(C)C)C(=O)O[C@H]1C] | Example 6, Step 2b | White Solid |

TABLE 1-continued

Compound Structure and Appearance

| Compound Number | Structure | Prepared According to Example | Appearance |
|---|---|---|---|
| F164 | 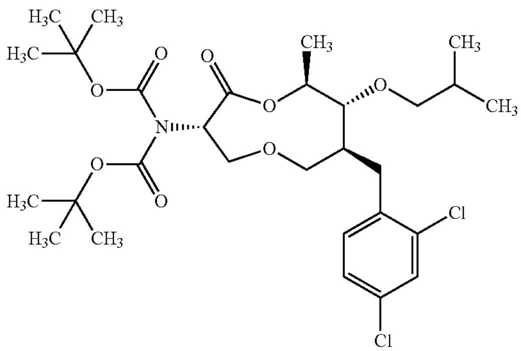 [SMILES: CC(C)CO[C@@H]1[C@@H](Cc2ccc(Cl)cc2Cl)COC[C@H](N(C(=O)OC(C)(C)C)C(=O)OC(C)(C)C)C(=O)O[C@H]1C] | Example 6, Step 2a-2 | Sticky White Solid |
| F165 | 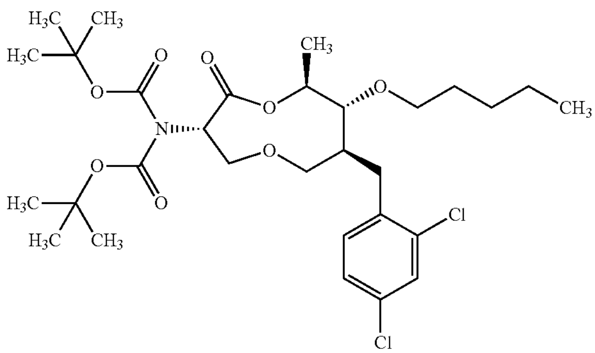 [SMILES: CCCCCO[C@@H]1[C@@H](Cc2ccc(Cl)cc2Cl)COC[C@H](N(C(=O)OC(C)(C)C)C(=O)OC(C)(C)C)C(=O)O[C@H]1C] | Example 6, Step 2a-2 | Clear Gel |
| F166 | 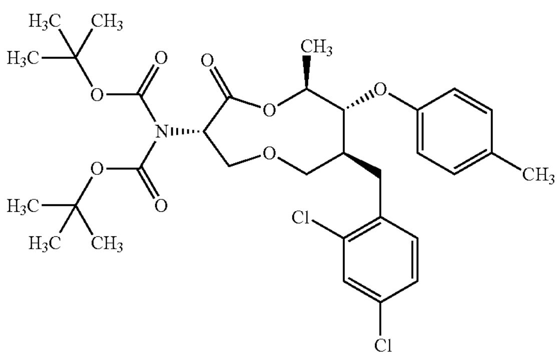 [SMILES: Cc1ccc(O[C@@H]2[C@@H](Cc3ccc(Cl)cc3Cl)COC[C@H](N(C(=O)OC(C)(C)C)C(=O)OC(C)(C)C)C(=O)O[C@H]2C)cc1] | Example 6, Step 2c | Clear Oil |
| F167 | 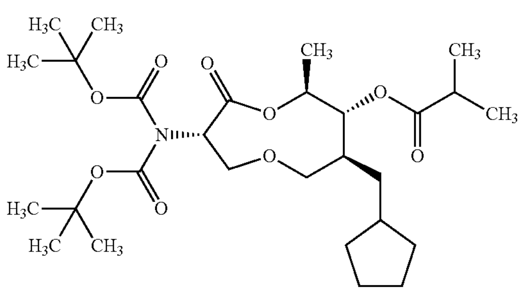 [SMILES: CC(C)C(=O)O[C@@H]1[C@@H](CC2CCCC2)COC[C@H](N(C(=O)OC(C)(C)C)C(=O)OC(C)(C)C)C(=O)O[C@H]1C] | Example 6, Step 2b | White Solid |

TABLE 1-continued

Compound Structure and Appearance

| Compound Number | Structure | Prepared According to Example | Appearance |
|---|---|---|---|
| F168 | 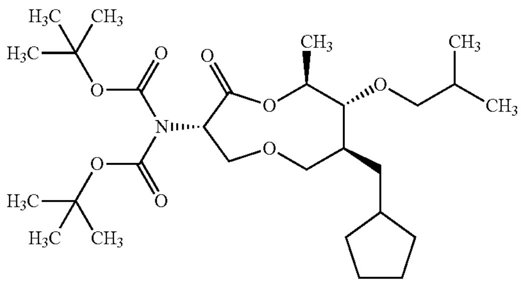 [SMILES: CC(C)CO[C@@H]1[C@@H](CC2CCCC2)COC[C@H](N(C(=O)OC(C)(C)C)C(=O)OC(C)(C)C)C(=O)O[C@H]1C] | Example 6, Step 2a-2 | Clear Oil |
| F169 | 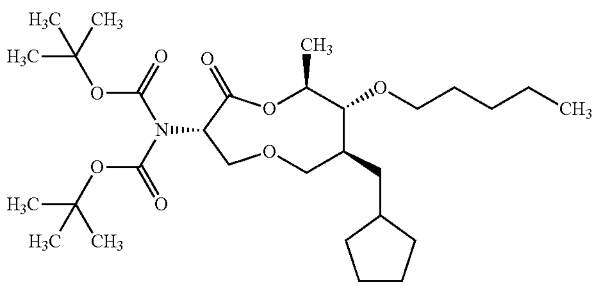 [SMILES: CCCCCO[C@@H]1[C@@H](CC2CCCC2)COC[C@H](N(C(=O)OC(C)(C)C)C(=O)OC(C)(C)C)C(=O)O[C@H]1C] | Example 6, Step 2 | Clear Oil |
| F170 | 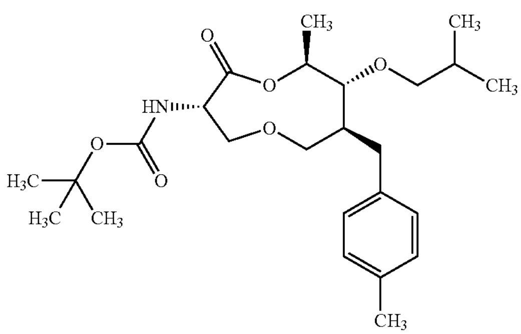 [SMILES: Cc1ccc(C[C@H]2COC[C@H](NC(=O)OC(C)(C)C)C(=O)O[C@@H](C)[C@@H]2OCC(C)C)cc1] | Example 4, Step 1 | Colorless, Sticky Oil. |
| F171 | 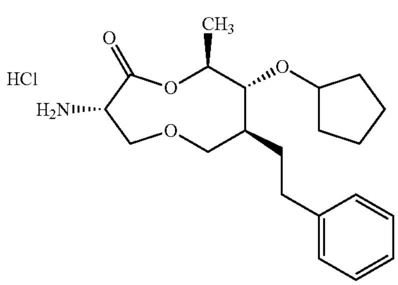 [SMILES: Cl ; C[C@@H]1OC(=O)[C@@H](N)COC[C@H](CCc2ccccc2)[C@H]1OC1CCCC1] | Example 6, Step 3a | White Solid |
| F172 | 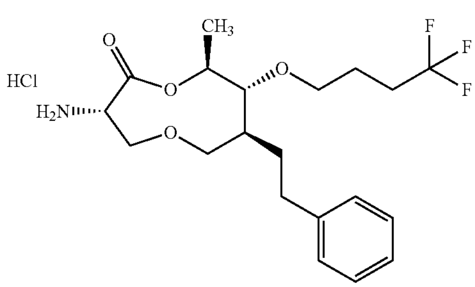 [SMILES: Cl ; C[C@@H]1OC(=O)[C@@H](N)COC[C@H](CCc2ccccc2)[C@H]1OCCCC(F)(F)F] | Example 6, Step 3a | White Solid |

TABLE 1-continued

Compound Structure and Appearance

| Compound Number | Structure | Prepared According to Example | Appearance |
|---|---|---|---|
| F173 | 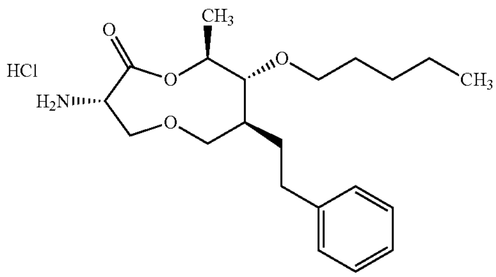 [SMILES: Cl ; CCCCCO[C@@H]1[C@@H](CCc2ccccc2)COC[C@H](N)C(=O)O[C@H]1C] | Example 6, Step 3a | White Solid |
| F174 | 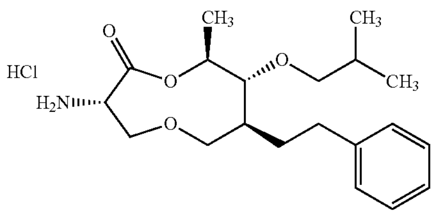 [SMILES: Cl ; CC(C)CO[C@@H]1[C@@H](CCc2ccccc2)COC[C@H](N)C(=O)O[C@H]1C] | Example 6, Step 3a | White Powder |
| F175 | 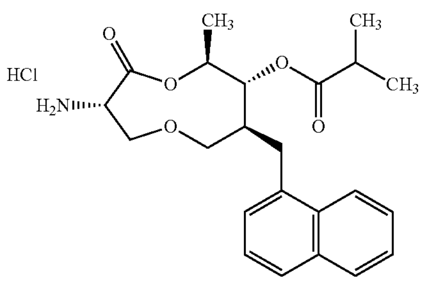 [SMILES: Cl ; CC(C)C(=O)O[C@@H]1[C@@H](Cc2cccc3ccccc23)COC[C@H](N)C(=O)O[C@H]1C] | Example 6, Step 3a | White Powder |
| F176 | 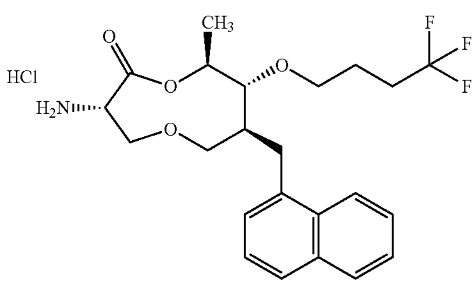 [SMILES: Cl ; C[C@@H]1OC(=O)[C@@H](N)COC[C@H](Cc2cccc3ccccc23)[C@H]1OCCCC(F)(F)F] | Example 6, Step 3a | White Powder |
| F177 | 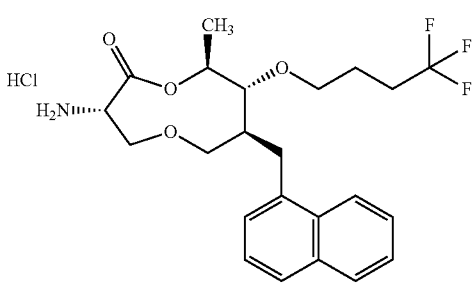 [SMILES: Cl ; C[C@@H]1OC(=O)[C@@H](N)COC[C@H](Cc2cccc3ccccc23)[C@H]1OCCCC(F)(F)F] | Example 6, Step 3a | White Powder |

TABLE 1-continued
Compound Structure and Appearance
| Compound Number | Structure | Prepared According to Example | Appearance |
|---|---|---|---|
| F178 | 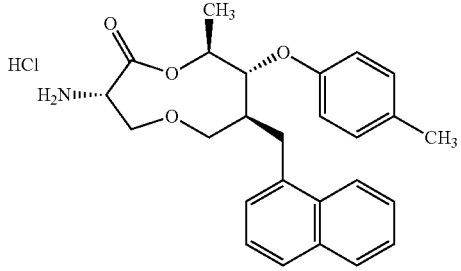 [SMILES: Cl ; Cc1ccc(O[C@@H]2[C@@H](Cc3cccc4ccccc34)COC[C@H](N)C(=O)O[C@H]2C)cc1] | Example 6, Step 3a | White Solid |
| F179 | 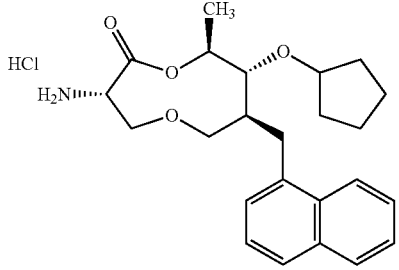 [SMILES: Cl ; C[C@@H]1OC(=O)[C@@H](N)COC[C@H](Cc2cccc3ccccc23)[C@H]1OC1CCCC1] | Example 6, Step 3a | White Powder |
| F180 | 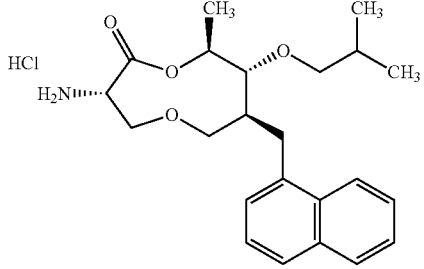 [SMILES: Cl ; CC(C)CO[C@@H]1[C@@H](Cc2cccc3ccccc23)COC[C@H](N)C(=O)O[C@H]1C] | Example 6, Step 3a | White Powder |
| F181 | 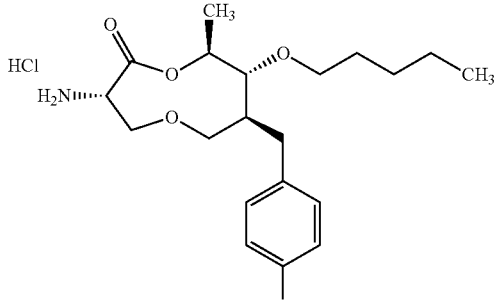 | Example 6, Step 3a | White Solid |
| F182 | 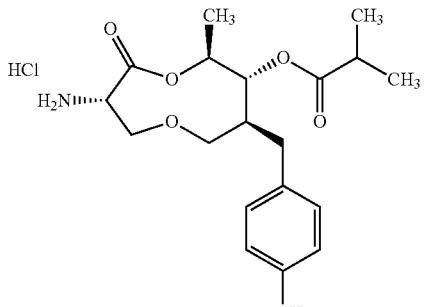 | Example 6, Step 3a | White Powder |

TABLE 1-continued

Compound Structure and Appearance

| Compound Number | Structure | Prepared According to Example | Appearance |
|---|---|---|---|
| F183 | 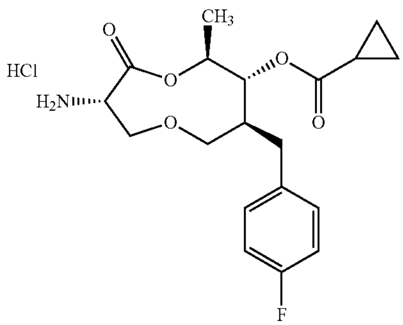 [SMILES: Cl ; C[C@@H]1OC(=O)[C@@H](N)COC[C@H](Cc2ccc(F)cc2)[C@H]1OC(=O)C1CC1] | Example 6, Step 3a | White Powder |
| F184 | 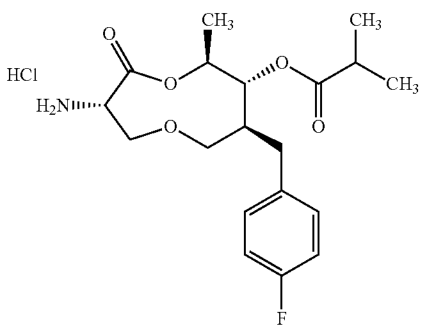 [SMILES: Cl ; CC(C)C(=O)O[C@@H]1[C@@H](Cc2ccc(F)cc2)COC[C@H](N)C(=O)O[C@H]1C] | Example 6, Step 3a | White Powder |
| F185 | 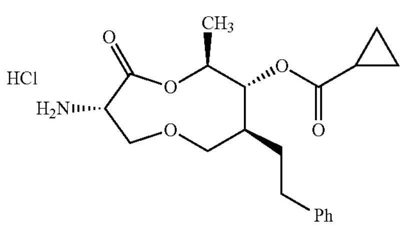 [SMILES: Cl ; C[C@@H]1OC(=O)[C@@H](N)COC[C@H](CCc2ccccc2)[C@H]1OC(=O)C1CC1] | Example 6, Step 3a | Colorless Oil |
| F186 | 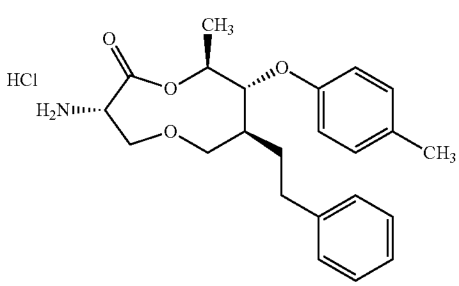 [SMILES: Cl ; Cc1ccc(O[C@@H]2[C@@H](CCc3ccccc3)COC[C@H](N)C(=O)O[C@H]2C)cc1] | Example 6, Step 3a | — |
| F187 | 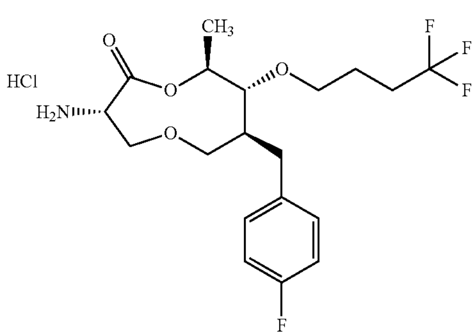 [SMILES: Cl ; C[C@@H]1OC(=O)[C@@H](N)COC[C@H](Cc2ccc(F)cc2)[C@H]1OCCCC(F)(F)F] | Example 6, Step 3a | — |

TABLE 1-continued

Compound Structure and Appearance

| Compound Number | Structure | Prepared According to Example | Appearance |
|---|---|---|---|
| F188 | 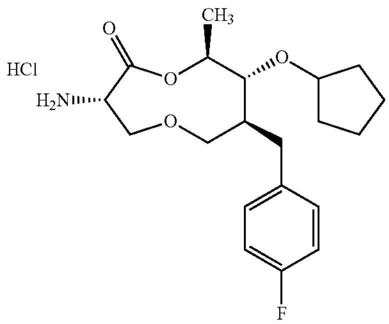 [SMILES: Cl ; C[C@@H]1OC(=O)[C@@H](N)COC[C@H](Cc2ccc(F)cc2)[C@H]1OC1CCCC1] | Example 6, Step 3a | — |
| F189 | 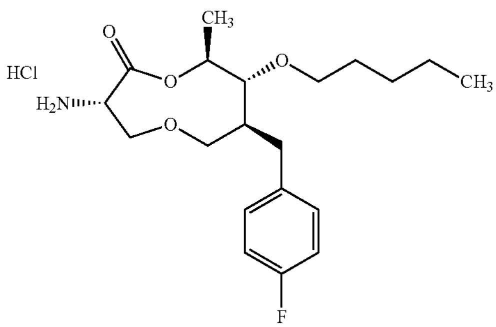 [SMILES: Cl ; CCCCCO[C@@H]1[C@@H](Cc2ccc(F)cc2)COC[C@H](N)C(=O)O[C@H]1C] | Example 6, Step 3a | Colorless Film |
| F190 | 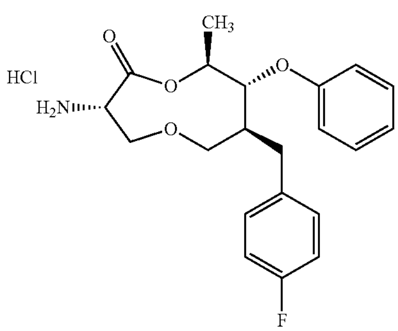 [SMILES: Cl ; C[C@@H]1OC(=O)[C@@H](N)COC[C@H](Cc2ccc(F)cc2)[C@H]1Oc1ccccc1] | Example 6, Step 3a | Colorless Oil |
| F191 | 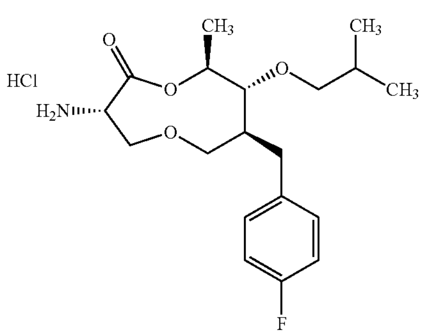 [SMILES: Cl ; CC(C)CO[C@@H]1[C@@H](Cc2ccc(F)cc2)COC[C@H](N)C(=O)O[C@H]1C] | Example 5, Step 1a | White Solid |

TABLE 1-continued
Compound Structure and Appearance
| Compound Number | Structure | Prepared According to Example | Appearance |
|---|---|---|---|
| F192 | 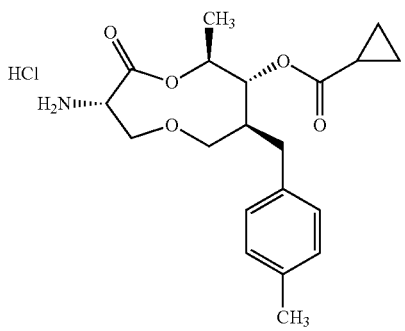 [SMILES: Cl ; Cc1ccc(C[C@H]2COC[C@H](N)C(=O)O[C@@H](C)[C@@H]2OC(=O)C2CC2)cc1] | Example 6, Step 3a | Pale Yellow Amorphous Solid |
| F193 | 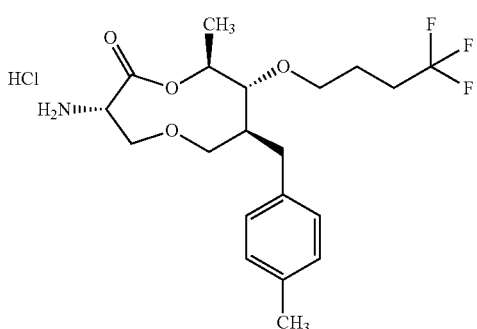 | Example 6, Step 3a | — |
| F194 | 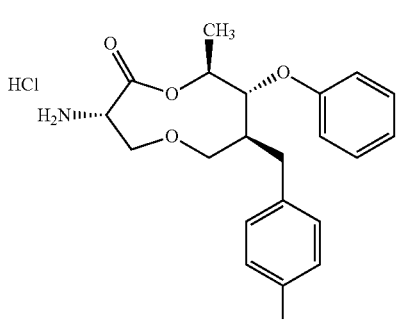 | Example 6, Step 3a | — |
| F195 | 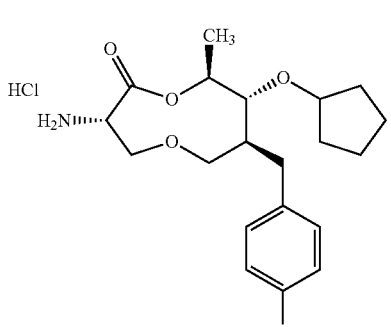 | Example 6, Step 3a | Colorless Film |

TABLE 1-continued
Compound Structure and Appearance
| Compound Number | Structure | Prepared According to Example | Appearance |
|---|---|---|---|
| F196 | 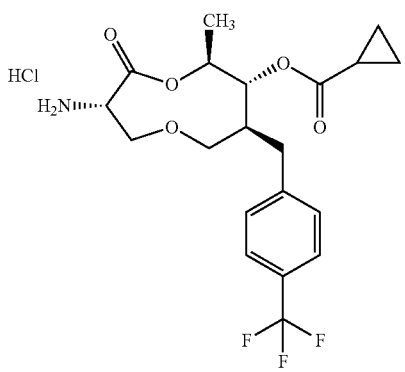 [SMILES: Cl ; C[C@@H]1OC(=O)[C@@H](N)COC[C@H](Cc2ccc(C(F)(F)F)cc2)[C@H]1OC(=O)C1CC1] | Example 6, Step 3a | — |
| F197 | 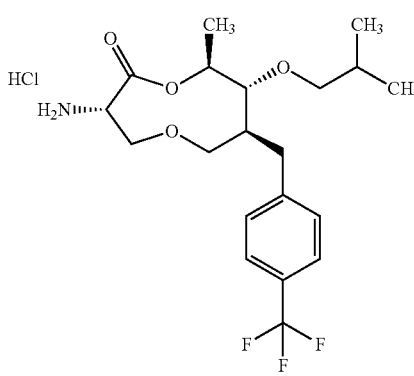 | Example 6, Step 3a | Colorless Oil |
| F198 | 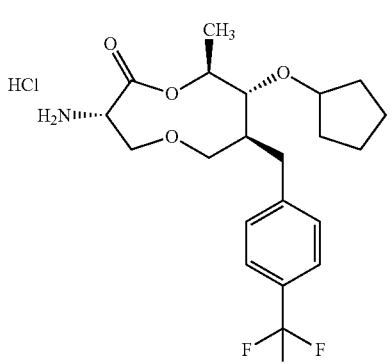 | Example 6, Step 3a | Colorless Oil |
| F199 | 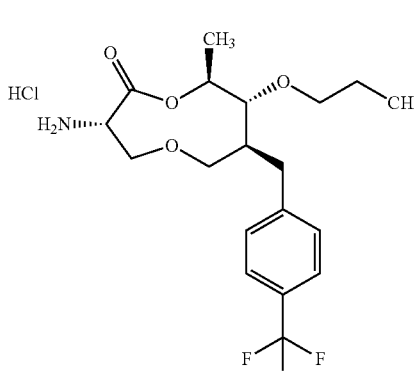 | Example 6, Step 3a | Colorless Oil |

TABLE 1-continued

Compound Structure and Appearance

| Compound Number | Structure | Prepared According to Example | Appearance |
|---|---|---|---|
| F200 | 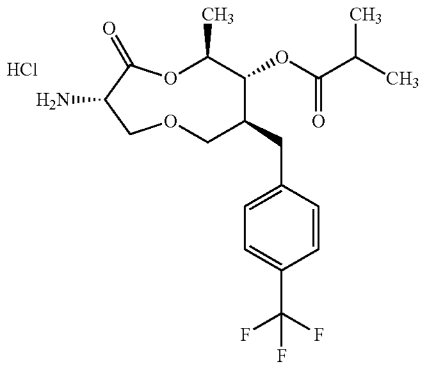 [SMILES: Cl ; CC(C)C(=O)O[C@@H]1[C@@H](Cc2ccc(C(F)(F)F)cc2)COC[C@H](N)C(=O)O[C@H]1C] | Example 6, Step 3a | Colorless Oil |
| F201 | 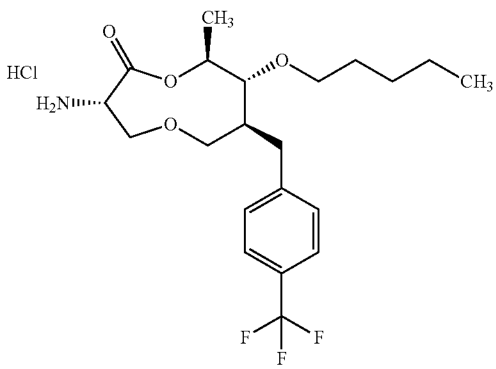 [SMILES: Cl ; CCCCCO[C@@H]1[C@@H](Cc2ccc(C(F)(F)F)cc2)COC[C@H](N)C(=O)O[C@H]1C] | Example 6, Step 3a | Colorless Film |
| F202 | 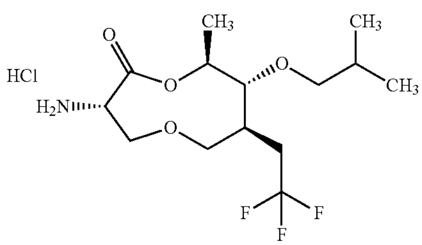 [SMILES: Cl ; CC(C)CO[C@@H]1[C@@H](CC(F)(F)F)COC[C@H](N)C(=O)O[C@H]1C] | Example 6, Step 3a | Colorless Oil |
| F203 | 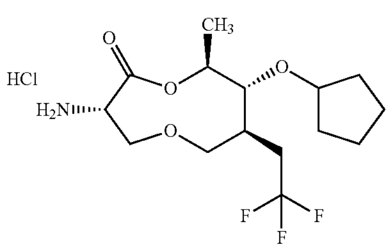 [SMILES: Cl ; C[C@@H]1OC(=O)[C@@H](N)COC[C@H](CC(F)(F)F)[C@H]1OC1CCCC1] | Example 6, Step 3a | Colorless Oil |
| F204 | 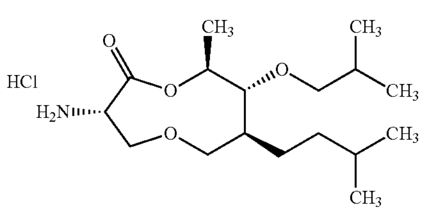 [SMILES: Cl ; CC(C)CC[C@H]1COC[C@H](N)C(=O)O[C@@H](C)[C@@H]1OCC(C)C] | Example 6, Step 3a | Colorless Semi Solid |

TABLE 1-continued

Compound Structure and Appearance

| Compound Number | Structure | Prepared According to Example | Appearance |
|---|---|---|---|
| F205 | 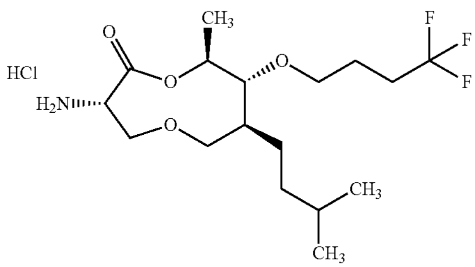 [SMILES: Cl ; CC(C)CC[C@H]1COC[C@H](N)C(=O)O[C@@H](C)[C@@H]1OCCCC(F)(F)F] | Example 6, Step 3a | Colorless Oil |
| F206 | 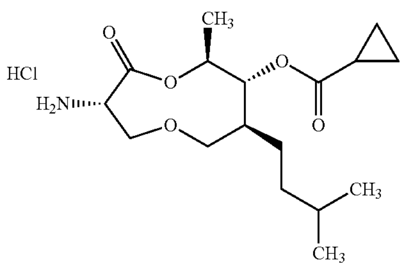 [SMILES: Cl ; CC(C)CC[C@H]1COC[C@H](N)C(=O)O[C@@H](C)[C@@H]1OC(=O)C1CC1] | Example 6, Step 3a | Colorless Oil |
| F207 | 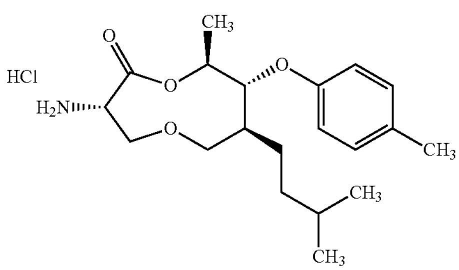 [SMILES: Cl ; Cc1ccc(O[C@@H]2[C@@H](CCC(C)C)COC[C@H](N)C(=O)O[C@H]2C)cc1] | Example 6, Step 3a | Colorless Film |
| F208 | 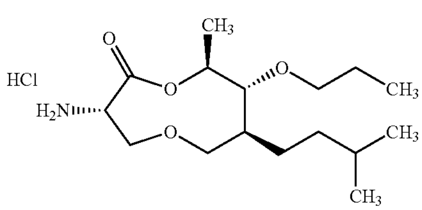 [SMILES: Cl ; CCCO[C@@H]1[C@@H](CCC(C)C)COC[C@H](N)C(=O)O[C@H]1C] | Example 6, Step 3a | — |
| F209 | 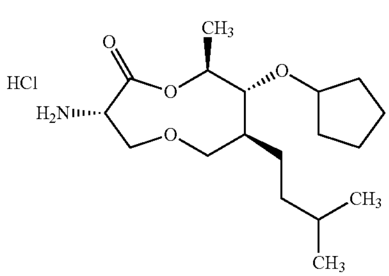 [SMILES: Cl ; CC(C)CC[C@H]1COC[C@H](N)C(=O)O[C@@H](C)[C@@H]1OC1CCCC1] | Example 6, Step 3a | Colorless Film |

153
154
TABLE 1-continued
Compound Structure and Appearance
| Compound Number | Structure | Prepared According to Example | Appearance |
|---|---|---|---|
| F210 | 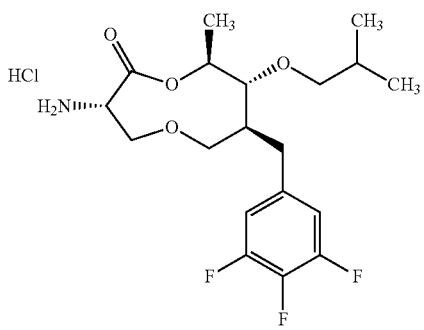 [SMILES: Cl ; CC(C)CO[C@@H]1[C@@H](Cc2cc(F)c(F)c(F)c2)COC[C@H](N)C(=O)O[C@H]1C] | Example 5, Step 1a | Colorless Solid |
| F211 | 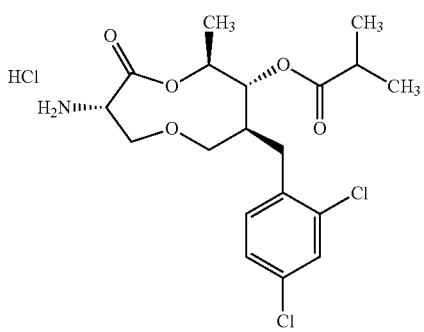 [SMILES: Cl ; CC(C)C(=O)O[C@@H]1[C@@H](Cc2ccc(Cl)cc2Cl)COC[C@H](N)C(=O)O[C@H]1C] | Example 6, Step 3a | White Solid |
| F212 | 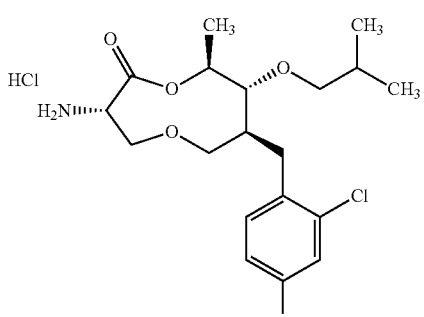 | Example 6, Step 3a | White Solid |
| F213 | 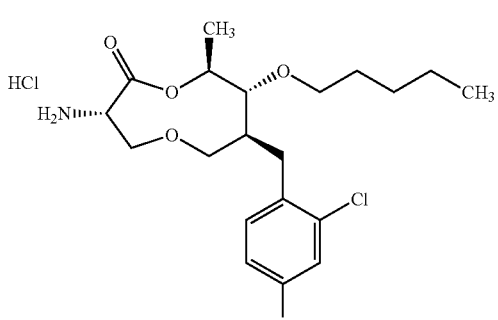 | Example 6, Step 3a | White Solid |

TABLE 1-continued

Compound Structure and Appearance

| Compound Number | Structure | Prepared According to Example | Appearance |
|---|---|---|---|
| F214 | 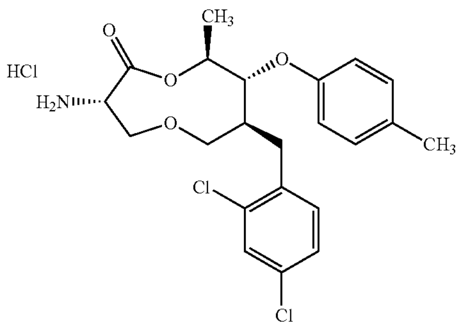 [SMILES: Cl ; Cc1ccc(O[C@@H]2[C@@H](Cc3ccc(Cl)cc3Cl)COC[C@H](N)C(=O)O[C@H]2C)cc1] | Example 6, Step 3a | Tan Solid |
| F215 | 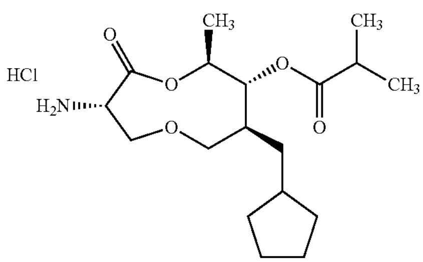 [SMILES: Cl ; CC(C)C(=O)O[C@@H]1[C@@H](CC2CCCC2)COC[C@H](N)C(=O)O[C@H]1C] | Example 6, Step 3a | White Solid |
| F216 | 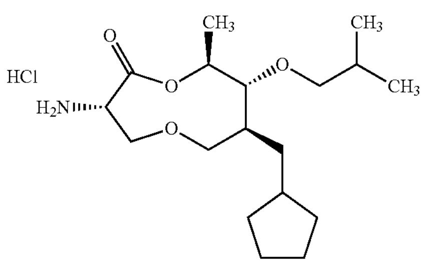 [SMILES: Cl ; CC(C)CO[C@@H]1[C@@H](CC2CCCC2)COC[C@H](N)C(=O)O[C@H]1C] | Example 6, Step 3a | White Solid |
| F217 | 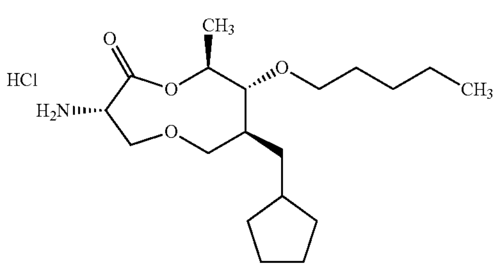 [SMILES: Cl ; CCCCCO[C@@H]1[C@@H](CC2CCCC2)COC[C@H](N)C(=O)O[C@H]1C] | Example 6, Step 3a | White Solid |
| F218 | 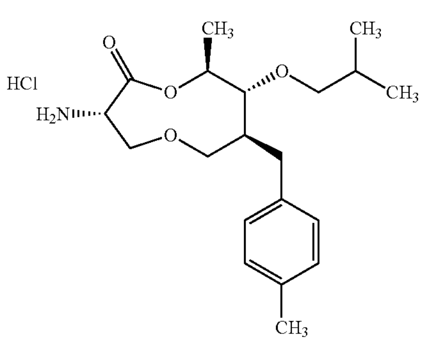 [SMILES: Cl ; Cc1ccc(C[C@H]2COC[C@H](N)C(=O)O[C@@H](C)[C@@H]2OCC(C)C)cc1] | Example 5, Step 1a | White Solid |

TABLE 2

Analytical Data

| Cmpd No. | MP (° C.) | IR (cm⁻¹) | Mass | ¹H NMR | ¹³C or ¹⁹F NMR |
|---|---|---|---|---|---|
| F1 | 51-58 | — | HRMS-ESI (m/z) [M + H]⁺ calcd for $C_{28}H_{37}N_2O_7$, 513.2595; found, 513.2600 | ¹H NMR (CDCl₃) δ 11.99 (s, 1H), 8.64 (d, J = 8.2 Hz, 1H), 7.99 (d, J = 5.2 Hz, 1H), 7.33-7.24 (m, 2H), 7.22-7.14 (m, 3H), 6.86 (d, J = 5.2 Hz, 1H), 5.07-4.90 (m, 2H), 4.14 (dd, J = 11.8, 6.4 Hz, 1H), 4.01-3.90 (m, 4H), 3.73 (dd, J = 11.4, 1.8 Hz, 1H), 3.68-3.58 (m, 2H), 3.23 (app t, J = 8.2 Hz, 1H), 2.76 (ddd, J = 13.7, 11.0, 4.7 Hz, 1H), 2.60 (ddd, J = 13.7, 10.3, 6.2 Hz, 1H), 2.10-1.96 (m, 1H), 1.79-1.37 (m, 13H) | — |
| F2 | 78-81 | — | HRMS-ESI (m/z) [M + H]⁺ calcd for $C_{27}H_{34}F_3N_2O_7$, 555.2313; found, 555.2327 | ¹H NMR (CDCl₃) δ 11.95 (s, 1H), 8.62 (d, J = 8.3 Hz, 1H), 8.00 (d, J = 5.2 Hz, 1H), 7.34-7.24 (m, 2H), 7.24-7.14 (m, 3H), 6.87 (d, J = 5.2 Hz, 1H), 5.07-4.92 (m, 2H), 4.12 (dd, J = 11.8, 7.0 Hz, 1H), 3.94 (s, 3H), 3.73 (dd, J = 10.9, 1.8 Hz, 1H), 3.68-3.60 (m, 2H), 3.60-3.53 (m, 1H), 3.53-3.45 (m, 1H), 3.10 (app t, J = 8.8 Hz, 1H), 2.79 (ddd, J = 14.3, 10.2, 4.8 Hz, 1H), 2.56 (ddd, J = 13.7, 9.8, 6.8 Hz, 1H), 2.23-2.06 (m, 2H), 1.93-1.83 (m, 1H), 1.83-1.74 (m, 2H), 1.73-1.67 (m, 1H), 1.62-1.48 (m, 1H), 1.45 (d, J = 6.4 Hz, 3H) | — |
| F3 | 96-98 | — | HRMS-ESI (m/z) [M + H]⁺ calcd for $C_{28}H_{39}N_2O_7$, 515.2752; found, 515.2767 | ¹H NMR (CDCl₃) δ 11.98 (s, 1H), 8.65 (d, J = 8.3 Hz, 1H), 7.99 (d, J = 5.2 Hz, 1H), 7.33-7.24 (m, 2H), 7.23-7.14 (m, 3H), 6.86 (d, J = 5.2 Hz, 1H), 5.07-4.93 (m, 2H), 4.10 (dd, J = 11.7, 7.0 Hz, 1H), 3.92 (s, 3H), 3.76 (dd, J = 11.1, 1.6 Hz, 1H), 3.67 (dd, J = 11.8, 6.4 Hz, 1H), 3.61 (dd, J = 11.0, 6.3 Hz, 1H), 3.57-3.40 (m, 2H), 3.07 (app t, J = 9.0 Hz, 1H), 2.77 (ddd, J = 13.7, 10.9, 4.7 Hz, 1H), 2.57 (ddd, J = 13.7, 10.4, 6.4 Hz, 1H), 2.06-1.90 (m, 1H), 1.77-1.64 (m, 1H), 1.60-1.48 (m, 3H), 1.47 (d, J = 6.3 Hz, 3H), 1.37-1.26 (m, 4H), 0.95-0.84 (m, 3H) | — |
| F4 | 117-120 | — | HRMS-ESI (m/z) [M + H]⁺ calcd for $C_{27}H_{37}N_2O_7$, 501.2595; found 501.2591 | ¹H NMR (CDCl₃) δ 11.98 (s, 1H), 8.64 (d, J = 8.2 Hz, 1H), 8.00 (d, J = 5.2 Hz, 1H), 7.33-7.24 (m, 2H), 7.23-7.15 (m, 3H), 6.87 (d, J = 5.2 Hz, 1H), 5.07-4.94 (m, 2H), 4.11 (dd, J = 11.8, 7.0 Hz, 1H), 3.93 (s, 3H), 3.75 (dd, J = 11.0, 1.6 Hz, 1H), 3.70-3.58 (m, 2H), 3.29 (dd, J = 8.3, 6.4 Hz, 1H), 3.23 (dd, J = 8.4, 6.4 Hz, 1H), 3.07 (app t, J = 9.0 Hz, 1H), 2.77 (ddd, J = 13.6, 10.8, 4.7 Hz, 1H), 2.57 (ddd, J = 13.7, 10.3, 6.6 Hz, 1H), 1.98 (dddd, J = 13.7, 10.9, 6.6, 3.0 Hz, 1H), 1.89-1.65 (m, 2H), 1.58-1.43 (m, 4H), 0.90 (app d, J = 6.7 Hz, 6H) | — |
| F5 | 139-142 | — | HRMS-ESI (m/z) | ¹H NMR (CDCl₃) δ 11.91 (s, 1H), 8.50 (d, J = 8.3 Hz, 1H), | — |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | [M + H]$^+$ calcd for C$_{30}$H$_{35}$N$_2$O$_8$, 551.2388; found 551.2388 | 8.01-7.92 (m, 2H), 7.89-7.82 (m, 1H), 7.74 (d, J = 8.2 Hz, 1H), 7.49 (dddd, J = 14.7, 8.1, 6.9, 1.5 Hz, 2H), 7.40 (dd, J = 8.2, 7.0 Hz, 1H), 7.30 (dd, J = 6.9, 1.2 Hz, 1H), 6.84 (d, J = 5.2 Hz, 1H), 5.20-5.02 (m, 3H), 4.04 (dd, J = 11.7, 7.3 Hz, 1H), 3.92 (s, 3H), 3.60 (d, J = 4.1 Hz, 2H), 3.43 (dd, J = 11.7, 7.1 Hz, 1H), 3.23 (dd, J = 14.2, 3.2 Hz, 1H), 2.79-2.64 (m, 2H), 2.36-2.23 (m, 1H), 1.43-1.37 (m, 3H), 1.29 (dd, J = 7.0, 3.6 Hz, 6H) | |
| F6 | 118-122 | — | HRMS-ESI (m/z) [M + H]$^+$ calcd for C$_{30}$H$_{34}$F$_3$N$_2$O$_7$, 591.2313; found 591.2315 | $^1$H NMR (CDCl$_3$) δ 11.93 (s, 1H), 8.48 (d, J = 8.4 Hz, 1H), 8.15-8.07 (m, 1H), 7.93 (d, J = 5.2 Hz, 1H), 7.84 (dd, J = 7.6, 2.0 Hz, 1H), 7.73 (d, J = 8.1 Hz, 1H), 7.55-7.42 (m, 2H), 7.39 (dd, J = 8.2, 6.9 Hz, 1H), 7.32 (dd, J = 7.0, 1.3 Hz, 1H), 6.81 (d, J = 5.2 Hz, 1H), 5.05-4.93 (m, 2H), 4.06 (dd, J = 11.7, 7.5 Hz, 1H), 3.89 (s, 4H), 3.80-3.72 (m, 1H), 3.57 (dd, J = 13.5, 2.9 Hz, 1H), 3.50 (dd, J = 10.8, 5.5 Hz, 1H), 3.45-3.37 (m, 1H), 3.36-3.25 (m, 2H), 2.82-2.71 (m, 1H), 2.39-2.23 (m, 2H), 2.15-1.87 (m, 3H), 1.54 (d, J = 6.4 Hz, 3H) | — |
| F7 | 116-120 | — | HRMS-ESI (m/z) [M + H]$^+$ calcd for C$_{31}$H$_{39}$N$_2$O$_7$, 551.2752; found 551.2762 | $^1$H NMR (CDCl$_3$) δ 11.94 (s, 1H), 8.48 (d, J = 8.3 Hz, 1H), 8.19 (dd, J = 8.4, 1.4 Hz, 1H), 7.93 (d, J = 5.2 Hz, 1H), 7.84 (dd, J = 7.9, 1.6 Hz, 1H), 7.73 (d, J = 8.2 Hz, 1H), 7.55-7.43 (m, 2H), 7.39 (dd, J = 8.1, 6.9 Hz, 1H), 7.33 (dd, J = 7.0, 1.3 Hz, 1H), 6.82 (d, J = 5.2 Hz, 1H), 5.04-4.93 (m, 2H), 4.06 (dd, J = 11.7, 7.5 Hz, 1H), 3.90 (s, 3H), 3.87-3.78 (m, 1H), 3.78-3.63 (m, 2H), 3.56-3.37 (m, 2H), 3.37-3.23 (m, 2H), 2.73 (app t, J = 12.8 Hz, 1H), 2.14-2.01 (m, 1H), 1.80-1.66 (m, 2H), 1.56 (d, J = 6.4 Hz, 3H), 1.51-1.33 (m, 4H), 0.93 (t, J = 7.1 Hz, 3H) | — |
| F8 | 94-98 | — | HRMS-ESI (m/z) [M + H]$^+$ calcd for C$_{33}$H$_{35}$N$_2$O$_7$, 571.2439; found 571.2448 | $^1$H NMR (CDCl$_3$) δ 11.94 (s, 1H), 8.50 (d, J = 8.4 Hz, 1H), 8.07 (dd, J = 8.4, 1.3 Hz, 1H), 7.92 (d, J = 5.2 Hz, 1H), 7.85-7.77 (m, 1H), 7.70 (d, J = 8.1 Hz, 1H), 7.54-7.40 (m, 2H), 7.35 (dd, J = 8.1, 7.0 Hz, 1H), 7.28 (dd, J = 7.0, 1.3 Hz, 1H), 7.17-7.10 (m, 2H), 7.06-6.99 (m, 2H), 6.80 (d, J = 5.2 Hz, 1H), 5.22-5.10 (m, 1H), 5.06 (app q, J = 7.9 Hz, 1H), 4.44 (app t, J = 9.0 Hz, 1H), 4.14-4.04 (m, 1H), 3.88 (s, 3H), 3.64-3.47 (m, 3H), 3.36 (dd, J = 11.7, 7.8 Hz, 1H), 2.69 (app t, J = 12.9 Hz, 1H), 2.38-2.24 (m, 4H), 1.44 (d, J = 6.4 Hz, 3H) | — |
| F9 | 78-85 | — | HRMS-ESI (m/z) | $^1$H NMR (CDCl$_3$) δ 11.94 (s, 1H), 8.45 (d, J = 8.4 Hz, 1H), | |

TABLE 2-continued

Analytical Data

| Cmpd No. | MP (° C.) | IR (cm⁻¹) | Mass | ¹H NMR | ¹³C or ¹⁹F NMR |
|---|---|---|---|---|---|
| | | | [M + H]⁺ calcd for C₃₁H₃₇N₂O₇, 549.2595; found 549.2599 | 8.15-8.08 (m, 1H), 7.94 (d, J = 5.2 Hz, 1H), 7.84 (dd, J = 8.1, 1.5 Hz, 1H), 7.73 (d, J = 8.1 Hz, 1H), 7.56-7.44 (m, 2H), 7.44-7.37 (m, 1H), 7.34 (dd, J = 7.0, 1.4 Hz, 1H), 6.83 (d, J = 5.2 Hz, 1H), 5.05-4.90 (m, 2H), 4.29-4.19 (m, 1H), 4.09 (dd, J = 11.6, 7.2 Hz, 1H), 3.91 (s, 3H), 3.75 (dd, J = 13.6, 2.8 Hz, 1H), 3.57-3.43 (m, 2H), 3.43-3.36 (m, 1H), 3.25 (dd, J = 11.7, 7.9 Hz, 1H), 2.76 (app dd, J = 13.7, 12.0 Hz, 1H), 2.08-1.96 (m, 1H), 1.93-1.75 (m, 6H), 1.65-1.55 (m, 5H) | |
| F10 | 78-80 | — | HRMS-ESI (m/z) [M + H]⁺ calcd for C₃₀H₃₇N₂O₇, 537.2595; found 537.2594 | ¹H NMR (CDCl₃) δ 11.94 (s, 1H), 8.48 (d, J = 8.4 Hz, 1H), 8.23-8.15 (m, 1H), 7.95 (d, J = 5.2 Hz, 1H), 7.88-7.80 (m, 1H), 7.73 (d, J = 8.1 Hz, 1H), 7.55-7.42 (m, 2H), 7.40 (dd, J = 8.1, 7.0 Hz, 1H), 7.33 (dd, J = 6.9, 1.3 Hz, 1H), 6.83 (d, J = 5.2 Hz, 1H), 5.06-4.93 (m, 2H), 4.06 (dd, J = 11.7, 7.5 Hz, 1H), 3.92 (s, 3H), 3.69 (dd, J = 13.7, 2.8 Hz, 1H), 3.60 (dd, J = 8.4, 6.6 Hz, 1H), 3.56-3.41 (m, 3H), 3.38-3.23 (m, 2H), 2.73 (dd, J = 13.7, 11.9 Hz, 1H), 2.11 (ddq, J = 14.6, 8.7, 2.6 Hz, 1H), 2.01 (p, J = 7.1, 6.7 Hz, 1H), 1.56 (d, J = 6.3 Hz, 3H), 1.05 (d, J = 2.3 Hz, 3H), 1.03 (d, J = 2.2 Hz, 3H) | — |
| F11 | 97-99 | — | HRMS-ESI (m/z) [M + H]⁺ calcd for C₂₈H₃₉N₂O₇, 515.2752; found, 515.2766 | ¹H NMR (CDCl₃) δ 11.96 (s, 1H), 8.55 (d, J = 8.4 Hz, 1H), 7.96 (d, J = 5.2 Hz, 1H), 7.14-7.04 (m, 4H), 6.84 (d, J = 5.2 Hz, 1H), 5.07-4.94 (m, 2H), 4.01 (dd, J = 11.7, 7.3 Hz, 1H), 3.92 (s, 3H), 3.67 (app dt, J = 8.6, 6.5 Hz, 1H), 3.60-3.49 (m, 2H), 3.49-3.38 (m, 2H), 3.19-3.07 (m, 2H), 2.34-2.23 (m, 4H), 2.00-1.87 (m, 1H), 1.67-1.55 (m, 2H), 1.51 (d, J = 6.3 Hz, 3H), 1.42-1.28 (m, 4H), 0.96-0.85 (m, 3H) | — |
| F12 | 67-72 | — | HRMS-ESI (m/z) [M + H]⁺ calcd for C₂₇H₃₅N₂O₈, 515.2388; found, 515.2400 | ¹H NMR (CDCl₃) δ 11.93 (s, 1H), 8.56 (d, J = 8.3 Hz, 1H), 7.96 (d, J = 5.2 Hz, 1H), 7.09 (d, J = 7.7 Hz, 2H), 7.03 (d, J = 8.0 Hz, 2H), 6.85 (d, J = 5.2 Hz, 1H), 5.09 (m, 2H), 4.97 (app t, J = 9.3 Hz, 1H), 4.02 (dd, J = 11.7, 7.3 Hz, 1H), 3.92 (s, 3H), 3.66-3.58 (m, 1H), 3.58-3.48 (m, 2H), 2.69 (dd, J = 13.9, 3.6 Hz, 1H), 2.61 (app p, J = 7.0 Hz, 1H), 2.31 (s, 3H), 2.24 (dd, J = 13.9, 11.4 Hz, 1H), 2.13-2.04 (m, 1H), 1.35 (d, J = 6.3 Hz, 3H), 1.22 (app dd, J = 7.0, 1.6 Hz, 6H) | — |
| F13 | 68-73 | — | HRMS-ESI (m/z) [M + H]⁺ calcd for | ¹H NMR (CDCl₃) δ 11.91 (s, 1H), 8.57 (d, J = 8.3 Hz, 1H), 7.98 (d, J = 5.2 Hz, 1H), 7.16-7.07 (m, 2H), | — |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | C$_{26}$H$_{30}$N$_2$O$_8$, 517.1981; found 517.2009 | 7.04-6.93 (m, 2H), 6.87 (d, J = 5.2 Hz, 1H), 5.17-5.01 (m, 2H), 4.97 (app t, J = 9.3 Hz, 1H), 4.04 (dd, J = 11.7, 7.2 Hz, 1H), 3.93 (s, 3H), 3.66-3.47 (m, 3H), 2.74 (dd, J = 14.2, 3.9 Hz, 1H), 2.29 (app dd, J = 14.1, 11.1 Hz, 1H), 2.14-2.01 (m, 1H), 1.70-1.59 (m, 1H), 1.36 (d, J = 6.3 Hz, 3H), 1.08-1.00 (m, 2H), 0.96-0.89 (m, 2H) | |
| F14 | 66-71 | — | HRMS-ESI (m/z) [M + H]$^+$ calcd for C$_{26}$H$_{32}$FN$_2$O$_8$, 519.2137; found 519.2160 | $^1$H NMR (CDCl$_3$) δ 11.91 (d, J = 0.6 Hz, 1H), 8.56 (d, J = 8.3 Hz, 1H), 7.98 (d, J = 5.2 Hz, 1H), 7.15-7.06 (m, 2H), 7.03-6.93 (m, 2H), 6.87 (d, J = 5.2 Hz, 1H), 5.18-5.01 (m, 2H), 4.98 (app t, J = 9.2 Hz, 1H), 4.05 (dd, J = 11.7, 7.2 Hz, 1H), 3.93 (s, 3H), 3.64-3.48 (m, 3H), 2.70 (dd, J = 14.1, 3.8 Hz, 1H), 2.61 (app p, J = 7.0 Hz, 1H), 2.29 (dd, J = 14.1, 11.4 Hz, 1H), 2.11-2.04 (m, 1H), 1.36 (d, J = 6.3 Hz, 3H), 1.22 (app dd, J = 7.0, 1.8 Hz, 6H) | — |
| F15 | — | — | HRMS-ESI (m/z) [M]$^+$ calcd for C$_{27}$H$_{32}$N$_2$O$_8$, 512.2159; found 512.2158 | $^1$H NMR (CDCl$_3$) δ 11.94 (s, 1H), 8.64 (d, J = 8.2 Hz, 1H), 8.01 (d, J = 5.2 Hz, 1H), 7.31-7.25 (m, 2H), 7.22-7.16 (m, 1H), 7.16-7.12 (m, 2H), 6.88 (d, J = 5.2 Hz, 1H), 5.13-5.01 (m, 2H), 4.94 (t, J = 9.3 Hz, 1H), 4.15-4.08 (m, 1H), 3.95 (s, 3H), 3.86 (dd, J = 10.9, 1.5 Hz, 1H), 3.80-3.62 (m, 3H), 2.77-2.67 (m, 1H), 2.54-2.43 (m, 1H), 1.90-1.80 (m, 1H), 1.68-1.61 (m, 1H), 1.57-1.48 (m, 1H), 1.34 (d, J = 6.3 Hz, 3H), 1.04-0.98 (m, 2H), 0.94-0.87 (m, 2H) | $^{13}$C NMR (CDCl$_3$) δ 174.16, 170.80, 168.94, 155.36, 148.76, 141.69, 140.65, 130.20, 128.41, 128.32, 125.95, 109.59, 76.27, 74.83, 74.52, 73.04, 56.10, 51.91, 43.86, 32.49, 31.26, 18.30, 12.87, 8.58 |
| F16 | — | — | HRMS-ESI (m/z) [M]$^+$ calcd for C$_{30}$H$_{34}$N$_2$O$_7$, 534.2366; found, 534.2377 | $^1$H NMR (CDCl$_3$) δ 11.95 (s, 1H), 8.65 (d, J = 8.3 Hz, 1H), 8.01 (d, J = 5.2 Hz, 1H), 7.25-7.18 (m, 2H), 7.18-7.11 (m, 1H), 7.10-7.05 (m, 2H), 7.04-6.99 (m, 2H), 6.88 (d, J = 5.2 Hz, 1H), 6.85-6.80 (m, 2H), 5.21-5.11 (m, 1H), 5.11-5.02 (m, 1H), 4.26-4.12 (m, 2H), 3.94 (s, 3H), 3.84-3.62 (m, 3H), 2.72-2.63 (m, 1H), 2.58-2.47 (m, 1H), 2.29 (s, 3H), 1.98-1.81 (m, 2H), 1.62-1.50 (m, 1H), 1.38 (d, J = 6.4 Hz, 3H) | $^{13}$C NMR (CDCl$_3$) δ 170.87, 168.96, 156.92, 155.36, 148.75, 141.68, 140.68, 130.55, 130.22, 130.15, 128.35, 128.31, 125.83, 115.27, 109.60, 81.88, 75.72, 74.57, 72.89, 56.10, 51.83, 45.35, 33.10, 31.19, 20.44, 19.04 |
| F17 | — | — | HRMS-ESI (m/z) [M]$^+$ calcd for C$_{26}$H$_{30}$F$_4$N$_2$O$_7$, 558.1989; found, 558.2001 | $^1$H NMR (CDCl$_3$) δ 11.92 (s, 1H), 8.54 (d, J = 8.3 Hz, 1H), 7.98 (d, J = 5.2 Hz, 1H), 7.20-7.09 (m, 2H), 7.07-6.94 (m, 2H), 6.86 (d, J = 5.2 Hz, 1H), 5.06-4.92 (m, 2H), 4.04 (dd, J = 11.7, 7.2 Hz, 1H), 3.94 (s, 3H), 3.80-3.70 (m, 1H), 3.68-3.57 (m, 1H), 3.51-3.40 (m, 3H), 3.18 (t, J = 8.9 Hz, 1H), 3.02 (dd, J = 13.7, 3.6 Hz, 1H), 2.37 (dd, J = 13.7, 11.6 Hz, 1H), 2.29-2.16 (m, 2H), 1.96-1.81 (m, 3H), 1.50 (d, J = 6.4 Hz, 3H) | $^{13}$C NMR (CDCl$_3$) δ 171.04, 168.92, 161.47 (d, J = 244.4 Hz), 155.35, 148.73, 140.64, 135.10 (d, J = 3.1 Hz), 130.44 (d, J = 7.6 Hz), 130.15, 128.44, 115.33 (d, J = 21.2 Hz), 109.59, 85.08, 75.41, 72.29, 72.18, 70.70, 56.08, 51.50, 47.46, 34.42, 30.73 (q, J = 29.0 Hz), 23.00 (q, J = 2.7 Hz), 18.77 |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| F18 | — | — | HRMS-ESI (m/z) [M]$^+$ calcd for C$_{27}$H$_{33}$FN$_2$O$_7$, 516.2272; found, 516.2280 | $^1$H NMR (CDCl$_3$) δ 11.95 (s, 1H), 8.53 (d, J = 8.3 Hz, 1H), 7.98 (d, J = 5.2 Hz, 1H), 7.19-7.09 (m, 2H), 7.04-6.92 (m, 2H), 6.86 (d, J = 5.3 Hz, 1H), 5.08-4.97 (m, 1H), 4.93 (dt, J = 8.3, 7.2 Hz, 1H), 4.11-4.03 (m, 2H), 3.93 (s, 3H), 3.49-3.42 (m, 2H), 3.40-3.29 (m, 2H), 3.15 (dd, J = 13.8, 3.6 Hz, 1H), 2.34 (dd, J = 13.7, 12.2 Hz, 1H), 1.88-1.54 (m, 7H), 1.60-1.49 (m, 5H) | $^{13}$C NMR (CDCl$_3$) δ 171.17, 168.89, 161.37 (d, J = 243.8 Hz), 155.33, 148.71, 140.61, 135.81 (d, J = 3.1 Hz), 130.45 (d, J = 7.9 Hz), 130.20, 115.24 (d, J = 21.2 Hz), 109.55, 83.58, 83.29, 76.27, 73.25, 72.52, 56.08, 51.77, 47.73, 34.34, 32.70, 32.62, 23.010, 23.006, 18.89 |
| F19 | — | — | HRMS-ESI (m/z) [M]$^+$ calcd for C$_{27}$H$_{35}$FN$_2$O$_7$, 518.2428; found, 518.2431 | $^1$H NMR (CDCl$_3$) δ 11.94 (s, 1H), 8.55 (d, J = 8.4 Hz, 1H), 8.02-7.95 (m, 1H), 7.18-7.11 (m, 2H), 7.03-6.94 (m, 2H), 6.86 (d, J = 5.2 Hz, 1H), 5.06-4.95 (m, 2H), 4.03 (dd, J = 11.7, 7.3 Hz, 1H), 3.93 (s, 3H), 3.72-3.61 (m, 1H), 3.59-3.39 (m, 4H), 3.19-3.07 (m, 2H), 2.33 (dd, J = 13.8, 11.8 Hz, 1H), 1.96-1.85 (m, 1H), 1.67-1.55 (m, 2H), 1.51 (d, J = 6.4 Hz, 3H), 1.41-1.31 (m, 4H), 0.96-0.87 (m, 3H) | $^{13}$C NMR (CDCl$_3$) δ 171.06, 168.91, 161.41 (d, J = 244.0 Hz), 155.33, 148.72, 140.63, 135.48 (d, J = 3.2 Hz), 130.50 (d, J = 7.8 Hz), 130.18, 115.24 (d, J = 21.2 Hz), 109.56, 84.92, 75.84, 72.98, 72.44, 72.33, 56.08, 51.55, 47.59, 34.38, 29.99, 28.34, 22.58, 18.75, 14.01 |
| F20 | — | — | — | $^1$H NMR (CDCl$_3$) δ 11.92 (s, 1H), 8.56 (d, J = 8.3 Hz, 1H), 7.99 (d, J = 5.2 Hz, 1H), 7.35-7.28 (m, 2H), 7.12-7.06 (m, 2H), 7.01-6.91 (m, 5H), 6.87 (d, J = 5.2 Hz, 1H), 5.25-5.14 (m, 1H), 5.13-4.99 (m, 1H), 4.33 (t, J = 8.9 Hz, 1H), 4.14-4.07 (m, 1H), 3.94 (s, 3H), 3.58 (d, J = 4.0 Hz, 2H), 3.49 (dd, J = 11.7, 7.3 Hz, 1H), 3.00 (dd, J = 13.8, 3.4 Hz, 1H), 2.33 (dd, J = 13.8, 11.6 Hz, 1H), 2.20-2.10 (m, 1H), 1.41 (d, J = 6.4 Hz, 3H) | $^{13}$C NMR (CDCl$_3$) δ 171.12, 168.95, 161.44 (d, J = 244.2 Hz), 159.04, 155.37, 148.75, 140.67, 135.01, 130.48 (d, J = 7.9 Hz), 130.14, 129.79, 121.43, 115.41, 115.24 (d, J = 20.8 Hz), 109.61, 81.76, 75.60, 72.26, 71.98, 56.10, 51.49, 47.76, 34.54, 18.98 |
| F21 | — | — | HRMS-ESI (m/z) [M]$^+$ calcd for C$_{26}$H$_{33}$FN$_2$O$_7$, 504.2272; found, 504.2273 | $^1$H NMR (CDCl$_3$) δ 11.94 (s, 1H), 8.54 (d, J = 8.4 Hz, 1H), 7.98 (d, J = 5.2 Hz, 1H), 7.18-7.11 (m, 2H), 7.01-6.95 (m, 2H), 6.86 (d, J = 5.3 Hz, 1H), 5.08-4.91 (m, 2H), 4.04 (dd, J = 11.7, 7.3 Hz, 1H), 3.94 (s, 3H), 3.54-3.38 (m, 4H), 3.33 (dd, J = 8.3, 6.3 Hz, 1H), 3.19-3.06 (m, 2H), 2.33 (dd, J = 13.8, 11.8 Hz, 1H), 1.90 (dq, J = 13.3, 6.8 Hz, 2H), 1.51 (d, J = 6.3 Hz, 3H), 0.96 (d, J = 6.7 Hz, 6H) | $^{13}$C NMR (CDCl$_3$) δ 171.08, 168.91, 161.42 (d, J = 244.3 Hz), 155.34, 148.72, 140.63, 135.50 (d, J = 3.1 Hz), 130.51 (d, J = 8.0 Hz), 130.19, 115.24 (d, J = 21.0 Hz), 109.56, 84.58, 79.44, 77.21, 75.84, 72.29, 56.09, 51.53, 47.68, 34.29, 29.19, 19.48, 18.80 |
| F22 | — | — | HRMS-ESI (m/z) [M]$^+$ calcd for C$_{27}$H$_{32}$N$_2$O$_8$, 512.2159; found, 512.2157 | $^1$H NMR (CDCl$_3$) δ 11.92 (s, 1H), 8.56 (d, J = 8.3 Hz, 1H), 7.98 (d, J = 5.2 Hz, 1H), 7.13-7.08 (m, 2H), 7.08-7.01 (m, 2H), 6.86 (d, J = 5.2 Hz, 1H), 5.15-5.02 (m, 2H), 4.97 (t, J = 9.3 Hz, 1H), 4.01 (dd, J = 11.7, 7.2 Hz, 1H), 3.93 (s, 3H), 3.68-3.62 (m, 1H), 3.58-3.48 (m, 2H), 2.74 (dd, J = 13.9, 3.7 Hz, 1H), 2.31 (s, 3H), 2.28-2.19 (m, 1H), 2.16-2.05 (m, 1H), 1.69-1.60 (m, 1H), 1.36 (d, J = 6.3 Hz, 3H), 1.07-1.01 (m, 2H), 0.96-0.89 (m, 2H) | $^{13}$C NMR (CDCl$_3$) δ 174.28, 171.02, 168.89, 155.35, 148.74, 140.62, 135.85, 135.82, 130.16, 129.22, 128.90, 109.57, 76.93, 74.43, 73.00, 72.54, 56.09, 51.71, 45.83, 34.51, 21.02, 18.26, 12.87, 8.67, 8.65 |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| F23 | — | — | HRMS-ESI (m/z) [M]$^+$ calcd for C$_{27}$H$_{33}$F$_3$N$_2$O$_7$, 554.2240; found, 554.2250 | $^1$H NMR (CDCl$_3$) δ 11.93 (s, 1H), 8.53 (d, J = 8.3 Hz, 1H), 7.98 (d, J = 5.2 Hz, 1H), 7.09 (q, J = 8.1 Hz, 4H), 6.86 (d, J = 5.2 Hz, 1H), 5.05-4.95 (m, 2H), 4.03 (dd, J = 11.7, 7.3 Hz, 1H), 3.93 (s, 3H), 3.80-3.69 (m, 1H), 3.68-3.56 (m, 1H), 3.55-3.49 (m, 1H), 3.49-3.40 (m, 2H), 3.18 (t, J = 8.9 Hz, 1H), 3.02 (dd, J = 13.6, 3.6 Hz, 1H), 2.39-2.28 (m, 4H), 2.27-2.16 (m, 2H), 2.01-1.90 (m, 1H), 1.89-1.80 (m, 2H), 1.49 (d, J = 6.4 Hz, 3H) | $^{13}$C NMR (CDCl$_3$) δ 171.11, 168.90, 155.33, 148.72, 140.63, 136.33, 135.77, 130.17, 129.21, 128.94, 127.09 (q, J = 276.1 Hz), 109.57, 85.10, 75.50, 72.45, 72.18, 70.55, 56.08, 51.49, 47.23, 34.78, 30.76 (q, J = 29.0 Hz), 22.99 (q, J = 3.1 Hz), 21.01, 18.79 |
| F24 | — | — | HRMS-ESI (m/z) [M]$^+$ calcd for C$_{29}$H$_{32}$N$_2$O$_7$, 520.2226; found, 520.2210 | $^1$H NMR (CDCl$_3$) δ 11.93 (s, 1H), 8.56 (d, J = 8.3 Hz, 1H), 7.98 (d, J = 5.2 Hz, 1H), 7.34-7.27 (m, 2H), 7.11-6.93 (m, 7H), 6.86 (d, J = 5.2 Hz, 1H), 5.25-5.14 (m, 1H), 5.05 (q, J = 7.6 Hz, 1H), 4.33 (t, J = 8.9 Hz, 1H), 4.08 (dd, J = 11.7, 7.3 Hz, 1H), 3.93 (s, 3H), 3.79-3.56 (m, 2H), 3.47 (dd, J = 11.7, 7.3 Hz, 1H), 3.01 (dd, J = 13.4, 3.0 Hz, 1H), 2.29 (m, 4H), 2.23-2.11 (m, 1H), 1.41 (d, J = 6.4 Hz, 3H) | $^{13}$C NMR (CDCl$_3$) δ 171.17, 168.92, 159.15, 155.35, 148.74, 140.65, 136.21, 135.68, 130.16, 129.74, 129.13, 128.98, 121.33, 115.48, 109.59, 81.89, 75.69, 72.16, 56.09, 51.49, 47.59, 34.82, 21.02, 19.01 |
| F25 | — | — | HRMS-ESI (m/z) [M]$^+$ calcd for C$_{28}$H$_{36}$N$_2$O$_7$, 512.2523; found, 512.2529 | $^1$H NMR (CDCl$_3$) δ 11.96 (s, 1H), 8.52 (d, J = 8.3 Hz, 1H), 7.98 (d, J = 5.2 Hz, 1H), 7.14-7.04 (m, 4H), 6.85 (d, J = 5.2 Hz, 1H), 5.02 (dq, J = 8.8, 6.5 Hz, 1H), 4.97-4.88 (m, 1H), 4.11-4.01 (m, 2H), 3.93 (s, 3H), 3.51-3.43 (m, 2H), 3.38-3.29 (m, 2H), 3.16 (dd, J = 13.7, 3.6 Hz, 1H), 2.33-2.25 (m, 4H), 1.92-1.62 (m, 7H), 1.61-1.49 (m, 5H) | $^{13}$C NMR (CDCl$_3$) δ 171.23, 168.87, 155.32, 148.71, 140.59, 137.07, 135.53, 130.22, 129.16, 128.97, 109.53, 83.56, 83.37, 76.34, 73.51, 72.38, 56.07, 51.77, 47.49, 34.63, 32.71, 32.62, 23.03, 23.00, 21.02, 18.90 |
| F26 | — | — | HRMS-ESI (m/z) [M]$^+$ calcd for C$_{27}$H$_{29}$F$_3$N$_2$O$_8$, 566.1876; found, 566.1897 | $^1$H NMR (CDCl$_3$) δ 11.90 (s, 1H), 8.58 (d, J = 8.3 Hz, 1H), 7.99 (d, J = 5.2 Hz, 1H), 7.56 (d, J = 8.1 Hz, 2H), 7.29 (d, J = 7.3 Hz, 2H), 6.87 (d, J = 5.2 Hz, 1H), 5.18-4.96 (m, 3H), 4.05 (dd, J = 11.8, 7.2 Hz, 1H), 3.94 (s, 3H), 3.67-3.50 (m, 3H), 2.82 (dd, J = 14.2, 4.3 Hz, 1H), 2.43 (dd, J = 14.2, 10.9 Hz, 1H), 2.22-2.06 (m, 1H), 1.66-1.55 (m, 1H), 1.37 (d, J = 6.3 Hz, 3H), 1.08-0.99 (m, 2H), 0.96-0.88 (m, 2H) | $^{13}$C NMR (CDCl$_3$) δ 174.25, 170.94, 168.92, 155.35, 148.74, 143.29, 140.65, 130.10, 129.31, 128.71 (q, J = 32.3 Hz), 125.45 (q, J = 3.8 Hz), 124.20 (q, J = 271.8 Hz), 109.61, 76.81, 74.26, 72.82, 72.62, 56.08, 51.66, 45.64, 35.09, 18.19, 12.77, 8.80, 8.71 |
| F27 | — | — | HRMS-ESI (m/z) [M]$^+$ calcd for C$_{27}$H$_{33}$F$_3$N$_2$O$_7$, 554.224; found, 554.2258 | $^1$H NMR (CDCl$_3$) δ 11.93 (s, 1H), 8.55 (d, J = 8.3 Hz, 1H), 7.98 (d, J = 5.2 Hz, 1H), 7.55 (d, J = 8.0 Hz, 2H), 7.32 (d, J = 7.9 Hz, 2H), 6.86 (d, J = 5.2 Hz, 1H), 5.08-4.95 (m, 2H), 4.04 (dd, J = 11.7, 7.2 Hz, 1H), 3.93 (s, 3H), 3.52-3.40 (m, 4H), 3.34 (dd, J = 8.3, 6.4 Hz, 1H), 3.25-3.11 (m, 2H), 2.50-2.37 (m, 1H), 2.02-1.93 (m, 1H), 1.93-1.82 (m, 1H), 1.51 (d, J = 6.3 Hz, 3H), 0.96 (d, J = 6.7 Hz, 6H) | $^{13}$C NMR (CDCl$_3$) δ 171.04, 168.93, 155.34, 148.72, 144.20, 140.64, 130.16, 129.45, 128.52 (q, J = 32.5 Hz), 125.39 (q, J = 3.8 Hz), 124.28 (q, J = 271.6 Hz), 109.58, 84.58, 79.56, 75.80, 72.34, 72.26, 56.08, 51.52, 47.48, 34.99, 29.18, 19.46, 18.80 |
| F28 | — | — | HRMS-ESI (m/z) [M]$^+$ | $^1$H NMR (CDCl$_3$) δ 11.94 (s, 1H), 8.54 (d, J = 8.2 Hz, 1H), 7.98 (d, J = 5.2 Hz, 1H), | $^{13}$C NMR (CDCl$_3$) δ 171.13, 168.92, 155.33, 148.71, |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | calcd for C$_{28}$H$_{33}$F$_3$N$_2$O$_7$, 566.2240; found, 566.2241 | 7.55 (d, J = 8.0 Hz, 2H), 7.32 (d, J = 8.0 Hz, 2H), 6.86 (d, J = 5.2 Hz, 1H), 5.09-4.98 (m, 1H), 4.94 (q, J = 7.4 Hz, 1H), 4.16-4.04 (m, 2H), 3.93 (s, 3H), 3.50-3.31 (m, 4H), 3.23 (dd, J = 13.7, 3.5 Hz, 1H), 2.45 (dd, J = 13.7, 12.2 Hz, 1H), 1.96-1.66 (m, 7H), 1.63-1.55 (m, 2H), 1.53 (d, J = 6.5 Hz, 3H) | 144.53, 140.63, 130.16, 129.40, 128.45 (q, J = 32.1 Hz), 125.38 (q, J = 3.8 Hz), 124.29 (q, J = 271.9 Hz), 109.58, 83.64, 83.25, 76.23, 73.16, 72.59, 56.07, 51.77, 47.48, 35.04, 32.70, 32.62, 23.00, 18.89 |
| F29 | — | — | HRMS-ESI (m/z) [M]$^+$ calcd for C$_{26}$H$_{31}$F$_3$N$_2$O$_7$, 540.2083; found, 540.2101 | $^1$H NMR (CDCl$_3$) δ 11.93 (s, 1H), 8.56 (d, J = 8.3 Hz, 1H), 7.98 (d, J = 5.2 Hz, 1H), 7.58-7.49 (m, 2H), 7.32 (d, J = 8.0 Hz, 2H), 6.86 (d, J = 5.2 Hz, 1H), 5.07-4.95 (m, 2H), 4.04 (dd, J = 11.7, 7.2 Hz, 1H), 3.93 (s, 3H), 3.66 (dt, J = 8.6, 6.6 Hz, 1H), 3.57-3.39 (m, 4H), 3.23-3.13 (m, 2H), 2.43 (dd, J = 13.7, 11.7 Hz, 1H), 2.03-1.91 (m, 1H), 1.70-1.59 (m, 2H), 1.52 (d, J = 6.4 Hz, 3H), 0.97 (t, J = 7.4 Hz, 3H) | $^{19}$F NMR (CDCl$_3$) δ −62.35 |
| F30 | — | — | HRMS-ESI (m/z) [M]$^+$ calcd for C$_{24}$H$_{31}$F$_3$N$_2$O$_8$, 568.2033; found, 568.2060 | $^1$H NMR (CDCl$_3$) δ 11.90 (s, 1H), 8.56 (d, J = 8.3 Hz, 1H), 7.99 (d, J = 5.2 Hz, 1H), 7.56 (d, J = 8.0 Hz, 2H), 7.27 (d, J = 8.0 Hz, 2H), 6.87 (d, J = 5.2 Hz, 1H), 5.19-4.96 (m, 3H), 4.06 (dd, J = 11.8, 7.2 Hz, 1H), 3.94 (s, 3H), 3.58-3.49 (m, 3H), 2.77 (dd, J = 14.0, 3.9 Hz, 1H), 2.59 (hept, J = 7.0 Hz, 1H), 2.41 (dd, J = 14.1, 11.4 Hz, 1H), 2.19-2.07 (m, 1H), 1.36 (d, J = 6.3 Hz, 3H), 1.22 (app dd, J = 7.0, 2.9 Hz, 6H) | $^{19}$F NMR (CDCl$_3$) δ −62.43 |
| F31 | — | — | HRMS-ESI (m/z) [M]$^+$ calcd for C$_{28}$H$_{35}$F$_3$N$_2$O$_7$, 568.2396; found, 568.2425 | $^1$H NMR (CDCl$_3$) δ 11.93 (s, 1H), 8.55 (d, J = 8.3 Hz, 1H), 7.98 (d, J = 5.2 Hz, 1H), 7.62-7.52 (m, 2H), 7.32 (d, J = 8.0 Hz, 2H), 6.86 (d, J = 5.2 Hz, 1H), 5.06-4.96 (m, 2H), 4.04 (dd, J = 11.7, 7.2 Hz, 1H), 3.93 (s, 3H), 3.73-3.65 (m, 1H), 3.59-3.51 (m, 1H), 3.51-3.39 (m, 3H), 3.23-3.13 (m, 2H), 2.43 (dd, J = 13.7, 11.7 Hz, 1H), 2.03-1.90 (m, 1H), 1.67-1.56 (m, 2H), 1.52 (d, J = 6.4 Hz, 3H), 1.41-1.29 (m, 4H), 0.94-0.87 (m, 3H) | $^{19}$F NMR (CDCl$_3$) δ −62.34 |
| F32 | — | — | HRMS-ESI (m/z) [M]$^+$ calcd for C$_{21}$H$_{29}$F$_3$N$_2$O$_7$, 478.1927; found, 478.1923 | $^1$H NMR (CDCl$_3$) δ 11.91 (s, 1H), 8.57 (d, J = 8.3 Hz, 1H), 8.00 (d, J = 5.2 Hz, 1H), 6.88 (d, J = 5.2 Hz, 1H), 5.09-4.91 (m, 2H), 4.13 (dd, J = 11.8, 7.3 Hz, 1H), 3.94 (s, 3H), 3.75-3.65 (m, 2H), 3.53 (dd, J = 11.8, 7.5 Hz, 1H), 3.42 (dd, J = 8.4, 6.4 Hz, 1H), 3.21 (dd, J = 8.4, 6.4 Hz, 1H), 3.12 (t, J = 8.8 Hz, 1H), 2.51-2.33 (m, 1H), 2.25-2.11 (m, 1H), 2.11-2.00 (m, 1H), 1.92-1.77 (m, 1H), 1.49 (d, J = 6.5 Hz, 3H), 0.93 (d, J = 6.7 Hz, 6H) | $^{13}$C NMR (CDCl$_3$) δ 171.00, 168.95, 155.36, 148.74, 140.67, 130.15, 127.00 (q, J = 277.3 Hz), 109.61, 83.19, 78.88, 75.68, 72.80, 72.22, 56.10, 51.39, 40.00, 32.61 (q, J = 28.3 Hz) 29.05, 19.30, 18.86 |
| F33 | — | — | HRMS-ESI (m/z) | $^1$H NMR (CDCl$_3$) δ 11.92 (s, 1H), 8.56 (d, J = 8.3 Hz, 1H), | $^{19}$F NMR (CDCl$_3$) δ −63.68 |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | [M]$^+$ calcd for C$_{22}$H$_{29}$F$_3$N$_2$O$_7$, 490.1927; found, 490.1929 | 8.00 (d, J = 5.2 Hz, 1H), 6.88 (d, J = 5.2 Hz, 1H), 5.04 (dq, J = 8.2, 6.5 Hz, 1H), 4.93 (td, J = 8.1, 6.7 Hz, 1H), 4.18 (dd, J = 11.7, 6.7 Hz, 1H), 4.04-3.90 (m, 4H), 3.69 (qd, J = 11.8, 4.2 Hz, 2H), 3.47 (dd, J = 11.7, 8.0 Hz, 1H), 3.28 (t, J = 7.8 Hz, 1H), 2.60-2.41 (m, 1H), 2.22-2.08 (m, 1H), 2.03-1.90 (m, 1H), 1.83-1.65 (m, 5H), 1.65-1.53 (m, 3H), 1.49 (d, J = 6.5 Hz, 3H) | |
| F34 | — | — | HRMS-ESI (m/z) [M]$^+$ calcd for C$_{24}$H$_{38}$N$_2$O$_7$, 466.2679; found, 466.2685 | $^1$H NMR (CDCl$_3$) δ 11.97 (s, 1H), 8.63 (d, J = 8.2 Hz, 1H), 7.99 (d, J = 5.2 Hz, 1H), 6.87 (d, J = 5.2 Hz, 1H), 5.08-4.93 (m, 2H), 4.06 (dd, J = 11.8, 7.0 Hz, 1H), 3.94 (s, 3H), 3.72-3.62 (m, 2H), 3.52 (dd, J = 10.8, 6.4 Hz, 1H), 3.35 (dd, J = 8.3, 6.4 Hz, 1H), 3.27 (dd, J = 8.3, 6.3 Hz, 1H), 3.03 (t, J = 9.1 Hz, 1H), 1.84 (hept, J = 6.6 Hz, 1H), 1.73-1.57 (m, 2H), 1.57-1.49 (m, 1H), 1.46 (d, J = 6.4 Hz, 3H), 1.36-1.22 (m, 1H), 1.21-1.08 (m, 2H), 0.93 (d, J = 6.7 Hz, 6H), 0.89 (app dd, J = 6.6, 3.5 Hz, 6H) | $^{13}$C NMR (CDCl$_3$) δ 170.88, 168.91, 155.30, 148.70, 140.62, 130.25, 109.54, 84.49, 78.95, 75.98, 75.35, 72.89, 56.07, 51.93, 45.81, 36.05, 29.13, 28.38, 26.71, 22.76, 22.42, 19.48, 18.89 |
| F35 | — | — | HRMS-ESI (m/z) [M]$^+$ calcd for C$_{24}$H$_{35}$F$_3$N$_2$O$_7$, 520.2396; found, 520.2407 | $^1$H NMR (CDCl$_3$) δ 11.95 (s, 1H), 8.62 (d, J = 8.3 Hz, 1H), 8.00 (d, J = 5.2 Hz, 1H), 6.87 (d, J = 5.2 Hz, 1H), 5.10-4.90 (m, 2H), 4.07 (dd, J = 11.8, 7.1 Hz, 1H), 3.94 (s, 3H), 3.70-3.60 (m, 3H), 3.60-3.49 (m, 2H), 3.07 (t, J = 8.9 Hz, 1H), 2.29-2.12 (m, 2H), 1.89-1.77 (m, 2H), 1.68-1.48 (m, 3H), 1.46 (d, J = 6.4 Hz, 3H), 1.36-1.24 (m, 1H), 1.23-1.08 (m, 2H), 0.92-0.86 (m, 6H) | $^{13}$C NMR (CDCl$_3$) δ 170.88, 168.93, 155.33, 148.72, 140.65, 130.21, 127.12 (q J = 276.0 Hz), 109.56, 84.96, 75.58, 74.93, 72.81, 70.28, 56.08, 51.84, 45.71, 35.99, 30.77 (q, J = 29.0 Hz), 28.33, 26.85 22.96 (q, J = 3.1 Hz), 22.74, 22.33, 18.90 |
| F36 | — | — | HRMS-ESI (m/z) [M]$^+$ calcd for C$_{24}$H$_{34}$N$_2$O$_8$, 478.2315; found, 478.2324 | $^1$H NMR (CDCl$_3$) δ 11.94 (s, 1H), 8.65 (d, J = 8.2 Hz, 1H), 8.00 (d, J = 5.1 Hz, 1H), 6.88 (d, J = 5.3 Hz, 1H), 5.12-5.01 (m, 2H), 4.88 (t, J = 9.4 Hz, 1H), 4.07 (dd, J = 11.8, 7.0 Hz, 1H), 3.94 (s, 3H), 3.81-3.70 (m, 2H), 3.59 (dd, J = 10.8, 7.1 Hz, 1H), 1.80-1.69 (m, 1H), 1.69-1.60 (m, 1H), 1.52-1.41 (m, 1H), 1.37-1.31 (m, 4H), 1.29-0.99 (m, 5H), 0.95-0.89 (m, 2H), 0.89-0.82 (m, 6H) | $^{13}$C NMR (CDCl$_3$) δ 174.11, 170.79, 168.92, 155.33, 148.73, 140.63, 130.19, 109.57, 76.49, 75.39, 74.56, 73.14, 56.08, 52.02, 44.50, 35.31, 28.19, 26.98, 22.69, 22.17, 18.31, 12.83, 8.41 |
| F37 | — | — | HRMS-ESI (m/z) [M]$^+$ calcd for C$_{27}$H$_{36}$N$_2$O$_7$, 500.2523; found, 500.2521 | $^1$H NMR (CDCl$_3$) δ 11.95 (s, 1H), 8.65 (d, J = 8.3 Hz, 1H), 8.00 (d, J = 5.1 Hz, 1H), 7.14-7.03 (m, 2H), 6.87 (d, J = 5.2 Hz, 1H), 6.85-6.77 (m, 2H), 5.15 (dt, J = 8.9, 6.4 Hz, 1H), 5.06 (dt, J = 8.3, 6.8 Hz, 1H), 4.21-4.06 (m, 2H), 3.94 (s, 3H), 3.79-3.59 (m, 3H), 2.29 (s, 3H), 1.87-1.77 (m, 1H), 1.63-1.49 (m, 1H), 1.37 (d, J = 6.4 Hz, 4H), 1.22-1.07 (m, 3H), 0.79 (d, J = 6.6 Hz, 3H), 0.75 (d, J = 6.5 Hz, 3H) | $^{13}$C NMR (CDCl$_3$) δ 170.90, 168.95, 157.07, 155.34, 148.73, 140.66, 130.38, 130.22, 130.06, 115.23, 109.58, 82.05, 75.82, 74.82, 72.86, 56.09, 51.87, 45.99, 35.93, 28.04, 27.00, 22.79, 22.13, 20.44, 19.09 |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| F38 | — | — | HRMS-ESI (m/z) [M]$^+$ calcd for C$_{23}$H$_{36}$N$_2$O$_7$, 452.2523; found, 452.2516 | $^1$H NMR (CDCl$_3$) δ 11.97 (s, 1H), 8.64 (d, J = 8.3 Hz, 1H), 7.99 (d, J = 5.2 Hz, 1H), 6.87 (d, J = 5.2 Hz, 1H), 5.08-4.91 (m, 2H), 4.06 (dd, J = 11.8, 7.0 Hz, 1H), 3.94 (s, 3H), 3.73-3.63 (m, 2H), 3.59-3.41 (m, 3H), 3.04 (t, J = 9.1 Hz, 1H), 1.71-1.50 (m, 5H), 1.47 (d, J = 6.4 Hz, 3H), 1.34-1.24 (m, 1H), 1.23-1.09 (m, 2H), 0.94 (t, J = 7.4 Hz, 3H), 0.89 (app dd, J = 6.6, 4.0 Hz, 6H) | $^{13}$C NMR (CDCl$_3$) δ 170.88, 168.91, 155.30, 148.69, 140.63, 130.23, 109.54, 84.76, 75.99, 75.32, 74.08, 72.88, 56.07, 51.91, 45.79, 36.01, 28.35, 26.79, 23.43, 22.78, 22.37, 18.85, 10.70 |
| F39 | — | — | HRMS-ESI (m/z) [M]$^+$ calcd for C$_{25}$H$_{38}$N$_2$O$_7$, 478.2679; found, 478.2686 | $^1$H NMR (CDCl$_3$) δ 11.98 (d, J = 0.6 Hz, 1H), 8.63 (d, J = 8.2 Hz, 1H), 7.99 (d, J = 5.2 Hz, 1H), 6.87 (dd, J = 5.3, 0.6 Hz, 1H), 5.07-4.90 (m, 2H), 4.16-4.04 (m, 1H), 4.02-3.96 (m, 1H), 3.94 (s, 3H), 3.69-3.59 (m, 2H), 3.55 (dd, J = 11.4, 6.3 Hz, 1H), 3.19 (t, J = 8.5 Hz, 1H), 1.79-1.60 (m, 1H), 1.59-1.50 (m, 4H), 1.47 (d, J = 6.4 Hz, 3H), 1.36-1.27 (m, 1H), 1.20-1.04 (m, 2H), 0.89 (app dd, J = 6.6, 4.4 Hz, 6H) | $^{13}$C NMR (CDCl$_3$) δ 170.91, 168.90, 155.30, 148.69, 140.60, 130.27, 109.52, 83.55, 83.23, 76.61, 76.32, 73.36, 56.06, 52.25, 46.20, 36.70, 32.59, 32.53, 28.43, 26.81, 23.06, 23.02, 22.73, 22.49, 18.94 |
| F40 | — | — | HRMS-ESI (m/z) [M]$^+$ calcd for C$_{26}$H$_{31}$F$_3$N$_2$O$_7$, 540.2083; found, 540.2091 | $^1$H NMR (CDCl$_3$) δ 11.92 (s, 1H), 8.55 (d, J = 8.3 Hz, 1H), 7.99 (d, J = 5.2 Hz, 1H), 6.90-6.77 (m, 3H), 5.08-4.93 (m, 2H), 4.06 (dd, J = 11.8, 7.2 Hz, 1H), 3.94 (s, 3H), 3.52-3.41 (m 4H) 3.30 (dd J = 8.4, 6.3 Hz, 1H), 3.17-3.00 (m, 2H), 2.33 (dd, J = 13.8, 11.8 Hz, 1H), 1.94-1.80 (m, 2H), 1.50 (d, J = 6.4 Hz, 3H), 0.96 (app dd, J = 6.7, 1.4 Hz, 6H) | $^{19}$F NMR (CDCl$_3$) δ −134.7 (dd, J = 20.4, 8.1 Hz), −163.8--164.1 (m) |
| F41 | 79-82 | — | HRMS-ESI (m/z) [M]$^+$ calcd for C$_{26}$H$_{30}$Cl$_2$N$_2$O$_8$, 568.1379; found, 568.1385 | $^1$H NMR (CDCl$_3$) δ 11.91 (s, 1H), 8.54 (d, J = 8.3 Hz, 1H), 7.98 (d, J = 5.2 Hz, 1H), 7.36 (s, 1H), 7.20-7.13 (m, 2H), 6.87 (d, J = 5.2 Hz, 1H), 5.18-4.96 (m, 3H), 4.10 (dd, J = 11.7, 7.3 Hz, 1H), 3.94 (s, 3H), 3.59-3.43 (m, 3H), 2.81 (dd, J = 13.9, 3.6 Hz, 1H), 2.62 (p, J = 7.0 Hz, 1H), 2.60-2.56 (m, 1H), 2.16 (bs, 1H), 1.36 (d, J = 6.3 Hz, 3H), 1.23 (d, J = 7.0 Hz, 6H) | $^{13}$C NMR (CDCl$_3$) δ 176.29, 171.06, 168.93, 155.36, 148.75, 140.64, 135.15, 134.89, 132.98, 132.37, 130.10, 129.51, 127.14, 109.61, 76.52, 74.17, 72.27, 71.61, 56.09, 51.46, 43.98, 34.22, 32.31, 19.04, 18.97, 18.16. |
| F42 | 60-64 | — | HRMS-ESI (m/z) [M]$^+$ calcd for C$_{26}$H$_{32}$Cl$_2$N$_2$O$_7$, 554.1585; found, 554.1584 | $^1$H NMR (CDCl$_3$) δ 11.94 (s, 1H), 8.56 (d, J = 8.1 Hz, 1H), 7.98 (d, J = 5.2 Hz, 1H), 7.36 (s, 1H), 7.26-7.10 (m, 2H), 6.86 (d, J = 5.3 Hz, 1H), 5.09-4.95 (m, 2H), 4.06 (dd, J = 11.7, 7.2 Hz, 1H), 3.93 (s, 3H), 3.51-3.40 (m, 4H), 3.36 (dd, J = 8.3, 6.5 Hz, 1H), 3.23-3.08 (m, 2H), 2.62-2.46 (m, 1H), 2.10-1.98 (m, 1H), 1.88 (dq, J = 13.2, 6.6 Hz, 1H), 1.51 (d, J = 6.4 Hz, 3H), 0.95 (d, J = 7.5 Hz, 6H) | $^{13}$C NMR (CDCl$_3$) δ 171.01, 168.91, 155.32, 148.71, 140.63, 136.12, 135.03, 132.57, 132.13, 130.15, 129.35, 127.09, 109.57, 84.92, 79.81, 75.84, 72.36, 60.38, 56.07, 51.57, 45.89, 32.10, 29.16, 19.48, 18.75 |
| F43 | 50-54 | — | HRMS-ESI (m/z) [M]$^+$ calcd for C$_{27}$H$_{34}$Cl$_2$N$_2$O$_7$ 568.1743; | $^1$H NMR (CDCl$_3$) δ 11.94 (s, 1H), 8.55 (d, J = 8.2 Hz, 1H), 7.98 (d, J = 5.2 Hz, 1H), 7.36 (s, 1H), 7.24-7.11 (m, 2H), 6.86 (d, J = 5.2 Hz, 1H), 5.09-4.92 (m, 2H), 4.06 (dd, J = 11.7, | $^{13}$C NMR (CDCl$_3$) δ 171.03, 168.92, 155.33, 148.71, 140.64, 136.10, 135.03, 132.59, 132.11, 130.16, |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | found, 568.1763 | 7.2 Hz, 1H), 3.93 (s, 3H), 3.74-3.63 (m, 1H), 3.57 (q, J = 8.4, 7.5 Hz, 1H), 3.50-3.37 (m, 3H), 3.24-3.08 (m, 2H), 2.62-2.48 (m, 1H), 2.07-1.98 (m, 1H), 1.64-1.55 (m, 2H), 1.51 (d, J = 6.4 Hz, 3H), 1.39-1.28 (m, 4H), 0.90 (t, J = 7.1 Hz, 3H) | 109.57, 85.20, 75.84, 73.35, 72.34, 72.19, 56.08, 51.54, 45.87, 32.17, 29.97, 28.33, 22.58, 18.72, 14.02 |
| F44 | 81-85 | — | HRMS-ESI (m/z) [M]$^+$ calcd for C$_{29}$H$_{30}$Cl$_2$N$_2$O$_7$, 588.1430; found, 588.1425 | $^1$H NMR (CDCl$_3$) δ 11.94 (s, 1H), 8.57 (d, J = 8.3 Hz, 1H), 7.97 (d, J = 5.2 Hz, 1H), 7.32 (s, 1H), 7.15 (s, 2H), 7.10 (d, J = 8.3 Hz, 2H), 6.91-6.83 (m, 3H), 5.26-5.13 (m, 1H), 5.06 (q, J = 7.5 Hz, 1H), 4.31 (t, J = 8.8 Hz, 1H), 4.20-4.04 (m, 1H), 3.92 (s, 3H), 3.65-3.37 (m, 3H), 3.05 (dd, J = 13.7, 3.5 Hz, 1H), 2.61-2.45 (m, 1H), 2.29 (s, 3H), 2.28-2.21 (m, 1H), 1.42 (d, J = 6.5 Hz, 3H) | $^{13}$C NMR (CDCl$_3$) δ 171.12, 168.97, 156.95, 155.35, 148.74, 140.67, 135.75, 134.96, 132.70, 132.22, 130.69, 130.20, 129.38, 127.05, 115.16, 109.63, 81.93, 77.32, 75.60, 72.16, 71.59, 56.09, 51.45, 46.08, 32.40, 20.45, 18.93 |
| F45 | 55-59 | — | HRMS-ESI (m/z) [M]$^+$ calcd for C$_{25}$H$_{36}$N$_2$O$_8$, 492.2472; found, 492.2488 | $^1$H NMR (CDCl$_3$) δ 11.94 (s, 1H), 8.61 (d, J = 8.2 Hz, 1H), 8.00 (d, J = 5.2 Hz, 1H), 6.88 (d, J = 5.1 Hz, 1H), 5.11-5.01 (m, 2H), 4.81 (t, J = 9.2 Hz, 1H), 4.10 (dd, J = 11.8, 7.2 Hz, 1H), 3.94 (s, 3H), 3.77-3.59 (m, 3H), 2.59 (hept, J = 7.0 Hz, 1H), 1.90-0.95 (m, 12H), 1.32 (d, J = 6.4 Hz, 3H), 1.20 (d, J = 7.0 Hz, 6H) | $^{13}$C NMR (CDCl$_3$) δ 176.19, 171.00, 168.92, 155.35, 148.75, 140.63, 130.19, 109.58, 74.52, 74.16, 72.60, 56.09, 51.75, 43.55, 37.20, 35.00, 34.26, 33.62, 32.13, 25.02, 19.03, 18.32 |
| F46 | 132-134 | — | HRMS-ESI (m/z) [M]$^+$ calcd for C$_{25}$H$_{38}$N$_2$O$_7$, 478.2679; found, 478.2673 | $^1$H NMR (CDCl$_3$) δ 11.97 (s, 1H), 8.61 (d, J = 8.2 Hz, 1H), 7.99 (d, J = 5.2 Hz, 1H), 6.87 (d, J = 5.2 Hz, 1H), 5.11-4.85 (m, 2H), 4.09 (dd, J = 11.7, 7.1 Hz, 1H), 3.94 (s, 3H), 3.71-3.47 (m, 3H), 3.37 (dd, J = 8.3, 6.3 Hz, 1H), 3.25 (dd, J = 8.2, 6.7 Hz, 1H), 2.98 (t, J = 8.9 Hz, 1H), 1.95-1.49 (m, 10H), 1.46 (d, J = 6.4 Hz, 3H), 1.31-1.21 (m, 1H), 1.15-1.05 (m, 2H), 0.92 (dd, J = 6.7, 4.3 Hz, 6H) | $^{13}$C NMR (CDCl$_3$) δ 171.04, 168.91, 155.31, 148.70, 140.61, 130.25, 109.54, 84.92, 79.14, 76.03, 74.47, 72.53, 56.06, 51.75, 44.72, 37.39, 34.94, 33.86, 32.01, 29.13, 25.05, 19.51, 18.83 |
| F47 | 109-111 | — | HRMS-ESI (m/z) [M]$^+$ calcd for C$_{26}$H$_{40}$N$_2$O$_7$, 492.2836; found, 492.2840 | $^1$H NMR (CDCl$_3$) δ 11.97 (s, 1H), 8.61 (d, J = 8.3 Hz, 1H), 7.99 (d, J = 5.2 Hz, 1H), 6.87 (d, J = 5.2 Hz, 1H), 5.09-4.85 (m, 2H), 4.08 (dd, J = 11.7, 7.1 Hz, 1H), 3.94 (s, 3H), 3.74-3.35 (m, 5H), 2.99 (t, J = 9.0 Hz, 1H), 1.96-1.83 (m, 1H), 1.83-1.71 (m, 2H), 1.72-1.48 (m, 8H), 1.47 (d, J = 6.4 Hz, 3H), 1.38-1.22 (m, 5H), 1.17-1.02 (m, 2H), 0.94-0.86 (m, 3H) | $^{13}$C NMR (CDCl$_3$) δ 171.05, 168.91, 155.32, 148.71, 140.62, 130.25, 109.54, 85.26, 76.03, 74.51, 72.55, 56.07, 51.75, 44.71, 37.40, 35.09, 33.85, 32.05, 29.95, 28.37, 25.10, 22.56, 18.80, 14.00 |
| F48 | — | — | HRMS-ESI (m/z) [M + H]$^+$ calcd for C$_{27}$H$_{37}$N$_2$O$_7$, 501.2595; found, 501.2602 | $^1$H NMR (CDCl$_3$) δ 11.95 (s, 1H), 8.54 (d, J = 8.3 Hz, 1H), 7.97 (d, J = 5.2 Hz, 1H), 7.09 (d, J = 2.1 Hz, 4H), 6.85 (d, J = 5.2 Hz, 1H), 5.01 (m, 2H), 3.92 (s, 3H), 4.02 (dd, J = 11.7, 7.3 Hz, 1H), 3.49 (d, J = 7.7 Hz, 1H), 3.44 (m, 3H), 3.34 (dd, J = 8.3, 6.5 Hz, 1H), 3.13 (m, 2H), 2.31 (s, 4H), 1.89 (dt, J = 13.2, 6.6 Hz, 2H), 1.50 (d, J = 6.4 Hz, 3H), 0.96 (d, J = 6.7 Hz, 6H) | $^{13}$C NMR (CDCl$_3$) δ 171.15, 168.90, 155.31, 148.71, 140.62, 136.76, 135.58, 130.20, 129.15, 129.05, 109.56, 84.61, 79.28, 75.92, 72.53, 72.16, 56.08, 51.53, 47.47, 34.60, 29.20, 21.03, 19.50, 18.83 |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| F49 | 59-64 | — | HRMS-ESI (m/z) [M + H]$^+$ calcd for C$_{29}$H$_{36}$F$_3$N$_2$O$_8$, 597.2418, found, 597.2446 | $^1$H NMR (CDCl$_3$) δ 8.65 (d, J = 8.7 Hz, 1H), 8.34 (d, J = 5.4 Hz, 1H), 7.33-7.24 (m, 2H), 7.24-7.13 (m, 3H), 7.01 (d, J = 5.4 Hz, 1H), 5.07-4.88 (m, 2H), 4.08 (dd, J = 11.7, 7.1 Hz, 1H), 3.90 (s, 3H), 3.71 (dd, J = 10.9, 1.7 Hz, 1H), 3.67-3.42 (m, 4H), 3.08 (app t, J = 8.9 Hz, 1H), 2.78 (ddd, J = 14.5, 10.3, 4.8 Hz, 1H), 2.55 (ddd, J = 13.7, 9.9, 6.8 Hz, 1H), 2.39 (s, 3H), 2.23-2.05 (m, 2H), 1.93-1.82 (m, 1H), 1.81-1.74 (m, 2H), 1.73-1.65 (m, 1H), 1.60-1.45 (m, 1H), 1.42 (d, J = 6.4 Hz, 3H) | — |
| F50 | 61-65 | — | HRMS-ESI (m/z) [M + H]$^+$ calcd for C$_{29}$H$_{39}$N$_2$O$_8$, 543.2701, found, 543.2714 | $^1$H NMR (CDCl$_3$) δ 8.66 (d, J = 7.9 Hz, 1H), 8.33 (d, J = 5.4 Hz, 1H), 7.33-7.23 (m, 2H), 7.23-7.14 (m, 3H), 7.00 (d, J = 5.4 Hz, 1H), 5.08-4.91 (m, 2H), 4.07 (dd, J = 11.7, 7.1 Hz, 1H), 3.89 (s, 3H), 3.73 (dd, J = 11.0, 1.6 Hz, 1H), 3.65-3.55 (m, 2H), 3.33-3.18 (m, 2H), 3.06 (app t, J = 9.0 Hz, 1H), 2.76 (ddd, J = 13.7, 10.9, 4.7 Hz, 1H), 2.56 (ddd, J = 13.7, 10.3, 6.4 Hz, 1H), 2.39 (s, 3H), 1.96 (dddd, J = 13.7, 10.9, 6.6, 3.0 Hz, 1H), 1.88-1.65 (m, 2H), 1.56-1.41 (m, 4H), 0.89 (app dd, J = 6.7, 0.7 Hz, 6H) | — |
| F51 | 104-108 | — | HRMS-ESI (m/z) [M + H]$^+$ calcd for C$_{32}$H$_{37}$N$_2$O$_9$, 593.2494; found, 593.2502 | $^1$H NMR (CDCl$_3$) δ 8.53 (d, J = 8.2 Hz, 1H), 8.27 (d, J = 5.4 Hz, 1H), 8.01-7.94 (m, 1H), 7.88-7.81 (m, 1H), 7.73 (d, J = 8.2 Hz, 1H), 7.55-7.43 (m, 2H), 7.39 (dd, J = 8.2, 7.0 Hz, 1H), 7.29 (dd, J = 7.0, 1.2 Hz, 1H), 6.96 (d, J = 5.4 Hz, 1H), 5.18-5.02 (m, 3H), 4.00 (dd, J = 11.7, 7.4 Hz, 1H), 3.86 (s, 3H), 3.58 (d, J = 4.2 Hz, 2H), 3.37 (dd, J = 11.7, 7.2 Hz, 1H), 3.22 (dd, J = 14.1, 3.1 Hz, 1H), 2.76-2.63 (m, 2H), 2.38 (s, 3H), 2.34-2.22 (m, 1H), 1.38 (d, J = 5.7 Hz, 3H), 1.28 (app dd, J = 7.0, 3.7 Hz, 6H) | — |
| F52 | 85-91 | — | HRMS-ESI (m/z) [M + H]$^+$ calcd for C$_{33}$H$_{41}$N$_2$O$_8$, 593.2857; found, 593.2867 | $^1$H NMR (CDCl$_3$) δ 8.51 (d, J = 8.5 Hz, 1H), 8.28 (d, J = 5.4 Hz, 1H), 8.19 (dd, J = 8.6, 1.4 Hz, 1H), 7.87-7.80 (m, 1H), 7.72 (d, J = 8.1 Hz, 1H), 7.55-7.42 (m, 2H), 7.39 (dd, J = 8.1, 7.0 Hz, 1H), 7.32 (dd, J = 6.9, 1.3 Hz, 1H), 6.96 (d, J = 5.4 Hz, 1H), 5.06-4.88 (m, 2H), 4.03 (dd, J = 11.7, 7.6 Hz, 1H), 3.91-3.77 (m, 4H), 3.77-3.62 (m, 2H), 3.57-3.38 (m, 2H), 3.32-3.20 (m, 2H), 2.76-2.65 (m, 1H), 2.38 (s, 3H), 2.11-2.04 (m, 1H), 1.79-1.67 (m, 2H), 1.54 (d, J = 6.4 Hz, 3H), 1.51-1.32 (m, 4H), 0.92 (t, J = 7.1 Hz, 3H) | — |
| F53 | — | — | HRMS-ESI (m/z) [M + H]$^+$ calcd for | $^1$H NMR (CDCl$_3$) δ 8.56 (d, J = 8.4 Hz, 1H), 8.31 (d, J = 5.4 Hz, 1H), 7.14-7.04 (m, 4H), 6.98 (d, J = 5.5 Hz, 1H), | $^{13}$C NMR (CDCl$_3$) δ 171.66, 168.83, 162.65, 159.40, 146.75, 141.13, |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | C$_{30}$H$_{41}$N$_2$O$_8$, 557.2857; found, 557.286 | 5.05-4.91 (m, 2H), 3.97 (dd, J = 11.7, 7.3 Hz, 1H), 3.88 (s, 3H), 3.72-3.61 (m, 1H), 3.59-3.46 (m, 2H), 3.46-3.34 (m, 2H), 3.17-3.05 (m, 2H), 2.38 (s, 3H), 2.31 (s, 3H), 2.28-2.23 (m, 1H), 1.99-1.86 (m, 1H), 1.66-1.55 (m, 2H), 1.49 (d, J = 6.3 Hz, 3H), 1.41-1.28 (m, 4H), 0.94-0.86 (m, 3H) | 137.49, 136.78, 135.54, 129.12, 129.11, 129.04, 109.91, 84.93, 75.71, 72.67, 72.37, 56.29, 51.61, 47.32, 34.72, 30.01, 28.36, 22.59, 21.02, 20.72, 18.80, 14.03. |
| F54 | 88-93 | — | HRMS-ESI (m/z) [M + H]$^+$ calcd for C$_{29}$H$_{37}$N$_2$O$_9$, 557.2494; found, 557.2497 | $^1$H NMR (CDCl$_3$) δ 8.58 (d, J = 8.3 Hz, 1H), 8.32 (d, J = 5.4 Hz, 1H), 7.13-7.06 (m, 2H), 7.06-6.96 (m, 3H), 5.13-5.00 (m, 2H), 4.95 (app t, J = 9.3 Hz, 1H), 3.98 (dd, J = 11.7, 7.3 Hz, 1H), 3.89 (s, 3H), 3.60 (dd, J = 10.8, 1.7 Hz, 1H), 3.55-3.41 (m, 2H), 2.67 (dd, J = 13.8, 3.5 Hz, 1H), 2.64-2.52 (m, 1H), 2.38 (s, 3H), 2.31 (s, 3H), 2.22 (dd, J = 13.7, 11.6 Hz, 1H), 2.14-2.01 (m, 1H), 1.33 (d, J = 6.3 Hz, 3H), 1.21 (app dd, J = 7.0, 1.6 Hz, 6H) | — |
| F55 | — | — | HRMS-ESI (m/z) [M + Na]$^+$ calc for C$_{30}$H$_{40}$N$_2$O$_8$Na, 579.2677; found, 579.2684 | $^1$H NMR (CDCl$_3$) δ 8.67 (d, J = 8.2 Hz, 1H), 8.33 (d, J = 5.4 Hz, 1H), 7.33-7.24 (m, 2H), 7.23-7.14 (m, 3H), 6.99 (d, J = 5.5 Hz, 1H), 5.08-4.90 (m, 2H), 4.07 (dd, J = 11.7, 7.1 Hz, 1H), 3.88 (s, 3H), 3.74 (dd, J = 10.9, 1.6 Hz, 1H), 3.65-3.55 (m, 2H), 3.55-3.39 (m, 2H), 3.06 (app t, J = 9.1 Hz, 1H), 2.76 (ddd, J = 13.7, 10.9, 4.7 Hz, 1H), 2.56 (ddd, J = 13.8, 10.4, 6.3 Hz, 1H), 2.39 (s, 3H), 2.02-1.89 (m, 1H), 1.76-1.64 (m, 1H), 1.59-1.41 (m, 6H), 1.37-1.24 (m, 4H), 0.93-0.84 (m, 3H) | $^{13}$C NMR (CDCl$_3$) δ 171.41, 168.84, 162.72, 159.42, 146.79, 142.18, 141.15, 137.52, 128.39, 128.36, 125.84, 109.95, 84.68, 75.68, 74.69, 73.08, 72.27, 56.30, 51.95, 45.18, 33.30, 31.11, 29.97, 28.37, 22.59, 20.74, 18.85, 14.03 |
| F56 | 74-79 | — | HRMS-ESI (m/z) [M + H]$^+$ calcd for C$_{28}$H$_{34}$FN$_2$O$_9$, 561.2243; found 561.2263 | $^1$H NMR (CDCl$_3$) δ 8.59 (d, J = 8.1 Hz, 1H), 8.32 (d, J = 5.4 Hz, 1H), 7.14-7.05 (m, 2H), 7.03-6.93 (m, 3H), 5.14-5.01 (m, 2H), 4.95 (app t, J = 9.3 Hz, 1H), 4.01 (dd, J = 11.7, 7.3 Hz, 1H), 3.89 (s, 3H), 3.61-3.43 (m, 3H), 2.68 (dd, J = 14.0, 3.8 Hz, 1H), 2.64-2.52 (m, 1H), 2.38 (s, 3H), 2.27 (dd, J = 14.1, 11.3 Hz, 1H), 2.11-1.98 (m, 1H), 1.33 (d, J = 6.3 Hz, 3H), 1.22 (app dd, J = 7.0, 1.8 Hz, 6H) | — |
| F57 | — | — | HRMS-ESI (m/z) [M]$^+$ calcd for C$_{28}$H$_{34}$FN$_2$O$_9$, 554.2264; found, 554.2267 | $^1$H NMR (CDCl$_3$) δ 8.67 (d, J = 8.4 Hz, 1H), 8.34 (d, J = 5.4 Hz, 1H), 7.30-7.25 (m, 2H), 7.21-7.11 (m, 3H), 7.01 (d, J = 5.5 Hz, 1H), 5.13-5.05 (m, 1H), 5.05-4.97 (m, 1H), 4.92 (t, J = 9.3 Hz, 1H), 4.08 (dd, J = 11.8, 7.2 Hz, 1H), 3.91 (s, 3H), 3.83 (dd, J = 10.9, 1.5 Hz, 1H), 3.72-3.62 (m, 2H), 2.77-2.66 (m, 1H), 2.53-2.42 (m, 1H), 2.40 (s, 3H), 1.89-1.79 (m, 1H), 1.68-1.57 (m, 2H), 1.57-1.44 (m, | $^{13}$C NMR (CDCl$_3$) δ 174.16, 171.34, 168.86, 162.71, 159.45, 146.76, 141.76, 141.11, 137.56, 128.39, 128.32, 125.92, 109.95, 76.26, 74.46, 74.34, 73.14, 56.31, 51.94, 43.87, 32.45, 31.32, 20.73, 18.30, 12.88, 8.55 |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | | 1H), 1.32 (d, J = 6.3 Hz, 3H), 1.04-0.96 (m, 2H), 0.93-0.85 (m, 2H) | |
| F58 | — | — | HRMS-ESI (m/z) [M]$^+$ calcd for C$_{32}$H$_{36}$N$_2$O$_8$, 576.2472; found, 576.2492 | $^1$H NMR (CDCl$_3$) δ 8.67 (d, J = 8.3 Hz, 1H), 8.35 (d, J = 5.5 Hz, 1H), 7.24-7.18 (m, 2H), 7.18-7.10 (m, 1H), 7.09-7.05 (m, 2H), 7.03-6.98 (m, 3H), 6.85-6.79 (m, 2H), 5.17-5.03 (m, 2H), 4.19 (t, J = 8.9 Hz, 1H), 4.12 (dd, J = 11.7, 7.2 Hz, 1H), 3.91 (s, 3H), 3.80 (dd, J = 10.9, 1.7 Hz, 1H), 3.72 (dd, J = 10.9, 6.5 Hz, 1H), 3.62 (dd, J = 11.7, 6.7 Hz, 1H), 2.72-2.61 (m, 1H), 2.57-2.46 (m, 1H), 2.40 (s, 3H), 2.28 (s, 3H), 1.97-1.80 (m, 2H), 1.60-1.47 (m, 1H), 1.36 (d, J = 6.4 Hz, 3H) | $^{13}$C NMR (CDCl$_3$) δ 171.39, 168.87, 162.73, 159.44, 156.97, 146.79, 141.76, 141.14, 137.55, 130.48, 130.13, 128.35, 128.29, 125.80, 115.27, 109.95, 81.87, 75.55, 74.33, 73.05, 56.31, 51.91, 45.40, 33.08, 31.25, 20.74, 20.43, 19.06 |
| F59 | — | — | HRMS-ESI (m/z) [M]$^+$ calcd for C$_{30}$H$_{31}$FN$_2$O$_8$, 566.2064; found, 566.2073 | $^1$H NMR (CDCl$_3$) δ 8.59 (d, J = 8.5 Hz, 1H), 8.33 (d, J = 5.5 Hz, 1H), 7.36-7.28 (m, 2H), 7.15-7.04 (m, 2H), 7.04-6.87 (m, 6H), 5.22-5.12 (m, 1H), 5.05 (dt, J = 8.6, 7.4 Hz, 1H), 4.30 (t, J = 8.9 Hz, 1H), 4.10-4.03 (m, 1H), 3.90 (s, 3H), 3.55 (d, J = 4.1 Hz, 2H), 3.43 (dd, J = 11.7, 7.4 Hz, 1H), 2.98 (dd, J = 13.8, 3.3 Hz, 1H), 2.39 (s, 3H), 2.31 (dd, J = 13.8, 11.6 Hz, 1H), 2.19-2.07 (m, 1H), 1.38 (d, J = 6.4 Hz, 3H) | $^{13}$C NMR (CDCl$_3$) δ 171.64, 168.85, 162.71, 161.42 (d, J = 244.2 Hz), 159.44, 159.08, 146.77, 141.07, 137.55, 135.07, 130.49 (d, J = 7.8 Hz), 129.77, 121.37, 115.42, 115.20 (d, J = 21.2 Hz), 109.96, 81.77, 75.41, 72.42, 71.74, 56.31, 51.57, 47.76, 34.57, 20.73, 18.99 |
| F60 | — | — | ESIMS m/z 546 [M$^+$] | $^1$H NMR (CDCl$_3$) δ 8.56 (d, J = 8.5 Hz, 1H), 8.32 (d, J = 5.4 Hz, 1H), 7.20-7.09 (m, 2H), 7.03-6.93 (m, 3H), 4.99 (ddd, J = 9.0, 7.9, 6.8 Hz, 2H), 4.00 (dd, J = 11.7, 7.3 Hz, 1H), 3.90 (s, 3H), 3.50-3.28 (m, 5H), 3.20-3.02 (m, 2H), 2.38 (s, 3H), 2.30 (dd, J = 13.7, 11.7 Hz, 1H), 1.88 (ddt, J = 13.3, 8.6, 4.8 Hz, 2H), 1.48 (d, J = 6.4 Hz, 3H), 0.96 (d, J = 6.7 Hz, 6H) | $^{19}$F NMR (CDCl$_3$) δ −117.24 |
| F61 | — | — | HRMS-ESI (m/z) [M]$^+$ calcd for C$_{29}$H$_{34}$N$_2$O$_9$, 554.2264; found, 554.2270 | $^1$H NMR (CDCl$_3$) δ 8.59 (d, J = 8.4 Hz, 1H), 8.32 (d, J = 5.4 Hz, 1H), 7.14-6.96 (m, 5H), 5.12-5.01 (m, 2H), 4.94 (t, J = 9.3 Hz, 1H), 3.97 (dd, J = 11.7, 7.3 Hz, 1H), 3.90 (s, 3H), 3.65-3.57 (m, 1H), 3.54-3.43 (m, 2H), 2.72 (dd, J = 14.0, 3.7 Hz, 1H), 2.38 (s, 3H), 2.31 (s, 3H), 2.26-2.18 (m, 1H), 2.14-2.04 (m, 1H), 1.69-1.61 (m, 1H), 1.34 (d, J = 6.3 Hz, 3H), 1.07-1.01 (m, 2H), 0.97-0.86 (m, 2H) | $^{13}$C NMR (CDCl$_3$) δ 174.28, 171.55, 168.85, 162.65, 159.43, 146.72, 141.09, 137.54, 135.88, 135.80, 129.20, 128.90, 109.91, 76.96, 74.25, 72.66, 56.29, 51.73, 45.83, 34.56, 21.02, 20.72, 18.26, 12.88, 8.64, 8.61 |
| F62 | — | — | HRMS-ESI (m/z) [M]$^+$ calcd for C$_{29}$H$_{35}$F$_3$N$_2$O$_8$, 596.2346; found, 596.2353 | $^1$H NMR (CDCl$_3$) δ 8.56 (d, J = 8.5 Hz, 1H), 8.32 (d, J = 5.5 Hz, 1H), 7.15-7.04 (m, 4H), 6.99 (d, J = 5.5 Hz, 1H), 5.04-4.91 (m, 2H), 3.99 (dd, J = 11.7, 7.4 Hz, 1H), 3.89 (s, 3H), 3.79-3.65 (m, 1H), 3.63-3.54 (m, 1H), 3.52-3.32 (m, 3H), 3.16 (t, J = 9.0 Hz, 1H), 3.00 (dd, J = 13.6, 3.6 Hz, 1H), 2.38 (s, 3H), 2.32 (s, 4H), 2.28-2.14 (m, 2H), 1.99-1.90 (m, 1H), | $^{13}$C NMR (CDCl$_3$) δ 171.65, 168.84, 162.66, 159.42, 146.74, 141.10, 137.51, 136.40, 135.72, 129.18, 128.95, 127.11 (q, J = 276.0 Hz), 109.91, 85.06, 75.31, 72.31, 72.16, 70.41, 56.29, 51.55, 47.18, 34.80, 30.77 (q, J = 29.1 Hz), 23.00 (q, J = 3.3 Hz), |

TABLE 2-continued

Analytical Data

| Cmpd No. | MP (° C.) | IR (cm⁻¹) | Mass | ¹H NMR | ¹³C or ¹⁹F NMR |
|---|---|---|---|---|---|
| | | | | 1.90-1.79 (m, 2H), 1.47 (d, J = 6.4 Hz, 3H) | 21.01, 20.72, 18.81 |
| F63 | — | — | HRMS-ESI (m/z) [M]⁺ calcd for $C_{31}H_{34}N_2O_8$, 562.2315; found, 562.2339 | ¹H NMR (CDCl₃) δ 8.58 (d, J = 8.4 Hz, 1H), 8.33 (d, J = 5.4 Hz, 1H), 7.35-7.28 (m, 2H), 7.09-6.91 (m, 8H), 5.21-5.11 (m, 1H), 5.05 (dt, J = 8.6, 7.5 Hz, 1H), 4.30 (t, J = 8.8 Hz, 1H), 4.04 (dd, J = 11.7, 7.4 Hz, 1H), 3.90 (s, 3H), 3.61-3.52 (m, 2H), 3.42 (dd, J = 11.7, 7.4 Hz, 1H), 2.99 (dd, J = 13.3, 2.9 Hz, 1H), 2.39 (s, 3H), 2.29 (s, 3H), 2.28-2.21 (m, 1H), 2.20-2.14 (m, 1H), 1.39 (d, J = 6.4 Hz, 3H) | ¹³C NMR (CDCl₃) δ 171.70, 168.85, 162.68, 159.43, 159.19, 141.10, 137.54, 136.27, 135.63, 129.71, 129.10, 128.98, 121.26, 115.49, 109.94, 81.91, 75.51, 72.32, 71.93, 56.31, 53.43, 51.57, 47.60, 34.85, 21.01, 20.73, 19.03 |
| F64 | — | — | HRMS-ESI (m/z) [M]⁺ calcd for $C_{30}H_{38}N_2O_8$, 554.2628; found, 554.2639 | ¹H NMR (CDCl₃) δ 8.54 (d, J = 8.4 Hz, 1H), 8.32 (d, J = 5.4 Hz, 1H), 7.13-7.04 (m, 4H), 6.99 (d, J = 5.5 Hz, 1H), 5.04-4.88 (m, 2H), 4.08 (td, J = 5.6, 3.6 Hz, 1H), 4.01 (dd, J = 11.6, 7.0 Hz, 1H), 3.89 (s, 3H), 3.50-3.41 (m, 2H), 3.35-3.24 (m, 2H), 3.14 (dd, J = 13.7, 3.5 Hz, 1H), 2.38 (s, 3H), 2.31 (s, 3H), 2.27 (dd, J = 13.5, 12.1 Hz, 1H), 1.91-1.63 (m, 7H), 1.63-1.52 (m, 2H), 1.50 (d, J = 6.5 Hz, 3H) | ¹³C NMR (CDCl₃) δ 171.77, 168.86, 162.63, 159.40, 146.73, 141.20, 137.49, 137.15, 135.49, 129.13, 128.99, 109.87, 83.51, 83.43, 76.13, 73.22, 72.55, 56.29, 51.85, 47.49, 34.67, 32.73, 32.63, 23.02, 22.99, 21.02, 20.73, 18.93 |
| F65 | — | — | HRMS-ESI (m/z) [M]⁺ calcd for $C_{29}H_{35}F_3N_2O_8$, 596.2346; found, 596.2358 | ¹H NMR (CDCl₃) δ 8.57 (d, J = 8.5 Hz, 1H), 8.32 (d, J = 5.5 Hz, 1H), 7.55 (d, J = 8.0 Hz, 2H), 7.31 (d, J = 8.0 Hz, 2H), 7.00 (d, J = 5.5 Hz, 1H), 5.05-4.94 (m, 2H), 4.00 (dd, J = 11.7, 7.3 Hz, 1H), 3.90 (s, 3H), 3.52-3.28 (m, 5H), 3.21-3.10 (m, 2H), 2.47-2.35 (m, 4H), 2.02-1.83 (m, 2H), 1.49 (d, J = 6.3 Hz, 3H), 0.96 (d, J = 6.7 Hz, 6H) | ¹³C NMR (CDCl₃) δ 171.57, 168.83, 162.68, 159.42, 146.74, 144.26, 141.11, 137.52, 129.45, 128.49 (q, J = 32.2 Hz), 125.37 (q, J = 3.7 Hz), 109.91, 84.54, 79.41, 75.59, 72.48, 71.94, 56.29, 51.57, 47.42, 35.02, 29.18, 20.71, 19.46, 18.81 |
| F66 | — | — | HRMS-ESI (m/z) [M]⁺ calcd for $C_{30}H_{35}F_3N_2O_8$, 608.2346; found, 608.2360 | ¹H NMR (CDCl₃) δ 8.55 (d, J = 8.2 Hz, 1H), 8.32 (d, J = 5.4 Hz, 1H), 7.55 (d, J = 8.0 Hz, 2H), 7.32 (d, J = 8.0 Hz, 2H), 7.00 (d, J = 5.5 Hz, 1H), 5.05-4.88 (m, 2H), 4.18-3.97 (m, 2H), 3.90 (s, 3H), 3.49-3.37 (m, 2H), 3.36-3.26 (m, 2H), 3.21 (dd, J = 13.6, 3.5 Hz, 1H), 2.49-2.40 (m, 1H), 2.38 (s, 3H), 1.96-1.55 (m, 9H), 1.51 (d, J = 6.5 Hz, 3H) | ¹³C NMR (CDCl₃) δ 171.66, 168.84, 162.66, 159.41, 146.75, 144.59, 141.14, 137.51, 129.41, 128.43 (q, J = 32.4 Hz), 125.34 (q, J = 3.9 Hz), 124.30 (q, J = 271.9 Hz), 109.91, 83.58, 83.29, 76.01, 72.84, 72.75, 56.29, 51.83, 47.46, 35.08, 32.72, 32.63, 23.00, 20.72, 18.91 |
| F67 | — | — | HRMS-ESI (m/z) [M]⁺ calcd for $C_{29}H_{33}F_3N_2O_9$, 610.2138; found, 610.2139 | ¹H NMR (CDCl₃) δ 8.66-8.51 (m, 1H), 8.32 (d, J = 5.4 Hz, 1H), 7.59-7.50 (m, 2H), 7.26 (d, J = 8.0 Hz, 2H), 7.00 (d, J = 5.5 Hz, 1H), 5.14-5.03 (m, 2H), 4.98 (t, J = 9.3 Hz, 1H), 4.02 (dd, J = 11.7, 7.3 Hz, 1H), 3.90 (s, 3H), 3.58-3.42 (m, 3H), 2.75 (dd, J = 14.1, 3.9 Hz, 1H), 2.61-2.52 (m, 1H), 2.44-2.32 (m, 4H), 2.17-2.06 (m, 1H), 1.34 (d, J = 6.3 Hz, 3H), 1.21 (app dd, J = 7.0, 2.8 Hz, 6H) | ¹⁹F NMR (CDCl₃) δ −62.43 |
| F68 | — | — | HRMS-ESI (m/z) [M]⁺ calcd for | ¹H NMR (CDCl₃) δ 8.74-8.59 (m, 1H), 8.33 (d, J = 5.4 Hz, 1H), 7.00 (d, J = 5.4 Hz, 1H), 5.02 (dt, J = 8.4, 6.7 Hz, | ¹³C NMR (CDCl₃) δ 171.42, 168.84, 162.69, 159.40, 146.76, 141.19, |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | C$_{26}$H$_{40}$N$_2$O$_8$, 508.2785; found, 508.2786 | 1H), 4.95 (dq, J = 9.3, 6.4 Hz, 1H), 4.02 (dd, J = 11.8, 7.1 Hz, 1H), 3.90 (s, 3H), 3.65 (dd, J = 10.6, 1.5 Hz, 1H), 3.59 (dd, J = 11.8, 6.4 Hz, 1H), 3.50 (dd, J = 10.7, 6.6 Hz, 1H), 3.34 (dd, J = 8.4, 6.4 Hz, 1H), 3.26 (dd, J = 8.3, 6.3 Hz, 1H), 3.01 (t, J = 9.1 Hz, 1H), 2.39 (s, 3H), 1.83 (hept, J = 6.6 Hz, 1H), 1.71-1.48 (m, 3H), 1.44 (d, J = 6.4 Hz, 3H), 1.36-1.23 (m, 1H), 1.20-1.07 (m, 2H), 0.92 (d, J = 6.7 Hz, 6H), 0.88 (app dd, J = 6.6, 3.4 Hz, 6H) | 137.50, 109.88, 84.40, 78.81, 75.80, 75.04, 73.02, 56.29, 51.97, 45.74, 35.99, 29.13, 28.40, 26.73, 22.76, 22.43, 20.73, 19.49, 18.90 |
| F69 | — | — | HRMS-ESI (m/z) [M]$^+$ calcd for C$_{29}$H$_{38}$N$_2$O$_8$, 542.2628; found, 542.2634 | $^1$H NMR (CDCl$_3$) δ 8.68 (d, J = 8.3 Hz, 1H), 8.34 (d, J = 5.4 Hz, 1H), 7.12-7.04 (m, 2H), 7.01 (d, J = 5.5 Hz, 1H), 6.85-6.75 (m, 2H), 5.18-5.01 (m, 2H), 4.17-4.02 (m, 2H), 3.91 (s, 3H), 3.72 (dd, J = 10.9, 1.6 Hz, 1H), 3.62 (dd, J = 11.4, 6.7 Hz, 2H), 2.39 (s, 3H), 2.28 (s, 3H), 1.90-1.77 (m, 1H) 1.60-1.47 (m, 1H), 1.43-1.31 (m, 4H), 1.22-1.07 (m, 3H), 0.78 (d, J = 6.6 Hz, 3H), 0.74 (d, J = 6.6 Hz, 3H) | $^{13}$C NMR (CDCl$_3$) δ 171.43, 168.85, 162.72, 159.43, 157.12, 146.78, 141.15, 137.54, 130.30, 130.04, 115.23, 109.92, 82.03, 75.65, 74.56, 73.01, 56.30, 51.93, 45.98, 35.88, 28.04, 27.01, 22.78, 22.12 20.73, 20.43, 19.10 |
| F70 | — | — | HRMS ESI (m/z) [M]$^+$ calcd for C$_{25}$H$_{38}$N$_2$O$_8$, 494.2628; found, 494.2632 | $^1$H NMR (CDCl$_3$) δ 8.66 (d, J = 8.4 Hz, 1H), 8.33 (d, J = 5.4 Hz, 1H), 7.00 (d, J = 5.5 Hz, 1H), 5.02 (ddd, J = 8.4, 7.2, 6.4 Hz, 1H), 4.94 (dq, J = 9.2, 6.4 Hz, 1H), 4.02 (dd, J = 11.8, 7.1 Hz, 1H), 3.90 (s, 3H), 3.70-3.41 (m, 5H), 3.02 (t, J = 9.2 Hz, 1H), 2.39 (s, 3H), 1.71-1.48 (m, 5H), 1.45 (d, J = 6.3 Hz, 3H), 1.36-1.21 (m, 1H), 1.22-1.08 (m, 2H), 0.94 (t, J = 7.4 Hz, 3H), 0.88 (app dd, J = 6.6, 3.9 Hz, 6H) | $^{13}$C NMR (CDCl$_3$) δ 171.42, 168.84, 162.69, 159.40, 146.75, 141.18, 137.50, 109.88, 84.69, 75.81, 75.01, 73.95, 73.02, 56.29, 51.95, 45.72, 35.96, 28.37, 26.81, 23.44, 22.77, 22.37, 20.72, 18.87, 10.69 |
| F71 | — | — | HRMS ESI (m/z) [M]$^+$ calcd for C$_{27}$H$_{40}$N$_2$O$_8$, 520.2785; found, 520.2802 | $^1$H NMR (CDCl$_3$) δ 8.65 (d, J = 8.2 Hz, 1H), 8.34 (d, J = 5.4 Hz, 1H), 7.00 (d, J = 5.5 Hz, 1H), 5.03-4.89 (m, 2H), 4.06 (dd, J = 11.8, 6.6 Hz, 1H), 4.02-3.95 (m, 1H), 3.90 (s, 3H), 3.68-3.47 (m, 3H), 3.16 (t, J = 8.5 Hz, 1H), 2.39 (s, 3H), 1.79-1.59 (m, 7H), 1.59-1.48 (m, 4H), 1.45 (d, J = 6.5 Hz, 3H), 1.37-1.22 (m, 1H), 1.18-1.01 (m, 2H), 0.88 (app dd, J = 6.6, 4.3 Hz, 6H) | $^{13}$C NMR (CDCl$_3$) δ 171.44, 168.85, 162.67, 159.39, 146.74, 141.25, 137.49, 109.85, 83.57, 83.18, 76.33, 76.13, 73.53, 56.28, 52.31, 46.18, 36.66, 32.62, 32.55, 28.46, 26.85, 23.06, 23.02, 22.73, 22.50, 20.73, 18.97 |
| F72 | — | — | HRMS-ESI (m/z) [M]$^+$ calcd for C$_{28}$H$_{33}$F$_3$N$_2$O$_8$, 582.2189; found, 582.2197 | $^1$H NMR (CDCl$_3$) δ 8.58 (d, J = 8.6 Hz, 1H), 8.32 (d, J = 5.4 Hz, 1H), 7.00 (d, J = 5.5 Hz, 1H), 6.81 (dd, J = 8.3, 6.4 Hz, 2H), 5.06-4.91 (m, 2H), 4.02 (dd, J = 11.7, 7.2 Hz, 1H), 3.90 (s, 3H), 3.51-3.36 (m, 4H), 3.29 (dd, J = 8.3, 6.3 Hz, 1H), 3.10 (t, J = 9.0 Hz, 1H), 3.04 (dd, J = 13.8, 3.4 Hz, 1H), 2.38 (s, 3H), 2.31 (dd, J = 13.8, 11.8 Hz, 1H), 1.87 (dt, J = 13.3, 6.7 Hz, 2H), 1.48 (d, J = 6.4 Hz, 3H), 0.95 (app dd, J = 6.7, 1.3 Hz, 6H) | $^{19}$F NMR (CDCl$_3$) δ −134.78 (d, J = 20.5 Hz), −163.99 (t, J = 21.0 Hz) |

TABLE 2-continued

Analytical Data

| Cmpd No. | MP (° C.) | IR (cm⁻¹) | Mass | ¹H NMR | ¹³C or ¹⁹F NMR |
|---|---|---|---|---|---|
| F73 | 93-97 | — | HRMS-ESI (m/z) [M]⁺ calcd for $C_{28}H_{32}Cl_2N_2O_9$, 610.1485; found, 610.1498 | ¹H NMR (CDCl₃) δ 8.57 (d, J = 7.7 Hz, 1H), 8.32 (d, J = 5.4 Hz, 1H), 7.35 (d, J = 1.9 Hz, 1H), 7.25-7.07 (m, 2H), 7.00 (d, J = 5.5 Hz, 1H), 5.21-4.78 (m, 3H), 4.06 (dd, J = 11.7, 7.3 Hz, 1H), 3.90 (s, 3H), 3.63-3.28 (m, 3H), 2.79 (dd, J = 13.9, 3.5 Hz, 1H), 2.61 (dt, J = 14.0, 7.0 Hz, 1H), 2.55-2.44 (m, 1H), 2.39 (s, 3H), 2.18-2.10 (m, 1H), 1.34 (d, J = 6.3 Hz, 3H), 1.22 (d, J = 7.0 Hz, 6H) | ¹³C NMR (CDCl₃) δ 176.30, 171.57, 168.84, 162.67, 159.44, 146.74, 141.02, 137.54, 135.21, 134.88, 132.93, 132.38, 129.47, 127.11, 109.96, 76.57, 73.96, 72.41, 71.29, 56.30, 51.52, 44.02, 34.22, 32.33, 20.72, 18.97, 18.16 |
| F74 | 69-73 | — | HRMS-ESI (m/z) [M]⁺ calcd for $C_{28}H_{34}Cl_2N_2O_8$, 596.1692; found, 596.1707 | ¹H NMR (CDCl₃) δ 8.58 (d, J = 7.7 Hz, 1H), 8.32 (d, J = 5.4 Hz, 1H), 7.36 (d, J = 1.7 Hz, 1H), 7.24-7.11 (m, 2H), 7.00 (d, J = 5.5 Hz, 1H), 5.00 (p, J = 7.5, 7.0 Hz, 2H), 4.02 (dd, J = 11.7, 7.3 Hz, 1H), 3.89 (s, 3H), 3.58-3.23 (m, 5H), 3.23-3.02 (m, 2H), 2.60-2.46 (m, 1H), 2.38 (s, 3H), 2.08-1.98 (m, 1H), 1.89 (dq, J = 13.2, 6.6 Hz, 1H), 1.49 (d, J = 6.4 Hz, 3H), 0.95 (dd, J = 6.7, 1.1 Hz, 6H) | ¹³C NMR (CDCl₃) δ 171.54, 168.83, 162.68, 159.41, 146.75, 141.11, 137.51, 136.18, 135.04, 132.53, 132.14, 129.33, 127.08, 109.92, 84.94, 79.71, 75.64, 72.53, 71.92, 56.30, 51.64, 45.90, 32.12, 29.17, 20.72, 19.49, 18.77 |
| F75 | 55-59 | — | HRMS-ESI (m/z) [M]⁺ calcd for $C_{29}H_{36}Cl_2N_2O_8$, 610.1849; found, 610.1862 | ¹H NMR (CDCl₃) δ 8.57 (d, J = 7.7 Hz, 1H), 8.32 (d, J = 5.4 Hz, 1H), 7.36 (d, J = 1.8 Hz, 1H), 7.25-7.10 (m, 2H), 7.00 (d, J = 5.5 Hz, 1H), 5.07-4.89 (m, 2H), 4.02 (dd, J = 11.7, 7.3 Hz, 1H), 3.90 (s, 3H), 3.75-3.62 (m, 1H), 3.61-3.50 (m, 1H), 3.42-3.37 (m, 3H), 3.23-2.97 (m, 2H), 2.54 (dd, J = 13.6, 12.2 Hz 1H), 2.39 (s, 3H), 2.06-1.96 (m, 1H), 1.62-1.57 (m, 2H), 1.49 (d, J = 6.4 Hz, 3H), 1.43-1.19 (m, 4H), 0.89 (d, J = 6.7 Hz, 3H) | ¹³C NMR (CDCl₃) δ 171.57, 168.84, 162.68, 159.42, 146.75, 141.12, 137.51, 136.17, 135.04, 132.55, 132.12, 129.34, 127.08, 109.92, 85.22, 73.24, 72.50, 71.87, 56.30, 51.61, 45.87, 32.18, 31.59, 29.97, 28.33, 22.66, 20.72, 18.72, 14.01 |
| F76 | 97-101 | — | HRMS-ESI (m/z) [M]⁺ calcd for $C_{31}H_{32}Cl_2N_2O_8$, 630.1536; found, 630.1531 | ¹H NMR (CDCl₃) δ 8.59 (d, J = 7.8 Hz, 1H), 8.32 (d, J = 5.4 Hz, 1H), 7.32 (s, 1H), 7.14 (d, J = 1.1 Hz, 2H), 7.10 (d, J = 8.3 Hz, 2H), 7.00 (d, J = 5.5 Hz, 1H), 6.88 (d, J = 8.6 Hz, 2H), 5.22-5.10 (m, 1H), 5.04 (q, J = 7.6 Hz, 1H), 4.28 (t, J = 8.8 Hz, 1H), 4.08 (dd, J = 11.7, 7.4 Hz, 1H), 3.89 (s, 3H), 3.56 (dd, J = 11.1, 6.3 Hz, 1H), 3.48 (d, J = 10.3 Hz, 1H), 3.40 (dd, J = 11.6, 7.6 Hz, 1H), 3.04 (dd, J = 13.7, 3.5 Hz, 1H), 2.57-2.45 (m, 1H), 2.39 (s, 3H), 2.29 (s, 3H), 2.28-2.17 (m, 1H), 1.40 (d, J = 6.4 Hz, 3H) | ¹³C NMR (CDCl₃) δ 171.62, 168.84, 162.71, 159.45, 156.98, 146.77, 141.08, 137.55, 135.80, 134.97, 132.67, 132.22, 130.64, 130.18, 129.37, 127.03, 115.16, 109.97, 81.99, 75.40, 72.37, 71.35, 56.31, 51.54, 46.13, 32.39, 20.73, 20.44, 18.94 |
| F77 | 66-69 | — | HRMS-ESI (m/z) [M]⁺ calcd for $C_{27}H_{38}N_2O_9$, 534.2577; found, 534.2581 | ¹H NMR (CDCl₃) δ 8.64 (d, J = 7.8 Hz, 1H), 8.33 (d, J = 5.4 Hz, 1H), 7.01 (d, J = 5.5 Hz, 1H), 5.12-5.04 (m, 1H), 5.01 (dd, J = 9.3, 6.4 Hz, 1H), 4.79 (t, J = 9.3 Hz, 1H), 4.07 (dd, J = 11.7, 7.3 Hz, 1H), 3.90 (s, 3H), 3.72 (d, J = 10.7 Hz, 1H), 3.65-3.54 (m, 2H), 2.58 (p, J = 7.0 Hz, 1H), 2.39 (s, 3H), 1.90-1.69 (m, 4H), | ¹³C NMR (CDCl₃) δ 176.17, 171.52, 168.81, 162.67, 159.43, 146.74, 141.07, 137.53, 109.95, 74.32, 73.78, 72.68, 56.29, 51.76, 43.57, 37.19, 35.02, 34.25, 33.62, 32.13, 25.01, 20.70, 18.96, 18.31 |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | | 1.61-1.45 (m, 4H), 1.30 (d, J = 6.4 Hz, 3H), 1.20 (d, J = 7.0 Hz, 6H), 1.11-0.94 (m, 4H) | |
| F78 | 56-59 | — | HRMS-ESI (m/z) [M]$^+$ calcd for C$_{27}$H$_{40}$N$_2$O$_8$, 520.2785; found, 520.2798 | $^1$H NMR (CDCl$_3$) δ 8.62 (d, J = 7.5 Hz, 1H), 8.34 (d, J = 5.4 Hz, 1H), 7.00 (d, J = 5.5 Hz, 1H), 5.04-4.97 (m, 1H), 4.94 (dd, J = 9.1, 6.4 Hz, 1H), 4.05 (dd, J = 11.7, 7.2 Hz, 1H), 3.90 (s, 3H), 3.62 (d, J = 9.6 Hz, 1H), 3.56-3.47 (m, 2H), 3.36 (dd, J = 8.3, 6.2 Hz, 1H), 3.23 (dd, J = 8.3, 6.6 Hz, 1H), 2.96 (t, J = 9.0 Hz, 1H), 2.39 (s, 3H), 1.93-1.71 (m, 4H), 1.69-1.47 (m, 5H), 1.44 (d, J = 6.4 Hz, 3H), 1.30-1.19 (m, 2H), 1.15-1.01 (m, 2H), 0.92 (dd, J = 6.7, 4.5 Hz, 6H) | $^{13}$C NMR (CDCl$_3$) δ 171.59, 168.85, 162.68, 159.41, 146.75, 141.20, 109.88, 84.88, 79.01, 75.87, 74.17, 72.68, 56.29, 51.80, 44.70, 37.39, 34.95, 33.89, 32.03, 29.14, 25.09, 20.72, 19.53, 18.86 |
| F79 | 46-51 | — | HRMS-ESI (m/z) [M]$^+$ calcd for C$_{28}$H$_{42}$N$_2$O$_8$, 534.2941; found, 534.2945 | $^1$H NMR (CDCl$_3$) δ 8.63 (d, J = 7.6 Hz, 1H), 8.33 (d, J = 5.4 Hz, 1H), 7.00 (d, J = 5.5 Hz, 1H), 5.01 (q, J = 7.1 Hz, 1H), 4.93 (dd, J = 9.1, 6.4 Hz, 1H), 4.04 (dd, J = 11.7, 7.2 Hz, 1H), 3.90 (s, 3H), 3.67-3.41 (m, 5H), 2.96 (t, J = 9.1 Hz, 1H), 2.39 (s, 3H), 1.95-1.83 (m, 1H), 1.82-1.71 (m, 2H), 1.67-1.47 (m, 8H), 1.44 (d, J = 6.4 Hz, 3H), 1.37-1.23 (m, 5H), 1.15-1.01 (m, 2H), 0.90 (t, J = 7.2 Hz, 3H) | $^{13}$C NMR (CDCl$_3$) δ 171.58, 168.81, 162.67, 159.40, 146.75, 141.17, 137.49, 109.90, 85.23, 75.84, 74.21, 72.50, 56.28, 51.79, 44.69, 37.39, 35.09, 33.85, 32.05, 29.94, 28.36, 25.06, 22.56, 20.70, 18.81, 14.00 |
| F80 | — | — | HRMS-FAB (m/z) [M + Na]$^+$ calcd for C$_{29}$H$_{38}$N$_2$O$_8$Na, 565.2520; found, 565.2516 | $^1$H NMR (CDCl$_3$) δ 8.56 (d, J = 7.8 Hz, 1H), 8.31 (d, J = 5.4 Hz, 1H), 7.08 (d, J = 2.4 Hz, 4H), 6.98 (d, J = 5.5 Hz, 1H), 4.99 (m, 2H), 3.98 (dd, J = 11.7, 7.4 Hz, 1H), 3.88 (s, 3H), 3.40 (m, 6H), 3.11 (m, 2H), 2.38 (s, 3H), 2.31 (s, 3H), 2.26 (m, 1H), 1.90 (ddd, J = 19.8, 13.5, 6.8 Hz, 2H), 1.48 (d, J = 6.4 Hz, 3H), 0.95 (d, J = 6.7 Hz, 6H) | $^{13}$C NMR (CDCl$_3$) δ 171.68, 168.84, 162.66, 159.41, 146.75, 141.13, 137.49, 136.82, 135.54, 129.13, 129.06, 109.91, 84.57, 79.12, 75.72, 72.32, 72.25, 56.30, 51.59, 47.41, 34.62, 29.19, 21.03, 20.73, 19.51, 18.85 |
| F81 | 45-50 | — | HRMS-ESI (m/z) [M + H]$^+$ calcd for C$_{31}$H$_{41}$N$_2$O$_9$, 585.2807; found, 585.2831 | $^1$H NMR (CDCl$_3$) δ 8.49 (d, J = 8.0 Hz, 1H), 8.29 (d, J = 5.4 Hz, 1H), 7.33-7.24 (m, 2H), 7.22-7.15 (m, 3H), 6.96 (d, J = 5.4 Hz, 1H), 5.78-5.69 (m, 2H), 5.05-4.93 (m, 2H), 4.19-4.08 (m, 1H), 4.02-3.92 (m, 1H), 3.91 (s, 3H), 3.76-3.55 (m, 3H), 3.22 (app t, J = 8.3 Hz, 1H), 2.76 (ddd, J = 13.8, 11.1, 4.7 Hz, 1H), 2.60 (ddd, J = 13.7, 10.5, 6.1 Hz, 1H), 2.11-1.96 (m, 4H), 1.78-1.39 (m, 13H) | — |
| F82 | — | — | HRMS-ESI (m/z) [M + H]$^+$ calcd for C$_{30}$H$_{41}$N$_2$O$_9$, 573.2807; found, 573.2807 | $^1$H NMR (CDCl$_3$) δ 8.49 (d, J = 8.0 Hz, 1H), 8.29 (d, J = 5.4 Hz, 1H), 7.33-7.23 (m, 2H), 7.23-7.14 (m, 3H), 6.96 (d, J = 5.4 Hz, 1H), 5.74 (ab q, J = 7.9 Hz, 2H), 5.05 (app dt, J = 8.1, 6.8 Hz, 1H), 4.97 (dq, J = 9.0, 6.4 Hz, 1H), 4.11 (dd, J = 11.7, 7.1 Hz, 1H), 3.91 (s, 3H), 3.74 (dd, J = 10.9, 1.7 Hz, 1H), 3.67-3.57 (m, 2H), 3.29 (dd, J = 8.4, 6.4 Hz, 1H), 3.23 (dd, J = 8.3, 6.4 Hz, 1H), 3.07 (app t, J = 9.1 Hz, 1H), 2.77 (ddd, J = 13.5, 10.9, 4.7 Hz, 1H), 2.56 (ddd, J = 13.7, | $^{13}$C NMR (CDCl$_3$) δ 171.51, 170.27, 163.21, 160.20, 145.81, 143.92, 142.17, 142.15, 128.37, 125.81, 109.71, 89.40, 84.33, 78.62, 75.65, 74.59, 73.05, 56.20, 52.17, 45.13, 33.29, 30.99, 29.07, 20.88, 19.44, 19.41, 18.88 |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | | 10.3, 6.5 Hz, 1H), 2.07 (s, 3H), 1.97 (dddd, J = 13.7, 10.8, 6.6, 3.0 Hz, 1H), 1.85-1.77 (m, 1H), 1.77-1.66 (m, 1H), 1.51 (ddd, J = 10.3, 8.4, 5.1 Hz, 1H), 1.45 (d, J = 6.4 Hz, 3H), 0.90 (app d, J = 6.7 Hz, 6H) | |
| F83 | 58-64 | — | HRMS-ESI (m/z) [M + H]$^+$ calcd for C$_{33}$H$_{39}$N$_2$O$_{10}$, 623.2599; found, 623.2611 | $^1$H NMR (CDCl$_3$) δ 8.37 (d, J = 8.1 Hz, 1H), 8.24 (d, J = 5.3 Hz, 1H), 8.02-7.94 (m, 1H), 7.89-7.81 (m, 1H), 7.74 (d, J = 8.2 Hz, 1H), 7.56-7.43 (m, 2H), 7.40 (dd, J = 8.2, 7.0 Hz, 1H), 7.30 (dd, J = 7.1, 1.2 Hz, 1H), 6.92 (d, J = 5.4 Hz, 1H), 5.71 (d, J = 6.5 Hz, 2H), 5.17-5.06 (m, 3H), 4.04 (dd, J = 11.6, 7.4 Hz, 1H), 3.89 (s, 3H), 3.60 (d, J = 4.2 Hz, 2H), 3.40 (dd, J = 11.7, 7.1 Hz, 1H), 3.23 (dd, J = 14.2, 3.1 Hz, 1H), 2.77-2.63 (m, 2H), 2.29 (app ddt, J = 12.2, 8.1, 3.9 Hz, 1H), 2.04 (s, 3H), 1.39 (d, J = 5.6 Hz, 3H), 1.29 (app dd, J = 7.0, 3.9 Hz, 6H) | — |
| F84 | 61-68 | — | HRMS-ESI (m/z) [M + H]$^+$ calcd for C$_{33}$H$_{38}$F$_3$N$_2$O$_9$, 663.2524; found, 663.2538 | $^1$H NMR (CDCl$_3$) δ 8.33 (d, J = 8.2 Hz, 1H), 8.23 (d, J = 5.4 Hz, 1H), 8.16-8.08 (m, 1H), 7.85 (dd, J = 7.9, 1.6 Hz, 1H), 7.74 (d, J = 8.1 Hz, 1H), 7.55-7.43 (m, 2H), 7.40 (dd, J = 8.2, 7.0 Hz, 1H), 7.33 (dd, J = 7.0, 1.3 Hz, 1H), 6.92 (d, J = 5.4 Hz, 1H), 5.74-5.68 (m, 2H), 5.09-4.90 (m, 2H), 4.07 (dd, J = 11.7, 7.5 Hz, 1H), 3.88 (s, 4H), 3.77 (app dt, J = 8.8, 6.0 Hz, 1H), 3.58 (dd, J = 13.6, 2.9 Hz, 1H), 3.52 (dd, J = 10.8, 5.7 Hz, 1H), 3.46-3.38 (m, 1H), 3.36-3.24 (m, 2H), 2.82-2.71 (m, 1H), 2.40-2.23 (m, 2H), 2.15-1.90 (m, 6H), 1.54 (d, J = 6.4 Hz, 3H) | $^{19}$F NMR (CDCl$_3$) δ −66.36 |
| F85 | 83-88 | — | HRMS-ESI (m/z) [M + H]$^+$ calcd for C$_{36}$H$_{39}$N$_2$O$_9$, 643.2650; found, 643.2639 | $^1$H NMR (CDCl$_3$) δ 8.36 (d, J = 8.2 Hz, 1H), 8.23 (d, J = 5.3 Hz, 1H), 8.12-8.05 (m, 1H), 7.85-7.78 (m, 1H), 7.70 (d, J = 8.1 Hz, 1H), 7.55-7.41 (m, 2H), 7.36 (dd, J = 8.2, 7.0 Hz, 1H), 7.28 (dd, J = 7.0, 1.3 Hz, 1H), 7.18-7.10 (m, 2H), 7.06-6.99 (m, 2H), 6.91 (d, J = 5.4 Hz, 1H), 5.72 (s, 2H), 5.20-5.03 (m, 2H), 4.44 (app t, J = 9.1 Hz, 1H), 4.15-4.06 (m, 1H), 3.87 (s, 3H), 3.66-3.48 (m, 3H), 3.34 (dd, J = 11.6, 7.8 Hz, 1H), 2.69 (app t, J = 12.9 Hz, 1H), 2.38-2.25 (m, 4H), 2.05 (s, 3H), 1.44 (d, J = 6.4 Hz, 3H) | — |
| F86 | — | — | HRMS-ESI (m/z) [M + H]$^+$ calcd for C$_{34}$H$_{41}$N$_2$O$_9$, 621.2807; found, 621.2824 | $^1$H NMR (CDCl$_3$) δ 8.31 (d, J = 8.2 Hz, 1H), 8.22 (d, J = 5.4 Hz, 1H), 8.12 (dd, J = 8.3, 1.4 Hz, 1H), 7.83 (dd, J = 7.9, 1.5 Hz, 1H), 7.72 (d, J = 8.0 Hz, 1H), 7.56-7.43 (m, 2H), 7.39 (dd, J = 8.1, 7.0 Hz, 1H), 7.34 (dd, J = 7.0, 1.4 Hz, 1H), 6.91 (d, J = 5.4 Hz, 1H), 5.75-5.67 (m, 2H), 5.04-4.90 (m, | $^{13}$C NMR (CDCl$_3$) δ 171.96, 170.27, 163.16, 160.17, 145.76, 143.88, 142.15, 136.10, 133.99, 132.12, 128.76, 127.71, 127.02, 125.95, 125.49, 125.33, 124.10, 109.69, 89.39, |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | | 2H), 4.29-4.19 (m, 1H), 4.08 (dd, J = 11.6, 7.2 Hz, 1H), 3.87 (s, 3H), 3.74 (dd, J = 13.5, 2.8 Hz, 1H), 3.56-3.36 (m, 3H), 3.23 (dd, J = 11.6, 7.9 Hz, 1H), 2.80-2.68 (m, 1H), 2.10-1.95 (m, 4H), 1.93-1.79 (m, 6H), 1.65-1.53 (m, 5H) | 84.12, 83.39, 76.62, 72.18, 56.19, 51.76, 46.75, 33.00, 32.52, 32.42, 23.06, 23.00, 20.86, 18.99 |
| F87 | — | — | HRMS-ESI (m/z) [M + H]$^+$ calcd for C$_{33}$H$_{41}$N$_2$O$_9$, 609.2807; found, 609.2813 | $^1$H NMR (CDCl$_3$) δ 8.34 (d, J = 8.2 Hz, 1H), 8.23 (d, J = 5.3 Hz, 1H), 8.20 (dd, J = 8.5, 1.4 Hz, 1H), 7.83 (dd, J = 7.9, 1.7 Hz, 1H), 7.72 (d, J = 8.1 Hz, 1H), 7.54-7.42 (m, 2H), 7.39 (dd, J = 8.1, 7.0 Hz, 1H), 7.33 (dd, J = 7.0, 1.3 Hz, 1H), 6.91 (d, J = 5.4 Hz, 1H), 5.71 (s, 2H), 5.09-5.00 (m, 1H), 5.00-4.91 (m, 1H), 4.05 (dd, J = 11.6, 7.5 Hz, 1H), 3.88 (s, 3H), 3.73-3.64 (m, 1H), 3.60 (dd, J = 8.4, 6.5 Hz, 1H), 3.56-3.40 (m, 3H), 3.35-3.22 (m, 2H), 2.71 (dd, J = 13.7, 11.9 Hz, 1H), 2.16-1.97 (m, 5H), 1.55 (d, J = 6.3 Hz, 3H), 1.03 (app dd, J = 6.7, 2.2 Hz, 6H) | $^{13}$C NMR (CDCl$_3$) δ 171.88, 170.25, 163.15, 160.15, 145.75, 143.87, 142.08, 135.79, 133.96, 132.12, 128.70, 127.78, 127.05, 125.87, 125.48, 125.28, 124.23, 109.68, 89.36, 85.24, 80.79, 76.12, 71.98, 71.49, 56.17, 51.59, 46.91, 32.60, 29.35, 20.85, 19.60, 19.58, 18.79 |
| F88 | 39-43 | — | HRMS ESI (m/z) [M + H]$^+$ calcd for C$_{31}$H$_{43}$N$_2$O$_9$, 587.2963; found, 587.2981 | $^1$H NMR (CDCl$_3$) δ 8.40 (d, J = 8.2 Hz, 1H), 8.26 (d, J = 5.4 Hz, 1H), 7.14-7.04 (m, 4H), 6.94 (d, J = 5.4 Hz, 1H), 5.76-5.67 (m, 2H), 5.08-4.92 (m, 2H), 4.00 (dd, J = 11.7, 7.3 Hz, 1H), 3.89 (s, 3H), 3.67 (app dt, J = 8.7, 6.6 Hz, 1H), 3.59-3.48 (m, 2H), 3.48-3.36 (m, 2H), 3.19-3.06 (m, 2H), 2.35-2.22 (m, 4H), 2.05 (s, 3H), 1.99-1.86 (m, 1H), 1.67-1.54 (m, 2H), 1.50 (d, J = 6.3 Hz, 3H), 1.43-1.27 (m, 4H), 0.94-0.85 (m, 3H) | — |
| F89 | 43-47 | — | HRMS-ESI (m/z) [M + H]$^+$ calcd for C$_{30}$H$_{39}$N$_2$O$_{10}$, 587.2599; found, 587.2625 | $^1$H NMR (CDCl$_3$) δ 8.42 (d, J = 8.1 Hz, 1H), 8.26 (d, J = 5.4 Hz, 1H), 7.09 (d, J = 7.7 Hz, 2H), 7.03 (d, J = 8.0 Hz, 2H), 6.95 (d, J = 5.4 Hz, 1H), 5.71 (s, 2H), 5.14-5.02 (m, 2H), 4.96 (app t, J = 9.3 Hz, 1H), 4.02 (dd, J = 11.7, 7.3 Hz, 1H), 3.90 (s, 3H), 3.65-3.57 (m, 1H), 3.57-3.44 (m, 2H), 2.68 (dd, J = 14.0, 3.6 Hz, 1H), 2.60 (app p, J = 7.0 Hz, 1H), 2.31 (s, 3H), 2.23 (dd, J = 13.9, 11.4 Hz, 1H), 2.14-2.02 (m, 4H), 1.34 (d, J = 6.3 Hz, 3H), 1.22 (app dd, J = 7.0, 1.6 Hz, 6H) | — |
| F90 | 59-64 | — | HRMS-ESI (m/z) [M + H]$^+$ calcd for C$_{29}$H$_{34}$FN$_2$O$_{10}$, 589.2192; found, 589.2220 | $^1$H NMR (CDCl$_3$) δ 8.43 (d, J = 8.1 Hz, 1H), 8.27 (d, J = 5.4 Hz, 1H), 7.16-7.07 (m, 2H), 7.03-6.92 (m, 3H), 5.76-5.68 (m, 2H), 5.08 (m, 2H), 4.96 (app t, J = 9.3 Hz, 1H), 4.03 (dd, J = 11.7, 7.2 Hz, 1H), 3.91 (s, 3H), 3.65-3.57 (m, 1H), 3.57-3.47 (m, 2H), 2.73 (dd, J = 14.1, 3.9 Hz, 1H), 2.29 (dd, J = 14.1, 11.1 Hz, 1H), 2.14-2.00 (m, 4H), | — |

TABLE 2-continued

Analytical Data

| Cmpd No. | MP (° C.) | IR (cm⁻¹) | Mass | ¹H NMR | ¹³C or ¹⁹F NMR |
|---|---|---|---|---|---|
| | | | | 1.70-1.58 (m, 1H), 1.35 (d, J = 6.3 Hz, 3H), 1.06-1.00 (m, 2H), 0.95-0.89 (m, 2H) | |
| F91 | 52-56 | — | HRMS-ESI (m/z) [M + H]⁺ calcd for $C_{29}H_{36}FN_2O_{10}$, 591.2349; found, 591.2368 | ¹H NMR (CDCl₃) δ 8.42 (d, J = 8.1 Hz, 1H), 8.27 (d, J = 5.4 Hz, 1H), 7.15-7.06 (m, 2H), 7.02-6.93 (m, 3H), 5.72 (s, 2H), 5.09 (m, 2H), 4.97 (app t, J = 9.3 Hz, 1H), 4.04 (dd, J = 11.7, 7.3 Hz, 1H), 3.91 (s, 3H), 3.63-3.45 (m, 3H), 2.68 (dd, J = 14.1, 3.7 Hz, 1H), 2.59 (app hept, J = 7.0 Hz, 1H), 2.28 (dd, J = 14.1, 11.3 Hz, 1H), 2.11-1.99 (m, 4H), 1.34 (d, J = 6.3 Hz, 3H), 1.22 (app dd, J = 7.0, 1.8 Hz, 6H) | — |
| F92 | — | — | HRMS-ESI (m/z) [M]⁺ calcd for $C_{30}H_{36}N_2O_{10}$, 584.2377; found, 584.2370 | ¹H NMR (CDCl₃) δ 8.50 (d, J = 8.0 Hz, 1H), 8.29 (d, J = 5.3 Hz, 1H), 7.31-7.24 (m, 2H), 6.96 (d, J = 5.4 Hz, 1H), 5.77-5.70 (m, 2H), 5.15-5.08 (m, 1H), 5.07-4.98 (m, 1H), 4.94 (t, J = 9.3 Hz, 1H), 4.11 (dd, J = 11.8, 7.2 Hz, 1H), 3.92 (s, 3H), 3.88-3.81 (m, 1H), 3.74-3.64 (m, 2H), 2.79-2.66 (m, 1H), 2.53-2.41 (m, 1H), 2.08 (s, 3H), 1.88-1.79 (m, 1H), 1.65-1.58 (m, 2H), 1.57-1.45 (m, 1H), 1.33 (d, J = 6.2 Hz, 3H), 1.05-0.96 (m, 2H), 0.93-0.86 (m, 2H) | ¹³C NMR (CDCl₃) δ 174.15, 171.44, 170.28, 163.22, 160.23, 145.79, 144.01, 142.11, 141.76, 128.39, 128.32, 125.92, 109.74, 89.43, 76.28, 74.55, 74.33, 73.21, 56.21, 52.21, 43.89, 32.46, 31.32, 20.88, 18.31, 12.87, 8.54 |
| F93 | — | — | HRMS-ESI (m/z) [M]⁺ calcd for $C_{29}H_{34}F_4N_2O_9$, 630.2200; found, 630.2211 | ¹H NMR (CDCl₃) δ 8.39 (d, J = 8.2 Hz, 1H), 8.27 (d, J = 5.3 Hz, 1H), 7.19-7.09 (m, 2H), 7.04-6.90 (m, 3H), 5.76-5.67 (m, 2H), 5.07-4.93 (m, 2H), 4.04 (dd, J = 11.7, 7.3 Hz, 1H), 3.91 (s, 3H), 3.77-3.67 (m, 1H), 3.67-3.54 (m, 1H), 3.48-3.37 (m, 3H), 3.17 (t, J = 8.9 Hz, 1H), 3.01 (dd, J = 13.8, 3.6 Hz, 1H), 2.42-2.30 (m, 1H), 2.29-2.15 (m, 2H), 2.06 (s, 3H), 1.98-1.80 (m, 3H), 1.48 (d, J = 6.4 Hz, 3H) | ¹³C NMR (CDCl₃) δ 171.68, 170.26, 163.18, 161.45 (d, J = 244.3 Hz), 160.21, 145.78, 143.94, 142.07, 135.18 (d, J = 3.0 Hz), 130.45 (d, J = 7.7 Hz), 127.07 (q, J = 276.0 Hz), 115.29 (d, J = 21.1 Hz), 109.73, 89.38, 85.07, 75.23, 72.44, 71.94, 70.62, 56.20, 51.81, 47.46, 34.44, 30.73 (q, J = 29.3 Hz), 23.00 (q, J = 3.1 Hz), 20.86, 18.79 |
| F94 | — | — | HRMS-ESI (m/z) [M]⁺ calcd for $C_{30}H_{37}FN_2O_9$ 588.2483; found, 588.2504 | ¹H NMR (CDCl₃) δ 8.38 (d, J = 8.1 Hz, 1H), 8.27 (d, J = 5.3 Hz, 1H), 7.19-7.09 (m, 2H), 7.02-6.89 (m, 3H), 5.77-5.68 (m, 2H), 5.05-4.91 (m, 2H), 4.13-4.02 (m, 2H), 3.90 (s, 3H), 3.50-3.38 (m, 2H), 3.38-3.27 (m, 2H), 3.14 (dd, J = 13.6, 3.5 Hz, 1H), 2.33 (dd, J = 13.7, 12.2 Hz, 1H), 2.06 (s, 3H), 1.90-1.68 (m, 7H), 1.62-1.47 (m, 5H) | ¹³C NMR (CDCl₃) δ 171.80, 170.26, 163.15, 161.35 (d, J = 243.7 Hz), 160.20, 145.76, 143.94, 142.14, 135.90 (d, J = 3.1 Hz), 130.47 (d, J = 7.5 Hz), 115.20 (d, J = 21.4), 109.69, 89.40, 83.56, 83.33, 76.08, 73.00, 72.70, 56.19, 52.08, 47.76, 34.36, 32.71, 32.62, 23.00, 20.86, 18.91 |
| F95 | — | — | HRMS-ESI (m/z) [M]⁺ calcd for $C_{30}H_{39}FN_2O_9$, 590.2640; found, 590.2658 | ¹H NMR (CDCl₃) δ 8.40 (d, J = 8.2 Hz, 1H), 8.31-8.22 (m, 1H), 7.19-7.08 (m, 2H), 7.03-6.92 (m, 3H), 5.76-5.68 (m, 2H), 5.07-4.90 (m, 2H), 4.02 (dd, J = 11.7, 7.3 Hz, 1H), 3.90 (s, 3H), 3.74-3.61 (m, 1H), 3.57-3.49 (m, 1H), 3.49-3.35 (m, 3H), 3.20-3.05 (m, 2H), 2.32 (dd, J = 13.7, | ¹³C NMR (CDCl₃) δ 171.71, 170.26, 163.18, 161.40 (d, J = 244.0 Hz), 160.21, 145.78, 143.94, 142.13, 135.56 (d, J = 3.2 Hz), 130.52 (d, J = 7.7 Hz), 115.21 (d, J = 21.2 Hz), 109.71, 89.40, 84.91, 75.65, |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | | 11.7 Hz, 1H), 2.06 (s, 3H), 1.95-1.82 (m, 1H), 1.66-1.53 (m, 2H), 1.52-1.44 (m, 3H), 1.41-1.30 (m, 4H), 0.96-0.87 (m, 3H) | 72.89, 72.50, 72.18, 56.19, 51.85, 47.60, 34.40, 30.00, 28.34, 22.58, 20.86, 18.77, 14.01 |
| F96 | — | — | HRMS-ESI (m/z) [M]$^+$ calcd for C$_{29}$H$_{37}$FN$_2$O$_9$, 576.2483; found 576.2491 | $^1$H NMR (CDCl$_3$) δ 8.40 (d, J = 8.1 Hz, 1H), 8.26 (d, J = 5.3 Hz, 1H), 7.15 (dd, J = 8.5, 5.5 Hz, 2H), 7.02-6.89 (m, 3H), 5.74-5.70 (m, 2H), 5.01 (ddd, J = 15.6, 8.7, 6.8 Hz, 2H), 4.03 (dd, J = 11.7, 7.3 Hz, 1H), 3.90 (s, 3H), 3.52-3.36 (m, 4H), 3.33 (dd, J = 8.4, 6.4 Hz, 1H), 3.18-3.06 (m, 2H), 2.31 (dd, J = 13.7, 11.7 Hz, 1H), 2.06 (s, 3H), 1.98-1.82 (m, 2H), 1.50 (d, J = 6.4 Hz, 3H), 0.96 (d, J = 6.7 Hz, 6H) | $^{13}$C NMR (CDCl$_3$) δ 171.72, 170.25, 163.17, 161.39 (d, J = 243.9 Hz), 160.20, 145.78, 143.92, 142.12, 135.59 (d, J = 3.0 Hz), 130.52 (d, J = 8.0 Hz), 115.20 (d, J = 21.2 Hz), 109.71, 89.39, 84.55, 79.34, 75.64, 72.45, 72.07, 56.19, 51.84, 47.69, 34.30, 29.18, 20.86, 19.48, 18.81 |
| F97 | — | — | HRMS-ESI (m/z) [M]$^+$ calcd for C$_{30}$H$_{36}$N$_2$O$_{10}$, 584.2730; found, 584.2734 | $^1$H NMR (CDCl$_3$) δ 8.43 (d, J = 8.1 Hz, 1H), 8.27 (d, J = 5.3 Hz, 1H), 7.12-7.08 (m, 2H), 7.07-7.02 (m, 2H), 6.94 (d, J = 5.4 Hz, 1H), 5.74-5.67 (m, 2H), 5.08 (s, 2H), 4.95 (t, J = 9.3 Hz, 1H), 4.01 (dd, J = 11.7, 7.3 Hz, 1H), 3.90 (s, 3H), 3.63 (dd, J = 10.6, 1.6 Hz, 1H), 3.57-3.44 (m, 2H), 2.73 (dd, J = 14.0, 3.7 Hz 1H) 2.31 (s, 3H) 2.29-2.17 (m, 1H), 2.15-2.07 (m, 1H), 2.06 (s, 2H), 1.70-1.60 (m, 2H), 1.35 (d, J = 6.3 Hz, 3H), 1.09-1.00 (m, 2H), 0.96-0.87 (m, 2H) | $^{13}$C NMR (CDCl$_3$) δ 174.27, 171.65, 170.27, 163.16, 160.21, 145.75, 143.99, 142.07, 135.90, 135.80, 129.20, 128.90, 109.71, 89.42, 76.98, 74.24, 72.72, 56.20, 52.01, 45.85, 34.56, 21.02, 20.87, 18.27, 12.88, 8.64, 8.61 |
| F98 | — | — | HRMS-ESI (m/z) [M]$^+$ calcd for C$_{30}$H$_{33}$F$_3$N$_2$O$_{10}$, 638.2087; found, 638.2109 | $^1$H NMR (CDCl$_3$) δ 8.44 (d, J = 8.1 Hz, 1H), 8.27 (d, J = 5.4 Hz, 1H), 7.55 (d, J = 8.0 Hz, 2H), 7.28 (d, J = 7.9 Hz, 2H), 6.95 (d, J = 5.4 Hz, 1H), 5.72 (s, 2H), 5.15-5.03 (m, 2H), 4.98 (t, J = 9.3 Hz, 1H), 4.04 (dd, J = 11.7, 7.2 Hz, 1H), 3.91 (s, 3H), 3.63-3.48 (m, 3H), 2.80 (dd, J = 14.3, 4.3 Hz, 1H), 2.42 (dd, J = 14.2, 10.8 Hz, 1H), 2.23-2.10 (m, 1H), 2.06 (s, 3H), 1.65-1.56 (m, 1H), 1.35 (d, J = 6.3 Hz, 3H), 1.07-0.99 (m, 2H), 0.97-0.86 (m, 2H) | $^{13}$C NMR (CDCl$_3$) δ 174.26, 171.56, 170.26, 163.19, 160.23, 145.77, 144.02, 143.36, 142.03, 129.31, 128.70 (q, J = 32.4 Hz), 125.44 (q, J = 3.7 Hz), 124.22 (q, J = 271.8 Hz), 109.75, 89.39, 76.88, 74.07, 72.84, 72.61, 56.21, 51.98, 45.67, 35.15, 20.86, 18.21, 12.79, 8.77, 8.68 |
| F99 | — | — | HRMS-ESI (m/z) [M]$^+$ calcd for C$_{30}$H$_{37}$F$_3$N$_2$O$_9$, 626.2451; found 626.2461 | $^1$H NMR (CDCl$_3$) δ 8.40 (d, J = 8.2 Hz, 1H), 8.27 (d, J = 5.4 Hz, 1H), 7.55 (d, J = 8.0 Hz, 2H), 7.31 (d, J = 8.0 Hz, 2H), 6.95 (d, J = 5.4 Hz, 1H), 5.72 (s, 2H), 5.07-4.95 (m, 2H), 4.03 (dd, J = 11.7, 7.3 Hz, 1H), 3.91 (s, 3H), 3.53-3.38 (m, 4H), 3.33 (dd, J = 8.3, 6.4 Hz, 1H), 3.23-3.09 (m, 2H), 2.42 (dd, J = 13.7, 11.8 Hz, 1H), 2.06 (s, 3H), 2.02-1.94 (m, 1H), 1.94-1.82 (m, 1H), 1.50 (d, J = 6.4 Hz, 3H), 0.96 (d, J = 6.7 Hz, 6H) | $^{13}$C NMR (CDCl$_3$) δ 171.67, 170.26, 163.18, 160.20, 145.78, 144.27, 143.94, 142.10, 129.45, 128.48 (q, J = 32.1 Hz), 125.37 (q, J = 3.7 Hz), 124.28 (q, J = 271.8 Hz), 109.71, 89.39, 84.56, 79.48, 75.60, 72.52, 72.01, 56.19, 51.83, 47.48, 35.02, 29.19, 20.86, 19.46, 18.81 |
| F100 | — | — | HRMS-ESI (m/z) [M]$^+$ calcd for C$_{31}$H$_{37}$F$_3$N$_2$O$_9$, 638.2451; found, | $^1$H NMR (CDCl$_3$) δ 8.38 (d, J = 8.0 Hz, 1H), 8.27 (d, J = 5.3 Hz, 1H), 7.55 (d, J = 8.0 Hz, 2H), 7.31 (d, J = 8.0 Hz, 2H), 6.95 (d, J = 5.4 Hz, 1H), 5.72 (s, 2H), 5.05-4.92 (m, 2H), 4.16-4.02 (m, 2H), 3.91 (s, | $^{13}$C NMR (CDCl$_3$) δ 171.77, 170.26, 163.16, 160.20, 145.77, 144.59, 143.94, 142.12, 129.41, 128.42 (q, J = 32.6 Hz), 125.36 (q, J = 3.7 Hz), |

TABLE 2-continued

Analytical Data

| Cmpd No. | MP (° C.) | IR (cm⁻¹) | Mass | ¹H NMR | ¹³C or ¹⁹F NMR |
|---|---|---|---|---|---|
| | | | 638.2472 | 3H), 3.43 (qd, J = 11.5, 3.9 Hz, 2H), 3.38-3.29 (m, 2H), 3.22 (dd, J = 13.6, 3.5 Hz, 1H), 2.44 (dd, J = 13.6, 12.2 Hz, 1H), 2.05 (s, 3H), 1.96-1.68 (m, 7H), 1.61-1.55 (m, 2H), 1.52 (d, J = 6.5 Hz, 3H) | 124.29 (q, J = 271.8 Hz) 109.71, 89.39, 83.62, 83.29, 76.04, 72.90, 72.77, 56.19, 52.07, 47.50, 35.08, 32.72, 32.62, 23.00, 20.86, 18.91 |
| F101 | — | — | HRMS-ESI (m/z) [M]⁺ calcd for C₂₉H₃₅F₃N₂O₉ 612.2295; found, 612.2324 | ¹H NMR (CDCl₃) δ 8.40 (d, J = 8.1 Hz, 1H), 8.27 (d, J = 5.4 Hz, 1H), 7.59-7.49 (m, 2H), 7.32 (d, J = 8.0 Hz, 2H), 6.95 (d, J = 5.4 Hz, 1H), 5.76-5.69 (m, 2H), 5.08-4.95 (m, 2H), 4.03 (dd, J = 11.7, 7.3 Hz, 1H), 3.91 (s, 3H), 3.66 (dt, J = 8.6, 6.6 Hz, 1H), 3.56-3.37 (m, 4H), 3.23-3.13 (m, 2H), 2.42 (dd, J = 13.7, 11.7 Hz, 1H), 2.06 (s, 3H), 2.01-1.89 (m, 1H), 1.69-1.58 (m, 2H), 1.51 (d, J = 6.4 Hz, 3H), 0.97 (t, J = 7.4 Hz, 3H) | ¹⁹F NMR (CDCl₃) δ −62.35 |
| F102 | — | — | HRMS-ESI (m/z) [M]⁺ calcd for C₃₀H₃₅F₃N₂O₁₀, 640.2244; found, 640.2271 | ¹H NMR (CDCl₃) δ 8.42 (d, J = 8.1 Hz, 1H), 8.27 (d, J = 5.4 Hz, 1H), 7.60-7.51 (m, 2H), 7.27 (d, J = 8.1 Hz, 2H), 6.95 (d, J = 5.4 Hz, 1H), 5.72 (d, J = 0.7 Hz, 2H), 5.15-5.04 (m, 2H), 4.99 (t, J = 9.2 Hz, 1H), 4.05 (dd, J = 11.7, 7.2 Hz, 1H), 3.91 (s, 3H), 3.58-3.45 (m, 3H), 2.76 (dd, J = 14.2, 3.8 Hz, 1H), 2.58 (hept, J = 7.0 Hz, 1H), 2.40 (dd, J = 14.1, 11.4 Hz, 1H), 2.17-2.07 (m, 1H), 2.06 (s, 3H), 1.35 (d, J = 6.3 Hz, 3H), 1.21 (app dd, J = 7.0, 2.8 Hz, 6H) | ¹⁹F NMR (CDCl₃) δ −62.43 |
| F103 | — | — | HRMS-ESI (m/z) [M]⁺ calcd for C₃₁H₃₉F₃N₂O₉, 640.2608; found, 640.2636 | ¹H NMR (CDCl₃) δ 8.40 (d, J = 8.2 Hz, 1H), 8.30-8.22 (m, 1H), 7.55 (dt, J = 8.7, 1.5 Hz, 2H), 7.32 (d, J = 7.9 Hz, 2H), 6.94 (d, J = 5.4 Hz, 1H), 5.76-5.68 (m, 2H), 5.07-4.93 (m, 2H), 4.03 (dd, J = 11.7, 7.3 Hz, 1H), 3.91 (s, 3H), 3.69 (dt, J = 8.6, 6.6 Hz, 1H), 3.54 (dt, J = 8.7, 6.6 Hz, 1H), 3.50-3.35 (m, 3H), 3.23-3.10 (m, 2H), 2.42 (dd, J = 13.7, 11.7 Hz, 1H), 2.06 (s, 3H), 2.01-1.89 (m, 1H), 1.65-1.56 (m, 2H), 1.51 (d, J = 6.4 Hz, 3H), 1.36 (tq, J = 4.9, 2.8, 2.2 Hz, 4H), 0.95-0.86 (m, 3H) | ¹⁹F NMR (CDCl₃) δ −62.34 |
| F104 | — | — | HRMS-ESI (m/z) [M]⁺ calcd for C₂₄H₃₃F₃N₂O₉, 550.2138; found, 550.2138 | ¹H NMR (CDCl₃) δ 8.43 (d, J = 8.2 Hz, 1H), 8.29 (d, J = 5.3 Hz, 1H), 6.96 (d, J = 5.4 Hz, 1H), 5.73 (d, J = 1.2 Hz, 2H), 5.08-4.93 (m, 2H), 4.12 (dd, J = 11.7, 7.3 Hz, 1H), 3.91 (s, 3H), 3.68 (d, J = 4.0 Hz, 2H), 3.50 (dd, J = 11.7, 7.5 Hz, 1H), 3.42 (dd, J = 8.4, 6.4 Hz, 1H), 3.20 (dd, J = 8.4, 6.4 Hz, 1H), 3.11 (t, J = 8.8 Hz, 1H), 2.48-2.31 (m, 1H), 2.27-2.11 (m, 1H), 2.11-20.3 (m, 4H), 1.92-1.79 (m, 1H), 1.48 (d, J = 6.4 Hz, 3H), 0.93 (dd, J = 6.6, 1.0 Hz, 6H) | ¹³C NMR (CDCl₃) δ 171.63, 170.27, 163.22, 160.22, 145.80, 143.97, 142.06, 127.03 (q, J = 277.0 Hz), 109.75, 89.39, 83.18, 78.80, 75.48, 72.64, 72.40, 56.21, 51.73, 40.04, 32.64 (q, J = 28.0 Hz), 29.05, 20.87, 19.30, 18.86 |
| F105 | — | — | HRMS-ESI (m/z) [M]⁺ | ¹H NMR (CDCl₃) δ 8.42 (d, J = 8.1 Hz, 1H), 8.29 (d, J = 5.3 Hz, 1H), 6.96 (d, J = 5.4 Hz, | ¹⁹F NMR (CDCl₃) δ −63.66 |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | calcd for C$_{25}$H$_{33}$F$_3$N$_2$O$_9$, 562.2138; found, 562.2154 | 1H), 5.79-5.69 (m, 2H), 5.06-4.90 (m, 2H), 4.24-4.13 (m, 1H), 4.03-3.95 (m, 1H), 3.91 (s, 3H), 3.75-3.59 (m, 2H), 3.43 (dd, J = 11.7, 8.0 Hz, 1H), 3.27 (t, J = 7.8 Hz, 1H), 2.58-2.41 (m, 1H), 2.18-2.09 (m, 1H), 2.07 (s, 3H), 2.02-1.93 (m, 1H), 1.82-1.64 (m, 5H), 1.61-1.52 (m, 3H), 1.48 (d, J = 6.5 Hz, 3H) | |
| F106 | — | — | HRMS-ESI (m/z) [M]$^+$ calcd for C$_{27}$H$_{42}$N$_2$O$_9$, 538.2890; found, 538.2912 | $^1$H NMR (CDCl$_3$) δ 8.49 (d, J = 8.0 Hz, 1H), 8.28 (d, J = 5.4 Hz, 1H), 6.95 (d, J = 5.5 Hz, 1H), 5.77-5.69 (m, 2H), 5.10-5.00 (m, 1H), 5.00-4.91 (m, 1H), 4.06 (dd, J = 11.8, 7.1 Hz, 1H), 3.91 (s, 3H), 3.70-3.57 (m, 2H), 3.51 (dd, J = 10.8, 6.6 Hz, 1H), 3.34 (dd, J = 8.3, 6.4 Hz, 1H), 3.26 (dd, J = 8.3, 6.4 Hz, 1H), 3.02 (t, J = 9.2 Hz, 1H), 2.07 (s, 3H), 1.84 (hept, J = 6.7 Hz, 1H), 1.69-1.56 (m, 2H), 1.48-1.42 (m, 3H), 1.35-1.23 (m, 2H), 1.18-1.07 (m, 2H), 0.92 (d, J = 6.7 Hz, 6H), 0.88 (app dd, J = 6.6, 3.2 Hz, 6H) | $^{13}$C NMR (CDCl$_3$) δ 171.53, 170.27, 163.21, 160.20, 145.79, 143.92, 142.21, 109.68, 89.44, 84.44, 78.86, 75.81, 75.10, 73.08, 56.19, 52.23, 45.79, 36.01, 29.14, 28.40, 27.97, 26.74, 22.76, 22.43, 20.88, 19.49, 18.91 |
| F107 | — | — | HRMS-ESI (m/z) [M]$^+$ calcd for C$_{27}$H$_{39}$F$_3$N$_2$O$_9$, 592.2608; found, 592.2622 | $^1$H NMR (CDCl$_3$) δ 8.48 (d, J = 8.1 Hz, 1H), 8.28 (d, J = 5.3 Hz, 1H), 6.96 (d, J = 5.4 Hz, 1H), 5.78-5.67 (m, 2H), 5.05 (dt, J = 8.1, 6.8 Hz, 1H), 4.94 (dq, J = 9.0, 6.4 Hz, 1H), 4.06 (dd, J = 11.7, 7.1 Hz, 1H), 3.91 (s, 3H), 3.70-3.48 (m, 5H), 3.06 (t, J = 9.0 Hz, 1H), 2.29-2.12 (m, 2H), 2.07 (s, 3H), 1.90-1.79 (m, 2H), 1.66-1.48 (m, 3H), 1.44 (d, J = 6.4 Hz, 3H), 1.38-1.07 (m, 3H), 0.93-087 (m, 6H) | $^{19}$F NMR (CDCl$_3$) δ −66.42 |
| F108 | — | — | HRMS-ESI (m/z) [M]$^+$ calcd for C$_{27}$H$_{38}$N$_2$O$_{10}$, 550.2526; found, 550.2536 | $^1$H NMR (CDCl$_3$) δ 8.51 (d, J = 8.0 Hz, 1H), 8.28 (d, J = 5.3 Hz, 1H), 6.96 (d, J = 5.4 Hz, 1H), 5.80-5.67 (m, 2H), 5.15-5.06 (m, 1H), 5.06-4.96 (m, 1H), 4.87 (t, J = 9.5 Hz, 1H), 4.07 (dd, J = 11.8, 7.1 Hz, 1H), 3.91 (s, 3H), 3.82-3.65 (m, 2H), 3.59 (dd, J = 10.8, 7.2 Hz, 1H), 2.07 (s, 3H), 1.79-1.69 (m, 1H), 1.69-1.59 (m, 1H), 1.45 (dq, J = 13.0, 6.5 Hz, 1H), 1.32 (d, J = 6.3 Hz, 3H), 1.29-1.19 (m, 2H), 1.17-1.06 (m, 2H), 1.06-0.98 (m, 2H), 0.95-0.89 (m, 2H), 0.89-0.80 (m, 6H) | $^{13}$C NMR (CDCl$_3$) δ 174.11, 171.42, 170.26, 163.21, 160.21, 145.78, 143.97, 142.11, 109.73, 89.41, 76.51, 75.12, 74.38, 73.31, 56.20, 52.32, 44.51, 35.28, 28.18, 27.00, 22.69, 22.16, 20.87, 18.32, 12.84, 8.48, 8.38 |
| F109 | — | — | HRMS-ESI (m/z) [M]$^+$ calcd for C$_{29}$H$_{35}$F$_3$N$_2$O$_9$, 612.2295; found, 612.2318 | $^1$H NMR (CDCl$_3$) δ 8.41 (d, J = 8.1 Hz, 1H), 8.27 (d, J = 5.4 Hz, 1H), 6.95 (d, J = 5.4 Hz, 1H), 6.82 (dd, J = 8.3, 6.4 Hz, 2H), 5.72 (s, 2H), 5.07-4.92 (m, 2H), 4.05 (dd, J = 11.8, 7.3 Hz, 1H), 3.91 (s, 3H), 3.52-3.38 (m, 4H), 3.30 (dd, J = 8.4, 6.3 Hz, 1H), 3.12 (t, J = 9.0 Hz, 1H), 3.05 (dd, J = 13.8, 3.2 Hz, 1H), 2.32 (dd, J = 13.8, 11.8 Hz, 1H), 2.06 (s, 3H), 1.93-1.81 (m, 2H), 1.49 (d, J = 6.4 Hz, 3H), 0.95 (dd, J = 6.6, 1.3 Hz, 6H) | $^{19}$F NMR (CDCl$_3$) δ −134.79 (dd, J = 20.4, 8.2 Hz), −163.72--164.43 (m) |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| F110 | 62-66 | — | HRMS-ESI (m/z) [M]$^+$ calcd for C$_{29}$H$_{34}$Cl$_2$N$_2$O$_{10}$, 640.1591; found, 640.1594 | $^1$H NMR (CDCl$_3$) δ 8.40 (d, J = 8.1 Hz, 1H), 8.27 (d, J = 5.4 Hz, 1H), 7.36 (d, J = 2.0 Hz, 1H), 7.24-7.07 (m, 2H), 6.95 (d, J = 5.4 Hz, 1H), 5.73-5.69 (m, 2H), 5.19-4.90 (m, 3H), 4.09 (dd, J = 11.7, 7.3 Hz, 1H), 3.91 (s, 3H), 3.63-3.33 (m, 3H), 2.78 (d, J = 3.6 Hz, 1H), 2.61 (p, J = 7.0 Hz, 1H), 2.48 (dd, J = 13.8, 12.0 Hz, 1H), 2.17-2.11 (m, 1H), 2.06 (s, 3H), 1.35 (d, J = 6.3 Hz, 3H), 1.22 (d, J = 7.6 Hz, 6H) | $^{13}$C NMR (CDCl$_3$) δ 176.31, 171.68, 163.18, 160.24, 145.76, 135.22, 134.90, 132.95, 132.40, 129.50, 127.12, 109.74, 89.42, 73.97, 72.50, 71.41, 56.21, 51.81, 44.03, 34.24, 32.37, 20.88, 19.05, 18.98, 18.19 |
| F111 | 49-53 | — | HRMS-ESI (m/z) [M]$^+$ calcd for C$_{29}$H$_{36}$Cl$_2$N$_2$O$_9$, 626.1798; found, 626.1804 | $^1$H NMR (CDCl$_3$) δ 8.40 (d, J = 8.1 Hz, 1H), 8.27 (d, J = 5.4 Hz, 1H), 7.36 (s, 1H), 7.27-7.12 (m, 2H), 6.95 (d, J = 5.4 Hz, 1H), 5.72 (s, 2H), 5.08-4.97 (m, 2H), 4.05 (dd, J = 11.7, 7.3 Hz, 1H), 3.90 (s, 3H), 3.55-3.28 (m, 5H), 3.28-3.04 (m, 2H), 2.66-2.43 (m, 1H), 2.06 (s, 3H), 1.98-1.76 (m, 2H), 1.50 (d, J = 6.4 Hz, 3H), 0.95 (d, J = 6.7 Hz, 6H) | $^{13}$C NMR (CDCl$_3$) δ 171.63, 170.25, 163.19, 160.20, 145.78, 143.92, 142.12, 136.19, 135.03, 132.52, 132.15, 129.32, 127.07, 109.72, 89.39, 84.94, 79.75, 75.65, 72.55, 72.01, 56.20, 51.89, 45.91, 32.13, 29.17, 20.86, 19.49, 18.77 |
| F112 | 53-57 | — | HRMS-ESI (m/z) [M]$^+$ calcd for C$_{30}$H$_{38}$Cl$_2$N$_2$O$_9$, 640.1954; found, 640.1962 | $^1$H NMR (CDCl$_3$) δ 8.41 (d, J = 8.0 Hz, 1H), 8.26 (d, J = 5.4 Hz, 1H), 7.36 (s, 1H), 7.25-7.06 (m, 2H), 6.95 (d, J = 5.4 Hz, 1H), 5.72 (s, 2H), 5.12-4.85 (m, 2H), 4.05 (dd, J = 11.7, 7.3 Hz, 1H), 3.90 (s, 3H), 3.75-3.64 (m, 1H), 3.62-3.52 (m, 1H), 3.47-3.38 (m, 3H), 3.26-3.08 (m, 2H), 2.63-2.43 (m, 1H), 2.13-1.97 (m, 1H), 2.06 (s, 3H), 1.69-1.54 (m, 2H), 1.50 (d, J = 6.4 Hz, 3H), 1.38-1.31 (m, 4H), 0.90 (t, J = 7.2 Hz, 3H) | $^{13}$C NMR (CDCl$_3$) δ 171.65, 170.23, 163.18, 160.20, 145.78, 143.92, 142.10, 136.17, 135.03, 132.52, 132.13, 129.33, 127.06, 109.73, 89.37, 85.22, 75.63, 73.28, 72.52, 71.95, 56.20, 51.86, 45.87, 32.20, 29.96, 28.32, 22.57, 20.86, 18.72, 14.01 |
| F113 | 70-74 | — | HRMS-ESI (m/z) [M]$^+$ calcd for C$_{32}$H$_{34}$Cl$_2$N$_2$O$_9$, 660.1641; found, 660.1647 | $^1$H NMR (CDCl$_3$) δ 8.42 (d, J = 8.1 Hz, 1H), 8.27 (d, J = 5.4 Hz, 1H), 7.32 (s, 1H), 7.15 (s, 2H), 7.10 (d, J = 8.4 Hz, 2H), 6.95 (d, J = 5.4 Hz, 1H), 6.88 (d, J = 8.5 Hz, 2H), 5.73 (s, 2H), 5.16 (dd, J = 8.9, 6.5 Hz, 1H), 5.07 (q, J = 7.6 Hz, 1H), 4.30 (t, J = 8.8 Hz, 1H), 4.12 (dd, J = 11.6, 7.4 Hz, 1H), 3.95-3.87 (m, 1H), 3.90 (s, 3H), 3.62-3.35 (m, 3H), 3.05 (dd, J = 13.7, 3.4 Hz, 1H), 2.57-2.46 (m, 1H), 2.29 (s, 3H), 2.07 (s, 3H), 1.41 (d, J = 6.4 Hz, 3H) | $^{13}$C NMR (CDCl$_3$) δ 171.73, 170.26, 163.21, 160.23, 156.98, 145.80, 143.97, 142.05, 135.80, 134.96, 132.65, 132.24, 130.64, 130.18, 129.36, 127.02, 115.14, 109.78, 89.38, 81.97, 75.40, 72.37, 71.38, 56.22, 51.77, 46.12, 32.42, 20.88, 20.44, 18.94 |
| F114 | 41-45 | — | HRMS-ESI (m/z) [M]$^+$ calcd for C$_{28}$H$_{40}$N$_2$O$_{10}$, 564.2683; found, 564.2687 | $^1$H NMR (CDCl$_3$) δ 8.47 (d, J = 8.0 Hz, 1H), 8.28 (d, J = 5.4 Hz, 1H), 6.96 (d, J = 5.4 Hz, 1H), 5.78-5.68 (m, 2H), 5.11 (q, J = 7.1 Hz, 1H), 5.02 (dd, J = 9.3, 6.4 Hz, 1H), 4.80 (t, J = 9.3 Hz, 1H), 4.10 (dd, J = 11.7, 7.3 Hz, 1H), 3.91 (s, 3H), 3.73 (d, J = 9.7 Hz, 1H), 3.67-3.53 (m, 2H), 2.59 (hept, J = 6.7 Hz, 1H), 2.07 (s, 3H), 1.93-1.67 (m, 4H), 1.59-1.48 (m, 4H), 1.31 (d, J = 6.4 Hz, 3H), 1.20 (d, J = 7.0 Hz, 6H), 1.14-0.91 (m, 4H) | $^{13}$C NMR (CDCl$_3$) δ 176.19, 171.63, 170.26, 163.19, 160.22, 145.77, 144.00, 142.10, 109.73, 89.42, 74.33, 73.88, 72.77, 56.20, 52.05, 43.59, 37.20, 35.04, 34.26, 33.63, 32.13, 25.02, 20.86, 18.97, 18.33 |

TABLE 2-continued

Analytical Data

| Cmpd No. | MP (° C.) | IR (cm⁻¹) | Mass | ¹H NMR | ¹³C or ¹⁹F NMR |
|---|---|---|---|---|---|
| F115 | — | — | HRMS-ESI (m/z) [M]⁺ calcd for C$_{28}$H$_{42}$N$_2$O$_9$, 550.2890; found, 550.2877 | ¹H NMR (CDCl$_3$) δ 8.46 (d, J = 8.0 Hz, 1H), 8.28 (d, J = 5.4 Hz, 1H), 6.95 (d, J = 5.4 Hz, 1H), 5.77-5.69 (m, 2H), 5.03 (q, J = 7.1 Hz, 1H), 4.95 (dd, J = 9.1, 6.4 Hz, 1H), 4.08 (dd, J = 11.7, 7.2 Hz, 1H), 3.91 (s, 3H), 3.63 (d, J = 10.6 Hz, 1H), 3.59-3.48 (m, 2H), 3.37 (dd, J = 8.3, 6.2 Hz, 1H), 3.24 (dd, J = 8.2, 6.7 Hz, 1H), 2.97 (t, J = 9.0 Hz, 1H), 2.07 (s, 3H) 1.93-1.70 (m, 4H), 1.70-1.48 (m, 6H), 1.45 (d, J = 6.4 Hz, 3H), 1.16-1.02 (m, 3H), 0.92 (dd, J = 6.7, 4.5 Hz, 6H) | ¹³C NMR (CDCl$_3$) δ 171.69, 170.25, 163.18, 160.20, 145.78, 142.23, 137.51, 131.24, 109.69, 89.43, 84.91, 74.23, 72.74, 56.19, 52.07, 44.74, 37.39, 34.97, 33.88, 32.02, 29.14, 25.09, 20.87, 19.53, 18.86 |
| F116 | — | — | HRMS-ESI (m/z) [M]⁺ calcd for C$_{29}$H$_{44}$N$_2$O$_9$, 564.3047; found, 564.3059 | ¹H NMR (CDCl$_3$) δ 8.46 (d, J = 8.1 Hz, 1H), 8.28 (d, J = 5.4 Hz, 1H), 6.96 (d, J = 5.4 Hz, 1H), 5.76-5.69 (m, 2H), 5.03 (q, J = 7.1 Hz, 1H), 4.94 (dd, J = 9.1, 6.4 Hz, 1H), 4.08 (dd, J = 11.7, 7.2 Hz, 1H), 3.91 (s, 3H), 3.67-3.42 (m, 5H), 2.98 (t, J = 9.0 Hz, 1H), 2.07 (s, 3H), 1.94-1.84 (m, 2H), 1.82-1.70 (m, 2H), 1.68-1.48 (m, 7H), 1.46 (d, J = 6.4 Hz, 3H), 1.39-1.21 (m, 5H), 1.17-1.01 (m, 2H), 0.94-0.86 (m, 3H) | ¹³C NMR (CDCl$_3$) δ 171.68, 170.24, 163.18, 160.19, 145.78, 143.91, 142.19, 109.70, 89.40, 85.24, 75.84, 74.23, 72.72, 56.19, 52.04, 44.72, 37.38, 35.10, 33.85, 32.04, 29.94, 28.36, 25.08, 22.55, 20.86, 18.81, 14.00 |
| F117 | — | — | HRMS-ESI (m/z) [M + Na]⁺ calcd for C$_{30}$H$_{40}$N$_2$O$_9$Na, 595.2626; found, 595.2620 | ¹H NMR (CDCl$_3$) δ 8.39 (d, J = 8.1 Hz, 1H), 8.26 (d, J = 5.4 Hz, 1H), 7.09 (m, 4H), 6.94 (d, J = 5.4 Hz, 1H), 5.72 (s, 2H), 5.00 (m, 2H), 4.01 (dd, J = 11.6, 7.4 Hz, 1H), 3.90 (s, 3H), 3.41 (m, 5H), 3.12 (m, 2H), 2.31 (s, 3H), 2.26 (d, J = 13.4 Hz, 1H), 2.05 (s, 3H), 1.89 (dd, J = 13.3, 6.6 Hz, 2H), 1.49 (d, J = 6.4 Hz, 3H), 0.96 (d, J = 6.7 Hz, 6H) | ¹³C NMR (CDCl$_3$) δ 171.78, 170.26, 163.15, 160.18, 145.76, 143.91, 142.14, 136.82, 135.53, 129.11, 129.05, 109.68, 89.40, 84.58, 79.17, 75.72, 72.33, 72.26, 56.18, 51.82, 47.44, 34.61, 29.18, 21.01, 20.87, 19.49, 18.84 |
| F118 | — | — | HRMS-ESI (m/z) [M]⁺ calcd for C$_{32}$H$_{40}$N$_2$O$_{10}$, 612.2683; found, 612.2705 | ¹H NMR (CDCl$_3$) δ 8.56 (d, J = 8.0 Hz, 1H), 8.28 (d, J = 5.4 Hz, 1H), 7.32-7.24 (m, 2H), 7.23-7.10 (m, 3H), 6.95 (d, J = 5.4 Hz, 1H), 5.81-5.72 (m, 2H), 5.18-5.08 (m, 1H), 5.08-4.98 (m, 1H), 4.94 (t, J = 9.3 Hz, 1H), 4.17-4.06 (m, 1H), 3.90 (s, 3H), 3.88-3.80 (m, 1H), 3.74-3.62 (m, 2H), 2.79-2.65 (m, 1H), 2.60-2.43 (m, 2H), 1.90-1.79 (m, 1H), 1.66-1.58 (m, 2H), 1.56-1.45 (m, 1H), 1.33 (d, J = 6.2 Hz, 3H), 1.15 (d, J = 7.0 Hz, 6H), 1.04-0.97 (m, 2H), 0.94-0.86 (m, 2H) | ¹³C NMR (CDCl$_3$) δ 176.26, 174.16, 171.45, 163.19, 160.22, 145.65, 144.23, 141.77, 128.39, 128.32, 125.92, 109.68, 89.78, 76.27, 74.47, 74.32, 73.16, 56.16, 52.17, 43.88, 33.86, 32.47, 31.32, 18.68, 18.30, 12.87, 8.54 |
| F119 | 57-60 | — | HRMS-ESI (m/z) [M]⁺ calcd for C$_{31}$H$_{38}$Cl$_2$N$_2$O$_{10}$, 668.1904; found, 668.1908 | ¹H NMR (CDCl$_3$) δ 8.46 (d, J = 8.1 Hz, 1H), 8.26 (d, J = 5.3 Hz, 1H), 7.36 (d, J = 1.9 Hz, 1H), 7.25-7.07 (m, 2H), 6.94 (d, J = 5.4 Hz, 1H), 5.84-5.70 (m, 2H), 5.18-4.86 (m, 3H), 4.09 (dd, J = 11.6, 7.4 Hz, 1H), 3.89 (s, 3H), 3.62-3.32 (m, 3H), 2.80 (dd, J = 13.9, 3.6 Hz, 1H), 2.70-2.39 (m, 3H), 2.27-2.08 (m, 1H), 1.35 (d, J = 6.3 Hz, 3H), 1.23 (d, J = 7.0 Hz, 6H), 1.14 (d, J = 7.0 Hz, 6H) | — |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| F120 | — | — | HRMS-ESI (m/z) [M]$^+$ calcd for C$_{31}$H$_{39}$F$_3$N$_2$O$_{10}$, 656.2557; found, 656.2569 | $^1$H NMR (CDCl$_3$) δ 8.41 (d, J = 8.2 Hz, 1H), 8.26 (d, J = 5.4 Hz, 1H), 7.61-7.50 (m, 2H), 7.32 (d, J = 8.0 Hz, 2H), 6.95 (d, J = 5.4 Hz, 1H), 5.80 (s, 2H), 5.04-4.95 (m, 2H), 4.08 (s, 2H), 4.03 (dd, J = 11.7, 7.3 Hz, 1H), 3.90 (s, 3H), 3.66 (dt, J = 8.6, 6.6 Hz, 1H), 3.63-3.47 (m, 3H), 3.47-3.36 (m, 3H), 3.23-3.12 (m, 2H), 2.43 (dd, J = 13.7, 11.7 Hz, 1H), 2.01-1.90 (m, 1H), 1.69-1.58 (m, 2H), 1.51 (d, J = 6.4 Hz, 3H), 1.22 (t, J = 7.0 Hz, 3H), 0.97 (t, J = 7.4 Hz, 3H) | $^{19}$F NMR (CDCl$_3$) δ −62.35 |
| F121 | — | — | HRMS-ESI (m/z) [M]$^+$ calcd for C$_{30}$H$_{44}$N$_2$O$_{11}$, 608.2945; found, 608.2950 | $^1$H NMR (CDCl$_3$) δ 8.48 (d, J = 8.1 Hz, 1H), 8.28 (d, J = 5.4 Hz, 1H), 6.97 (d, J = 5.4 Hz, 1H), 5.81 (s, 2H), 5.12-4.98 (m, 2H), 4.81 (t, J = 9.3 Hz, 1H), 4.10 (s, 3H), 3.91 (s, 3H), 3.76-3.56 (m, 6H), 2.58 (h, J = 7.0 Hz, 1H), 1.93-1.68 (m, 4H), 1.62-1.46 (m, 4H), 1.31 (d, J = 6.4 Hz, 3H), 1.25-1.17 (m, 9H), 1.12-0.94 (m, 3H) | $^{13}$C NMR (CDCl$_3$) δ 176.17, 171.61, 170.04, 163.14, 160.13, 145.81, 143.93, 141.93, 109.84, 89.39, 74.31, 73.85, 72.71, 67.77, 67.17, 56.23, 52.01, 43.55, 37.19, 35.02, 34.25, 33.61, 32.12, 25.00, 19.02, 18.31, 14.99 |
| F122 | — | — | HRMS-ESI (m/z) [M]$^+$ calcd for C$_{32}$H$_{42}$Cl$_2$N$_2$O$_{10}$, 684.2217; found, 684.2232 | $^1$H NMR (CDCl$_3$) δ 8.42 (d, J = 8.1 Hz, 1H), 8.26 (d, J = 5.4 Hz, 1H), 7.36 (s, 1H), 7.26-7.12 (m, 2H), 6.95 (d, J = 5.4 Hz, 1H), 5.80 (s, 2H), 5.08-4.91 (m, 2H), 4.09 (s, 2H), 4.05 (dd, J = 11.7, 7.3 Hz, 1H), 3.90 (s, 3H), 3.76-3.64 (m, 1H), 3.63-3.54 (m, 3H), 3.46-3.38 (m, 3H), 3.22-3.13 (m, 2H), 2.56 (dd, J = 13.6, 12.2 Hz, 1H), 2.08-1.95 (m, 1H), 1.65-1.56 (m, 2H), 1.50 (d, J = 6.4 Hz, 3H), 1.38-1.31 (m, 3H), 1.28-1.21 (m, 4H), 0.90 (t, J = 7.1 Hz, 3H) | $^{13}$C NMR (CDCl$_3$) δ 171.62, 170.01, 163.12, 160.10, 145.82, 143.86, 141.95, 136.17, 135.01, 132.51, 132.13, 129.31, 127.05, 109.83, 89.36, 85.20, 75.62, 73.28, 72.49, 71.95, 67.77, 67.16, 56.23, 51.83, 45.85, 32.19, 29.95, 28.31, 22.56, 18.71, 15.00, 14.00 |
| F123 | 96-99 | — | HRMS-ESI (m/z) [M]$^+$ calcd for C$_{31}$H$_{40}$Cl$_2$N$_2$O$_9$, 654.2111; found, 654.2141 | $^1$H NMR (CDCl$_3$) δ 8.55 (d, J = 7.7 Hz, 1H), 8.31 (d, J = 5.4 Hz, 1H), 7.36 (s, 1H), 7.25-7.12 (m, 2H), 6.99 (d, J = 5.5 Hz, 1H), 5.08-4.89 (m, 2H), 4.02 (dd, J = 11.7, 7.3 Hz, 1H), 3.88 (s, 3H), 3.81 (t, J = 6.6 Hz, 2H), 3.72-3.61 (m, 2H), 3.61-3.49 (m, 1H), 3.46-3.32 (m, 3H), 3.41 (s, 3H), 3.20-3.08 (m, 2H), 2.97 (t, J = 6.6 Hz, 2H), 2.59-2.48 (m, 1H), 2.05-1.95 (m, 1H), 1.65-1.54 (m, 2H), 1.49 (d, J = 6.4 Hz, 3H), 1.38-1.31 (m, 3H), 0.90 (t, J = 7.1 Hz, 3H) | $^{13}$C NMR (CDCl$_3$) δ 171.57, 169.34, 162.64, 159.42, 146.81, 141.13, 137.35, 136.16, 135.02, 132.53, 132.12, 129.33, 127.07, 109.93, 85.20, 75.61, 73.24, 72.45, 71.84, 67.56, 58.77, 56.33, 51.58, 34.60, 32.19, 29.96, 28.32, 22.57, 18.71, 14.01 |
| F124 | — | — | ESIMS m/z 584 ([M + Na]$^+$) | $^1$H NMR (CDCl$_3$) δ 7.31-7.23 (m, 2H), 7.21-7.12 (m, 3H), 5.06 (app t, J = 7.4 Hz, 1H), 4.84 (dq, J = 8.3, 6.5 Hz, 1H), 4.19 (dd, J = 11.8, 7.3 Hz, 1H), 4.04-3.91 (m, 2H), 3.66 (d, J = 4.1 Hz, 2H), 3.22 (app t, J = 7.7 Hz, 1H), 2.76 (ddd, J = 13.6, 10.8, 4.8 Hz, 1H), 2.59 (ddd, J = 13.7, 10.3, 6.1 Hz, 1H), 2.04-1.92 (m, 1H), 1.77-1.46 (m, 28H), 1.43 (d, J = 6.5 Hz, 3H) | $^{13}$C NMR (CDCl$_3$) δ 169.88, 152.65, 128.35, 128.30, 125.75, 83.13, 82.95, 82.77, 75.93, 75.32, 71.84, 57.87, 45.13, 34.03, 32.59, 32.54, 30.65, 27.97, 27.94, 23.06, 23.04, 19.10 |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| F125 | — | — | ESIMS m/z 626 ([M + Na]$^+$) | $^1$H NMR (CDCl$_3$) δ 7.32-7.23 (m, 2H), 7.23-7.13 (m, 3H), 5.15 (dd, J = 8.4, 6.1 Hz, 1H), 4.91-4.79 (m, 1H), 4.23 (dd, J = 11.9, 6.2 Hz, 1H), 3.94 (dd, J = 11.9, 8.5 Hz, 1H), 3.73 (dd, J = 10.9, 1.6 Hz, 1H), 3.61 (dd, J = 11.0, 6.2 Hz, 1H), 3.57-3.41 (m, 2H), 3.10 (app t, J = 8.6 Hz, 1H), 2.78 (ddd, J = 13.8, 10.3, 4.8 Hz, 1H), 2.59-2.49 (m, 1H), 2.20-2.07 (m, 2H), 1.89-1.71 (m, 4H), 1.61-1.49 (m, 19H), 1.41 (d, J = 6.4 Hz, 3H) | $^{19}$F NMR (CDCl$_3$) δ −66.40 |
| F126 | — | — | ESIMS m/z 586 ([M + Na]$^+$) | $^1$H NMR (CDCl$_3$) δ 7.31-7.22 (m, 2H), 7.21-7.12 (m, 3H), 5.16 (dd, J = 8.5, 5.8 Hz, 1H), 4.84 (dq, J = 9.0, 6.3 Hz, 1H), 4.22 (dd, J = 11.9, 5.8 Hz, 1H), 3.93 (dd, J = 11.9, 8.5 Hz, 1H), 3.76 (dd, J = 10.9, 1.6 Hz, 1H), 3.56 (dd, J = 10.9, 6.4 Hz, 1H), 3.53-3.37 (m, 2H), 3.07 (app t, J = 8.9 Hz, 1H), 2.76 (ddd, J = 13.6, 10.9, 4.7 Hz, 1H), 2.55 (ddd, J = 13.7, 10.4, 6.3 Hz, 1H), 1.93 (dddd, J = 13.9, 10.9, 6.4, 3.2 Hz, 1H), 1.79-1.67 (m, 1H), 1.51 (s, 21H), 1.43 (d, J = 6.3 Hz, 3H), 1.35-1.23 (m, 4H), 0.96-0.82 (m, 3H) | $^{13}$C NMR (CDCl$_3$) δ 169.70, 152.67, 142.28, 128.36, 128.34, 125.79, 84.57, 82.96, 75.41, 75.21, 71.87, 71.68, 57.77, 44.75, 33.31, 31.00, 29.97, 28.38, 27.95, 22.59, 18.98, 14.02 |
| F127 | — | — | ESIMS m/z 573 ([M + Na]$^+$) | $^1$H NMR (CDCl$_3$) δ 7.31-7.22 (m, 2H), 7.21-7.13 (m, 3H), 5.16 (dd, J = 8.5, 5.8 Hz, 1H), 4.90-4.81 (m, 1H), 4.22 (dd, J = 11.9, 5.9 Hz, 1H), 3.93 (dd, J = 11.9, 8.5 Hz, 1H), 3.80-3.72 (m, 1H), 3.57 (dd, J = 10.9, 6.4 Hz, 1H), 3.30-3.16 (m, 2H), 3.07 (app t, J = 8.9 Hz, 1H), 2.84-2.67 (m, 1H), 2.61-2.45 (m, 1H), 1.93 (dddd, J = 13.8, 11.0, 6.5, 3.2 Hz, 1H), 1.85-1.68 (m, 2H), 1.54-1.49 (m, 19H), 1.43 (d, J = 6.4 Hz, 3H), 0.89 (d, J = 6.7 Hz, 6H) | $^{13}$C NMR (CDCl$_3$) δ 169.71, 152.68, 142.27, 128.36, 125.79, 84.24, 82.95, 78.20, 75.35, 75.13, 71.68, 57.77, 44.70, 33.31, 30.87, 29.08, 27.95, 19.46, 19.44, 19.03 |
| F128 | 130-132 | — | ESIMS m/z 622 ([M + Na]$^+$) | $^1$H NMR (CDCl$_3$) δ 8.01-7.93 (m, 1H), 7.84 (dd, J = 8.0, 1.5 Hz, 1H), 7.72 (d, J = 8.1 Hz, 1H), 7.54-7.41 (m, 2H), 7.37 (dd, J = 8.2, 7.0 Hz, 1H), 7.28 (dd, J = 7.0, 1.3 Hz, 1H), 5.20 (dd, J = 8.7, 5.7 Hz, 1H), 5.11 (app t, J = 9.3 Hz, 1H), 5.08-4.97 (m, 1H), 4.06 (dd, J = 11.8, 5.7 Hz, 1H), 3.86 (dd, J = 11.9, 8.7 Hz, 1H), 3.66 (d, J = 11.0 Hz, 1H), 3.50 (dd, J = 10.8, 6.4 Hz, 1H), 3.23 (dd, J = 14.0, 3.1 Hz, 1H), 2.74-2.55 (m, 2H), 2.37-2.20 (m, 1H), 1.42 (s, 18H), 1.37 (d, J = 6.2 Hz, 3H), 1.26 (app dd, J = 7.0, 4.4 Hz, 6H) | — |
| F129 | — | — | ESIMS m/z 662 ([M + Na]$^+$) | $^1$H NMR (CDCl$_3$) δ 8.13-8.06 (m, 1H), 7.84 (dd, J = 7.8, 1.7 Hz, 1H), 7.72 (dd, J = 8.1, 1.3 Hz, 1H), 7.54-7.41 (m, 2H), 7.38 (dd, J = 8.1, 6.9 Hz, | $^{19}$F NMR (CDCl$_3$) δ −66.36 |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | | 1H), 7.32 (dd, J = 7.1, 1.4 Hz, 1H), 5.12 (dd, J = 8.5, 6.8 Hz, 1H), 4.87 (dq, J = 9.0, 6.4 Hz, 1H), 4.04 (dd, J = 11.7, 6.8 Hz, 1H), 3.88 (dd, J = 11.7, 8.6 Hz, 1H), 3.84-3.76 (m, 1H), 3.77-3.66 (m, 1H), 3.56 (dd, J = 13.5, 3.0 Hz, 1H), 3.48-3.41 (m, 2H), 3.28 (app t, J = 8.9 Hz, 1H), 2.76 (app t, J = 12.4 Hz, 1H), 2.34-2.22 (m, 2H), 2.15-2.04 (m, 1H), 2.00-1.86 (m, 2H), 1.51 (d, J = 6.4 Hz, 3H), 1.43 (s, 18H), | |
| F130 | — | IR: 2932, 2873, 1743, 1707, 1356, 1121 | ESIMS m/z 622 ([M + H]$^+$) | $^1$H NMR (CDCl$_3$) δ 8.21-8.13 (m, 1H), 7.87-7.79 (m, 1H), 7.71 (dd, J = 8.0, 1.3 Hz, 1H), 7.54-7.41 (m, 2H), 7.42-7.28 (m, 2H), 5.12 (dd, J = 8.6, 6.7 Hz, 1H), 4.85 (dq, J = 9.2, 6.3 Hz, 1H), 4.03 (dd, J = 11.7, 6.7 Hz, 1H), 3.92-3.73 (m, 2H), 3.73-3.63 (m, 2H), 3.51-3.37 (m, 2H), 3.24 (app t, J = 9.1 Hz, 1H), 2.78-2.65 (m, 1H), 2.13-2.02 (m, 1H), 1.77-1.64 (m, 2H), 1.57-1.49 (m, 4H), 1.42 (m, 21H), 0.91 (t, J = 7.1 Hz, 3H) | — |
| F131 | — | — | ESIMS m/z 642 ([M + Na]$^+$) | $^1$H NMR (CDCl$_3$) δ 8.11-8.03 (m, 1H), 7.81 (dd, J = 7.9, 1.6 Hz, 1H), 7.69 (d, J = 8.1 Hz, 1H), 7.54-7.39 (m, 2H), 7.39-7.30 (m, 1H), 7.27 (dd, J = 7.0, 1.4 Hz, 1H), 7.16-7.08 (m, 2H), 7.03-6.95 (m, 2H), 5.17 (dd, J = 8.7, 6.5 Hz, 1H), 5.09-4.99 (m, 1H), 4.40 (app t, J = 9.0 Hz, 1H), 4.08 (dd, J = 11.7, 6.6 Hz, 1H), 3.91 (dd, J = 11.7, 8.7 Hz, 1H), 3.63-3.48 (m, 3H), 2.69-2.64 (m, 1H), 2.37-2.26 (m, 4H), 1.47-1.38 (m, 21H) | $^{13}$C NMR (CDCl$_3$) δ 169.99, 157.28, 152.59, 135.48, 133.98, 131.99, 130.55, 130.22, 128.67, 127.79, 127.09, 125.91, 125.43, 125.14, 124.04, 115.18, 83.05, 82.23, 75.40, 72.08, 70.65, 57.24, 46.50, 32.68, 27.84, 20.43, 19.10 |
| F132 | 49-55 | — | ESIMS m/z 620 ([M + Na]$^+$) | $^1$H NMR (CDCl$_3$) δ 8.09 (d, J = 8.3 Hz, 1H), 7.82 (dd, J = 8.1, 1.5 Hz, 1H), 7.74-7.67 (m, 1H), 7.54-7.41 (m, 2H), 7.40-7.31 (m, 2H), 5.05 (app t, J = 7.7 Hz, 1H), 4.90-4.79 (m, 1H), 4.21-4.12 (m, 1H), 3.94 (dd, J = 11.7, 7.5 Hz, 1H), 3.88 (dd, J = 11.7, 8.0 Hz, 1H), 3.73 (dd, J = 13.6, 2.9 Hz, 1H), 3.53-3.35 (m, 3H), 2.71 (app t, J = 12.8 Hz, 1H), 2.07-1.96 (m, 1H), 1.90-1.70 (m, 6H), 1.63-1.49 (m, 5H), 1.38 (s, 18H) | — |
| F133 | 57-63 | — | ESIMS m/z 608 ([M + Na]$^+$) | $^1$H NMR (CDCl$_3$) δ 8.17 (dd, J = 8.0, 1.6 Hz, 1H), 7.82 (dd, J = 7.7, 1.8 Hz, 1H), 7.71 (d, J = 8.0 Hz, 1H), 7.51-7.40 (m, 2H), 7.37 (dd, J = 8.1, 6.9 Hz, 1H), 7.32 (dd, J = 7.0, 1.4 Hz, 1H), 5.12 (dd, J = 8.6, 6.5 Hz, 1H), 4.93-4.83 (m, 1H), 4.02 (dd, J = 11.7, 6.5 Hz, 1H), 3.86 (dd, J = 11.8, 8.6 Hz, 1H), 3.68 (dd, J = 13.6, 2.8 Hz, 1H), 3.59-3.36 (m, 4H), 3.23 (app t, J = 9.1 Hz, 1H), 2.74-2.63 (m, 1H), | — |

TABLE 2-continued

Analytical Data

| Cmpd No. | MP (° C.) | IR (cm⁻¹) | Mass | ¹H NMR | ¹³C or ¹⁹F NMR |
|---|---|---|---|---|---|
| | | | | 2.14-2.05 (m, 1H), 2.05-1.94 (m, 1H), 1.53 (d, J = 6.4 Hz, 3H), 1.41 (s, 18H), 1.01 (app dd, J = 6.7, 2.1 Hz, 6H) | |
| F134 | 100-103 | — | ESIMS m/z 586 ([M + Na]⁺) | ¹H NMR (CDCl₃) δ 7.08 (app s, 4H), 5.12 (dd, J = 8.6, 6.3 Hz, 1H), 4.91-4.81 (m, 1H), 4.07 (dd, J = 11.8, 6.3 Hz, 1H), 3.83 (dd, J = 11.8, 8.6 Hz, 1H), 3.68-3.58 (m, 1H), 3.57-3.45 (m, 2H), 3.36 (dd, J = 10.9, 6.2 Hz, 1H), 3.18-3.02 (m, 2H), 2.37-2.26 (m, 4H), 2.00-1.89 (m, 1H), 1.64-1.55 (m, 2H), 1.51-1.44 (m, 21H), 1.39-1.27 (m, 4H), 0.94-0.85 (m, 3H) | — |
| F135 | — | — | ESIMS m/z 586 ([M + Na]⁺) | ¹H NMR (CDCl₃) δ 7.07 (d, J = 7.9 Hz, 2H), 7.01 (d, J = 8.1 Hz, 2H), 5.19 (dd, J = 8.7, 5.8 Hz, 1H), 5.02-4.90 (m, 2H), 4.12 (dd, J = 11.9, 5.8 Hz, 1H), 3.86 (dd, J = 11.9, 8.7 Hz, 1H), 3.64 (d, J = 10.6 Hz, 1H), 3.45 (dd, J = 10.8, 6.7 Hz, 1H), 2.67 (dd, J = 13.9, 3.7 Hz, 1H), 2.61-2.51 (m, 1H), 2.32-2.20 (m, 4H), 2.16-2.04 (m, 1H), 1.49 (s, 18H), 1.32 (d, J = 5.5 Hz, 3H), 1.19 (app dd, J = 7.0, 1.5 Hz, 6H) | ¹³C NMR (CDCl₃) δ 176.14, 169.82, 152.55, 135.97, 135.63, 129.08, 128.92, 82.95, 76.78, 73.88, 73.23, 71.24, 57.60, 45.58, 34.43, 34.15, 27.89, 20.96, 18.97, 18.95, 18.38 |
| F136 | 131-133 | — | ESIMS m/z 588 ([M + Na]⁺) | ¹H NMR (CDCl₃) δ 7.15-7.04 (m, 2H), 7.01-6.92 (m, 2H), 5.19 (dd, J = 8.7, 5.6 Hz, 1H), 5.02-4.89 (m, 2H), 4.13 (dd, J = 11.9, 5.7 Hz, 1H), 3.87 (dd, J = 11.9, 8.7 Hz, 1H), 3.64 (d, J = 10.8 Hz, 1H), 3.44 (dd, J = 10.9, 6.7 Hz, 1H), 2.71 (dd, J = 14.1, 4.1 Hz, 1H), 2.30 (dd, J = 14.2, 10.8 Hz, 1H), 2.17-2.03 (m, 1H), 1.66-1.57 (m, 1H), 1.49 (s, 18H), 1.33 (d, J = 5.6 Hz, 3H), 1.06-0.96 (m, 2H), 0.95-0.85 (m, 2H) | — |
| F137 | — | — | ESIMS m/z 590 ([M + Na]⁺) | ¹H NMR (CDCl₃) δ 7.13-7.05 (m, 2H), 7.00-6.91 (m, 2H), 5.18 (dd, J = 8.7, 5.7 Hz, 1H), 5.02-4.89 (m, 2H), 4.13 (dd, J = 11.9, 5.8 Hz, 1H), 3.87 (dd, J = 11.9, 8.6 Hz, 1H), 3.62 (d, J = 10.8 Hz, 1H), 3.45 (dd, J = 10.9, 6.6 Hz, 1H), 2.66 (dd, J = 14.0, 3.8 Hz, 1H), 2.57 (app p, J = 7.0 Hz, 1H), 2.29 (dd, J = 14.1, 11.1 Hz, 1H), 2.11-2.01 (m, 1H), 1.49 (s, 18H), 1.32 (d, J = 5.6 Hz, 3H), 1.20 (app dd, J = 7.0, 1.8 Hz, 6H) | ¹³C NMR (CDCl₃) δ 176.22, 169.76, 161.45 (d, JCF = 244.4 Hz), 152.60, 134.77 (d, JCF = 3.3 Hz), 130.45 (d, JCF = 7.8 Hz), 115.21 (d, JCF = 21.1 Hz), 83.07, 76.72, 73.81, 73.08, 71.36, 57.58, 45.72, 34.18, 34.11, 27.91, 18.99, 18.96, 18.38 |
| F138 | — | — | ESIMS m/z 585 ([M + Na]⁺) | ¹H NMR (CDCl₃) δ 7.30-7.23 (m, 2H), 7.20-7.14 (m, 1H), 7.14-7.10 (m, 2H), 5.23 (dd, J = 8.8, 5.0 Hz, 1H), 4.97-4.88 (m, 2H), 4.26 (dd, J = 12.0, 5.0 Hz, 1H), 3.95 (dd, J = 12.0, 8.8 Hz, 1H), 3.89 (dd, J = 10.8, 1.3 Hz, 1H), 3.61 (dd, J = 10.8, 7.2 Hz, 1H), 2.74-2.63 (m, 1H), 2.51-2.40 (m, 1H), 1.88 (q, J = 9.2, 8.0 Hz, 1H), 1.66-1.45 (m, 21H), 1.30 (d, J = 5.8 Hz, 3H), | ¹³C NMR (CDCl₃) δ 174.15, 169.50, 152.65, 141.92, 129.08, 128.37, 128.29, 125.87, 83.08, 76.37, 74.11, 72.11, 57.93, 43.64, 32.43, 31.39, 27.96, 18.41, 12.90, 8.50 |

TABLE 2-continued

Analytical Data

| Cmpd No. | MP (° C.) | IR (cm⁻¹) | Mass | ¹H NMR | ¹³C or ¹⁹F NMR |
|---|---|---|---|---|---|
| F139 | — | (Thin Film) 2979, 2921, 1742, 1705, 1507, 1355, 1234, 1169, 1143, 1120 | HRMS-ESI (m/z) [M]⁺ calcd for C$_{33}$H$_{45}$NO$_8$, 583.3145; found, 583.3159 | 1.03-0.97 (m, 2H), 0.93-0.85 (m, 2H) $^1$H NMR (CDCl$_3$) δ 7.23-7.16 (m, 2H), 7.16-7.09 (m, 1H), 7.09-7.03 (m, 2H), 7.01-6.96 (m, 2H), 6.83-6.78 (m, 2H), 5.20 (dd, J = 8.5, 5.9 Hz, 1H), 5.05-4.94 (m, 1H), 1.89-1.77 (m, 1H), 4.27 (dd, J = 11.9, 6.0 Hz, 1H), 4.20 (t, J = 8.8 Hz, 1H), 4.04-3.94 (m, 1H), 3.83 (d, J = 10.8 Hz, 1H), 3.72-3.63 (m, 1H), 2.70-2.60 (m, 1H), 2.57-2.44 (m, 1H), 2.28 (s, 3H), 2.00-1.90 (m, 1H), 1.56-1.48 (m, 19H), 1.35 (d, J = 6.5 Hz, 3H) | — |
| F140 | — | — | ESIMS m/z 631 ([M + Na]⁺) | $^1$H NMR (CDCl$_3$) δ 7.17-7.09 (m, 2H), 7.02-6.91 (m, 2H), 5.11 (dd, J = 8.4, 6.6 Hz, 1H), 4.94-4.84 (m, 1H), 4.09 (dd, J = 11.8, 6.6 Hz, 1H), 3.92-3.81 (m, 1H), 3.74-3.65 (m, 1H), 3.60-3.53 (m, 1H), 3.53-3.44 (m, 1H), 3.43-3.33 (m, 1H), 3.17 (t, J = 8.6 Hz, 1H), 2.97 (dd, J = 13.7, 3.7 Hz, 1H), 2.47-2.34 (m, 1H), 2.27-2.13 (m, 2H), 1.97-1.89 (m, 1H), 1.89-1.79 (m, 2H), 1.49 (s, 18H), 1.46 (d, J = 6.4 Hz, 3H) | $^{13}$C NMR (CDCl$_3$) δ 169.88, 161.42 (d, J = 244.2 Hz), 152.64, 135.32 (d, J = 3.3 Hz), 130.50 (d, J = 7.8 Hz), 127.09 (q, J = 275.9 Hz), 115.17 (d, J = 21.2 Hz), 84.96, 83.07, 74.85, 72.42, 71.03, 70.14, 57.38, 47.05, 34.28, 30.74 (q, J = 29.3 Hz), 27.91, 22.99, 18.92 |
| F141 | — | — | ESIMS m/z 589 ([M + Na]⁺) | $^1$H NMR (CDCl$_3$) δ 7.18-7.10 (m, 2H), 7.02-6.87 (m, 2H), 5.03 (t, J = 7.7 Hz, 1H), 4.91-4.80 (m, 1H), 4.07-3.96 (m, 2H), 3.94-3.83 (m, 1H), 3.48-3.37 (m, 2H), 3.31 (t, J = 8.0 Hz, 1H), 3.08 (d, J = 3.7 Hz, 1H), 2.41-2.29 (m, 1H), 1.87-1.58 (m, 8H), 1.48 (s, 22H) | $^{13}$C NMR (CDCl$_3$) δ 170.15, 161.33 (d, J = 243.7 Hz), 152.60, 136.06, 130.49 (d, J = 7.6 Hz), 115.09 (d, J = 21.0 Hz), 83.18, 83.00, 75.90, 72.86, 71.09, 57.51, 47.32, 34.10, 32.67, 32.60, 27.90, 23.03, 19.02 |
| F142 | — | — | ESIMS m/z 590 ([M + Na]⁺) | $^1$H NMR (CDCl$_3$) δ 7.18-7.11 (m, 2H), 7.00-6.91 (m, 2H), 5.12 (dd, J = 8.6, 6.3 Hz, 1H), 4.90-4.81 (m, 1H), 4.13-4.04 (m, 1H), 3.85 (dd, J = 11.8, 8.6 Hz, 1H), 3.63 (dt, J = 8.7, 6.6 Hz, 1H), 3.56-3.46 (m, 2H), 3.40-3.30 (m, 1H), 3.17-3.02 (m, 2H), 2.34 (dd, J = 13.9, 11.4 Hz, 1H), 1.97-1.82 (m, 1H), 1.65-1.54 (m, 2H), 1.48 (s, 21H), 1.39-1.29 (m, 4H), 0.94-0.86 (m, 3H) | $^{13}$C NMR (CDCl$_3$) δ 169.91, 161.36 (d, J = 243.6 Hz), 152.62, 135.67 (d, J = 3.2 Hz), 130.56 (d, J = 7.8 Hz), 115.08 (d, J = 21.1 Hz), 84.78, 83.01, 75.36, 72.74, 72.43, 71.00, 57.43, 47.15, 34.28, 29.98, 28.33, 27.91, 22.57, 18.88, 14.00 |
| F143 | — | — | ESIMS m/z 479 ([M + Na]⁺) | $^1$H NMR (CDCl$_3$) δ 7.19-7.08 (m, 2H), 7.03-6.91 (m, 2H), 5.12 (d, J = 8.3 Hz, 1H), 4.95 (dq, J = 9.2, 6.4 Hz, 1H), 4.59 (q, J = 7.5 Hz, 1H), 3.90 (dd, J = 11.7, 7.2 Hz, 1H), 3.50-3.20 (m, 5H), 3.16-3.01 (m, 2H), 2.28 (t, J = 12.8 Hz, 1H), 1.94-1.76 (m, 2H), 1.48 (d, J = 6.4 Hz, 3H), 1.42 (s, 9H), 0.95 (d, J = 6.7 Hz, 6H) | $^{19}$F NMR (CDCl$_3$) δ −117.2 |
| F144 | — | — | ESIMS m/z 585 ([M + Na]⁺) | $^1$H NMR (CDCl$_3$) δ 7.08 (d, J = 7.9 Hz, 2H), 7.02 (d, J = 8.0 Hz, 2H), 5.18 (dd, J = 8.7, 5.6 Hz, 1H), 5.02-4.89 (m, 2H), 4.11 (dd, J = 11.9, 5.6 Hz, 1H), 3.85 (dd, J = 11.9, 8.8 Hz, 1H), 3.66 (d, J = 10.7 Hz, 1H), 3.43 (dd, J = 10.8, 6.9 Hz, | $^{13}$C NMR (CDCl$_3$) δ 174.27, 169.80, 152.58, 136.04, 135.66, 129.08, 128.93, 83.06, 77.12, 74.03, 73.63, 71.40, 57.69, 45.52, 34.53, 27.93, 21.00, 18.37, |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | | 1H), 2.70 (dd, J = 14.0, 3.8 Hz, 1H), 2.31 (s, 3H), 2.25 (dd, J = 13.9, 11.0 Hz, 1H), 2.18-2.02 (m, 1H), 1.67-1.60 (m, 1H), 1.49 (s, 18H), 1.33 (d, J = 5.7 Hz, 3H), 1.07-0.99 (m, 2H), 0.92-0.85 (m, 2H) | 12.90, 8.57, 8.56 |
| F145 | — | — | ESIMS m/z 627 ([M + Na]$^+$) | $^1$H NMR (CDCl$_3$) δ 7.14-7.03 (m, 4H), 5.11 (dd, J = 8.5, 6.5 Hz, 1H), 4.94-4.82 (m, 1H), 4.12-4.03 (m, 1H), 3.85 (dd, J = 11.8, 8.5 Hz, 1H), 3.73-3.63 (m, 1H), 3.61-3.47 (m, 2H), 3.45-3.35 (m, 1H), 3.17 (t, J = 8.8 Hz, 1H), 2.97 (dd, J = 13.7, 3.8 Hz, 1H), 2.42-2.32 (m, 1H), 2.32 (s, 3H), 2.25-2.13 (m, 2H), 2.02-1.91 (m, 1H), 1.87-1.78 (m, 2H), 1.48 (s, 18H), 1.45 (d, J = 6.3 Hz, 3H) | $^{13}$C NMR (CDCl$_3$) δ 169.95, 152.62, 136.54, 135.60, 129.08, 129.00, 127.11 (q, J = 276.1 Hz), 84.97, 83.04, 74.94, 72.74, 70.96, 69.97, 57.42, 46.79, 34.67, 30.77 (q, J = 29.0 Hz), 27.91, 22.96 (q, J = 3.0 Hz), 21.00, 18.94. |
| F146 | — | (Thin Film) 2979, 2931, 1742, 1705, 1491, 1392, 1366, 1237, 1204, 1169, 1142, 1120 | HRMS-ESI (m/z) [M]$^+$ calcd for C$_{32}$H$_{43}$NO$_8$, 569.2989; found, 569.3001 | $^1$H NMR (CDCl$_3$) δ 7.31-7.26 (m, 2H), 7.07-6.99 (m, 4H), 6.98-6.92 (m, 3H), 5.16 (dd, J = 8.5, 6.6 Hz, 1H), 5.10-4.99 (m, 1H), 4.30 (t, J = 8.7 Hz, 1H), 4.12 (dd, J = 11.8, 6.6 Hz, 1H), 3.90 (dd, J = 11.8, 8.6 Hz, 1H), 3.60 (d, J = 10.9 Hz, 1H), 3.57-3.46 (m, 1H), 2.97 (dd, J = 13.6, 3.3 Hz, 1H), 2.29 (m, 4H), 2.24-2.13 (m, 1H), 1.49 (s, 18H), 1.38 (d, J = 6.4 Hz, 3H) | — |
| F147 | — | — | ESIMS m/z 585 ([M + Na]$^+$) | $^1$H NMR (CDCl$_3$) δ 7.08 (m, 4H), 5.03 (t, J = 7.7 Hz, 1H), 4.92-4.81 (m, 1H), 4.10-4.02 (m, 1H), 4.02-3.95 (m, 1H), 3.93-3.83 (m, 1H), 3.44 (d, J = 5.3 Hz, 2H), 3.30 (t, J = 8.1 Hz, 1H), 3.10 (dd, J = 13.7, 3.7 Hz, 1H), 2.31 (s, 4H), 1.92-1.81 (m, 1H), 1.81-1.64 (m, 5H), 1.47 (m, 24H) | $^{13}$C NMR (CDCl$_3$) δ 170.22, 152.58, 137.28, 135.37, 129.03, 83.22, 83.16, 82.96, 75.97, 73.09, 71.04, 57.56, 47.11, 34.44, 32.70, 32.60, 27.90, 23.04, 23.02, 21.01, 19.05 |
| F148 | — | — | ESMIS m/z 638 ([M + Na]$^+$) | $^1$H NMR (CDCl$_3$) δ 7.53 (d, J = 8.0 Hz, 2H), 7.30-7.24 (m, 2H), 15.19 (dd, J = 8.7, 5.6 Hz, 1H), 5.01-4.88 (m, 2H), 4.14 (dd, J = 12.0, 5.7 Hz, 1H), 3.87 (dd, J = 12.0, 8.7 Hz, 1H), 3.62 (d, J = 11.0 Hz, 1H), 3.46 (dd, J = 10.9, 6.5 Hz, 1H), 2.78 (dd, J = 14.0, 4.6 Hz, 1H), 2.47-2.32 (m, 1H), 2.22-2.09 (m, 1H), 1.56-1.51 (m, 1H), 1.49 (s, 18H), 1.33 (d, J = 5.6 Hz, 3H), 1.02-0.95 (m, 2H), 0.93-0.82 (m, 2H) | $^{19}$F NMR (CDCl$_3$) δ −62.4 |
| F149 | — | — | ESIMS m/z 627 ([M + Na]$^+$) | $^1$H NMR (CDCl$_3$) δ 7.53 (d, J = 7.8 Hz, 2H), 7.31 (d, J = 8.0 Hz, 2H), 5.12 (dd, J = 8.5, 6.4 Hz, 1H), 4.93-4.84 (m, 1H), 4.12-4.04 (m, 1H), 3.85 (dd, J = 11.8, 8.5 Hz, 1H), 3.51-3.40 (m, 2H), 3.40-3.25 (m, 2H), 3.19-3.09 (m, 2H), 2.44 (t, J = 12.7 Hz, 1H), 2.03-1.93 (m, 1H), 1.93-1.79 (m, 1H), 1.51-1.44 (m, 21H), 0.94 (dd, J = 6.7, 1.0 Hz, 6H) | $^{19}$F NMR (CDCl$_3$) δ −62.4 |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| F150 | — | — | ESIMS m/z 639 ([M + Na]$^+$) | $^1$H NMR (CDCl$_3$) δ 7.53 (d, J = 8.0 Hz, 2H), 7.31 (d, J = 8.0 Hz, 2H), 5.04 (t, J = 7.7 Hz, 1H), 4.92-4.83 (m, 1H), 4.09-3.97 (m, 2H), 3.94-3.84 (m, 1H), 3.47-3.37 (m, 2H), 3.32 (t, J = 8.0 Hz, 1H), 3.17 (dd, J = 13.9, 3.5 Hz, 1H), 2.47 (t, J = 12.8 Hz, 1H), 1.95-1.83 (m, 1H), 1.83-1.61 (m, 6H), 1.55-1.51 (m, 1H), 1.51-1.45 (m, 22H) | $^{19}$F NMR (CDCl$_3$) δ −62.4 |
| F151 | — | — | ESIMS m/z 613 ([M + Na]$^+$) | $^1$H NMR (CDCl$_3$) δ 7.58-7.48 (m, 2H), 7.31 (d, J = 8.0 Hz, 2H), 5.12 (dd, J = 8.5, 6.3 Hz, 1H), 4.94-4.82 (m, 1H), 4.13-4.05 (m, 1H), 3.90-3.81 (m, 1H), 3.66-3.59 (m, 1H), 3.48 (dt, J = 8.6, 6.6 Hz, 2H), 3.40-3.31 (m, 1H), 3.20-3.10 (m, 2H), 2.45 (t, J = 12.6 Hz, 1H), 2.00 (dd, J = 9.0, 4.3 Hz, 1H), 1.65-1.54 (m, 2H), 1.55-1.42 (m, 21H), 0.95 (t, J = 7.4 Hz, 3H) | $^{19}$F NMR (CDCl$_3$) δ −62.3 |
| F152 | — | — | ESIMS m/z 641 ([M + Na]$^+$) | $^1$H NMR (CDCl$_3$) δ 7.58-7.49 (m, 2H), 7.26 (d, J = 7.8 Hz, 2H), 5.19 (dd, J = 8.7, 5.8 Hz, 1H), 5.04-4.94 (m, 2H), 4.17-4.08 (m, 1H), 3.89 (dd, J = 11.9, 8.7 Hz, 1H), 3.64-3.55 (m, 1H), 3.50-3.42 (m, 1H), 2.74 (dd, J = 14.1, 4.0 Hz, 1H), 2.61-2.49 (m, 1H), 2.41 (dd, J = 14.0, 11.2 Hz, 1H), 2.19-2.09 (m, 1H), 1.49 (s, 18H), 1.33 (d, J = 5.8 Hz, 3H), 1.19 (app dd, J = 7.0, 2.6 Hz, 6H) | $^{19}$F NMR (CDCl$_3$) δ −62.4 |
| F153 | — | — | ESIMS m/z 641 ([M + Na]$^+$) | $^1$H NMR (CDCl$_3$) δ 7.57-7.48 (m, 2H), 7.31 (d, J = 8.1 Hz, 2H), 5.12 (dd, J = 8.5, 6.3 Hz, 1H), 4.93-4.84 (m, 1H), 4.08 (dd, J = 11.9, 6.4 Hz, 1H), 3.85 (dd, J = 11.8, 8.6 Hz, 1H), 3.64 (dt, J = 8.7, 6.6 Hz, 1H), 3.57-3.44 (m, 2H), 3.36 (dd, J = 11.0, 5.9 Hz, 1H), 3.21-3.10 (m, 2H), 2.45 (t, J = 12.6 Hz, 1H), 2.04-1.89 (m, 1H), 1.64-1.53 (m, 2H), 1.53-1.42 (m, 21H), 1.41-1.27 (m, 4H), 0.94-0.82 (m, 3H) | $^{19}$F NMR (CDCl$_3$) δ −62.3 |
| F154 | — | — | ESIMS m/z 551 ([M + Na]$^+$) | $^1$H NMR (CDCl$_3$) δ 5.11 (dd, J = 8.3, 6.7 Hz, 1H), 4.94-4.82 (m, 1H), 4.23-4.15 (m, 1H), 3.93 (dd, J = 11.9, 8.3 Hz, 1H), 3.75-3.59 (m, 2H), 3.37 (dd, J = 8.4, 6.4 Hz, 1H), 3.18 (dd, J = 8.4, 6.4 Hz, 1H), 3.11 (t, J = 8.5 Hz, 1H), 2.44-2.28 (m, 1H), 2.28-2.13 (m, 1H), 2.10-2.01 (m, 1H), 1.88-1.77 (m, 1H), 1.51 (s, 18H), 1.45 (d, J = 6.5 Hz, 3H), 0.91 (d, J = 6.6 Hz, 6H) | $^{19}$F NMR (CDCl$_3$) δ −63.3 |
| F155 | — | — | ESIMS m/z 562 ([M + Na]$^+$) | $^1$H NMR (CDCl$_3$) δ 5.04-4.96 (m, 1H), 4.89 (q, J = 6.8 Hz, 1H), 4.20-4.10 (m, 1H), 4.05-3.90 (m, 2H), 3.78-3.69 (m, 1H), 3.68-3.59 (m, 1H), 2.29-2.15 (m, 1H), 3.27 (t, J = 7.1 Hz, 1H), 2.52-2.35 (m, 1H), 2.03-1.94 (m, 1H), | $^{19}$F NMR (CDCl$_3$) δ −63.7 |

TABLE 2-continued

Analytical Data

| Cmpd No. | MP (° C.) | IR (cm⁻¹) | Mass | ¹H NMR | ¹³C or ¹⁹F NMR |
|---|---|---|---|---|---|
| | | | | 1.78-1.61 (m, 5H), 1.59-1.48 (m, 21H), 1.44 (d, J = 6.6 Hz, 3H) | |
| F156 | — | — | ESIMS m/z 539 ([M + Na]⁺) | ¹H NMR (CDCl₃) δ 5.14 (dd, J = 8.5, 5.7 Hz, 1H), 4.89-4.78 (m, 1H), 4.18 (dd, J = 11.9, 5.7 Hz, 1H), 3.89 (dd, J = 11.9, 8.5 Hz, 1H), 3.71-3.64 (m, 1H), 3.45 (dd, J = 10.9, 6.4 Hz, 1H), 3.31 (dd, J = 8.3, 6.5 Hz, 1H), 3.24 (dd, J = 8.3, 6.3 Hz, 1H), 3.02 (t, J = 8.9 Hz, 1H), 1.89-1.78 (m, 1H), 1.68-1.45 (m, 20H), 1.42 (d, J = 6.3 Hz, 3H), 1.35-1.05 (m, 4H), 0.91 (d, J = 6.7 Hz, 6H), 0.87 (app dd, J = 6.6, 2.6 Hz, 6H) | ¹³C NMR (CDCl₃) δ 169.75, 152.67, 84.31, 82.96, 78.41, 75.49, 71.64, 57.84, 45.24, 35.99, 29.12, 28.41, 27.94, 26.61, 22.75, 22.43, 19.49, 19.02 |
| F157 | — | — | ESIMS m/z 593 ([M + Na]⁺) | ¹H NMR (CDCl₃) δ 5.14 (dd, J = 8.5, 5.9 Hz, 1H), 4.89-4.79 (m, 1H), 4.19 (dd, J = 11.9, 5.9 Hz, 1H), 3.90 (dd, J = 12.0, 8.5 Hz, 1H), 3.71-3.57 (m, 2H), 3.57-3.43 (m, 2H), 3.06 (t, J = 8.8 Hz, 1H), 2.26-2.12 (m, 2H), 1.86-1.76 (m, 2H), 1.65 (s, 2H), 1.51 (s, 18H), 1.41 (d, J = 6.3 Hz, 3H), 1.35-1.02 (m, 4H), 0.88 (dd, J = 6.6, 4.0 Hz, 6H) | ¹⁹F NMR (CDCl₃) δ −66.4 |
| F158 | — | — | ESIMS m/z 550 ([M + Na]⁺) | ¹H NMR (CDCl₃) δ 5.22 (dd, J = 8.7, 4.8 Hz, 1H), 4.96-4.81 (m, 2H), 4.23 (dd, J = 12.0, 4.9 Hz, 1H), 3.91 (dd, J = 12.0, 8.8 Hz, 1H), 3.80 (dd, J = 10.8, 1.3 Hz, 1H), 3.50 (dd, J = 10.8, 7.3 Hz, 1H), 1.83-1.73 (m, 1H), 1.65-1.58 (m, 1H), 1.51 (s, 18H), 1.48-1.38 (m, 1H), 1.29 (d, J = 5.9 Hz, 3H), 1.28-1.11 (m, 1H), 1.22-1.11 (m, 2H), 1.09-0.98 (m, 3H), 0.93-0.87 (m, 2H), 0.86-0.81 (m, 6H) | ¹³C NMR (CDCl₃) δ 174.09, 169.53, 152.64, 83.02, 76.56, 76.20, 74.16, 72.12, 58.02, 44.11, 35.18, 28.23, 27.94, 27.02, 22.68, 22.16, 18.40, 12.86, 8.42, 8.33 |
| F159 | — | (Thin Film) 2954, 2932, 2870, 1743, 1706, 1507, 1392, 1365, 1235, 1167, 1144, 1118 | HRMS-ESI (m/z) [M]⁺ calcd for C₃₀H₄₇NO₈, 549.3302; found, 549.3322 | ¹H NMR (CDCl₃) δ 7.10-7.01 (m, 2H), 6.84-6.76 (m, 2H), 5.18 (dd, J = 8.5, 5.8 Hz, 1H), 5.04-4.94 (m, 1H), 4.23 (dd, J = 11.9, 5.9 Hz, 1H), 4.13 (t, J = 8.9 Hz, 1H), 3.95 (dd, J = 11.9, 8.5 Hz, 1H), 3.74 (dd, J = 11.0, 1.5 Hz, 1H), 3.58 (dd, J = 11.0, 6.8 Hz, 1H), 2.28 (s, 3H), 1.91-1.78 (m, 1H), 1.56-1.45 (m, 20H), 1.34 (d, J = 6.4 Hz, 3H), 1.22-1.04 (m, 3H), 0.77 (d, J = 6.6 Hz, 3H), 0.73 (d, J = 6.6 Hz, 3H) | — |
| F160 | — | — | — | ¹H NMR (CDCl₃) δ 5.15 (dd, J = 8.5, 5.7 Hz, 1H), 4.87-4.78 (m, 1H), 4.18 (dd, J = 11.9, 5.7 Hz, 1H), 3.89 (dd, J = 11.9, 8.5 Hz, 1H), 3.71-3.63 (m, 1H), 3.55-3.38 (m, 3H), 3.03 (t, J = 9.0 Hz, 1H), 1.67-1.52 (m, 5H), 1.50 (s, 18H), 1.43 (d, J = 6.4 Hz, 3H), 1.36-1.04 (m, 3H), 0.93 (t, J = 7.4 Hz, 3H), 0.88 (d, J = 3.1 Hz, 3H), 0.87 (d, J = 3.1 Hz, 3H) | ¹³C NMR (CDCl₃) δ 169.74, 152.65, 84.57, 82.95, 75.51, 73.54, 71.61, 57.81, 45.23, 35.94, 28.37, 27.93, 26.70, 23.43, 22.76, 22.38, 18.97, 10.69 |
| F161 | — | — | ESIMS m/z 551 ([M + Na]⁺) | ¹H NMR (CDCl₃) δ 5.04 (t, J = 7.4 Hz, 1H), 4.86-4.75 (m, 1H), 4.14 (dd, J = 11.8, 7.1 Hz, 1H), 4.00-3.92 (m, 2H), | ¹³C NMR (CDCl₃) δ 169.95, 152.63, 83.27, 82.94, 82.87, 76.01, 75.71, 71.67, 57.88, |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | | | | 3.62-3.50 (m, 2H), 3.18 (t, J = 8.1 Hz, 1H), 1.77-1.59 (m, 7H), 1.56-1.46 (m, 22H), 1.43 (d, J = 6.5 Hz, 3H), 1.36-1.22 (m, 1H), 1.19-1.05 (m, 2H), 0.90-0.80 (m, 6H) | 45.58, 36.81, 32.61, 32.52, 28.41, 27.92, 26.45, 23.08, 23.05, 22.73, 22.47, 19.05 |
| F162 | — | — | ESIMS m/z 512 ([M + Na]$^+$) | $^1$H NMR (CDCl$_3$) δ 6.85-6.73 (m, 2H), 5.16 (d, J = 8.3 Hz, 1H), 5.02-4.89 (m, 1H), 4.63-4.52 (m, 1H), 4.00-3.87 (m, 1H), 3.50-3.22 (m, 5H), 3.13-2.97 (m, 2H), 2.37-2.21 (m, 1H), 1.93-1.74 (m, 2H), 1.51-1.45 (d, J = 6.3 Hz, 3H), 1.45-1.37 (s, 9H), 1.00-0.89 (m, 6H) | $^{19}$F NMR (CDCl$_3$) δ −134.8 (dd, J = 20.9, 9.2 Hz), −163.9-−164.2 (m) |
| F163 | — | — | ESIMS m/z 641 ([M + Na]$^+$) | $^1$H NMR (CDCl$_3$) δ 7.34 (d, J = 1.7 Hz, 1H), 7.19-7.13 (m, 2H), 5.17 (dd, J = 8.6, 6.2 Hz, 1H), 5.02-4.92 (m, 2H), 4.13 (dd, J = 11.8, 6.2 Hz, 1H), 3.90 (dd, J = 11.8, 8.7 Hz, 1H), 3.5-3.44 (m, 2H), 2.78 (dd, J = 13.8, 3.6 Hz, 1H), 2.59 (h, J = 7.0 Hz, 1H), 2.46 (t, J = 12.8 Hz, 1H), 2.16 (bs, 1H), 1.49 (s, 18H), 1.33 (d, J = 5.9 Hz, 3H), 1.22-1.20 (m, 6H) | $^{13}$C NMR (CDCl$_3$) δ 176.32, 169.77, 152.61, 135.36, 134.93, 132.83, 132.45, 129.41, 126.99, 83.12, 77.23, 73.78, 71.17, 57.40, 43.77, 34.22, 32.23, 27.91, 19.03, 18.94, 18.30 |
| F164 | — | — | ESIMS m/z 628 ([M + Na]$^+$) | $^1$H NMR (CDCl$_3$) δ 7.35 (d, J = 2.1 Hz, 1H), 7.23-7.15 (m, 2H), 5.11 (dd, J = 8.4, 6.6 Hz, 1H), 4.89 (dd, J = 8.8, 6.4 Hz, 1H), 4.07 (dd, J = 11.8, 6.5 Hz, 1H), 3.87 (dd, J = 11.8, 8.5 Hz, 1H), 3.46-3.28 (m, 3H), 3.19-3.11 (m, 2H), 2.54 (t, J = 12.9 Hz, 1H), 2.05 (bs, 1H), 1.86 (dp, J = 13.2, 6.6 Hz, 1H), 1.52-1.46 (m, 4H), 1.48 (s, 18H), 0.93 (d, J = 6.7 Hz, 6H) | — |
| F165 | — | — | ESIMS m/z 641 ([M + Na]$^+$) | $^1$H NMR (CDCl$_3$) δ 7.35 (d, J = 2.1 Hz, 1H), 7.25-7.06 (m, 2H), 5.11 (dd, J = 8.3, 6.6 Hz, 1H), 4.88 (dd, J = 8.9, 6.4 Hz, 1H), 4.07 (dd, J = 11.8, 6.6 Hz, 1H), 3.87 (dd, J = 11.8, 8.5 Hz, 1H), 3.70-3.59 (m, 1H), 3.55-3.49 (m, 1H), 3.46-3.27 (m, 2H), 3.24-3.08 (m, 2H), 2.55 (t, J = 12.8 Hz, 1H), 2.08-1.98 (m, 1H), 1.65-1.29 (m, 9H), 1.48 (s, 18H), 0.89 (t, J = 7.0 Hz, 3H) | — |
| F166 | — | — | ESIMS m/z 539 ([M − t-BOC]$^+$) | $^1$H NMR (CDCl$_3$) δ 7.31 (d, J = 1.8 Hz, 1H), 7.17-7.11 (m, 2H), 7.08 (d, J = 8.2 Hz, 2H), 6.85 (d, J = 8.6 Hz, 2H), 5.16 (dd, J = 8.3, 6.9 Hz, 1H), 5.05 (dq, J = 8.5, 6.4 Hz, 1H), 4.27 (t, J = 8.6 Hz, 1H), 4.13 (dd, J = 11.8, 6.8 Hz, 1H), 3.93 (dd, J = 11.8, 8.5 Hz, 1H), 3.58-3.43 (m, 2H), 3.04 (dd, J = 13.7, 3.5 Hz, 1H), 2.52 (t, J = 12.7 Hz, 1H), 2.33-2.19 (m, 1H), 2.28 (s, 3H), 1.49 (s, 18H), 1.39 (d, J = 6.4 Hz, 3H) | — |
| F167 | — | — | ESIMS m/z 565 ([M + Na]$^+$) | $^1$H NMR (CDCl$_3$) δ 5.20 (dd, J = 8.6, 5.7 Hz, 1H), 4.96-4.89 (m, 1H), 4.79 (t, J = 9.0 Hz, 1H), 4.23 (dd, J = 11.9, 5.7 Hz, 1H), 3.93 (dd, J = 11.9, 8.7 Hz, 1H), 3.75 (d, J = 10.7 Hz, | — |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| | — | — | | 1H), 3.56 (dd, J = 10.9, 7.1 Hz, 1H), 2.56 (h, J = 7.0 Hz, 1H), 1.91-1.42 (m, 8H), 1.51 (s, 18H), 1.29 (d, J = 6.3 Hz, 3H), 1.19 (d, J = 7.0 Hz, 6H), 1.13-0.93 (m, 4H) | |
| F168 | — | — | ESIMS m/z 551 ([M + Na]$^+$) | $^1$H NMR (CDCl$_3$) δ 5.11 (dd, J = 8.3, 6.5 Hz, 1H), 4.89-4.78 (m, 1H), 4.18 (dd, J = 11.8, 6.4 Hz, 1H), 3.91 (dd, J = 11.8, 8.4 Hz, 1H), 3.62 (d, J = 10.7 Hz, 1H), 3.51 (dd, J = 10.9, 6.3 Hz, 1H), 3.33 (dd, J = 8.3, 6.3 Hz, 1H), 3.21 (dd, J = 8.3, 6.6 Hz, 1H), 2.97 (t, J = 8.7 Hz, 1H), 2.88 (t, J = 7.6 Hz, 2H), 2.71 (t, J = 7.6 Hz, 2H), 1.97-1.45 (m, 6H), 1.50 (s, 18H), 1.42 (d, J = 6.4 Hz, 3H), 1.32-1.22 (m, 1H), 1.15-1.00 (m, 2H), 0.91 (dd, J = 6.7, 4.2 Hz, 6H) | — |
| F169 | — | — | ESIMS m/z 565 ([M + Na]$^+$) | — | — |
| F170 | — | — | ESIMS m/z 473 ([M + Na]$^+$) | $^1$H NMR (CDCl$_3$) δ 7.07 (m, 4H), 5.14 (d, J = 8.2 Hz, 1H), 4.95 (dq, J = 9.2, 6.4 Hz, 1H), 4.59 (q, J = 7.3 Hz, 1H), 3.87 (dd, J = 11.5, 7.3 Hz, 1H), 3.44 (t, J = 7.4 Hz, 2H), 3.31 (dddd, J = 24.1, 18.8, 10.5, 6.8 Hz, 3H), 3.10 (dd, J = 10.4, 6.6 Hz, 2H), 2.31 (s, 3H), 2.24 (t, J = 12.7 Hz, 1H), 1.87 (dt, J = 13.2, 6.6 Hz, 2H), 1.47 (d, J = 6.4 Hz, 3H), 1.41 (s, 9H), 0.95 (d, J = 6.7 Hz, 6H) | $^{13}$C NMR (CDCl$_3$) δ 172.24, 154.95, 136.81, 135.52, 129.10, 129.01, 84.66, 80.02, 79.21, 75.57, 72.86, 72.48, 52.97, 47.40, 34.56, 29.17, 28.27, 21.01, 19.48, 18.80 |
| F171 | — | — | ESIMS m/z 362 ([M + H]$^+$) | — | — |
| F172 | — | — | ESIMS m/z 404 ([M + H]$^+$) | — | — |
| F173 | — | — | ESIMS m/z 364 ([M + H]$^+$) | — | — |
| F174 | — | — | ESIMS m/z 350 ([M + H]$^+$) | — | — |
| F175 | — | — | ESIMS m/z 400 ([M + H]$^+$) | — | — |
| F176 | — | — | ESIMS m/z 440 ([M + H]$^+$) | — | — |
| F177 | — | — | ESIMS m/z 401 ([M + H]$^+$) | — | — |
| F178 | — | — | ESIMS m/z 420 ([M + H]$^+$) | — | — |
| F179 | — | — | ESIMS m/z 398 ([M + H]$^+$) | — | — |
| F180 | — | — | ESIMS m/z 404 ([M + H]$^+$) | — | — |
| F181 | — | — | ESIMS m/z 364 ([M + H]$^+$) | — | — |
| F182 | — | — | ESIMS m/z 364 ([M + H]$^+$) | — | — |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| F183 | — | — | ESIMS m/z 366 ([M + H]$^+$) | — | — |
| F184 | — | — | ESIMS m/z 368 ([M + H]$^+$) | — | — |
| F185 | — | — | HRMS-ESI (m/z) [M + H]$^+$ calcd for C$_{20}$H$_{28}$NO$_5$, 362.1962; found, 362.1956 | — | — |
| F186 | — | — | — | — | — |
| F187 | — | — | HRMS-ESI (m/z) [M]$^+$ calcd for C$_{19}$H$_{25}$F$_4$NO$_4$, 407.172; found, 407.1726 | — | — |
| F188 | — | — | HRMS-ESI (m/z) [M + H]$^+$ calcd for C$_{20}$H$_{29}$FNO$_4$, 366.2075; found, 366.2082 | — | — |
| F189 | — | — | ESIMS m/z 368 ([M + H]$^+$) | — | — |
| F190 | — | — | ESIMS m/z 374 ([M + H]$^+$) | — | — |
| F191 | — | — | ESIMS m/z 354 ([M + H]$^+$) | — | — |
| F192 | — | — | HRMS-ESI (m/z) [M + H]$^+$ calcd for C$_{20}$H$_{28}$NO$_5$, 362.1962; found, 362.1963 | — | — |
| F193 | — | — | HRMS-ESI (m/z) [M]$^+$ calcd for C$_{20}$H$_{28}$F$_3$NO$_4$, 403.1970; found, 403.1973 | — | — |
| F194 | — | — | — | — | — |
| F195 | — | — | ESIMS m/z 362 ([M + H]$^+$) | — | — |
| F196 | — | — | — | — | — |
| F197 | — | — | ESIMS m/z 404 ([M + H]$^+$) | — | — |
| F198 | — | — | ESIMS m/z 416 ([M + H]$^+$) | — | — |
| F199 | — | — | ESIMS m/z 390 ([M + H]$^+$) | — | — |
| F200 | — | — | ESIMS m/z 418 ([M + H]$^+$) | — | — |

TABLE 2-continued

Analytical Data

| Cmpd No. | MP (° C.) | IR (cm$^{-1}$) | Mass | $^1$H NMR | $^{13}$C or $^{19}$F NMR |
|---|---|---|---|---|---|
| F201 | — | — | ESIMS m/z 418 ([M + H]$^+$) | — | — |
| F202 | — | — | ESIMS m/z 328 ([M + H]$^+$) | — | — |
| F203 | — | — | ESIMS m/z 340 ([M + H]$^+$) | — | — |
| F204 | — | — | ESIMS m/z 316 ([M + H]$^+$) | — | — |
| F205 | — | — | HRMS-ESI (m/z) [M]$^+$ calcd for C$_{17}$H$_{30}$F$_3$NO$_4$, 369.2127; found, 369.2126 | — | — |
| F206 | — | — | HRMS-ESI (m/z) [M]$^+$ calcd for C$_{17}$H$_{29}$NO$_5$, 327.2046; found, 327.2053 | — | — |
| F207 | — | — | HRMS-ESI (m/z) [M]$^+$ calcd for C$_{20}$H$_{31}$NO$_4$, 349.2253; found, 349.2240 | — | — |
| F208 | — | — | ESIMS m/z 302 ([M + H]$^+$) | — | — |
| F209 | — | — | ESIMS m/z 328 ([M + H]$^+$) | — | — |
| F210 | — | — | HRMS-ESI (m/z) [M]$^+$ calcd for C$_{19}$H$_{26}$F$_3$NO$_4$, 389.1814; found, 389.1831 | — | — |
| F211 | — | — | ESIMS m/z 419 ([M + H]$^+$) | $^1$H NMR (DMSO-d$_6$) δ 8.51 (bs, 3H), 7.61 (d, J = 2.1 Hz, 1H), 7.40 (dd, J = 8.3, 2.1 Hz, 1H), 7.35 (d, J = 8.3 Hz, 1H), 5.08-5.00 (m, 1H), 4.89 (t, J = 9.4 Hz, 1H), 4.47-4.44 (m, 1H), 3.95 (dd, J = 12.4, 7.0 Hz, 1H), 3.65-3.45 (m, 3H), 2.71 (dd, J = 13.8, 3.7 Hz, 1H), 2.64 (p, J = 7.0 Hz, 1H), 2.38-2.32 (m, 1H), 2.11-2.01 (m, 1H), 1.27 (d, J = 6.3 Hz, 3H), 1.15 (d, J = 7.0 Hz, 6H) | — |
| F212 | — | — | ESIMS m/z 404.3 ([M + H]$^+$) | — | — |
| F213 | — | — | ESIMS m/z 418.23 ([M + H]$^+$) | — | — |
| F214 | — | — | ESIMS m/z 438.2 ([M + H]$^+$) | — | — |
| F215 | — | — | HRMS-ESI (m/z) | — | — |

TABLE 2-continued

Analytical Data

| Cmpd No. | MP (°C.) | IR (cm$^{-1}$) | Mass | $^1$H NMR | $^{13}$C or $^{19}$F NMR |
|---|---|---|---|---|---|
| | | | [M]$^+$ calcd for C$_{18}$H$_{31}$NO$_5$, 341.2202; found, 341.2201 | | |
| F216 | — | — | ESIMS m/z 328.4 ([M + H]$^+$) | — | — |
| F217 | — | — | ESIMS m/z 342.4 ([M + H]$^+$) | — | — |
| F218 | 81-84 | — | ESIMS m/z 351 ([M + H]$^+$) | $^1$H NMR (CDCl$_3$) δ 7.08 (t, J = 2.7 Hz, 4H), 4.91 (dq, J = 9.2, 6.4 Hz, 1H), 3.84 (dd, J = 11.6, 7.5 Hz, 1H), 3.76 (m, 1H), 3.71 (d, J = 7.7 Hz, 1H), 3.64 (m, 1H), 3.47 (dd, J = 8.3, 6.4 Hz, 1H), 3.41 (dd, J = 10.7, 6.1 Hz, 1H), 3.31 (m, 2H), 3.13 (d, J = 9.0 Hz, 1H), 3.09 (m, 1H), 3.04 (m, 2H), 2.31 (s, 3H), 1.87 (m, 2H), 1.61 (s, 1H), 1.47 (d, J = 6.4 Hz, 3H), 0.95 (dd, J = 6.7, 1.6 Hz, 6H) | — |

*$^1$H NMR were run at 400 MHz unless noted otherwise
*$^{13}$C NMR were run at 101 MHz unless noted otherwise
*$^{19}$F NMR were run at 376 MHz unless noted otherwise

TABLE 3

Biological Testing Rating Scale
Rating Table for Fungal Pathogens

| % Control | Rating |
|---|---|
| 80-100 | A |
| More than 0-Less than 80 | B |
| Not Tested | C |
| No activity noticed in this bioassay | D |

TABLE 4

Biological Activity - Disease Control in High and Low Volume Applications

| Cmpd. No. | PUCCRT* | | | | SEPTTR* | | | |
| | 1DP* Rate | | 3DC* | | 1DP* Rate | | 3DC* | |
| | 121.5 g/H* | 100 ppm* | 121.5 g/H* | 100 ppm* | 121.5 g/H* | 100 ppm* | 121.5 g/H* | 100 ppm* |
|---|---|---|---|---|---|---|---|---|
| F1 | C | A | C | A | C | A | C | B |
| F2 | C | A | C | B | C | A | C | A |
| F3 | C | A | C | A | C | A | C | A |
| F4 | C | A | C | A | C | A | C | A |
| F5 | C | B | C | B | C | A | C | B |
| F6 | C | B | C | D | C | A | C | B |
| F7 | C | A | C | B | C | A | C | B |
| F8 | C | A | C | B | C | A | C | B |
| F9 | C | A | C | D | C | A | C | A |

TABLE 4-continued

Biological Activity - Disease Control in High and Low Volume Applications

| Cmpd. No. | PUCCRT* | | | | SEPTTR* | | | |
|---|---|---|---|---|---|---|---|---|
| | 1DP* | | 3DC* | | 1DP* | | 3DC* | |
| | Rate | | | | Rate | | | |
| | 121.5 g/H* | 100 ppm* | 121.5 g/H* | 100 ppm* | 121.5 g/H* | 100 ppm* | 121.5 g/H* | 100 ppm* |
| F10 | C | A | C | D | C | A | C | B |
| F11 | C | A | C | B | C | A | C | A |
| F12 | C | A | C | A | C | A | C | A |
| F13 | C | A | C | A | C | A | C | A |
| F14 | C | A | C | A | C | A | C | A |
| F15 | C | A | C | B | C | A | C | A |
| F16 | C | A | C | B | C | A | C | B |
| F17 | C | A | C | B | C | A | C | A |
| F18 | C | A | C | A | C | A | C | B |
| F19 | C | A | C | A | C | A | C | A |
| F20 | C | C | C | C | C | C | C | C |
| F21 | C | A | C | A | C | A | C | A |
| F22 | C | B | C | B | C | D | C | B |
| F23 | C | A | C | B | C | A | C | B |
| F24 | C | A | C | B | C | A | C | B |
| F25 | C | A | C | B | C | A | C | A |
| F26 | C | B | C | D | C | A | C | B |
| F27 | C | A | C | B | C | A | C | B |
| F28 | C | A | C | B | C | A | C | B |
| F29 | C | A | C | B | C | A | C | A |
| F30 | C | A | C | D | C | A | C | B |
| F31 | C | B | C | D | C | A | C | B |
| F32 | C | A | C | B | C | A | C | B |
| F33 | C | B | C | D | C | A | C | B |
| F34 | C | A | C | A | C | A | C | A |
| F35 | C | A | C | D | C | A | C | B |
| F36 | C | A | C | B | C | A | C | A |
| F37 | C | A | C | B | C | A | C | A |
| F38 | C | A | C | A | C | A | C | A |
| F39 | C | A | C | A | C | A | C | A |
| F40 | C | B | C | D | C | A | C | A |
| F41 | C | A | C | D | C | A | C | A |
| F42 | C | A | C | A | C | A | C | A |
| F43 | C | B | C | D | C | A | C | B |
| F44 | C | A | C | D | C | D | C | D |
| F45 | C | A | C | B | C | A | C | A |
| F46 | C | A | C | A | C | A | C | A |
| F47 | C | A | C | A | C | A | C | A |
| F48 | C | A | C | A | C | A | C | B |
| F49 | A | A | B | A | A | A | A | A |
| F50 | C | A | C | A | C | A | C | A |
| F51 | C | A | C | B | C | A | C | A |
| F52 | C | A | C | B | C | A | C | A |
| F53 | A | A | B | A | A | A | B | A |
| F54 | A | A | B | A | A | A | A | A |
| F55 | C | A | C | A | C | A | C | A |
| F56 | C | A | C | A | C | A | C | A |
| F57 | A | A | B | A | A | A | A | A |
| F58 | A | A | B | A | A | A | A | A |
| F59 | A | A | B | A | A | A | A | A |
| F60 | A | A | A | A | A | A | A | A |
| F61 | A | A | B | A | A | A | B | A |
| F62 | A | A | B | A | A | A | A | A |
| F63 | A | A | B | A | A | A | A | A |
| F64 | C | A | C | A | C | A | C | A |
| F65 | A | A | B | A | A | A | A | A |
| F66 | A | A | B | B | A | A | B | B |
| F67 | C | A | C | A | C | A | C | B |
| F68 | A | A | A | A | A | A | A | A |
| F69 | A | A | B | A | A | A | A | A |
| F70 | C | A | C | A | C | A | C | A |
| F71 | C | A | C | A | C | A | C | A |
| F72 | A | A | A | A | A | A | A | A |
| F73 | A | A | B | A | A | A | A | A |
| F74 | C | A | C | A | C | A | C | A |
| F75 | A | A | B | A | A | A | A | A |
| F76 | A | A | B | D | A | B | D | D |
| F77 | A | A | A | A | A | A | A | A |
| F78 | C | A | C | A | C | A | C | A |
| F79 | A | A | B | A | A | A | A | A |
| F80 | A | A | A | A | A | A | A | A |

TABLE 4-continued

Biological Activity - Disease Control in High and Low Volume Applications

| Cmpd. No. | PUCCRT* | | | | SEPTTR* | | | |
|---|---|---|---|---|---|---|---|---|
| | 1DP* | | 3DC* | | 1DP* | | 3DC* | |
| | Rate | | | | Rate | | | |
| | 121.5 g/H* | 100 ppm* | 121.5 g/H* | 100 ppm* | 121.5 g/H* | 100 ppm* | 121.5 g/H* | 100 ppm* |
| F81 | C | A | C | A | C | A | C | A |
| F82 | A | A | A | A | A | A | A | A |
| F83 | A | A | B | A | B | A | A | A |
| F84 | C | A | C | A | C | A | C | D |
| F85 | C | A | C | B | C | A | C | B |
| F86 | C | A | C | A | C | A | C | A |
| F87 | A | A | B | A | A | A | A | A |
| F88 | C | A | C | A | C | A | C | A |
| F89 | C | A | C | A | C | A | C | A |
| F90 | C | A | C | A | C | A | C | A |
| F91 | C | A | C | A | C | A | C | A |
| F92 | A | A | A | A | A | A | A | A |
| F93 | A | A | A | A | A | A | A | A |
| F94 | A | A | A | A | A | A | A | A |
| F95 | C | A | C | A | C | A | C | A |
| F96 | A | A | A | A | A | A | A | A |
| F97 | A | A | A | A | A | A | A | B |
| F98 | A | A | B | A | A | A | B | A |
| F99 | A | A | B | A | A | A | A | A |
| F100 | A | A | B | A | A | A | B | A |
| F101 | C | A | C | A | C | A | C | A |
| F102 | C | A | C | A | C | A | C | A |
| F103 | C | A | C | A | C | A | C | B |
| F104 | A | A | A | A | A | A | A | A |
| F105 | A | A | A | A | A | A | A | A |
| F106 | A | A | A | A | A | A | A | A |
| F107 | A | A | A | A | A | A | A | A |
| F108 | A | A | A | A | A | A | A | A |
| F109 | A | A | A | A | A | A | A | A |
| F110 | A | A | B | A | A | A | A | A |
| F111 | C | A | C | A | C | A | C | A |
| F112 | A | C | B | C | A | C | A | C |
| F113 | A | C | D | C | D | C | D | C |
| F114 | A | A | A | A | A | A | A | A |
| F115 | A | A | A | A | A | A | A | A |
| F116 | A | A | A | A | A | A | A | A |
| F117 | A | A | A | A | A | A | A | A |
| F118 | A | A | A | A | A | A | A | A |
| F119 | C | A | C | A | C | A | C | A |
| F120 | C | A | C | B | C | A | C | A |
| F121 | A | A | A | A | A | A | A | A |
| F122 | A | C | B | C | A | C | D | C |
| F123 | A | C | D | C | A | C | D | C |

*PUCCRT—Wheat Brown Rust (*Puccinia triticina*)
*SEPTTR—Wheat Leaf Blotch (*Septoria tritici*)
*1DP—1 Day Protectant
*3DC—3 Day Curative

TABLE 5

Biological Activity - Disease Control at 100 ppm

| Compound. Number | ALTESO* | CERCBE* | COLLLA* 1DP* | ERYSCI* | ERYSGH* |
|---|---|---|---|---|---|
| F60 | C | A | C | A | C |
| F73 | B | A | A | B | C |
| F80 | A | A | A | A | A |
| F82 | B | B | A | B | C |
| F83 | D | A | A | D | A |
| F96 | A | A | A | A | A |
| F105 | B | A | A | B | C |
| F107 | A | A | C | A | B |
| F108 | A | A | C | A | A |
| F110 | A | A | A | B | C |
| F114 | A | A | A | A | A |
| F117 | A | A | A | A | A |

TABLE 5-continued

Biological Activity - Disease Control at 100 ppm

| Compound. Number | ALTESO* | CERCBE* | COLLLA* 1DP* | ERYSCI* | ERYSGH* |
|---|---|---|---|---|---|
| F122 | A | A | A | B | A |
| F123 | A | A | A | A | A |

*ALTESO—Tomato Early Blight (*Alternaria solani*)
*CERCBE—Leaf Spot of Sugar Beets (*Cercospora beticola*)
*COLLLA—Cucumber Anthracnose (*Glomerella lagenarium*; Anamorph: *Colletotricum lagenarium*)
*ERYSCI—Powdery Mildew of Cucumber (*Erysiphe cichoracearum*)
*ERYSGH—Barley Powdery Mildew (*Blumeria graminis* f.sp. *hordei*; Synonym: *Erysiphe graminis* f.sp. *hordei*)
*1DP—1 Day Protectant

TABLE 6

Biological Activity - Disease Control at 100 ppm

| Compound. Number | ERYSGT* | LEPTNO* | PYRIOR* | RHYNSE* 1DP* | UNCINE* | VENTIN* |
|---|---|---|---|---|---|---|
| F60 | C | C | C | C | A | C |
| F73 | C | C | A | A | C | C |
| F80 | A | A | A | C | B | B |
| F82 | C | C | A | A | C | C |
| F83 | C | A | A | A | B | A |
| F96 | A | A | A | C | A | C |
| F105 | C | C | A | A | C | C |
| F107 | C | C | A | A | B | C |
| F108 | C | C | A | A | A | C |
| F110 | C | C | A | A | C | C |
| F114 | C | C | A | A | A | A |
| F117 | A | A | A | C | A | A |
| F122 | C | A | C | A | A | A |
| F123 | C | A | C | A | A | B |

*ERYSGT—Wheat Powdery Mildew (*Blumeria graminis* f. sp. *tritici*; Synonym: *Erysiphe graminis* f. sp. *tritici*)
*LEPTNO—Wheat Glume Blotch (*Leptosphaeria nodorum*)
*PYRIOR—Rice Blast (*Magnaporthe grisea*; Anamorph: *Pyricularia oryzae*)
*RHYNSE—Barley Scald (*Rhyncosporium secalis*)
*UNCINE—Grape Powdery Mildew (*Uncinula necator*)
*VENTIN—Apple Scab (*Venturia inaequalis*)
*1DP—1 Day Protectant

TABLE 7

Biological Activity - Disease Control at 25 ppm

| Compound Number | PHAKPA* | |
|---|---|---|
| | 1DP* | 3DC* |
| F106 | A | A |
| F107 | A | B |
| F108 | A | A |
| F109 | A | B |
| F114 | A | B |
| F122 | B | D |
| F123 | B | D |

*PHAKPA—Asian Soybean Rust (*Phakopsora pachyrhizi*)
*1DP—1 Day Protectant
*3DC—3 Day Curative

What is claimed is:

1. A method for the control and/or the prevention of fungal growth comprising the steps of:
   applying a fungicidally effective amount of at least one compound of Formula I

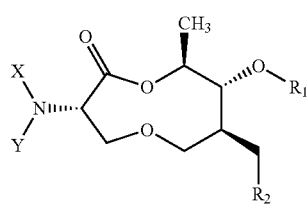

wherein:
X is H or C(O)R$_3$;
Y is H, C(O)R$_3$, or Q;
Q is

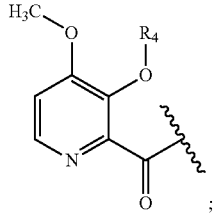

R$_1$ is chosen from H, alkyl, alkenyl, aryl, —Si(R$_6$)$_3$, or —C(O)R$_6$, each optionally substituted with 0, 1 or multiple R$_5$;

R$_2$ is chosen from H, alkyl, aryl, heteroaryl, or arylalkyl, each optionally substituted with 0, 1 or multiple R$_5$;

R$_3$ is chosen from alkoxy, or benzyloxy, each optionally substituted with 0, 1, or multiple R$_5$;

R$_4$ is chosen from H, —C(O)R$_7$, or —CH$_2$OC(O)R$_7$;

R$_5$ is chosen from H, alkyl, alkenyl, halo, haloalkyl, alkoxy, aryl, heteroaryl, heterocyclyl, or —C(O)R$_6$;

R$_6$ is chosen from alkyl, alkenyl, haloalkyl, alkoxy, aryl or heteroaryl; and

R$_7$ is chosen from alkyl or alkoxy, each optionally substituted with 0, 1, or multiple R$_6$;

with the proviso that R$_2$ is not unsubstituted phenyl or unsubstituted cyclohexyl;

to at least one selected from the group consisting of: a fungi, an animal, an inert surface, a plant, an area adjacent to a plant, soil adapted to support growth of a plant, and a seed adapted to produce a plant.

2. The method according to claim 1, wherein X and Y are independently chosen from H or C(O)R$_3$.

3. The method according to claim 2, wherein R$_1$ is chosen from H, alkyl, alkenyl, aryl, —Si(R$_6$)$_3$, or —C(O)R$_6$, each optionally substituted with 0, 1 or multiple R$_5$.

4. The method according to claim 3, wherein $R_2$ is chosen from H, alkyl, aryl, heteroaryl, or arylalkyl, each optionally substituted with 0, 1 or multiple $R_5$.

5. The method according to claim 1, wherein X is H and Y is Q.

6. The method according to claim 5, wherein $R_1$ is chosen from H, alkyl, alkenyl, aryl, —Si($R_6$)$_3$, or —C(O)$R_6$, each optionally substituted with 0, 1 or multiple $R_5$.

7. The method according to claim 6, wherein $R_2$ is chosen from H, alkyl, aryl, heteroaryl, or arylalkyl, each optionally substituted with 0, 1 or multiple $R_5$.

8. The method according to claim 7, wherein $R_4$ is H, —C(O)$R_7$, or —CH$_2$OC(O)$R_7$.

9. The method according to claim 8, wherein $R_7$ is alkyl or alkoxy, each optionally substituted with 0, 1, or multiple $R_6$.

10. The method according to claim 1, wherein:
at least one compound of said Formula I is applied in combination with a phytologically acceptable carrier material.

11. The method according to claim 10, wherein:
the compound of Formula I is admixed with a phytologically acceptable carrier material.

12. The method according to claim 1, wherein:
the compound of Formula I is applied in combination with at least one agriculturally active ingredient selected from the group consisting of: fungicides, insecticides, nematocides, miticides, arthropodicides, bactericides and combinations thereof.

13. The method according to claim 12, wherein:
the compound of Formula I is admixed with at least one agriculturally active ingredient selected from the group consisting of: fungicides, insecticides, nematocides, miticides, arthropodicides, bactericides and combinations thereof.

14. The method according to claim 1, wherein the compound of Formula I is suitable for the control of at least one fungal pathogen selected from the group consisting of: *Mycosphaerella graminicola*; anamorph: *Septoria tritici, Puccinia triticina, Puccinia striiformis, Venturia inaequalis, Ustilago maydis, Uncinula necator, Rhynchosporium secalis, Magnaporthe grisea, Pseudoperonospora cubensis, Phakopsora pachyrhizi, Leptosphaeria nodorum, Blumeria graminis* f. sp. *tritici, Blumeria graminis* f. sp. *hordei, Erysiphe cichoracearum, Glomerella lagenarium, Cercospora beticola, Alternaria solani*, and *Pyrenophora teres*.

15. The method according to claim 1, wherein the compound of Formula I is suitable for the control of a fungal pathogen comprising *Septoria tritici, Puccinia triticina*, and *Phakopsora pachyrhizi*.

16. The method according to claim 12, wherein the compound of Formula I is suitable for the control of at least one fungal pathogen selected from the group consisting of *Mycosphaerella graminicola*; anamorph: *Septoria tritici, Puccinia triticina, Puccinia striiformis, Venturia inaequalis, Ustilago maydis, Uncinula necator, Rhynchosporium secalis, Magnaporthe grisea, Pseudoperonospora cubensis, Phakopsora pachyrhizi, Leptosphaeria nodorum, Blumeria graminis* f. sp. *tritici, Blumeria graminis* f. sp. *hordei, Erysiphe cichoracearum, Glomerella lagenarium, Cercospora beticola, Alternaria solani*, and *Pyrenophora teres*.

17. The method according to claim 13, wherein the compound of Formula I is suitable for the control of at least one fungal pathogen selected from the group consisting of *Mycosphaerella graminicola*; anamorph: *Septoria tritici, Puccinia triticina, Puccinia striiformis, Venturia inaequalis, Ustilago maydis, Uncinula necator, Rhynchosporium secalis, Magnaporthe grisea, Pseudoperonospora cubensis, Phakopsora pachyrhizi, Leptosphaeria nodorum, Blumeria graminis* f. sp. *tritici, Blumeria graminis* f. sp. *hordei, Erysiphe cichoracearum, Glomerella lagenarium, Cercospora beticola, Alternaria solani*, and *Pyrenophora teres*.

18. The method according to claim 12, wherein the compound of Formula I is suitable for the control of a fungal pathogen comprising *Septoria tritici, Puccinia triticina*, and *Phakopsora pachyrhizi*.

19. The method according to claim 13, wherein the compound of Formula I is suitable for the control of a fungal pathogen comprising *Septoria tritici, Puccinia triticina*, and *Phakopsora pachyrhizi*.

20. The method according to claim 1, wherein the compound of Formula I is applied to a root of the plant or foliage of the plant.

* * * * *